US012760316B2

(12) United States Patent
Mason et al.

(10) Patent No.: US 12,760,316 B2
(45) Date of Patent: Oct. 13, 2026

(54) IgG VARIANTS FOR INDUCTION OF IMMUNE RESPONSE WITHOUT ADJUVANT

(71) Applicant: ARIZONA BOARD OF REGENTS ON BEHALF OF ARIZONA STATE UNIVERSITY, Scottsdale, AZ (US)

(72) Inventors: Hugh Mason, Phoenix, AZ (US); Andrew Diamos, Tempe, AZ (US); Mary Pardhe, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1022 days.

(21) Appl. No.: 17/801,110

(22) PCT Filed: Feb. 22, 2021

(86) PCT No.: PCT/US2021/019090
§ 371 (c)(1),
(2) Date: Aug. 19, 2022

(87) PCT Pub. No.: WO2021/168434
PCT Pub. Date: Aug. 26, 2021

(65) Prior Publication Data

US 2023/0105415 A1 Apr. 6, 2023

Related U.S. Application Data

(60) Provisional application No. 62/980,012, filed on Feb. 21, 2020.

(51) Int. Cl.

| | |
|---|---|
| ***A61K 39/385*** | (2006.01) |
| ***A61K 39/12*** | (2006.01) |
| ***A61K 39/395*** | (2006.01) |
| ***C12N 15/62*** | (2006.01) |
| ***C12N 15/82*** | (2006.01) |
| *A61K 39/00* | (2006.01) |

(52) U.S. Cl.
CPC .......... *C12N 15/8258* (2013.01); *A61K 39/12* (2013.01); *A61K 39/385* (2013.01); *A61K 39/395* (2013.01); *C12N 15/62* (2013.01); *A61K 2039/6056* (2013.01); *C07K 2317/34* (2013.01); *C07K 2317/60* (2013.01); *C07K 2319/30* (2013.01); *C12N 2770/16034* (2013.01)

(58) Field of Classification Search
None
See application file for complete search history.

(56) References Cited

U.S. PATENT DOCUMENTS

| | | | | |
|---|---|---|---|---|
| 8,970,056 | B2 | 3/2015 | Solheim | |
| 10,835,867 | B2 | 11/2020 | Penunuri | |
| 11,058,766 | B2 * | 7/2021 | Mason | A61K 39/12 |
| 11,865,174 | B2 * | 1/2024 | Mason | A61P 31/20 |
| 12,257,302 | B2 * | 3/2025 | Mason | A61K 39/12 |
| 2007/0298042 | A1 | 12/2007 | Hart | |
| 2013/0045205 | A1 | 2/2013 | Mason | |
| 2014/0339169 | A1 | 11/2014 | Zeren | |
| 2018/0051545 | A1 | 2/2018 | Johnson | |
| 2019/0002534 | A1 | 1/2019 | Thomas, Jr. | |
| 2019/0336596 | A1 | 11/2019 | Mason | |

OTHER PUBLICATIONS

Schroeder et al., Journal of Allergy and Clinical Immunology, 2010, 125(2) S2:S41-S52 (Year: 2010).*
Huang et al., Vaccine, 2010, 106(1):9-17 (Year: 2010).*
Tsouchnikas, G., Zlatkovic, J., Jarmer, J., Strauß, J., Vratskikh, O., Kundi, M., et al. (2015) "Immunization with Immune Complexes Modulates the Fine Specificity of Antibody Responses to a Flavivirus Antigen." J. Virol., 89, 7970-8.
Tusé, D., Tu, T., and McDonald, K. A. (2014). "Manufacturing Economics of Plant-Made Biologics: Case Studies in Therapeutic and Industrial Enzymes." Biomed Res. Int. 2014, 1-16. doi:10.1155/2014/256135.
Van Montfoort, N., Mangsbo, S.M., Camps, M.G.M., van Maren, W.W.C., Verhaart, I.E.C., Waisman, A., et al. (2012) "Circulating specific antibodies enhance systemic cross-priming by delivery of complexed antigen to dendritic cells in vivo." Eur. J. Immunol., 42, 598-606.
Vannice, K.S., Cassetti, M.C., Eisinger, R.W., Hombach, J., Knezevic, I., Marston, H.D., et al. (2019) "Demonstrating vaccine effectiveness during a waning epidemic: A WHO/NIH meeting report on approaches to development and licensure of Zika vaccine candidates." Vaccine, 37, 863-868.
Wang, G., de Jong, R.N., van den Bremer, E.T.J., Beurskens, F.J., Labrijn, A.F., Ugurlar, D., et al. (2016) "Molecular Basis of Assembly and Activation of Complement Component C1 in Complex with Immunoglobulin G1 and Antigen." Mol. Cell, 63, 135-145.
Wang, Q., Chung, C.-Y., Chough, S., and Betenbaugh, M.J. (2018) "Antibody glycoengineering strategies in mammalian cells." Biotechnol. Bioeng., 115, 1378-1393.
Webster, G. et al., "A polymeric immunoglobulin-antigen fusion protein strategy for enhancing vaccine immunogenicity", Plant Biotechnology Journal, Dec. 2018 (available online Apr. 2018), vol. 16, No. 12, pp. 1983-1996 <DOI:10.1111/pbi.12932>.
West, E.E., Kolev, M., and Kemper, C. (2018) "Complement and the Regulation of T Cell Responses." Annu. Rev. Immunol., 36, 309-338.
Wilson, J.A., Hevey, M., Bakken, R., Guest, S., Bray, M., Schmaljohn, A.L., and Hart, M.K. (2000) "Epitopes involved in antibody-mediated protection from Ebola virus." Science, 287, 1664-6.

(Continued)

*Primary Examiner* — Stacy B Chen
(74) *Attorney, Agent, or Firm* — FULLER IP LAW LLC; Rodney J. Fuller

(57) ABSTRACT

The disclosure relates to immunoglobulin variants that are useful for the design of vaccinations against a variety of pathogens and their method of production and use. In some aspects, the immunoglobulin variants are variants of IgG, for example, the 6D8 antibody.

5 Claims, 35 Drawing Sheets

Specification includes a Sequence Listing.

(56) References Cited

OTHER PUBLICATIONS

Yan, B., Boyd, D., Kaschak, T., Tsukuda, J., Shen, A., Lin, Y., et al. (2012) "Engineering Upper Hinge Improves Stability and Effector Function of a Human IgG1." J. Biol. Chem., 287, 5891-5897.

Yang, M. et al., "Immunization of Zika virus envelope protein domain III induces specific and neutralizing immune responses against Zika virus", Vaccine, Jul. 2017 (available online Jun. 2017), vol. 35, No. 33, pp. 4287-4294 <DOI:10.1016/j.vaccine.2017.04.052>.

Yang, M. et al., "Plant-produced Zika virus envelope protein elicits neutralizing immune responses that correlate with protective immunity against Zika virus in mice", Plant Biotechnology Journal, Feb. 2018 (available online Jul. 2017), vol. 16, No. 2, pp. 572-580 <DOI:10.1111/pbi.12796>.

Zeitlin, L. et al., "Enhanced potency of a fucose-free monoclonal antibody being developed as an Ebola virus immunoprotectant", Proceedings of the National Academy of Sciences of the United States of America, Dec. 2011, vol. 108, No. 51, pp. 20690-20694 <DOI:10.1073/pnas.1108360108>.

Zeng, F., Yang, C., Gao, X., Li, X., Zhang, Z., and Gong, R. (2018) "Comprehensive elucidation of the structural and functional roles of engineered disulfide bonds in antibody Fc fragment." J. Biol. Chem., 293, 19127-19135.

Zhang, D., Armstrong, A.A., Tam, S.H., McCarthy, S.G., Luo, J., Gilliland, G.L., and Chiu, M.L. (2017) "Functional optimization of agonistic antibodies to OX40 receptor with novel Fc mutations to promote antibody multimerization." MAbs, 9, 1129-1142.

Zhang, Y., Zhou, Z., Zhu, S.L., Zu, X., Wang, Z., Zhang, L. ke, et al. (2019) "A novel RSV F-Fc fusion protein vaccine reduces lung injury induced by respiratory syncytial virus infection." Antiviral Res., 165, 11-22.

Alam, A. et al., "Technoeconomic Modeling of Plant-Based Griththsin Manufacturing", Frontiers in Bioengineering and Biotechnology, Jul. 2018, vol. 6, No. 102, 13 pages <DOI:10.3389/fbioe.2018.00102>.

Bournazos, S. and Ravetch, J. V. (2017) "Fcγ Receptor Function and the Design of Vaccination Strategies." Immunity, 47, 224-233.

Buyel, J.F. (2019) "Plant molecular farming—Integration and exploitation of side streams to achieve sustainable biomanufacturing." Front. Plant Sci., 9.

Carter, P.J. (2011) "Introduction to current and future protein therapeutics: A protein engineering perspective." Exp. Cell Res., 317, 1261-1269.

Castilho, A. et al., "Glyco-engineering in plants to produce human-like N-glycan structures", Biotechnology Journal, Sep. 2012 (available online Aug. 2012), vol. 7, No. 9, pp. 1088-1098 <DOI:10.1002/biot.201200032>.

Chargelegue, D. et al., "Highly Immunogenic and Protective Recombinant Vaccine Candidate Expressed in Transgenic Plants", Infection and Immunity, Sep. 2005, vol. 73, No. 9, pp. 5915-5922 <DOI:10.1128/IAI.73.9.5915-5922.2005>.

Chen, Q. et al., "The potential of plants as a system for the development and production of human biologics", F1000 Research, May 2016, vol. 5, No. 912, 8 pages <DOI:10.12688/f1000research.8010.1>.

Czajkowsky, D.M., Hu, J., Shao, Z., and Pleass, R.J. (2012) "Fc-fusion proteins: New developments and future perspectives." EMBO Mol. Med., 4, 1015-1028.

D'Eall, C., Pon, R.A., Rossotti, M.A., Krahn, N., Spearman, M., Callaghan, D., et al. (2019) "Modulating antibody-dependent cellular cytotoxicity of epidermal growth factor receptor-specific heavy-chain antibodies through hinge engineering." Immunol. Cell Biol.

Dekkers, G., Bentlage, A.E.H., Stegmann, T.C., Howie, H.L., Lissenberg-Thunnissen, S., Zimring, J., et al. (2017) "Affinity of human IgG subclasses to mouse Fc gamma receptors." MAbs, 9, 767-773.

Dent, M., Hurtado, J., Paul, A.M., Sun, H., Lai, H., Yang, M., et al. (2016) "Plant-produced anti-dengue virus monoclonal antibodies exhibit reduced antibody-dependent enhancement of infection activity." J. Gen. Virol., 97, 3280-3290.

Diamos et al., "5' and 3' Untranslated Regions Strongly Enhance Performance of Geminiviral Replicons in *Nicotiana benthamiana* Leaves", Front Plant Sci, (Feb. 24, 2016), vol. 7, No. 200, pp. 1-15.

Diamos, A. et al., "Codelivery of improved immune complex and virus-like particle vaccines containing Zika virus envelope domain III synergistically enhances immunogenicity", Vaccine, Apr. 2020 (available online Mar. 2020), vol. 38, No. 18, pp. 3455-3463 <DOI:10.1016/j.vaccine.2020.02.089>.

Diamos, A. et al., "Vaccine synergy with virus-like particle and immune complex platforms for delivery of human papillomavirus L2 antigen", Vaccine, Jan. 2019 (available online Nov. 2018), vol. 37, No. 1, pp. 137-144 <DOI:10.1016/j.vaccine.2018.11.021>.

Diebolder, C.A., Beurskens, F.J., de Jong, R.N., Koning, R.I., Strumane, K., Lindorfer, M.A., et al. (2014) "Complement Is Activated by IgG Hexamers Assembled at the Cell Surface." Science (80-. )., 343, 1260-1263.

Fletcher, E.A.K., van Maren, W., Cordfunke, R., Dinkelaar, J., Codee, J.D.C., van der Marel, G., et al. (2018) "Formation of Immune Complexes with a Tetanus-Derived B Cell Epitope Boosts Human T Cell Responses to Covalently Linked Peptides in an Ex Vivo Blood Loop System." J. Immunol., 201, 87-97.

Forthal, D.N., Gach, J.S., Landucci, G., Jez, J., Strasser, R., Kunert, R., and Steinkellner, H. (2010) "Fc-Glycosylation Influences Fcγ Receptor Binding and Cell-Mediated Anti-HIV Activity of Monoclonal Antibody 2G12." J. Immunol., 185, 6876-6882.

Getahun, A. and Heyman, B. (2006) "How antibodies act as natural adjuvants." Immunol. Lett., 104, 38-45.

Gupta, S.K. and Shukla, P. (2018) "Glycosylation control technologies for recombinant therapeutic proteins." Appl. Microbiol. Biotechnol., 102, 10457-10468.

Harry W. Schroeder, Lisa Cavacini, "Structure and function of immunoglobulins", Journal of Allergy and Clinical Immunology, Elsevier, Amsterdam, NL, Amsterdam, NL, (Feb. 1, 2010), vol. 125, No. 2, doi:10.1016/j.jaci.2009.09.046, ISSN 0091-6749, pp. S41-S52, XP055713825.

He, Junyun, Lai, H., Engle, M., Gorlatov, S., Gruber, C., Steinkellner, H., et al. (2014) "Generation and Analysis of Novel Plant-Derived Antibody-Based Therapeutic Molecules against West Nile Virus." PLoS One, 9, e93541.

Heider, K.-H., Kiefer, K., Zenz, T., Volden, M., Stilgenbauer, S., Ostermann, E., et al. (2011) "A novel Fc-engineered monoclonal antibody to CD37 with enhanced ADCC and high proapoptotic activity for treatment of B-cell malignancies." Blood, 118, 4159-4168.

Hioe, C.E., Kumar, R., Upadhyay, C., Jan, M., Fox, A., Itri, V., et al. (2018) "Modulation of Antibody Responses to the V1V2 and V3 Regions of HIV-1 Envelope by Immune Complex Vaccines." Front. Immunol., 9, 2441.

Ho, N.I., Camps, M.G.M., de Haas, E.F.E., Trouw, L.A., Verbeek, J.S., and Ossendorp, F. (2017) "C1q-Dependent Dendritic Cell Cross-Presentation of In Vivo-Formed Antigen-Antibody Complexes." J. Immunol., 198, 4235-4243.

Huang, Z. et al., "Conformational analysis of hepatitis B surface antigen fusions in an Agrobacterium-mediated transient expression system", Plant Biotechnology Journal, May 2004 (available online Mar. 2004), vol. 2, No. 3, pp. 241-249 <DOI:10.1111/j.1467-7652.2004.00068.x>.

Huber, V.C., McKeon, R.M., Brackin, M.N., Miller, L.A., Keating, R., Brown, S.A., et al. (2006) "Distinct contributions of vaccine-induced immunoglobulin G1 (IgG1) and IgG2a antibodies to protective immunity against influenza." Clin. Vaccine Immunol., 13, 981-990.

Hurtado, J., Acharya, D., Lai, H., Sun, H., Kallolimath, S., Steinkellner, H., et al. (2020) "In vitro and in vivo efficacy of anti-chikungunya virus monoclonal antibodies produced in wild-type and glycoengineered Nicotiana benthamiana plants." Plant Biotechnol. J.

Kallolimath, S. and Steinkellner, H. (2015) "Glycosylation of plant produced human antibodies." Hum. Antibodies, 23, 45-48.

Kim, M-Y. et al., "Novel vaccination approach for dengue infection based on recombinant immune complex universal platform", Vaccine, Apr. 2015 (available Feb. 2015), vol. 33, No. 15, pp. 1830-1838 <DOI:10.1016/j.vaccine.2015.02.036>.

(56) References Cited

OTHER PUBLICATIONS

Kim, M-Y. et al., "Plant-expressed Fc-fusion protein tetravalent dengue vaccine with inherent adjuvant properties", Plant Biotechnology Journal, Jul. 2018 (available online Dec. 2017), vol. 16, No. 7, pp. 1283-1294 <DOI:10.1111/pbi.12869>.
Lagassé, H.A.D., Hengel, H., Golding, B., and Sauna, Z.E. (2019) "Fc-Fusion Drugs Have FcγR/C1q Binding and Signaling Properties That May Affect Their Immunogenicity." AAPS J., 21, 62.
Lazar, G.A., Dang, W., Karki, S., Vafa, O., Peng, J.S., Hyun, L., et al. (2006) "Engineered antibody Fc variants with enhanced effector function." Proc. Natl. Acad. Sci. U. S. A., 103, 4005-10.
Lyon, G. M., Mehta, A. K., Varkey, J. B., Brantly, K., Plyler, L., McElroy, A. K., et al. (2014). Clinical Care of Two Patients with Ebola Virus Disease in the United States. N. Engl. J. Med. 371, 2402-2409. doi:10.1056/nejmoa1409838.
Ma, J.K.C., Christou, P., Chikwamba, R., Haydon, H., Paul, M., Ferrer, M.P., et al. (2013) "Realising the value of plant molecular pharming to benefit the poor in developing countries and emerging economies." Plant Biotechnol. J., 11, 1029-1033.
Marusic, C. et al., "N-glycan engineering of a plant-produced anti-CD20-hIL-2 immunocytokine significantly enhances its effector functions", Biotechnology and Bioengineering, Mar. 2018 (available online Nov. 2017), vol. 115, No. 3, pp. 565-576 <DOI:10.1002/bit.26503>.
Mason, H.S. (2016) "Recombinant immune complexes as versatile and potent vaccines." Hum. Vaccin. Immunother., 12, 988-989.
Mastrangeli, R., Palinsky, W., and Bierau, H. (2019) "Glycoengineered antibodies: towards the next-generation of immunotherapeutics." Glycobiology, 29, 199-210.
Mekhaiel, D.N.A., Czajkowsky, D.M., Andersen, J.T., Shi, J., El-Faham, M., Doenhoff, M., et al. (2011) "Polymeric human Fc-fusion proteins with modified effector functions." Sci. Rep., 1.
Nandi, S. et al., "Techno-economic analysis of a transient plant-based platform for monoclonal antibody production", mAbs, Sep. 2016 (available online Aug. 2016), vol. 8, No. 8, pp. 1456-1466 <DOI:10.1080/19420862.2016.1227901>.
Olinger, G. G., Pettitt, J., Kim, D., Working, C., Bohorov, O., Bratcher, B., et al. (2012). "Delayed treatment of Ebola virus infection with plant-derived monoclonal antibodies provides protection in rhesus macaques." Proc. Natl. Acad. Sci. U. S. A. 109, 18030-5. doi:10.1073/pnas.1213709109.
Pepponi, I. et al., "Plant-derived recombinant immune complexes as self-adjuvanting TB immunogens for mucosal boosting of BCG", Plant Biotechnology Journal, Sep. 2014 (available online Mar. 2014), vol. 12, No. 7, pp. 840-850 <DOI:10.1111/pbi.12185>.
Phoolcharoen, W. et al., "A nonreplicating subunit vaccine protects mice against lethal Ebola virus challenge", Proceedings of the National Academy of Sciences of the United States of America, Dec. 2011, vol. 108, No. 51, pp. 20695-20700 <DOI:10.1073/pnas.1117715108>.
Phoolcharoen, W. et al., "Expression of an immunogenic Ebola immune complex in Nicotiana benthamiana", Plant Biotechnology Journal, Sep. 2011 (available online Feb. 2011), vol. 9, No. 7, pp. 807-816 <DOI:10.1111/j.467-7652.2011.00593.x>.
Qiu, X., Wong, G., Audet, J., Bello, A., Fernando, L., Alimonti, J. B., et al. (2014). Reversion of advanced Ebola virus disease in nonhuman primates with ZMapp. Nature 514, 47-53. doi:10.1038/nature13777.
Reed, S.G., Orr, M.T., and Fox, C.B. (2013) "Key roles of adjuvants in modern vaccines." Nat. Med., 19, 1597-1608.
Robbie, G.J., Criste, R., Dall'acqua, W.F., Jensen, K., Patel, N.K., Losonsky, G.A., and Griffin, M.P. (2013) "A novel investigational Fc-modified humanized monoclonal antibody, motavizumab-YTE, has an extended half-life in healthy adults." Antimicrob. Agents Chemother., 57, 6147-53.
Roopenian, D.C. and Akilesh, S. (2007) "FcRn: the neonatal Fc receptor comes of age." Nat. Rev. Immunol., 7, 715-725.
Santi, L. et al., "An efficient plant viral expression system generating orally immunogenic Norwalk virus-like particles", Vaccine, Mar. 2008 (available online Feb. 2008), vol. 26, No. 15, pp. 1846-1854 <DOI:10.1016/j.vaccine.2008.01.053>.
Strasser, R. et al., "Generation of glyco-engineered Nicotiana benthamiana for the production of monoclonal antibodies with a homogeneous human-like N-glycan structure", Plant Biotechnology Journal, May 2008 (available online Mar. 2008), vol. 6, No. 4, pp. 392-402 <DOI:10.1111/j.1467-7652.2008.00330.x>.
Sun, H., Chen, Q., and Lai, H. (2018) "Development of antibody therapeutics against flaviviruses." Int. J. Mol. Sci., 19.

* cited by examiner

Fig. 5A
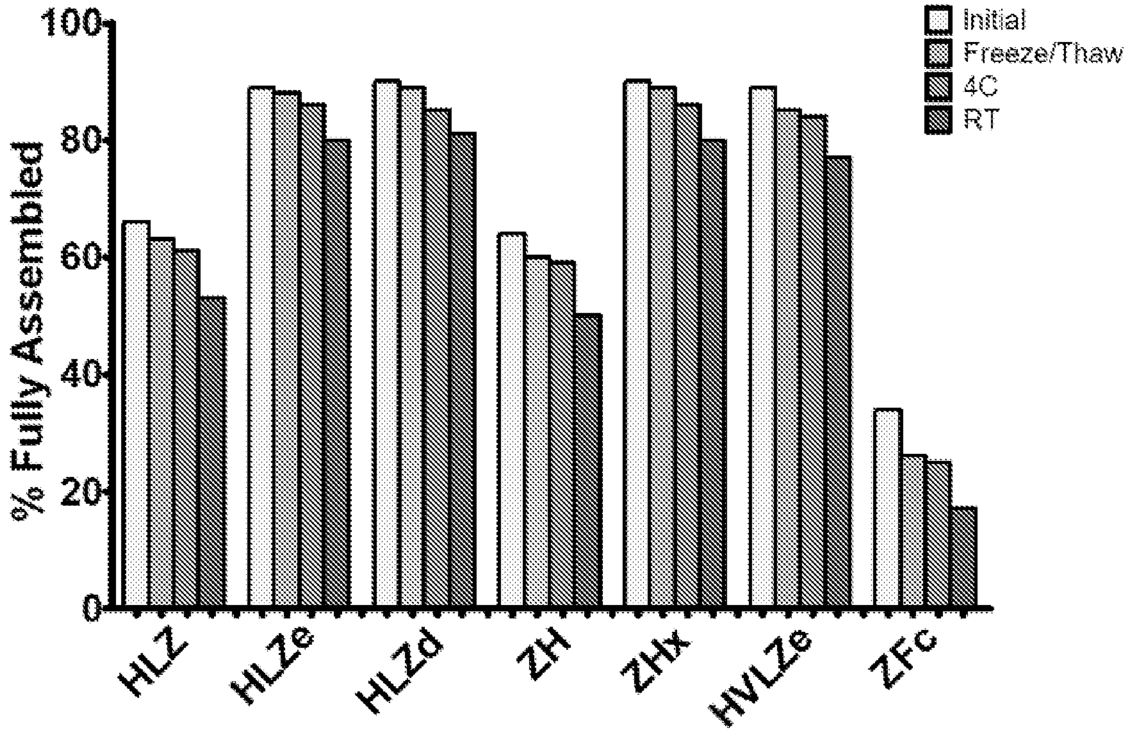
Fig. 5B C1q Binding
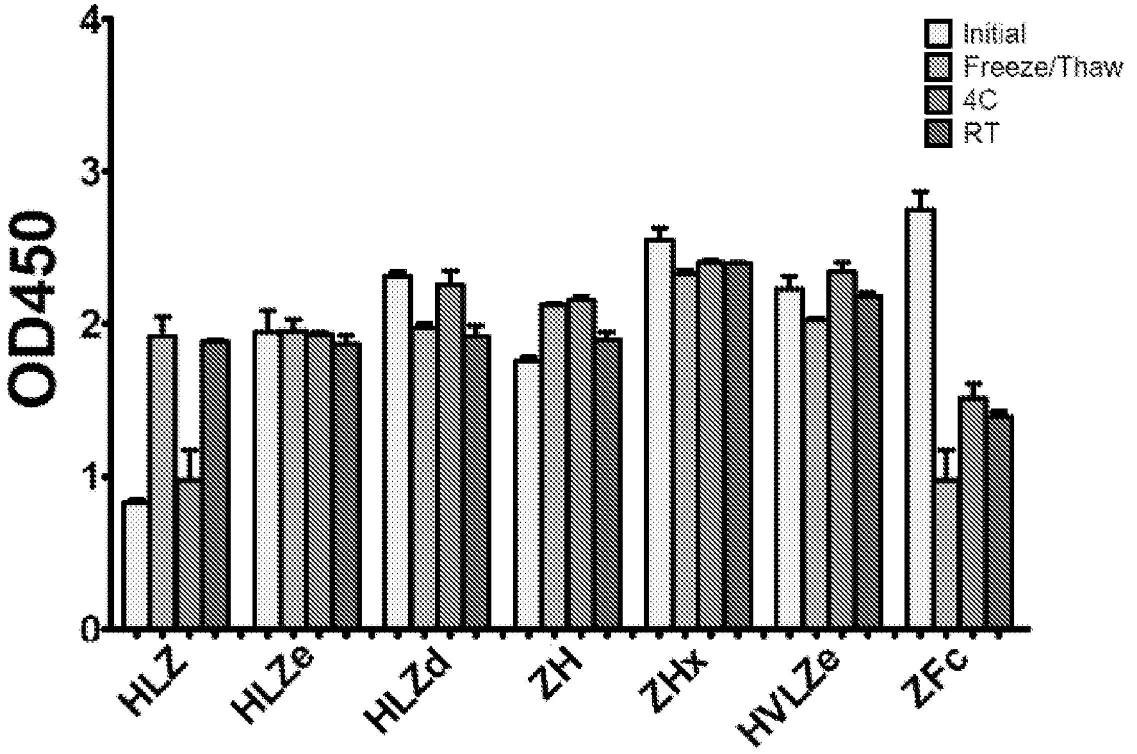

Fig. 10 C1q Binding
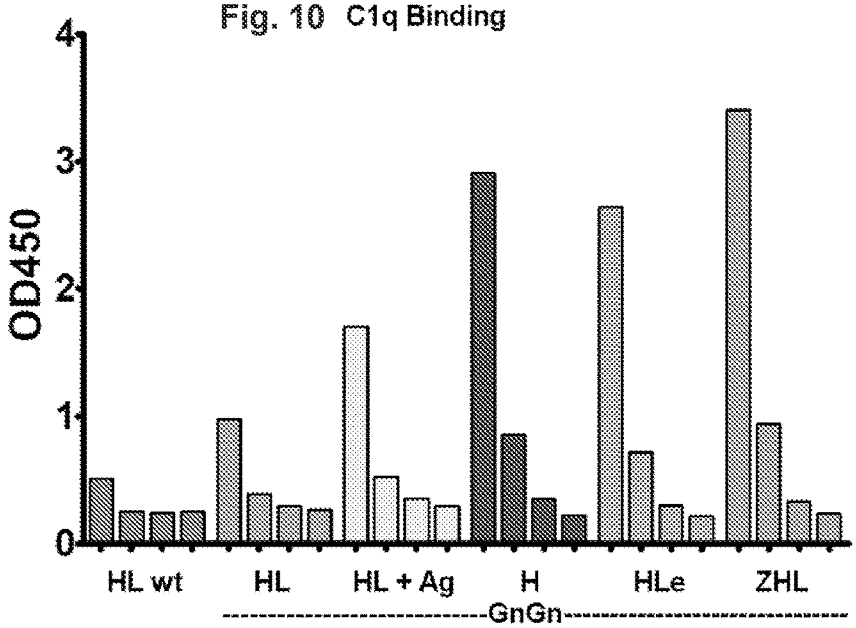
Fig. 11
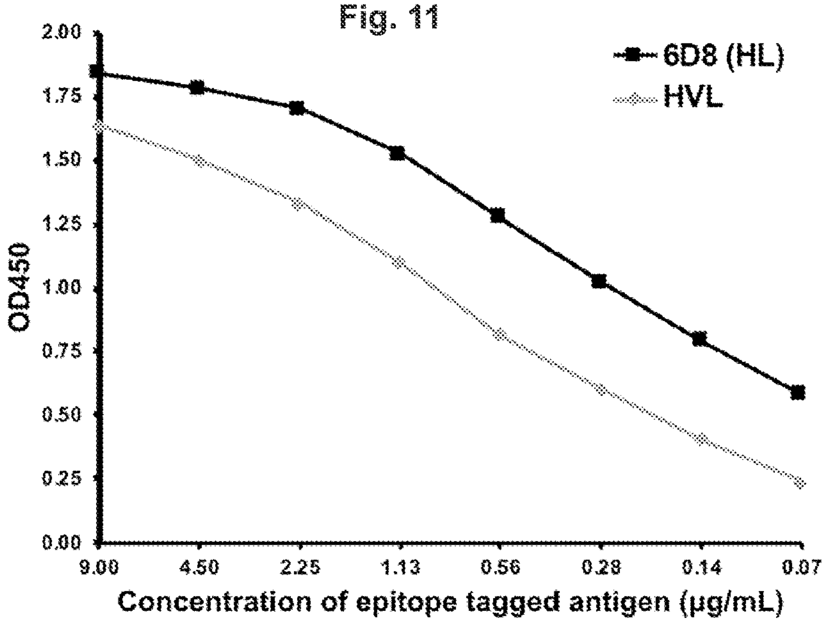
Fig. 12
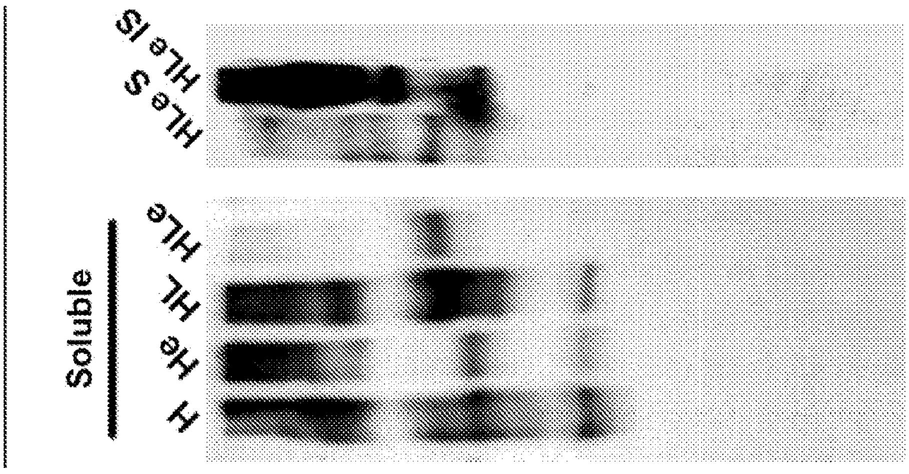

Fig. 16 MNV-1 Binding
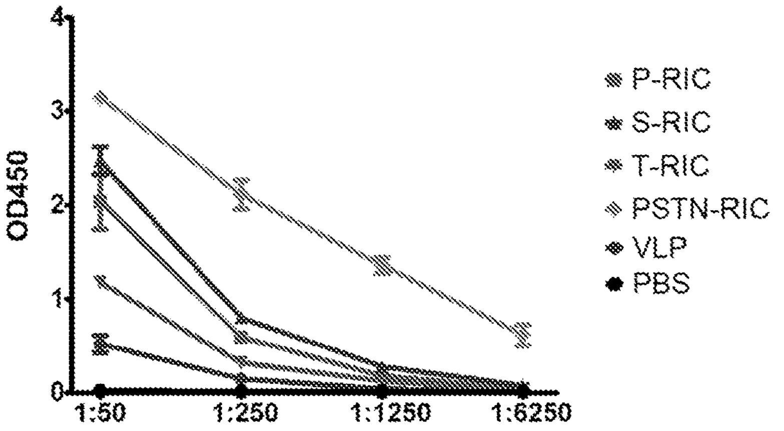
Fig. 17 GI.I VLP Binding
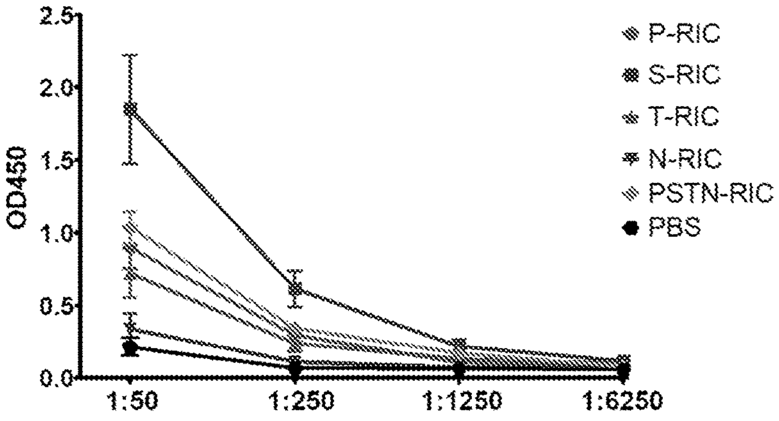

SEQUENCE LISTING

```
<160> NUMBER OF SEQ ID NOS: 79

<210> SEQ ID NO 1
<211> LENGTH: 6
<212> TYPE: PRT
<213> ORGANISM: Artificial Sequence
<220> FEATURE:
<223> OTHER INFORMATION: epitope

<400> SEQUENCE: 1
```

Tyr Lys Leu Asp Ile Ser
1 5

<210> SEQ ID NO 2
<211> LENGTH: 9
<212> TYPE: PRT
<213> ORGANISM: Artificial Sequence
<220> FEATURE:
<223> OTHER INFORMATION: epitope

<400> SEQUENCE: 2

Val Tyr Lys Leu Asp Ile Ser Glu Ala
1 5

<210> SEQ ID NO 3
<211> LENGTH: 9
<212> TYPE: PRT
<213> ORGANISM: Artificial Sequence
<220> FEATURE:
<223> OTHER INFORMATION: epitope

<400> SEQUENCE: 3

Val Tyr Lys Leu Asp Ile Ser Glu Ala
1 5

<210> SEQ ID NO 4
<211> LENGTH: 7
<212> TYPE: PRT
<213> ORGANISM: Artificial Sequence
<220> FEATURE:
<223> OTHER INFORMATION: epitope

<400> SEQUENCE: 4

Tyr Lys Leu Asp Ile Ser Glu
1 5

<210> SEQ ID NO 5
<211> LENGTH: 101
<212> TYPE: PRT
<213> ORGANISM: Artificial Sequence
<220> FEATURE:
<223> OTHER INFORMATION: CH1 domain

<400> SEQUENCE: 5

Thr Lys Gly Pro Ser Val Phe Pro Leu Ala Pro Ser Ser Lys Ser Thr
1 5 10 15

Ser Gly Gly Thr Ala Ala Leu Gly Cys Leu Val Lys Asp Tyr Phe Pro
20 25 30

Glu Pro Val Thr Val Ser Trp Asn Ser Gly Ala Leu Thr Ser Gly Val
35 40 45

His Thr Phe Pro Ala Val Leu Gln Ser Ser Gly Leu Tyr Ser Leu Ser
50 55 60

Ser Val Val Thr Val Pro Ser Ser Ser Leu Gly Thr Gln Thr Tyr Ile
65 70 75 80

Cys Asn Val Asn His Lys Pro Ser Asn Thr Lys Val Asp Lys Lys Val
85 90 95

Glu Pro Lys Ser Cys
100

<210> SEQ ID NO 6
<211> LENGTH: 120
<212> TYPE: PRT
<213> ORGANISM: Artificial Sequence
<220> FEATURE:

```
<223> OTHER INFORMATION: CH2 domain

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Ala Pro Ile Glu
            100                 105                 110

Lys Thr Ile Ser Lys Ala Lys Gly
        115                 120


<210> SEQ ID NO 7
<211> LENGTH: 106
<212> TYPE: PRT
<213> ORGANISM: Artificial Sequence
<220> FEATURE:
<223> OTHER INFORMATION: CH3 domain

<400> SEQUENCE: 7

Gln Pro Arg Glu Pro Gln Val Tyr Thr Leu Pro Pro Ser Arg Asp Glu
1               5                   10                  15

Leu Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
        35                  40                  45

Asn Tyr Lys Thr Thr Pro Pro Val Leu Asp Ser Asp Gly Ser Phe Phe
    50                  55                  60

Leu Tyr Ser Lys Leu Thr Val Asp Lys Ser Arg Trp Gln Gln Gly Asn
65                  70                  75                  80

Val Phe Ser Cys Ser Val Met His Glu Ala Leu His Asn His Tyr Thr
                85                  90                  95

Gln Lys Ser Leu Ser Leu Ser Pro Gly Lys
            100                 105


<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8

gcgggatcca agggcgtgtc atactcc                                          27


<210> SEQ ID NO 9
<211> LENGTH: 30
<212> TYPE: DNA
<213> ORGANISM: Artificial Sequence
<220> FEATURE:
<223> OTHER INFORMATION: primer
```

<400> SEQUENCE: 9
acagagctct taagtgctac cactcctgtg 30

<210> SEQ ID NO 10
<211> LENGTH: 40
<212> TYPE: DNA
<213> ORGANISM: Artificial Sequence
<220> FEATURE:
<223> OTHER INFORMATION: primer

<400> SEQUENCE: 10
ctagtgttta caagctggac atatctgagg cataagagct 40

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
cttatgcctc agatatgtcc agcttgtaaa ca 32

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
tttgagctct tactcagata tgtccagctt gtaaac 36

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
aatcccacta tccttcgc 18

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
ctagttacaa gctggacata tctgagtaag agct 34

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
cttactcaga tatgtccagc ttgtaa 26

<210> SEQ ID NO 16
<211> LENGTH: 31

<212> TYPE: DNA
<213> ORGANISM: Artificial Sequence
<220> FEATURE:
<223> OTHER INFORMATION: primer

<400> SEQUENCE: 16
ctagttacaa gctggacata tcttaagagc t 31

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
cttaagatat gtccagcttg taa 23

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
aagcttgttg ttgtgactcc gag 23

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
cggactagta gctgaagaca ctgtgac 27

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
cgtgctagcc ttgatctcca ctttggtc 28

<210> SEQ ID NO 21
<211> LENGTH: 17977
<212> TYPE: DNA
<213> ORGANISM: Artificial Sequence
<220> FEATURE:
<223> OTHER INFORMATION: pBYR11eM-h6D8ZE3

<400> SEQUENCE: 21
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360

```
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
```

```
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtcaag   3780
gcaccactgt cacagtgtct tcagctagca ccaaaggtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgctct gaccagtgga gtgcacacct   3960
ttccagctgt tcttcagtcc tcaggattgt attctcttag cagtgttgtg actgttccat   4020
cctcaagctt gggcactcag acctacatct gcaatgtgaa tcacaaaccc agcaacacca   4080
aggttgacaa gaaagttgag cccaagtctt gtgacaagac tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtgga agtgcacaat gccaagacaa   4320
agccgagaga ggaacagtac aacagcacgt acagggttgt ctcagttctc actgttctcc   4380
atcaagattg gttgaatggc aaagagtaca agtgcaaggt ctccaacaaa gccctcccag   4440
cccccattga gaagaccatt tccaaagcga aagggcaacc ccgtgaacca caagtgtaca   4500
cacttcctcc atctcgcgat gaactgacca agaaccaggt cagcttgact tgcctggtga   4560
aaggcttcta tccctctgac atagctgtag agtgggagag caatgggcaa ccggagaaca   4620
actacaagac tacacctccc gttctcgatt ctgacggctc cttcttcctc tacagcaagc   4680
tcacagtgga caagagcagg tggcaacaag ggaatgtctt ctcatgctcc gtgatgcatg   4740
aggctcttca caatcactac acacagaaga gtctctcctt gtctccgggt aaaggaggtg   4800
gcggatcagg tggaggcggt tcaggcggag gtggatccaa gggcgtgtca tactccttgt   4860
gtaccgctgc cttcacattc accaagatcc cggctgaaac actccacgga accgttaccg   4920
tggaggtcca atacgccggt acagatggac cttgcaaggt tccagctcag atggcggtgg   4980
acatgcaaac tcttacccca gttggaaggt tgattaccgc taaccccgtt atcactgaaa   5040
gcactgagaa ctctaagatg atgttggaac ttgatccacc attcggtgac tcttacattg   5100
```

-continued tcattggtgt gggagagaag aagatcaccc accactggca caggagtggt agcactagtc 5160
ataacactcc tgtttacaag ctggacatat ctgaggcaac tcaataagag ctcaaagcag 5220
aatgctgagc taaaagaaag gctttttcca ttttcgagag acaatgagaa aagaagaaga 5280
agaagaagaa gaagaagaag aagaaaagag taaataataa agccccacag gaggcgaagt 5340
tcttgtagct ccatgttatc taagttattg atattgtttg ccctatattt tatttctgtc 5400
attgtgtatg ttttgttcag tttcgagaat tctcgattaa aaatcccaat tatatttggt 5460
ctaatttagt ttggtattga gtaaaacaaa ttcgaaccaa accaaaatat aaatatatag 5520
tttttatata tatgccttta agacttttta tagaattttc tttaaaaaat atctagaaat 5580
atttgcgact cttctggcat gtaatatttc gttaaatatg aagtgctcca tttttattaa 5640
ctttaaataa ttggttgtac gatcactttc ttatcaagtg ttactaaaat gcgtcaatct 5700
ctttgttctt ccatattcat atgtcaaaat ctatcaaaat tcttatatat ctttttcgaa 5760
tttgaagtga aatttcgata atttaaaatt aaatagaaca tatcattatt taggtatcat 5820
attgattttt atacttaatt actaaatttg gttaactttg aaagtgtaca tcaacgaaaa 5880
attagtcaaa cgactaaaat aaataaatat catgtgttat taagaaaatt ctcctataag 5940
aatattttaa tagatcatat gtttgtaaaa aaaattaatt tttactaaca catatattta 6000
cttatcaaaa atttgacaaa gtaagattaa aataatattc atctaacaaa aaaaaaacca 6060
gaaaatgctg aaaacccggc aaaaccgaac caatccaaac cgatatagtt ggtttggttt 6120
gattttgata taaaccgaac caactcggtc catttgcacc cctaatcata atagctttaa 6180
tatttcaaga tattattaag ttaacgttgt caatatcctg gaaattttgc aaaatgaatc 6240
aagcctatat ggctgtaata tgaatttaaa agcagctcga tgtggtggta atatgtaatt 6300
tacttgattc taaaaaaata tcccaagtat taataatttc tgctaggaag aaggttagct 6360
acgatttaca gcaaagccag aatacaaaga accataaagt gattgaagct cgaaatatac 6420
gaaggaacaa atatttttaa aaaaatacgc aatgacttgg aacaaaagaa agtgatatat 6480
tttttgttct taaacaagca tcccctctaa agaatggcag ttttcctttg catgtaacta 6540
ttatgctccc ttcgttacaa aaattttgga ctactattgg gaacttcttc tgaaaatagt 6600
ggtaccgagt gtacttcaag tcagttggaa atcaataaaa tgattatttt atgaatatat 6660
ttcattgtgc aagtagatag aaattacata tgttacataa cacacgaaat aaacaaaaaa 6720
acacaatcca aaacaaacac cccaaacaaa ataacactat atatatcctc gtatgaggag 6780
aggcacgttc agtgactcga cgattcccga gcaaaaaaag tctccccgtc acacatatag 6840
tgggtgacgc aattatcttc aaagtaatcc ttctgttgac ttgtcattga taacatccag 6900
tcttcgtcag gattccaaag aattatagaa gggatcggtc aacatggtgg agcacgacac 6960
acttgtctac tccaaaaata tcaaagatac agtctcagaa gaccaaaggg caattgagac 7020
ttttcaacaa agggtaatat ccggaaacct cctcggattc cattgcccag ctatctgtca 7080
ctttattgtg aagatagtgg aaaaggaagg tggctcctac aaatgccatc attgcgataa 7140
aggaaaggcc atcgttgaag atgcctctgc cgacagtggt cccaaagatg gacccccacc 7200
cacgaggagc atcgtggaaa aagaagacgt tccaaccacg tcttcaaagc aagtggattg 7260
atgtgataac atggtggagc acgacacact tgtctactcc aaaaatatca aagatacagt 7320
ctcagaagac caaagggcaa ttgagacttt tcaacaaagg gtaatatccg gaaacctcct 7380
cggattccat tgcccagcta tctgtcactt tattgtgaag atagtggaaa aggaaggtgg 7440
ctcctacaaa tgccatcatt gcgataaagg aaaggccatc gttgaagatg cctctgccga 7500

```
cagtggtccc aaagatggac ccccacccac gaggagcatc gtggaaaaag aagacgttcc   7560
aaccacgtct tcaaagcaag tggattgatg tgatatctcc actgacgtaa gggatgacgc   7620
acaatcccac tatccttcgc aagacccttc ctctatataa ggaagttcat ttcatttgga   7680
gaggacctcg agtattttta caacaattac caacaacaac aaacaacaaa caacattaca   7740
attactattt acaatctaga acaatgggat ggtcttgcat cattctcttc ttggtagcca   7800
cagctacagg tgtccactcc gatgttttga tgactcaaag ccctctctca cttcctgtga   7860
ctcttggaca gcccgcatcc atatcttgca gatctagtca gagtattgtt catagtaacg   7920
gcaacaccta cttggaatgg tatctgcaga aaccaggcca gtctccaaag cttctgatct   7980
acaaggcttc caatcgtttc tctggtgtcc cagacaggtt tagtggcagt ggatcaggga   8040
ctgacttcac attgaagatc agcagagttg aggctgaaga tgcgggagtg tactattgtc   8100
ttcaaggttc acatgttccg tcaacgtttg gaggtgggac caaagtggag atcaagactg   8160
ttgcggcgcc atctgtcttc atctttcctc catctgatga acaactcaag tctggaactg   8220
cttctgttgt gtgccttctg aacaacttct atcctagaga agccaaagta cagtggaagg   8280
ttgacaatgc tcttcaatca ggtaactccc aggagagtgt cacagagcaa gattccaagg   8340
attccaccta cagcctctca agtaccttga cgttgagcaa ggcagactat gagaaacaca   8400
aagtgtacgc atgcgaagtc actcatcagg gcctgtcatc acccgtgaca aagagcttca   8460
acaggggaga gtgttaggta ccgagctcga agtgacatca caaagttgaa ggtaataaag   8520
ccaaattaat taagacattt tcataatgat gtcaagaatg caaagcaaat tgcataactg   8580
cctttatgca aaacattaat ataatataaa ttataaagaa ctgcgctctc tgcttcttat   8640
tttcttagct tcatttatta gtcactagct gttcagaatt ttcagtatct tttgatatta   8700
ctaagaacct aatcacacaa tgtatattct tatgcaggaa aagcagaatg ctgagctaaa   8760
agaaaggctt tttccatttt cgagagacaa tgagaaaaga agaagaagaa gaagaagaag   8820
aagaagaaga aaagagtaaa taataaagcc ccacaggagg cgaagttctt gtagctccat   8880
gttatctaag ttattgatat tgtttgccct atattttatt tctgtcattg tgtatgtttt   8940
gttcagtttc gatctccttg caaaatgcag agattatgag atgaataaac taagttatat   9000
tattatacgt gttaatattc tcctcctctc tctagctagc cttttgtttt ctctttttct   9060
tatttgattt tctttaaatc aatccatttt aggagagggc cagggagtga tccagcaaaa   9120
catgaagatt agaagaaact tccctctttt ttttcctgaa aacaatttaa cgtcgagatt   9180
tatctctttt tgtaatggaa tcatttctac agttatgacg aattctcgat taaaaatccc   9240
aattatattt ggtctaattt agtttggtat tgagtaaaac aaattcgaac caaaccaaaa   9300
tataaatata tagtttttat atatatgcct ttaagacttt ttatagaatt ttctttaaaa   9360
aatatctaga aatatttgcg actcttctgg catgtaatat ttcgttaaat atgaagtgct   9420
ccatttttat taactttaaa taattggttg tacgatcact ttcttatcaa gtgttactaa   9480
aatgcgtcaa tctctttgtt cttccatatt catatgtcaa aatctatcaa aattcttata   9540
tatctttttc gaatttgaag tgaaatttcg ataatttaaa attaaataga acatatcatt   9600
atttaggtat catattgatt tttatactta attactaaat ttggttaact ttgaaagtgt   9660
acatcaacga aaaattagtc aaacgactaa aataaataaa tatcatgtgt tattaagaaa   9720
attctcctat aagaatattt taatagatca tatgtttgta aaaaaaatta atttttacta   9780
acacatatat ttacttatca aaaatttgac aaagtaagat taaaataata ttcatctaac   9840
```

```
aaaaaaaaaa ccagaaaatg ctgaaaaccc ggcaaaaccg aaccaatcca aaccgatata   9900
gttggtttgg tttgattttg atataaaccg aaccaactcg gtccatttgc acccctaatc   9960
ataatagctt taatatttca agatattatt aagttaacgt tgtcaatatc ctggaaattt  10020
tgcaaaatga atcaagccta tatggctgta atatgaattt aaaagcagct cgatgtggtg  10080
gtaatatgta atttacttga ttctaaaaaa atatcccaag tattaataat ttctgctagg  10140
aagaaggtta gctacgattt acagcaaagc cagaatacaa agaaccataa agtgattgaa  10200
gctcgaaata tacgaaggaa caaatatttt taaaaaaata cgcaatgact tggaacaaaa  10260
gaaagtgata tattttttgt tcttaaacaa gcatcccctc taaagaatgg cagttttcct  10320
ttgcatgtaa ctattatgct cccttcgtta caaaaatttt ggactactat tgggaacttc  10380
ttctgaaaat agtggtaccg agtgtacttc aagtcagttg gaaatcaata aaatgattat  10440
tttatgaata tatttcattg tgcaagtaga tagaaattac atatgttaca taacacacga  10500
aataaacaaa aaaacacaat ccaaaacaaa caccccaaac aaaataacac tatatatatc  10560
ctcgtatgag gagaggcacg ttcagtgact cgacgattcc cgagcaaaaa aagtctcccc  10620
gtcacacata tagtgggtga cgcaattatc ttcaaagtaa tccttctgtt gacttgtcat  10680
tgataacatc cagtcttcgt caggattgca aagaattata gaagggatcc caccttttat  10740
tttcttcttt tttccatatt tagggttgac agtgaaatca gactggcaac ctattaattg  10800
cttccacaat gggacgaact tgaaggggat gtcgtcgatg atattatagg tggcgtgttc  10860
atcgtagttg gtgaagtcga tggtcccgtt ccagtagttg tgtcgcccga gacttctagc  10920
ccaggtggtc tttccggtac gagttggtcc gcagatgtag aggctggggt gtctgacccc  10980
agtccttccc tcatcctggt tagatcggcc atccactcaa ggtcagattg tgcttgatcg  11040
taggagacag gatgtatgaa agtgtaggca tcgatgctta catgatatag gtgcgtctct  11100
ctccagttgt gcagatcttc gtggcagcgg agatctgatt ctgtgaaggg cgacacgtac  11160
tgctcaggtt gtggaggaaa taatttgttg gctgaatatt ccagccattg aagctttgtt  11220
gcccattcat gagggaactc ttctttgatc atgtcaagat actcctcctt agacgttgca  11280
gtctggataa tagttcgcca tcgtgcgtca gatttgcgag gagacacctt atgatctcgg  11340
aaatctcctc tggttttaat atctccgtcc tttgatatgt aatcaaggac ttgtttagag  11400
tttctagctg gctggatatt agggtgattt ccttcaaaat cgaaaaaaga aggatcccta  11460
atacaaggtt ttttatcaag ctggataaga gcatgatagt gggtagtgcc atcttgatga  11520
agctcagaag caacaccaag gaagaaaata agaaaaggtg tgagtttctc ccagagaaac  11580
tggaataaat catctctttg agatgagcac ttggggtagg taaggaaaac atatttagat  11640
tggagtctga agttcttgct agcagaaggc atgttgttgt gactccgagg ggttgcctca  11700
aactctatct tataaccggc gtggaggcat ggaggcaagg gcattttggt aatttaagta  11760
gttagtggaa aatgacgtca tttacttaaa gacgaagtct tgcgacaagg ggggcccacg  11820
ccgaatttta atattaccgg cgtggcccca ccttatcgcg agtgctttag cacgagcggt  11880
ccagatttaa agtagaaaag ttcccgccca ctagggttaa aggtgttcac actataaaag  11940
catatacgat gtgatggtat ttgatggagc gtatattgta tcaggtattt ccgtcggata  12000
cgaattattc gtacggccgg accggtcccc taggccggcc aattcgagat cggccgcggc  12060
tgagtggctc cttcaatcgt tgcggttctg tcagttccaa acgtaaaacg gcttgtcccg  12120
cgtcatcggc gggggtcata acgtgactcc cttaattctc cgctcatgat cagattgtcg  12180
tttcccgcct tcagtttaaa ctatcagtgt ttgacaggat atattggcgg gtaaacctaa  12240
```

gagaaaagag cgtttattag aataatcgga tatttaaaag ggcgtgaaaa ggtttatccg 12300
ttcgtccatt tgtatgtgca tgccaaccac agggttcccc agatctggcg ccggccagcg 12360
agacgagcaa gattggccgc cgcccgaaac gatccgacag cgcgcccagc acaggtgcgc 12420
aggcaaattg caccaacgca tacagcgcca gcagaatgcc atagtgggcg gtgacgtcgt 12480
tcgagtgaac cagatcgcgc aggaggcccg gcagcaccgg cataatcagg ccgatgccga 12540
cagcgtcgag cgcgacagtg ctcagaatta cgatcagggg tatgttgggt ttcacgtctg 12600
gcctccggag actgtcatac gcgtaaaaag gccgcgttgc tggcgttttt ccataggctc 12660
cgcccccctg acgagcatca caaaaatcga cgctcaagtc agaggtggcg aaacccgaca 12720
ggactataaa gataccaggc gtttccccct ggaagctccc tcgtgcgctc tcctgttccg 12780
accctgccgc ttaccggata cctgtccgcc tttctccctt cgggaagcgt ggcgctttct 12840
catagctcac gctgtaggta tctcagttcg gtgtaggtcg ttcgctccaa gctgggctgt 12900
gtgcacgaac cccccgttca gcccgaccgc tgcgccttat ccggtaacta tcgtcttgag 12960
tccaacccgg taagacacga cttatcgcca ctggcagcag ccactggtaa caggattagc 13020
agagcgaggt atgtaggcgg tgctacagag ttcttgaagt ggtggcctaa ctacggctac 13080
actagaagga cagtatttgg tatctgcgct ctgctgaagc cagttacctt cggaaaaaga 13140
gttggtagct cttgatccgg caaacaaacc accgctggta gcggtggttt ttttgtttgc 13200
aagcagcaga ttacgcgcag aaaaaaagga tctcaagaag atcctttgat cttttctacg 13260
gggtctgacg ctcagtggaa cgaaaactca cgttaaggga ttttggtcat gagattatca 13320
aaaaggatct tcacctagat ccttttaaat taaaaatgaa gttttaaatc aatctaaagt 13380
atatatgagt aaacttggtc tgcagttgcc atgttttacg gcagtgagag cagagatagc 13440
gctgatgtcc ggcggtgctt ttgccgttac gcaccacccc gtcagtagct gaacaggagg 13500
gacagctgat agacacagaa gccactggag cacctcaaaa acaccatcat acactaaatc 13560
agtaagttgg cagcatcacc cataattgtg gtttcaaaat cggctccgtc gatactatgt 13620
tatacgccaa ctttgaaaac aactttgaaa aagctgtttt ctggtattta aggttttaga 13680
atgcaaggaa cagtgaattg gagttcgtct tgttataatt agcttcttgg ggtatcttta 13740
aatactgtag aaaagaggaa ggaaataata aatggctaaa atgagaatat caccggaatt 13800
gaaaaaactg atcgaaaaat accgctgcgt aaaagatacg gaaggaatgt ctcctgctaa 13860
ggtatataag ctggtgggag aaaatgaaaa cctatattta aaaatgacgg acagccggta 13920
taaagggacc acctatgatg tggaacggga aaaggacatg atgctatggc tggaaggaaa 13980
gctgcctgtt ccaaaggtcc tgcactttga acggcatgat ggctggagca atctgctcat 14040
gagtgaggcc gatggcgtcc tttgctcgga agagtatgaa gatgaacaaa gccctgaaaa 14100
gattatcgag ctgtatgcgg agtgcatcag gctctttcac tccatcgaca tatcggattg 14160
tccctatacg aatagcttag acagccgctt agccgaattg gattacttac tgaataacga 14220
tctggccgat gtggattgcg aaaactggga agaagacact ccatttaaag atccgcgcga 14280
gctgtatgat tttttaaaga cggaaaagcc cgaagaggaa cttgtctttt cccacggcga 14340
cctgggagac agcaacatct ttgtgaaaga tggcaaagta agtggcttta ttgatcttgg 14400
gagaagcggc agggcggaca agtggtatga cattgccttc tgcgtccggt cgatcaggga 14460
ggatatcggg gaagaacagt atgtcgagct atttttgac ttactgggga tcaagcctga 14520
ttgggagaaa ataaaatatt atattttact ggatgaattg ttttagtacc tagatgtggc 14580
gcaacgatgc cggcgacaag caggagcgca ccgacttctt ccgcatcaag tgttttggct 14640
ctcaggccga ggcccacggc aagtatttgg gcaaggggtc gctggtattc gtgcagggca 14700
agattcggaa taccaagtac gagaaggacg gccagacggt ctacgggacc gacttcattg 14760
ccgataaggt ggattatctg gacaccaagg caccaggcgg gtcaaatcag gaataagggc 14820
acattgcccc ggcgtgagtc ggggcaatcc cgcaaggagg gtgaatgaat cggacgtttg 14880
accggaaggc atacaggcaa gaactgatcg acgcggggtt ttccgccgag gatgccgaaa 14940
ccatcgcaag ccgcaccgtc atgcgtgcgc cccgcgaaac cttccagtcc gtcggctcga 15000
tggtccagca agctacggcc aagatcgagc gcgacagcgt gcaactggct ccccctgccc 15060
tgcccgcgcc atcggccgcc gtggagcgtt cgcgtcgtct cgaacaggag gcggcaggtt 15120
tggcgaagtc gatgaccatc gacacgcgag gaactatgac gaccaagaag cgaaaaaccg 15180
ccggcgagga cctggcaaaa caggtcagcg aggccaagca ggccgcgttg ctgaaacaca 15240
cgaagcagca gatcaaggaa atgcagcttt ccttgttcga tattgcgccg tggccggaca 15300
cgatgcgagc gatgccaaac gacacggccc gctctgccct gttcaccacg cgcaacaaga 15360
aaatcccgcg cgaggcgctg caaaacaagg tcattttcca cgtcaacaag gacgtgaaga 15420
tcacctacac cggcgtcgag ctgcgggccg acgatgacga actggtgtgg cagcaggtgt 15480
tggagtacgc gaagcgcacc cctatcggcg agccgatcac cttcacgttc tacgagcttt 15540
gccaggacct gggctggtcg atcaatggcc ggtattacac gaaggccgag gaatgcctgt 15600
cgcgcctaca ggcgacggcg atgggcttca cgtccgaccg cgttgggcac ctggaatcgg 15660
tgtcgctgct gcaccgcttc cgcgtcctgg accgtggcaa gaaaacgtcc cgttgccagg 15720
tcctgatcga cgaggaaatc gtcgtgctgt ttgctggcga ccactacacg aaattcatat 15780
gggagaagta ccgcaagctg tcgccgacgg cccgacggat gttcgactat ttcagctcgc 15840
accgggagcc gtacccgctc aagctggaaa ccttccgcct catgtgcgga tcggattcca 15900
cccgcgtgaa gaagtggcgc gagcaggtcg gcgaagcctg cgaagagttg cgaggcagcg 15960
gcctggtgga acacgcctgg gtcaatgatg acctggtgca ttgcaaacgc tagggccttg 16020
tggggtcagt tccggctggg ggttcagcag ccagcgcttt actggcattt caggaacaag 16080
cgggcactgc tcgacgcact tgcttcgctc agtatcgctc gggacgcacg gcgcgctcta 16140
cgaactgccg ataaacagag gattaaaatt gacaattcaa tggcaaggac tgccagcgct 16200
gccatttttg gggtgaggcc gttcgcggcc gaggggcgca gcccctgggg ggatgggagg 16260
cccgcgttag cgggccggga gggttcgaga aggggggca ccccccttcg gcgtgcgcgg 16320
tcacgcgcac agggcgcagc cctggttaaa aacaaggttt ataaatattg gtttaaaagc 16380
aggttaaaag acaggttagc ggtggccgaa aaacgggcgg aaacccttgc aaatgctgga 16440
ttttctgcct gtggacagcc cctcaaatgt caataggtgc gcccctcatc tgtcagcact 16500
ctgcccctca agtgtcaagg atcgcgcccc tcatctgtca gtagtcgcgc ccctcaagtg 16560
tcaataccgc agggcactta tccccaggct tgtccacatc atctgtggga aactcgcgta 16620
aaatcaggcg ttttcgccga tttgcgaggc tggccagctc cacgtcgccg gccgaaatcg 16680
agcctgcccc tcatctgtca acgccgcgcc gggtgagtcg gcccctcaag tgtcaacgtc 16740
cgcccctcat ctgtcagtga gggccaagtt ttccgcgagg tatccacaac gccggcggcc 16800
gcggtgtctc gcacacggct tcgacggcgt ttctggcgcg tttgcagggc catagacggc 16860
cgccagccca gcggcgaggg caaccagccc ggtgagcgtc gcaaaggcgc tcggtcttgc 16920
cttgctcgtc gagatctggg gtcgatcagc cggggatgca tcaggccgac agtcggaact 16980

```
tcgggtcccc gacctgtacc attcggtgag caatggatag gggagttgat atcgtcaacg  17040
ttcacttcta aagaaatagc gccactcagc ttcctcagcg gctttatcca gcgatttcct  17100
attatgtcgg catagttctc aagatcgaca gcctgtcacg gttaagcgag aaatgaataa  17160
gaaggctgat aattcggatc tctgcgaggg agatgatatt tgatcacagg cagcaacgct  17220
ctgtcatcgt tacaatcaac atgctaccct ccgcgagatc atccgtgttt caaacccggc  17280
agcttagttg ccgttcttcc gaatagcatc ggtaacatga gcaaagtctg ccgccttaca  17340
acggctctcc cgctgacgcc gtcccggact gatgggctgc ctgtatcgag tggtgatttt  17400
gtgccgagct gccggtcggg gagctgttgg ctggctggtg gcaggatata ttgtggtgta  17460
aacaaattga cgcttagaca acttaataac acattgcgga cgtttttaat gtactggggt  17520
ggtttttctt ttcaccagtg agacgggcaa cagctgattg cccttcaccg cctggccctg  17580
agagagttgc agcaagcggt ccacgctggt ttgccccagc aggcgaaaat cctgtttgat  17640
ggtggttccg aaatcggcaa aatcccttat aaatcaaaag aatagcccga gatagggttg  17700
agtgttgttc cagtttggaa caagagtcca ctattaaaga acgtggactc caacgtcaaa  17760
gggcgaaaaa ccgtctatca gggcgatggc ccactacgtg aaccatcacc caaatcaagt  17820
tttttggggt cgaggtgccg taaagcacta aatcggaacc ctaaagggag cccccgattt  17880
agagcttgac ggggaaagcc ggcgaacgtg gcgagaaagg aagggaagaa agcgaaagga  17940
gcgggcgcca ttcaggctgc gcaactgttg ggaaggg                           17977
```

```
<210> SEQ ID NO 22
<211> LENGTH: 17686
<212> TYPE: DNA
<213> ORGANISM: Artificial Sequence
<220> FEATURE:
<223> OTHER INFORMATION: pBYR11eMa-BAZE3-Hgp371

<400> SEQUENCE: 22
```

```
cgatcggtcg attcatagaa gattagattt ttcatagtat tttttaaag taaaccttta     60
actacggtta ggacactttt aagttaaatt taatttgaac ccttaaatta atttttaaaa    120
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
```

ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980
gctgtccata aaaccgccca gtctagctat cgccatgtaa gcccactgca agctacctgc 2040
tttctctttg cgcttgcgtt ttcccttgtc cagatagccc agtagctgac attcatccgg 2100
ggtcagcacc gtttctgcgg actggctttc tacgtgttcc gcttccttta gcagcccttg 2160
cgccctgagt gcttgcggca gcgtgaagct ggcgcgccgc tctagcagaa ggcatgttgt 2220
tgtgactccg aggggttgcc tcaaactcta tcttataacc ggcgtggagg catggaggca 2280
agggcatttt ggtaatttaa gtagttagtg gaaaatgacg tcatttactt aaagacgaag 2340
tcttgcgaca aggggggccc acgccgaatt ttaatattac cggcgtggcc ccaccttatc 2400
gcgagtgctt tagcacgagc ggtccagatt taaagtagaa aagttcccgc ccactagggt 2460
taaaggtgtt cacactataa aagcatatac gatgtgatgg tatttgataa agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat ggctaacaag cacctctcat 3420

```
tgtctctctt ccttgtgctc cttggtcttt ctgcttctct tgcttctggt aagggcgtgt   3480
catactcctt gtgtaccgct gccttcacat tcaccaagat cccggctgaa acactccacg   3540
gaaccgttac cgtggaggtc caatacgccg gtacagatgg accttgcaag gttccagctc   3600
agatggcggt ggacatgcaa actcttaccc cagttggaag gttgattacc gctaaccccg   3660
ttatcactga aagcactgag aactctaaga tgatgttgga acttgatcca ccattcggtg   3720
actcttacat tgtcattggt gtgggagaga agaagatcac ccaccactgg cacaggagtg   3780
gtagcactag tggtggatca ggaggttctg gtggttctgg aggttcagga tccgatgttc   3840
agcttcttga gtctggaggt ggtcttgtgc aacctggagg ttccttgaga ctctcctgtg   3900
cagcttcagg gtttgacttc agtaggtact ggatgagttg ggttcgtcaa gctcctggga   3960
aaggactaga atggattgga gagatcaatc cagattcaag taccatcaac tatactccat   4020
ctctgaagga tcgcttcacc atttccagag acaatgccaa gaacacgttg tatcttcaga   4080
tgaacagctt gaggactgaa gacacagcct tgtactactg cacaagacag ggctatggct   4140
acaactactg ggtcaaggc accactgtca cagtgtcttc agctagcacc aaaggtccat   4200
cggtctttcc actggcacct tcttccaaga gtacttctgg aggcacagct gcactgggtt   4260
gtcttgtcaa ggactacttt ccagaacctg ttacggtttc gtggaactca ggtgctctga   4320
ccagtggagt gcacaccttt ccagctgttc ttcagtcctc aggattgtat tctcttagca   4380
gtgttgtgac tgttccatcc tcaagcttgg gcactcagac ctacatctgc aatgtgaatc   4440
acaaacccag caacaccaag gttgacaaga aagttgagcc caagtcttgt gacaagactc   4500
atacgtgtcc accgtgccca gcacctgaac ttcttggagg accgtcagtc ttcttgtttc   4560
ctccaaagcc taaggatacc ttgatgatct ccaggactcc tgaagtcaca tgtgtagttg   4620
tggatgtgag ccatgaagat cctgaggtga agttcaactg gtatgtggat ggtgtggaag   4680
tgcacaatgc caagacaaag ccgagagagg aacagtacaa cagcacgtac agggttgtct   4740
cagttctcac tgttctccat caagattggt tgaatggcaa agagtacaag tgcaaggtct   4800
ccaacaaagc cctcccagcc cccattgaga agaccatttc caaagcgaaa gggcaacccc   4860
gtgaaccaca agtgtacaca cttcctccat ctcgcgatga actgaccaag aaccaggtca   4920
gcttgacttg cctggtgaaa ggcttctatc cctctgacat agctgtagag tgggagagca   4980
atgggcaacc ggagaacaac tacaagacta cacctcccgt tctcgattct gacggctcct   5040
tcttcctcta cagcaagctc acagtggaca agagcaggtg gcaacaaggg aatgtcttct   5100
catgctccgt gatgcatgag gctcttcaca atcactacac acagaagagt ctctccttgt   5160
ctccgggtaa aggaggtggc ggatcaggtg gaggcggttc aggcggaggt ggatcccata   5220
acactcctgt ttacaagctg gacatatctg aggcaactca ataagagctc gaagtgacat   5280
cacaaagttg aaggtaataa agccaaatta attaagacat tttcataatg atgtcaagaa   5340
tgcaaagcaa attgcataac tgcctttatg caaaacatta atataatata aattataaag   5400
aactgcgctc tctgcttctt attttcttag cttcatttat tagtcactag ctgttcagaa   5460
ttttcagtat cttttgatat tactaagaac ctaatcacac aatgtatatt cttatgcagg   5520
aaaagcagaa tgctgagcta aaagaaaggc tttttccatt ttcgagagac aatgagaaaa   5580
gaagaagaag aagaagaaga agaagaagaa gaaaagagta aataataaag ccccacagga   5640
ggcgaagttc ttgtagctcc atgttatcta agttattgat attgtttgcc ctatatttta   5700
tttctgtcat tgtgtatgtt ttgttcagtt tcgatctcct tgcaaaatgc agagattatg   5760
```

```
agatgaataa actaagttat attattatac gtgttaatat tctcctcctc tctctagcta   5820
gccttttgtt ttctcttttt cttatttgat tttctttaaa tcaatccatt ttaggagagg   5880
gccagggagt gatccagcaa aacatgaaga ttagaagaaa cttccctctt ttttttcctg   5940
aaaacaattt aacgtcgaga tttatctctt tttgtaatgg aatcatttct acagttatga   6000
cgaattgtac atcaacgaaa aattagtcaa acgactaaaa taaataaata tcatgtgtta   6060
ttaagaaaat tctcctataa gaatatttta atagatcata tgtttgtaaa aaaaattaat   6120
ttttactaac acatatattt acttatcaaa aatttgacaa agtaagatta aaataatatt   6180
catctaacaa aaaaaaaacc agaaaatgct gaaaacccgg caaaaccgaa ccaatccaaa   6240
ccgatatagt tggtttggtt tgattttgat ataaaccgaa ccaactcggt ccatttgcac   6300
ccctaatcat aatagcttta atatttcaag atattattaa gttaacgttg tcaatatcct   6360
ggaaattttg caaaatgaat caagcctata tggctgtaat atgaatttaa aagcagctcg   6420
atgtggtggt aatatgtaat ttacttgatt ctaaaaaaat atcccaagta ttaataattt   6480
ctgctaggaa gaaggttagc tacgatttac agcaaagcca gaatacaaag aaccataaag   6540
tgattgaagc tcgaaatata cgaaggaaca aatattttta aaaaaatacg caatgacttg   6600
gaacaaaaga aagtgatata ttttttgttc ttaaacaagc atcccctcta aagaatggca   6660
gttttccttt gcatgtaact attatgctcc cttcgttaca aaaattttgg actactattg   6720
ggaacttctt ctgaaaatag tggtaccgag tgtacttcaa gtcagttgga aatcaataaa   6780
atgattattt tatgaatata tttcattgtg caagtagata gaaattacat atgttacata   6840
acacacgaaa taaacaaaaa aacacaatcc aaaacaaaca ccccaaacaa aataacacta   6900
tatatatcct cgtatgagga gaggcacgtt cagtgactcg acgattcccg agcaaaaaaa   6960
gtctccccgt cacacatata gtgggtgacg caattatctt caaagtaatc cttctgttga   7020
cttgtcattg ataacatcca gtcttcgtca ggattccaaa gaattataga agggatcggt   7080
caacatggtg gagcacgaca cacttgtcta ctccaaaaat atcaaagata cagtctcaga   7140
agaccaaagg gcaattgaga cttttcaaca aagggtaata tccggaaacc tcctcggatt   7200
ccattgccca gctatctgtc actttattgt gaagatagtg gaaaaggaag gtggctccta   7260
caaatgccat cattgcgata aaggaaaggc catcgttgaa gatgcctctg ccgacagtgg   7320
tcccaaagat ggacccccac ccacgaggag catcgtggaa aaagaagacg ttccaaccac   7380
gtcttcaaag caagtggatt gatgtgataa catggtggag cacgacacac ttgtctactc   7440
caaaaatatc aaagatacag tctcagaaga ccaaagggca attgagactt ttcaacaaag   7500
ggtaatatcc ggaaacctcc tcggattcca ttgcccagct atctgtcact ttattgtgaa   7560
gatagtggaa aaggaaggtg gctcctacaa atgccatcat tgcgataaag gaaaggccat   7620
cgttgaagat gcctctgccg acagtggtcc caaagatgga cccccaccca cgaggagcat   7680
cgtggaaaaa gaagacgttc caaccacgtc ttcaaagcaa gtggattgat gtgatatctc   7740
cactgacgta agggatgacg cacaatccca ctatccttcg caagaccctt cctctatata   7800
aggaagttca tttcatttgg agaggacctc gagaaacaaa caaaatcaac aaatatagaa   7860
aataacgcat ttccaattct ttgaaatttc tgcaacatct agaacaatgg gatggtcttg   7920
catcattctc ttcttggtag ccacagctac aggtgtccac tccgatgttt tgatgactca   7980
aagccctctc tcacttcctg tgactcttgg acagcccgca tccatatctt gcagatctag   8040
tcagagtatt gttcatagta acggcaacac ctacttggaa tggtatctgc agaaaccagg   8100
ccagtctcca aagcttctga tctacaaggc ttccaatcgt ttctctggtg tcccagacag   8160
```

```
gtttagtggc agtggatcag ggactgactt cacattgaag atcagcagag ttgaggctga   8220
agatgcggga gtgtactatt gtcttcaagg ttcacatgtt ccgtcaacgt ttggaggtgg   8280
gaccaaagtg gagatcaaga ctgttgcggc gccatctgtc ttcatctttc ctccatctga   8340
tgaacaactc aagtctggaa ctgcttctgt tgtgtgcctt ctgaacaact tctatcctag   8400
agaagccaaa gtacagtgga aggttgacaa tgctcttcaa tcaggtaact cccaggagag   8460
tgtcacagag caagattcca aggattccac ctacagcctc tcaagtacct tgacgttgag   8520
caaggcagac tatgagaaac acaaagtgta cgcatgcgaa gtcactcatc agggcctgtc   8580
atcacccgtg acaaagagct tcaacagggg agagtgttag gtaccgagct cgaagtgaca   8640
tcacaaagtt gaaggtaata aagccaaatt aattaagaca ttttcataat gatgtcaaga   8700
atgcaaagca aattgcataa ctgcctttat gcaaaacatt aatataatat aaattataaa   8760
gaactgcgct ctctgcttct tattttctta gcttcattta ttagtcacta gctgttcaga   8820
attttcagta tcttttgata ttactaagaa cctaatcaca caatgtatat tcttatgcag   8880
gaaaagcaga atgctgagct aaaagaaagg ctttttccat tttcgagaga caatgagaaa   8940
agaagaagaa gaagaagaag aagaagaaga agaaaagagt aaataataaa gccccacagg   9000
aggcgaagtt cttgtagctc catgttatct aagttattga tattgtttgc cctatatttt   9060
atttctgtca ttgtgtatgt tttgttcagt ttcgatctcc ttgcaaaatg cagagattat   9120
gagatgaata aactaagtta tattattata cgtgttaata ttctcctcct ctctctagct   9180
agccttttgt tttctctttt tcttatttga ttttctttaa atcaatccat tttaggagag   9240
ggccagggag tgatccagca aaacatgaag attagaagaa acttccctct ttttttttcct   9300
gaaaacaatt taacgtcgag atttatctct ttttgtaatg gaatcatttc tacagttatg   9360
acgaattgta catcaacgaa aaattagtca aacgactaaa ataaataaat atcatgtgtt   9420
attaagaaaa ttctcctata agaatatttt aatagatcat atgtttgtaa aaaaaattaa   9480
tttttactaa cacatatatt tacttatcaa aaatttgaca aagtaagatt aaaataatat   9540
tcatctaaca aaaaaaaaac cagaaaatgc tgaaaacccg gcaaaaccga accaatccaa   9600
accgatatag ttggtttggt ttgattttga tataaaccga accaactcgg tccatttgca   9660
cccctaatca taatagcttt aatatttcaa gatattatta agttaacgtt gtcaatatcc   9720
tggaaatttt gcaaaatgaa tcaagcctat atggctgtaa tatgaattta aaagcagctc   9780
gatgtggtgg taatatgtaa tttacttgat tctaaaaaaa tatcccaagt attaataatt   9840
tctgctagga agaaggttag ctacgattta cagcaaagcc agaatacaaa gaaccataaa   9900
gtgattgaag ctcgaaatat acgaaggaac aaatattttt aaaaaaatac gcaatgactt   9960
ggaacaaaag aaagtgatat attttttgtt cttaaacaag catcccctct aaagaatggc  10020
agttttcctt tgcatgtaac tattatgctc ccttcgttac aaaaattttg gactactatt  10080
gggaacttct tctgaaaata gtggtaccga gtgtacttca agtcagttgg aaatcaataa  10140
aatgattatt ttatgaatat atttcattgt gcaagtagat agaaattaca tatgttacat  10200
aacacacgaa ataaacaaaa aaacacaatc caaaacaaac accccaaaca aaataacact  10260
atatatatcc tcgtatgagg agaggcacgt tcagtgactc gacgattccc gagcaaaaaa  10320
agtctccccg tcacacatat agtgggtgac gcaattatct tcaaagtaat ccttctgttg  10380
acttgtcatt gataacatcc agtcttcgtc aggattgcaa agaattatag aagggatccc  10440
accttttatt ttcttctttt ttccatattt agggttgaca gtgaaatcag actggcaacc  10500
```

tattaattgc ttccacaatg ggacgaactt gaaggggatg tcgtcgatga tattataggt 10560
ggcgtgttca tcgtagttgg tgaagtcgat ggtcccgttc cagtagttgt gtcgcccgag 10620
acttctagcc caggtggtct ttccggtacg agttggtccg cagatgtaga ggctggggtg 10680
tctgacccca gtccttccct catcctggtt agatcggcca tccactcaag gtcagattgt 10740
gcttgatcgt aggagacagg atgtatgaaa gtgtaggcat cgatgcttac atgatatagg 10800
tgcgtctctc tccagttgtg cagatcttcg tggcagcgga gatctgattc tgtgaagggc 10860
gacacgtact gctcaggttg tggaggaaat aatttgttgg ctgaatattc cagccattga 10920
agctttgttg cccattcatg agggaactct tctttgatca tgtcaagata ctcctcctta 10980
gacgttgcag tctggataat agttcgccat cgtgcgtcag atttgcgagg agacacctta 11040
tgatctcgga aatctcctct ggttttaata tctccgtcct ttgatatgta atcaaggact 11100
tgtttagagt ttctagctgg ctggatatta gggtgatttc cttcaaaatc gaaaaaagaa 11160
ggatccctaa tacaaggttt tttatcaagc tggataagag catgatagtg ggtagtgcca 11220
tcttgatgaa gctcagaagc aacaccaagg aagaaaataa gaaaaggtgt gagtttctcc 11280
cagagaaact ggaataaatc atctctttga gatgagcact tggggtaggt aaggaaaaca 11340
tatttagatt ggagtctgaa gttcttgcta gcagaaggca tgttgttgtg actccgaggg 11400
gttgcctcaa actctatctt ataaccggcg tggaggcatg gaggcaaggg cattttggta 11460
atttaagtag ttagtggaaa atgacgtcat ttacttaaag acgaagtctt gcgacaaggg 11520
gggcccacgc cgaattttaa tattaccggc gtggccccac cttatcgcga gtgctttagc 11580
acgagcggtc cagatttaaa gtagaaaagt tcccgcccac tagggttaaa ggtgttcaca 11640
ctataaaagc atatacgatg tgatggtatt tgatggagcg tatattgtat caggtatttc 11700
cgtcggatac gaattattcg tacggccgga ccggtcccct aggccggcca attcgagatc 11760
ggccgcggct gagtggctcc ttcaatcgtt gcggttctgt cagttccaaa cgtaaaacgg 11820
cttgtcccgc gtcatcggcg gggtcataa cgtgactccc ttaattctcc gctcatgatc 11880
agattgtcgt ttcccgcctt cagtttaaac tatcagtgtt tgacaggata tattggcggg 11940
taaacctaag agaaaagagc gtttattaga ataatcggat atttaaaagg gcgtgaaaag 12000
gtttatccgt tcgtccattt gtatgtgcat gccaaccaca gggttcccca gatctggcgc 12060
cggccagcga gacgagcaag attggccgcc gcccgaaacg atccgacagc gcgcccagca 12120
caggtgcgca ggcaaattgc accaacgcat acagcgccag cagaatgcca tagtgggcgg 12180
tgacgtcgtt cgagtgaacc agatcgcgca ggaggcccgg cagcaccggc ataatcaggc 12240
cgatgccgac agcgtcgagc gcgacagtgc tcagaattac gatcaggggt atgttgggtt 12300
tcacgtctgg cctccggaga ctgtcatacg cgtaaaaagg ccgcgttgct ggcgtttttc 12360
cataggctcc gccccctga cgagcatcac aaaaatcgac gctcaagtca gaggtggcga 12420
aacccgacag gactataaag ataccaggcg tttccccctg gaagctccct cgtgcgctct 12480
cctgttccga ccctgccgct taccggatac ctgtccgcct ttctcccttc gggaagcgtg 12540
gcgctttctc atagctcacg ctgtaggtat ctcagttcgg tgtaggtcgt tcgctccaag 12600
ctgggctgtg tgcacgaacc ccccgttcag cccgaccgct gcgccttatc cggtaactat 12660
cgtcttgagt ccaacccggt aagacacgac ttatcgccac tggcagcagc cactggtaac 12720
aggattagca gagcgaggta tgtaggcggt gctacagagt tcttgaagtg gtggcctaac 12780
tacggctaca ctagaaggac agtatttggt atctgcgctc tgctgaagcc agttaccttc 12840
ggaaaaagag ttggtagctc ttgatccggc aaacaaacca ccgctggtag cggtggtttt 12900
tttgtttgca agcagcagat tacgcgcaga aaaaaaggat ctcaagaaga tcctttgatc 12960
ttttctacgg ggtctgacgc tcagtggaac gaaaactcac gttaagggat tttggtcatg 13020
agattatcaa aaaggatctt cacctagatc cttttaaatt aaaaatgaag ttttaaatca 13080
atctaaagta tatatgagta aacttggtct gcagttgcca tgttttacgg cagtgagagc 13140
agagatagcg ctgatgtccg gcggtgcttt tgccgttacg caccaccccg tcagtagctg 13200
aacaggaggg acagctgata gacacagaag ccactggagc acctcaaaaa caccatcata 13260
cactaaatca gtaagttggc agcatcaccc ataattgtgg tttcaaaatc ggctccgtcg 13320
atactatgtt atacgccaac tttgaaaaca actttgaaaa agctgttttc tggtatttaa 13380
ggttttagaa tgcaaggaac agtgaattgg agttcgtctt gttataatta gcttcttggg 13440
gtatctttaa atactgtaga aaagaggaag gaaataataa atggctaaaa tgagaatatc 13500
accggaattg aaaaaactga tcgaaaaata ccgctgcgta aaagatacgg aaggaatgtc 13560
tcctgctaag gtatataagc tggtgggaga aaatgaaaac ctatatttaa aaatgacgga 13620
cagccggtat aaagggacca cctatgatgt ggaacgggaa aaggacatga tgctatggct 13680
ggaaggaaag ctgcctgttc caaaggtcct gcactttgaa cggcatgatg gctggagcaa 13740
tctgctcatg agtgaggccg atggcgtcct ttgctcggaa gagtatgaag atgaacaaag 13800
ccctgaaaag attatcgagc tgtatgcgga gtgcatcagg ctctttcact ccatcgacat 13860
atcggattgt ccctatacga atagcttaga cagccgctta gccgaattgg attacttact 13920
gaataacgat ctggccgatg tggattgcga aaactgggaa gaagacactc catttaaaga 13980
tccgcgcgag ctgtatgatt ttttaaagac ggaaaagccc gaagaggaac ttgtcttttc 14040
ccacggcgac ctgggagaca gcaacatctt tgtgaaagat ggcaaagtaa gtggctttat 14100
tgatcttggg agaagcggca gggcggacaa gtggtatgac attgccttct gcgtccggtc 14160
gatcagggag gatatcgggg aagaacagta tgtcgagcta ttttttgact tactggggat 14220
caagcctgat tgggagaaaa taaaatatta tattttactg gatgaattgt tttagtacct 14280
agatgtggcg caacgatgcc ggcgacaagc aggagcgcac cgacttcttc cgcatcaagt 14340
gttttggctc tcaggccgag gcccacggca agtatttggg caaggggtcg ctggtattcg 14400
tgcagggcaa gattcggaat accaagtacg agaaggacgg ccagacggtc tacgggaccg 14460
acttcattgc cgataaggtg gattatctgg acaccaaggc accaggcggg tcaaatcagg 14520
aataagggca cattgccccg gcgtgagtcg gggcaatccc gcaaggaggg tgaatgaatc 14580
ggacgtttga ccggaaggca tacaggcaag aactgatcga cgcggggttt tccgccgagg 14640
atgccgaaac catcgcaagc cgcaccgtca tgcgtgcgcc ccgcgaaacc ttccagtccg 14700
tcggctcgat ggtccagcaa gctacggcca agatcgagcg cgacagcgtg caactggctc 14760
cccctgccct gcccgcgcca tcggccgccg tggagcgttc gcgtcgtctc gaacaggagg 14820
cggcaggttt ggcgaagtcg atgaccatcg acacgcgagg aactatgacg accaagaagc 14880
gaaaaaccgc cggcgaggac ctggcaaaac aggtcagcga ggccaagcag gccgcgttgc 14940
tgaaacacac gaagcagcag atcaaggaaa tgcagctttc cttgttcgat attgcgccgt 15000
ggccggacac gatgcgagcg atgccaaacg acacggcccg ctctgccctg ttcaccacgc 15060
gcaacaagaa aatcccgcgc gaggcgctgc aaaacaaggt cattttccac gtcaacaagg 15120
acgtgaagat cacctacacc ggcgtcgagc tgcgggccga cgatgacgaa ctggtgtggc 15180
agcaggtgtt ggagtacgcg aagcgcaccc ctatcggcga gccgatcacc ttcacgttct 15240
acgagctttg ccaggacctg ggctggtcga tcaatggccg gtattacacg aaggccgagg 15300
aatgcctgtc gcgcctacag gcgacggcga tgggcttcac gtccgaccgc gttgggcacc 15360
tggaatcggt gtcgctgctg caccgcttcc gcgtcctgga ccgtggcaag aaaacgtccc 15420
gttgccaggt cctgatcgac gaggaaatcg tcgtgctgtt tgctggcgac cactacacga 15480
aattcatatg ggagaagtac cgcaagctgt cgccgacggc ccgacggatg ttcgactatt 15540
tcagctcgca ccgggagccg tacccgctca agctggaaac cttccgcctc atgtgcggat 15600
cggattccac ccgcgtgaag aagtggcgcg agcaggtcgg cgaagcctgc gaagagttgc 15660
gaggcagcgg cctggtggaa cacgcctggg tcaatgatga cctggtgcat tgcaaacgct 15720
agggccttgt ggggtcagtt ccggctgggg gttcagcagc cagcgcttta ctggcatttc 15780
aggaacaagc gggcactgct cgacgcactt gcttcgctca gtatcgctcg ggacgcacgg 15840
cgcgctctac gaactgccga taaacagagg attaaaattg acaattcaat ggcaaggact 15900
gccagcgctg ccatttttgg ggtgaggccg ttcgcggccg aggggcgcag cccctggggg 15960
gatgggaggc ccgcgttagc gggccgggag ggttcgagaa ggggggggcac ccccccttcgg 16020 cgtgcgcggt cacgcgcaca gggcgcagcc ctggttaaaa acaaggttta taaatattgg 16080
tttaaaagca ggttaaaaga caggttagcg gtggccgaaa aacgggcgga aacccttgca 16140
aatgctggat tttctgcctg tggacagccc ctcaaatgtc aataggtgcg cccctcatct 16200
gtcagcactc tgcccctcaa gtgtcaagga tcgcgcccct catctgtcag tagtcgcgcc 16260
cctcaagtgt caataccgca gggcacttat ccccaggctt gtccacatca tctgtgggaa 16320
actcgcgtaa aatcaggcgt tttcgccgat ttgcgaggct ggccagctcc acgtcgccgg 16380
ccgaaatcga gcctgcccct catctgtcaa cgccgcgccg ggtgagtcgg cccctcaagt 16440
gtcaacgtcc gcccctcatc tgtcagtgag ggccaagttt tccgcgaggt atccacaacg 16500
ccggcggccg cggtgtctcg cacacggctt cgacggcgtt tctggcgcgt ttgcagggcc 16560
atagacggcc gccagcccag cggcgagggc aaccagcccg gtgagcgtcg caaaggcgct 16620
cggtcttgcc ttgctcgtcg agatctgggg tcgatcagcc ggggatgcat caggccgaca 16680
gtcggaactt cgggtccccg acctgtacca ttcggtgagc aatggatagg ggagttgata 16740
tcgtcaacgt tcacttctaa agaaatagcg ccactcagct tcctcagcgg ctttatccag 16800
cgatttccta ttatgtcggc atagttctca agatcgacag cctgtcacgg ttaagcgaga 16860
aatgaataag aaggctgata attcggatct ctgcgaggga gatgatattt gatcacaggc 16920
agcaacgctc tgtcatcgtt acaatcaaca tgctaccctc cgcgagatca tccgtgtttc 16980
aaacccggca gcttagttgc cgttcttccg aatagcatcg gtaacatgag caaagtctgc 17040
cgccttacaa cggctctccc gctgacgccg tcccggactg atgggctgcc tgtatcgagt 17100
ggtgattttg tgccgagctg ccggtcgggg agctgttggc tggctggtgg caggatatat 17160
tgtggtgtaa acaaattgac gcttagacaa cttaataaca cattgcggac gtttttaatg 17220
tactggggtg gtttttcttt tcaccagtga gacgggcaac agctgattgc ccttcaccgc 17280
ctggccctga gagagttgca gcaagcggtc cacgctggtt tgccccagca ggcgaaaatc 17340
ctgtttgatg gtggttccga aatcggcaaa atcccttata aatcaaaaga atagcccgag 17400
atagggttga gtgttgttcc agtttggaac aagagtccac tattaaagaa cgtggactcc 17460
aacgtcaaag ggcgaaaaac cgtctatcag ggcgatggcc cactacgtga accatcaccc 17520
aaatcaagtt ttttggggtc gaggtgccgt aaagcactaa atcggaaccc taaagggagc 17580
ccccgattta gagcttgacg gggaaagccg gcgaacgtgg cgagaaagga agggaagaaa 17640
gcgaaaggag cgggcgccat tcaggctgcg caactgttgg gaaggg 17686

<210> SEQ ID NO 23
<211> LENGTH: 17602
<212> TYPE: DNA
<213> ORGANISM: Artificial Sequence
<220> FEATURE:
<223> OTHER INFORMATION: pBYR11eMa-BAZE3-H

<400> SEQUENCE: 23
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980

```
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggcc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat ggctaacaag cacctctcat   3420
tgtctctctt ccttgtgctc cttggtcttt ctgcttctct tgcttctggt aagggcgtgt   3480
catactcctt gtgtaccgct gccttcacat tcaccaagat cccggctgaa acactccacg   3540
gaaccgttac cgtggaggtc caatacgccg gtacagatgg accttgcaag gttccagctc   3600
agatggcggt ggacatgcaa actcttaccc cagttggaag gttgattacc gctaaccccg   3660
ttatcactga aagcactgag aactctaaga tgatgttgga acttgatcca ccattcggtg   3720
actcttacat tgtcattggt gtgggagaga agaagatcac ccaccactgg cacaggagtg   3780
gtagcactag tggtggatca ggaggttctg gtggttctgg aggttcagga tccgatgttc   3840
agcttcttga gtctggaggt ggtcttgtgc aacctggagg ttccttgaga ctctcctgtg   3900
cagcttcagg gtttgacttc agtaggtact ggatgagttg ggttcgtcaa gctcctggga   3960
aaggactaga atggattgga gagatcaatc cagattcaag taccatcaac tatactccat   4020
ctctgaagga tcgcttcacc atttccagag acaatgccaa gaacacgttg tatcttcaga   4080
tgaacagctt gaggactgaa gacacagcct tgtactactg cacaagacag ggctatggct   4140
acaactactg gggtcaaggc accactgtca cagtgtcttc agctagcacc aaaggtccat   4200
cggtctttcc actggcacct tcttccaaga gtacttctgg aggcacagct gcactgggtt   4260
gtcttgtcaa ggactacttt ccagaacctg ttacggtttc gtggaactca ggtgctctga   4320
ccagtggagt gcacaccttt ccagctgttc ttcagtcctc aggattgtat tctcttagca   4380
```

gtgttgtgac tgttccatcc tcaagcttgg gcactcagac ctacatctgc aatgtgaatc 4440
acaaacccag caacaccaag gttgacaaga aagttgagcc caagtcttgt gacaagactc 4500
atacgtgtcc accgtgccca gcacctgaac ttcttggagg accgtcagtc ttcttgtttc 4560
ctccaaagcc taaggatacc ttgatgatct ccaggactcc tgaagtcaca tgtgtagttg 4620
tggatgtgag ccatgaagat cctgaggtga agttcaactg gtatgtggat ggtgtggaag 4680
tgcacaatgc caagacaaag ccgagagagg aacagtacaa cagcacgtac agggttgtct 4740
cagttctcac tgttctccat caagattggt tgaatggcaa agagtacaag tgcaaggtct 4800
ccaacaaagc cctcccagcc cccattgaga agaccatttc caaagcgaaa gggcaacccc 4860
gtgaaccaca agtgtacaca cttcctccat ctcgcgatga actgaccaag aaccaggtca 4920
gcttgacttg cctggtgaaa ggcttctatc cctctgacat agctgtagag tgggagagca 4980
atgggcaacc ggagaacaac tacaagacta cacctcccgt tctcgattct gacggctcct 5040
tcttcctcta cagcaagctc acagtggaca agagcaggtg gcaacaaggg aatgtcttct 5100
catgctccgt gatgcatgag gctcttcaca atcactacac acagaagagt ctctccttgt 5160
ctccgggtaa atgaggtacc gagctcgaag tgacatcaca aagttgaagg taataaagcc 5220
aaattaatta agacattttc ataatgatgt caagaatgca aagcaaattg cataactgcc 5280
tttatgcaaa acattaatat aatataaatt ataaagaact gcgctctctg cttcttattt 5340
tcttagcttc atttattagt cactagctgt tcagaatttt cagtatcttt tgatattact 5400
aagaacctaa tcacacaatg tatattctta tgcaggaaaa gcagaatgct gagctaaaag 5460
aaaggctttt tccattttcg agagacaatg agaaaagaag aagaagaaga agaagaagaa 5520
gaagaagaaa agagtaaata ataaagcccc acaggaggcg aagttcttgt agctccatgt 5580
tatctaagtt attgatattg tttgccctat attttatttc tgtcattgtg tatgttttgt 5640
tcagtttcga tctccttgca aaatgcagag attatgagat gaataaacta agttatatta 5700
ttatacgtgt taatattctc ctcctctctc tagctagcct tttgttttct ctttttctta 5760
tttgattttc tttaaatcaa tccattttag gagagggcca gggagtgatc cagcaaaaca 5820
tgaagattag aagaaacttc cctctttttt ttcctgaaaa caatttaacg tcgagattta 5880
tctcttttttg taatggaatc atttctacag ttatgacgaa ttgtacatca acgaaaaatt 5940
agtcaaacga ctaaaataaa taaatatcat gtgttattaa gaaaattctc ctataagaat 6000
attttaatag atcatatgtt tgtaaaaaaa attaattttt actaacacat atatttactt 6060
atcaaaaatt tgacaaagta agattaaaat aatattcatc taacaaaaaa aaaaccagaa 6120
aatgctgaaa acccggcaaa accgaaccaa tccaaaccga tatagttggt ttggtttgat 6180
tttgatataa accgaaccaa ctcggtccat ttgcacccct aatcataata gctttaatat 6240
ttcaagatat tattaagtta acgttgtcaa tatcctggaa attttgcaaa atgaatcaag 6300
cctatatggc tgtaatatga atttaaaagc agctcgatgt ggtggtaata tgtaatttac 6360
ttgattctaa aaaaatatcc caagtattaa taatttctgc taggaagaag gttagctacg 6420
atttacagca aagccagaat acaaagaacc ataaagtgat tgaagctcga aatatacgaa 6480
ggaacaaata tttttaaaaa aatacgcaat gacttggaac aaaagaaagt gatatatttt 6540
ttgttcttaa acaagcatcc cctctaaaga atggcagttt tcctttgcat gtaactatta 6600
tgctcccttc gttacaaaaa ttttggacta ctattgggaa cttcttctga aaatagtggt 6660
accgagtgta cttcaagtca gttggaaatc aataaaatga ttattttatg aatatatttc 6720

```
attgtgcaag tagatagaaa ttacatatgt tacataacac acgaaataaa caaaaaaaca   6780
caatccaaaa caaacacccc aaacaaaata acactatata tatcctcgta tgaggagagg   6840
cacgttcagt gactcgacga ttcccgagca aaaaaagtct ccccgtcaca catatagtgg   6900
gtgacgcaat tatcttcaaa gtaatccttc tgttgacttg tcattgataa catccagtct   6960
tcgtcaggat tccaaagaat tatagaaggg atcggtcaac atggtggagc acgacacact   7020
tgtctactcc aaaaatatca aagatacagt ctcagaagac caaagggcaa ttgagacttt   7080
tcaacaaagg gtaatatccg gaaacctcct cggattccat tgcccagcta tctgtcactt   7140
tattgtgaag atagtggaaa aggaaggtgg ctcctacaaa tgccatcatt gcgataaagg   7200
aaaggccatc gttgaagatg cctctgccga cagtggtccc aaagatggac ccccacccac   7260
gaggagcatc gtggaaaaag aagacgttcc aaccacgtct tcaaagcaag tggattgatg   7320
tgataacatg gtggagcacg acacacttgt ctactccaaa aatatcaaag atacagtctc   7380
agaagaccaa agggcaattg agacttttca acaaagggta atatccggaa acctcctcgg   7440
attccattgc ccagctatct gtcactttat tgtgaagata gtggaaaagg aaggtggctc   7500
ctacaaatgc catcattgcg ataaaggaaa ggccatcgtt gaagatgcct ctgccgacag   7560
tggtcccaaa gatggacccc cacccacgag gagcatcgtg gaaaaagaag acgttccaac   7620
cacgtcttca aagcaagtgg attgatgtga tatctccact gacgtaaggg atgacgcaca   7680
atcccactat ccttcgcaag acccttcctc tatataagga agttcatttc atttggagag   7740
gacctcgaga aacaaacaaa atcaacaaat atagaaaata acgcatttcc aattctttga   7800
aatttctgca acatctagaa caatgggatg gtcttgcatc attctcttct tggtagccac   7860
agctacaggt gtccactccg atgttttgat gactcaaagc cctctctcac ttcctgtgac   7920
tcttggacag cccgcatcca tatcttgcag atctagtcag agtattgttc atagtaacgg   7980
caacacctac ttggaatggt atctgcagaa accaggccag tctccaaagc ttctgatcta   8040
caaggcttcc aatcgtttct ctggtgtccc agacaggttt agtggcagtg gatcagggac   8100
tgacttcaca ttgaagatca gcagagttga ggctgaagat gcgggagtgt actattgtct   8160
tcaaggttca catgttccgt caacgtttgg aggtgggacc aaagtggaga tcaagactgt   8220
tgcggcgcca tctgtcttca tctttcctcc atctgatgaa caactcaagt ctggaactgc   8280
ttctgttgtg tgccttctga acaacttcta tcctagagaa gccaaagtac agtggaaggt   8340
tgacaatgct cttcaatcag gtaactccca ggagagtgtc acagagcaag attccaagga   8400
ttccacctac agcctctcaa gtaccttgac gttgagcaag gcagactatg agaaacacaa   8460
agtgtacgca tgcgaagtca ctcatcaggg cctgtcatca cccgtgacaa agagcttcaa   8520
caggggagag tgttaggtac cgagctcgaa gtgacatcac aaagttgaag gtaataaagc   8580
caaattaatt aagacatttt cataatgatg tcaagaatgc aaagcaaatt gcataactgc   8640
ctttatgcaa aacattaata taatataaat tataaagaac tgcgctctct gcttcttatt   8700
ttcttagctt catttattag tcactagctg ttcagaattt tcagtatctt ttgatattac   8760
taagaaccta atcacacaat gtatattctt atgcaggaaa agcagaatgc tgagctaaaa   8820
gaaaggcttt ttccattttc gagagacaat gagaaaagaa gaagaagaag aagaagaaga   8880
agaagaagaa aagagtaaat aataaagccc cacaggaggc gaagttcttg tagctccatg   8940
ttatctaagt tattgatatt gtttgcccta tattttattt ctgtcattgt gtatgttttg   9000
ttcagtttcg atctccttgc aaaatgcaga gattatgaga tgaataaact aagttatatt   9060
attatacgtg ttaatattct cctcctctct ctagctagcc ttttgttttc tctttttctt   9120
```

-continued

```
atttgatttt ctttaaatca atccatttta ggagagggcc agggagtgat ccagcaaaac   9180
atgaagatta gaagaaactt ccctcttttt tttcctgaaa acaatttaac gtcgagattt   9240
atctcttttt gtaatggaat catttctaca gttatgacga attgtacatc aacgaaaaat   9300
tagtcaaacg actaaaataa ataaatatca tgtgttatta agaaaattct cctataagaa   9360
tattttaata gatcatatgt ttgtaaaaaa aattaatttt tactaacaca tatatttact   9420
tatcaaaaat ttgacaaagt aagattaaaa taatattcat ctaacaaaaa aaaaaccaga   9480
aaatgctgaa aacccggcaa aaccgaacca atccaaaccg atatagttgg tttggtttga   9540
ttttgatata aaccgaacca actcggtcca tttgcacccc taatcataat agctttaata   9600
tttcaagata ttattaagtt aacgttgtca atatcctgga aattttgcaa aatgaatcaa   9660
gcctatatgg ctgtaatatg aatttaaaag cagctcgatg tggtggtaat atgtaattta   9720
cttgattcta aaaaaatatc ccaagtatta ataatttctg ctaggaagaa ggttagctac   9780
gatttacagc aaagccagaa tacaaagaac cataaagtga ttgaagctcg aaatatacga   9840
aggaacaaat atttttaaaa aaatacgcaa tgacttggaa caaaagaaag tgatatattt   9900
tttgttctta aacaagcatc ccctctaaag aatggcagtt ttcctttgca tgtaactatt   9960
atgctccctt cgttacaaaa attttggact actattggga acttcttctg aaaatagtgg  10020
taccgagtgt acttcaagtc agttggaaat caataaaatg attattttat gaatatattt  10080
cattgtgcaa gtagatagaa attacatatg ttacataaca cacgaaataa acaaaaaaac  10140
acaatccaaa acaaacaccc caaacaaaat aacactatat atatcctcgt atgaggagag  10200
gcacgttcag tgactcgacg attcccgagc aaaaaaagtc tccccgtcac acatatagtg  10260
ggtgacgcaa ttatcttcaa agtaatcctt ctgttgactt gtcattgata acatccagtc  10320
ttcgtcagga ttgcaaagaa ttatagaagg gatcccacct tttattttct tctttttcc  10380
atatttaggg ttgacagtga aatcagactg gcaacctatt aattgcttcc acaatgggac  10440
gaacttgaag ggatgtcgt cgatgatatt ataggtggcg tgttcatcgt agttggtgaa  10500
gtcgatggtc ccgttccagt agttgtgtcg cccgagactt ctagcccagg tggtctttcc  10560
ggtacgagtt ggtccgcaga tgtagaggct ggggtgtctg accccagtcc ttccctcatc  10620
ctggttagat cggccatcca ctcaaggtca gattgtgctt gatcgtagga gacaggatgt  10680
atgaaagtgt aggcatcgat gcttacatga tataggtgcg tctctctcca gttgtgcaga  10740
tcttcgtggc agcggagatc tgattctgtg aagggcgaca cgtactgctc aggttgtgga  10800
ggaaataatt tgttggctga atattccagc cattgaagct ttgttgccca ttcatgaggg  10860
aactcttctt tgatcatgtc aagatactcc tccttagacg ttgcagtctg gataatagtt  10920
cgccatcgtg cgtcagattt gcgaggagac accttatgat ctcggaaatc tcctctggtt  10980
ttaatatctc cgtcctttga tatgtaatca aggacttgtt tagagtttct agctggctgg  11040
atattagggt gatttccttc aaaatcgaaa aaagaaggat ccctaataca aggtttttta  11100
tcaagctgga taagagcatg atagtgggta gtgccatctt gatgaagctc agaagcaaca  11160
ccaaggaaga aaataagaaa aggtgtgagt ttctcccaga gaaactggaa taaatcatct  11220
ctttgagatg agcacttggg gtaggtaagg aaaacatatt tagattggag tctgaagttc  11280
ttgctagcag aaggcatgtt gttgtgactc cgaggggttg cctcaaactc tatcttataa  11340
ccggcgtgga ggcatggagg caagggcatt ttggtaattt aagtagttag tggaaaatga  11400
cgtcatttac ttaaagacga agtcttgcga caaggggggc ccacgccgaa ttttaatatt  11460
```

accggcgtgg ccccacctta tcgcgagtgc tttagcacga gcggtccaga tttaaagtag 11520
aaaagttccc gcccactagg gttaaaggtg ttcacactat aaaagcatat acgatgtgat 11580
ggtatttgat ggagcgtata ttgtatcagg tatttccgtc ggatacgaat tattcgtacg 11640
gccggaccgg tcccctaggc cggccaattc gagatcggcc gcggctgagt ggctccttca 11700
atcgttgcgg ttctgtcagt tccaaacgta aaacggcttg tcccgcgtca tcggcggggg 11760
tcataacgtg actcccttaa ttctccgctc atgatcagat tgtcgtttcc cgccttcagt 11820
ttaaactatc agtgtttgac aggatatatt ggcgggtaaa cctaagagaa aagagcgttt 11880
attagaataa tcggatattt aaaagggcgt gaaaaggttt atccgttcgt ccatttgtat 11940
gtgcatgcca accacagggt tccccagatc tggcgccggc cagcgagacg agcaagattg 12000
gccgccgccc gaaacgatcc gacagcgcgc ccagcacagg tgcgcaggca aattgcacca 12060
acgcatacag cgccagcaga atgccatagt gggcggtgac gtcgttcgag tgaaccagat 12120
cgcgcaggag gcccggcagc accggcataa tcaggccgat gccgacagcg tcgagcgcga 12180
cagtgctcag aattacgatc aggggtatgt tgggtttcac gtctggcctc cggagactgt 12240
catacgcgta aaaaggccgc gttgctggcg tttttccata ggctccgccc ccctgacgag 12300
catcacaaaa atcgacgctc aagtcagagg tggcgaaacc cgacaggact ataaagatac 12360
caggcgtttc cccctggaag ctccctcgtg cgctctcctg ttccgaccct gccgcttacc 12420
ggatacctgt ccgcctttct cccttcggga agcgtggcgc tttctcatag ctcacgctgt 12480
aggtatctca gttcggtgta ggtcgttcgc tccaagctgg gctgtgtgca cgaacccccc 12540
gttcagcccg accgctgcgc cttatccggt aactatcgtc ttgagtccaa cccggtaaga 12600
cacgacttat cgccactggc agcagccact ggtaacagga ttagcagagc gaggtatgta 12660
ggcggtgcta cagagttctt gaagtggtgg cctaactacg gctacactag aaggacagta 12720
tttggtatct gcgctctgct gaagccagtt accttcggaa aaagagttgg tagctcttga 12780
tccggcaaac aaaccaccgc tggtagcggt ggtttttttg tttgcaagca gcagattacg 12840
cgcagaaaaa aaggatctca agaagatcct ttgatctttt ctacggggtc tgacgctcag 12900
tggaacgaaa actcacgtta agggattttg gtcatgagat tatcaaaaag gatcttcacc 12960
tagatccttt taaattaaaa atgaagtttt aaatcaatct aaagtatata tgagtaaact 13020
tggtctgcag ttgccatgtt ttacggcagt gagagcagag atagcgctga tgtccggcgg 13080
tgcttttgcc gttacgcacc accccgtcag tagctgaaca ggagggacag ctgatagaca 13140
cagaagccac tggagcacct caaaaacacc atcatacact aaatcagtaa gttggcagca 13200
tcacccataa ttgtggtttc aaaatcggct ccgtcgatac tatgttatac gccaactttg 13260
aaaacaactt tgaaaaagct gttttctggt atttaaggtt ttagaatgca aggaacagtg 13320
aattggagtt cgtcttgtta taattagctt cttggggtat ctttaaatac tgtagaaaag 13380
aggaaggaaa taataaatgg ctaaaatgag aatatcaccg gaattgaaaa aactgatcga 13440
aaaataccgc tgcgtaaaag atacggaagg aatgtctcct gctaaggtat ataagctggt 13500
gggagaaaat gaaaacctat atttaaaaat gacggacagc cggtataaag ggaccaccta 13560
tgatgtggaa cgggaaaagg acatgatgct atggctggaa ggaaagctgc ctgttccaaa 13620
ggtcctgcac tttgaacggc atgatggctg gagcaatctg ctcatgagtg aggccgatgg 13680
cgtcctttgc tcggaagagt atgaagatga acaaagccct gaaaagatta tcgagctgta 13740
tgcggagtgc atcaggctct ttcactccat cgacatatcg gattgtccct atacgaatag 13800
cttagacagc cgcttagccg aattggatta cttactgaat aacgatctgg ccgatgtgga 13860

```
ttgcgaaaac tgggaagaag acactccatt taaagatccg cgcgagctgt atgatttttt  13920
aaagacggaa aagcccgaag aggaacttgt cttttcccac ggcgacctgg gagacagcaa  13980
catctttgtg aaagatggca aagtaagtgg ctttattgat cttgggagaa gcggcagggc  14040
ggacaagtgg tatgacattg ccttctgcgt ccggtcgatc agggaggata tcggggaaga  14100
acagtatgtc gagctatttt ttgacttact ggggatcaag cctgattggg agaaaataaa  14160
atattatatt ttactggatg aattgtttta gtacctagat gtggcgcaac gatgccggcg  14220
acaagcagga gcgcaccgac ttcttccgca tcaagtgttt tggctctcag gccgaggccc  14280
acggcaagta tttgggcaag gggtcgctgg tattcgtgca gggcaagatt cggaatacca  14340
agtacgagaa ggacggccag acggtctacg ggaccgactt cattgccgat aaggtggatt  14400
atctggacac caaggcacca ggcgggtcaa atcaggaata agggcacatt gccccggcgt  14460
gagtcggggc aatcccgcaa ggagggtgaa tgaatcggac gtttgaccgg aaggcataca  14520
ggcaagaact gatcgacgcg gggttttccg ccgaggatgc cgaaaccatc gcaagccgca  14580
ccgtcatgcg tgcgccccgc gaaaccttcc agtccgtcgg ctcgatggtc cagcaagcta  14640
cggccaagat cgagcgcgac agcgtgcaac tggctccccc tgccctgccc gcgccatcgg  14700
ccgccgtgga gcgttcgcgt cgtctcgaac aggaggcggc aggtttggcg aagtcgatga  14760
ccatcgacac gcgaggaact atgacgacca agaagcgaaa aaccgccggc gaggacctgg  14820
caaaacaggt cagcgaggcc aagcaggccg cgttgctgaa acacacgaag cagcagatca  14880
aggaaatgca gctttccttg ttcgatattg cgccgtggcc ggacacgatg cgagcgatgc  14940
caaacgacac ggcccgctct gccctgttca ccacgcgcaa caagaaaatc ccgcgcgagg  15000
cgctgcaaaa caaggtcatt ttccacgtca acaaggacgt gaagatcacc tacaccggcg  15060
tcgagctgcg ggccgacgat gacgaactgg tgtggcagca ggtgttggag tacgcgaagc  15120
gcacccctat cggcgagccg atcaccttca cgttctacga gctttgccag gacctgggct  15180
ggtcgatcaa tggccggtat tacacgaagg ccgaggaatg cctgtcgcgc ctacaggcga  15240
cggcgatggg cttcacgtcc gaccgcgttg ggcacctgga atcggtgtcg ctgctgcacc  15300
gcttccgcgt cctggaccgt ggcaagaaaa cgtcccgttg ccaggtcctg atcgacgagg  15360
aaatcgtcgt gctgtttgct ggcgaccact acacgaaatt catatgggag aagtaccgca  15420
agctgtcgcc gacggcccga cggatgttcg actatttcag ctcgcaccgg gagccgtacc  15480
cgctcaagct ggaaaccttc cgcctcatgt gcggatcgga ttccacccgc gtgaagaagt  15540
ggcgcgagca ggtcggcgaa gcctgcgaag agttgcgagg cagcggcctg gtggaacacg  15600
cctgggtcaa tgatgacctg gtgcattgca aacgctaggg ccttgtgggg tcagttccgg  15660
ctgggggttc agcagccagc gctttactgg catttcagga acaagcgggc actgctcgac  15720
gcacttgctt cgctcagtat cgctcgggac gcacggcgcg ctctacgaac tgccgataaa  15780
cagaggatta aaattgacaa ttcaatggca aggactgcca gcgctgccat ttttggggtg  15840
aggccgttcg cggccgaggg gcgcagcccc tggggggatg ggaggcccgc gttagcgggc  15900
cgggagggtt cgagaagggg gggcaccccc cttcggcgtg cgcggtcacg cgcacagggc  15960
gcagccctgg ttaaaaacaa ggtttataaa tattggttta aaagcaggtt aaaagacagg  16020
ttagcggtgg ccgaaaaacg ggcggaaacc cttgcaaatg ctggattttc tgcctgtgga  16080
cagcccctca aatgtcaata ggtgcgcccc tcatctgtca gcactctgcc cctcaagtgt  16140
caaggatcgc gcccctcatc tgtcagtagt cgcgcccctc aagtgtcaat accgcagggc  16200
```

-continued

```
acttatcccc aggcttgtcc acatcatctg tgggaaactc gcgtaaaatc aggcgttttc  16260

gccgatttgc gaggctggcc agctccacgt cgccggccga aatcgagcct gcccctcatc  16320

tgtcaacgcc gcgccgggtg agtcggcccc tcaagtgtca acgtccgccc ctcatctgtc  16380

agtgagggcc aagttttccg cgaggtatcc acaacgccgg cggccgcggt gtctcgcaca  16440

cggcttcgac ggcgtttctg gcgcgtttgc agggccatag acggccgcca gcccagcggc  16500

gagggcaacc agcccggtga gcgtcgcaaa ggcgctcggt cttgccttgc tcgtcgagat  16560

ctggggtcga tcagccgggg atgcatcagg ccgacagtcg gaacttcggg tccccgacct  16620

gtaccattcg gtgagcaatg gataggggag ttgatatcgt caacgttcac ttctaaagaa  16680

atagcgccac tcagcttcct cagcggcttt atccagcgat ttcctattat gtcggcatag  16740

ttctcaagat cgacagcctg tcacggttaa gcgagaaatg aataagaagg ctgataattc  16800

ggatctctgc gagggagatg atatttgatc acaggcagca acgctctgtc atcgttacaa  16860

tcaacatgct accctccgcg agatcatccg tgtttcaaac ccggcagctt agttgccgtt  16920

cttccgaata gcatcggtaa catgagcaaa gtctgccgcc ttacaacggc tctcccgctg  16980

acgccgtccc ggactgatgg gctgcctgta tcgagtggtg attttgtgcc gagctgccgg  17040

tcggggagct gttggctggc tggtggcagg atatattgtg gtgtaaacaa attgacgctt  17100

agacaactta ataacacatt gcggacgttt ttaatgtact ggggtggttt ttcttttcac  17160

cagtgagacg ggcaacagct gattgccctt caccgcctgg ccctgagaga gttgcagcaa  17220

gcggtccacg ctggtttgcc ccagcaggcg aaaatcctgt ttgatggtgg ttccgaaatc  17280

ggcaaaatcc cttataaatc aaaagaatag cccgagatag ggttgagtgt tgttccagtt  17340

tggaacaaga gtccactatt aaagaacgtg gactccaacg tcaaagggcg aaaaaccgtc  17400

tatcagggcg atggcccact acgtgaacca tcacccaaat caagtttttt ggggtcgagg  17460

tgccgtaaag cactaaatcg gaaccctaaa gggagccccc gatttagagc ttgacgggga  17520

aagccggcga acgtggcgag aaaggaaggg aagaaagcga aaggagcggg cgccattcag  17580

gctgcgcaac tgttgggaag gg                                           17602
```

<210> SEQ ID NO 24
<211> LENGTH: 14220
<212> TYPE: DNA
<213> ORGANISM: Artificial Sequence
<220> FEATURE:
<223> OTHER INFORMATION: pBYKEMd-HZE3

<400> SEQUENCE: 24

```
cgatcggtcg attcatagaa gattagattt ttcatagtat ttttttaaag taaaccttta     60

actacggtta ggacactttt aagttaaatt taatttgaac ccttaaatta atttttaaaa    120

tagataaata tcaatcatcc tgatatgctt ttgaaaaaat gaatgagaaa gatgattcaa    180

ttaaggccac attttaatca tgactaaaat aatatacagt ataatttcat atatatttgc    240

tttaaaaaaa aattgacaat ccattcgttt ctagcaataa atttcttcaa ccacaaatat    300

attaaagata actacggcat agaaacaaaa atctatgaag aatttttgta tacttcatat    360

gaaattaaaa aaaacttcat tgaacatcaa aataataata ataatcataa actcctcaat    420

atttatattc ctagcttctt gaattaaatt gtttacatat tcaacgatgt aaaaaaattat    480

ttctctatct attttcctta tatcatgcat ggtttcacat atatcaaagg ataaaagcaa    540

tctatgtaaa ttatctcact ttattaagtt ttctatctga attattgaga acgtagattt    600

ctttttgcac tatcccccaa taattagcaa aacacaccta gactagattt gttttgctaa    660
```

```
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
```

```
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtcaag   3780
gcaccactgt cacagtgtct tcagctagca ccaaaggtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgctct gaccagtgga gtgcacacct   3960
ttccagctgt tcttcagtcc tcaggattgt attctcttag cagtgttgtg actgttccat   4020
cctcaagctt gggcactcag acctacatct gcaatgtgaa tcacaaaccc agcaacacca   4080
aggttgacaa gaaagttgag cccaagtctt gtgacaagac tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtgga agtgcacaat gccaagacaa   4320
agccgagaga ggaacagtac aacagcacgt acagggttgt ctcagttctc actgttctcc   4380
atcaagattg gttgaatggc aaagagtaca agtgcaaggt ctccaacaaa gccctcccag   4440
cccccattga gaagaccatt tccaaagcga aagggcaacc ccgtgaacca caagtgtaca   4500
cacttcctcc atctcgcgat gaactgacca agaaccaggt cagcttgact tgcctggtga   4560
aaggcttcta tccctctgac atagctgtag agtgggagag caatgggcaa ccggagaaca   4620
actacaagac tacacctccc gttctcgatt ctgacggctc cttcttcctc tacagcaagc   4680
tcacagtgga caagagcagg tggcaacaag ggaatgtctt ctcatgctcc gtgatgcatg   4740
aggctcttca caatcactac acacagaaga gtctctcctt gtctccgggt aaaggaggtg   4800
gcggatcagg tggaggcggt tcaggcggag gtggatccaa gggcgtgtca tactccttgt   4860
gtaccgctgc cttcacattc accaagatcc cggctgaaac actccacgga accgttaccg   4920
tggaggtcca atacgccggt acagatggac cttgcaaggt tccagctcag atggcggtgg   4980
acatgcaaac tcttacccca gttggaaggt tgattaccgc taaccccgtt atcactgaaa   5040
gcactgagaa ctctaagatg atgttggaac ttgatccacc attcggtgac tcttacattg   5100
tcattggtgt gggagagaag aagatcaccc accactggca caggagtggt agcacttaag   5160
agctcgaagt gacatcacaa agttgaaggt aataaagcca aattaattaa gacattttca   5220
taatgatgtc aagaatgcaa agcaaattgc ataactgcct ttatgcaaaa cattaatata   5280
atataaatta taaagaactg cgctctctgc ttcttatttt cttagcttca tttattagtc   5340
actagctgtt cagaattttc agtatctttt gatattacta agaacctaat cacacaatgt   5400
```

atattcttat gcaggaaaag cagaatgctg agctaaaaga aaggcttttt ccattttcga 5460
gagacaatga gaaaagaaga agaagaagaa gaagaagaag aagaagaaaa gagtaaataa 5520
taaagcccca caggaggcga agttcttgta gctccatgtt atctaagtta ttgatattgt 5580
ttgccctata ttttatttct gtcattgtgt atgttttgtt cagtttcgat ctccttgcaa 5640
aatgcagaga ttatgagatg aataaactaa gttatattat tatacgtgtt aatattctcc 5700
tcctctctct agctagcctt ttgttttctc tttttcttat ttgattttct ttaaatcaat 5760
ccattttagg agagggccag ggagtgatcc agcaaaacat gaagattaga agaaacttcc 5820
ctcttttttt tcctgaaaac aatttaacgt cgagatttat ctctttttgt aatggaatca 5880
tttctacagt tatgacgaat tgtacatcaa cgaaaaatta gtcaaacgac taaaataaat 5940
aaatatcatg tgttattaag aaaattctcc tataagaata ttttaataga tcatatgttt 6000
gtaaaaaaaa ttaattttta ctaacacata tatttactta tcaaaaattt gacaaagtaa 6060
gattaaaata atattcatct aacaaaaaaa aaaccagaaa atgctgaaaa cccggcaaaa 6120
ccgaaccaat ccaaaccgat atagttggtt tggtttgatt ttgatataaa ccgaaccaac 6180
tcggtccatt tgcaccccta atcataatag ctttaatatt tcaagatatt attaagttaa 6240
cgttgtcaat atcctggaaa ttttgcaaaa tgaatcaagc ctatatggct gtaatatgaa 6300
tttaaaagca gctcgatgtg gtggtaatat gtaatttact tgattctaaa aaaatatccc 6360
aagtattaat aatttctgct aggaagaagg ttagctacga tttacagcaa agccagaata 6420
caaagaacca taaagtgatt gaagctcgaa atatacgaag gaacaaatat ttttaaaaaa 6480
atacgcaatg acttggaaca aaagaaagtg atatattttt tgttcttaaa caagcatccc 6540
ctctaaagaa tggcagtttt cctttgcatg taactattat gctcccttcg ttacaaaaat 6600
tttggactac tattgggaac ttcttctgaa aatagtggta ccgagtgtac ttcaagtcag 6660
ttggaaatca ataaaatgat tattttatga atatatttca ttgtgcaagt agatagaaat 6720
tacatatgtt acataacaca cgaaataaac aaaaaaacac aatccaaaac aaacacccca 6780
aacaaaataa cactatatat atcctcgtat gaggagaggc acgttcagtg actcgacgat 6840
tcccgagcaa aaaaagtctc cccgtcacac atatagtggg tgacgcaatt atcttcaaag 6900
taatccttct gttgacttgt cattgataac atccagtctt cgtcaggatt gcaaagaatt 6960
atagaaggga tcccaccttt tattttcttc ttttttccat atttagggtt gacagtgaaa 7020
tcagactggc aacctattaa ttgcttccac aatgggacga acttgaaggg gatgtcgtcg 7080
atgatattat aggtggcgtg ttcatcgtag ttggtgaagt cgatggtccc gttccagtag 7140
ttgtgtcgcc cgagacttct agcccaggtg gtctttccgg tacgagttgg tccgcagatg 7200
tagaggctgg ggtgtctgac cccagtcctt ccctcatcct ggttagatcg gccatccact 7260
caaggtcaga ttgtgcttga tcgtaggaga caggatgtat gaaagtgtag gcatcgatgc 7320
ttacatgata taggtgcgtc tctctccagt tgtgcagatc ttcgtggcag cggagatctg 7380
attctgtgaa gggcgacacg tactgctcag gttgtggagg aaataatttg ttggctgaat 7440
attccagcca ttgaagcttt gttgcccatt catgagggaa ctcttctttg atcatgtcaa 7500
gatactcctc cttagacgtt gcagtctgga taatagttcg ccatcgtgcg tcagatttgc 7560
gaggagacac cttatgatct cggaaatctc ctctggtttt aatatctccg tcctttgata 7620
tgtaatcaag gacttgttta gagtttctag ctggctggat attagggtga tttccttcaa 7680
aatcgaaaaa agaaggatcc ctaatacaag gttttttatc aagctggata agagcatgat 7740
agtgggtagt gccatcttga tgaagctcag aagcaacacc aaggaagaaa ataagaaaag 7800
gtgtgagttt ctcccagaga aactggaata aatcatctct ttgagatgag cacttggggt 7860
aggtaaggaa aacatattta gattggagtc tgaagttctt gctagcagaa ggcatgttgt 7920
tgtgactccg aggggttgcc tcaaactcta tcttataacc ggcgtggagg catggaggca 7980
agggcatttt ggtaatttaa gtagttagtg gaaaatgacg tcatttactt aaagacgaag 8040
tcttgcgaca aggggggccc acgccgaatt ttaatattac cggcgtggcc ccaccttatc 8100
gcgagtgctt tagcacgagc ggtccagatt taaagtagaa aagttcccgc ccactagggt 8160
taaaggtgtt cacactataa aagcatatac gatgtgatgg tatttgatgg agcgtatatt 8220
gtatcaggta tttccgtcgg atacgaatta ttcgtacggc cggaccggtc ccctaggccg 8280
gccaattcga gatcggccgc ggctgagtgg ctccttcaat cgttgcggtt ctgtcagttc 8340
caaacgtaaa acggcttgtc ccgcgtcatc ggcgggggtc ataacgtgac tcccttaatt 8400
ctccgctcat gatcagattg tcgtttcccg ccttcagttt aaactatcag tgtttgacag 8460
gatatattgg cgggtaaacc taagagaaaa gagcgtttat tagaataatc ggatatttaa 8520
aagggcgtga aaaggtttat ccgttcgtcc atttgtatgt gcatgccaac cacagggttc 8580
cccagatctg gcgccggcca gcgagacgag caagattggc cgccgcccga aacgatccga 8640
cagcgcgccc agcacaggtg cgcaggcaaa ttgcaccaac gcatacagcg ccagcagaat 8700
gccatagtgg gcggtgacgt cgttcgagtg aaccagatcg cgcaggaggc ccggcagcac 8760
cggcataatc aggccgatgc cgacagcgtc gagcgcgaca gtgctcagaa ttacgatcag 8820
gggtatgttg ggtttcacgt ctggcctccg gagactgtca tacgcgtaaa aaggccgcgt 8880
tgctggcgtt tttccatagg ctccgccccc ctgacgagca tcacaaaaat cgacgctcaa 8940
gtcagaggtg gcgaaacccg acaggactat aaagatacca ggcgtttccc cctggaagct 9000
ccctcgtgcg ctctcctgtt ccgaccctgc cgcttaccgg atacctgtcc gcctttctcc 9060
cttcgggaag cgtggcgctt tctcatagct cacgctgtag gtatctcagt tcggtgtagg 9120
tcgttcgctc caagctgggc tgtgtgcacg aaccccccgt tcagcccgac cgctgcgcct 9180
tatccggtaa ctatcgtctt gagtccaacc cggtaagaca cgacttatcg ccactggcag 9240
cagccactgg taacaggatt agcagagcga ggtatgtagg cggtgctaca gagttcttga 9300
agtggtggcc taactacggc tacactagaa ggacagtatt tggtatctgc gctctgctga 9360
agccagttac cttcggaaaa agagttggta gctcttgatc cggcaaacaa accaccgctg 9420
gtagcggtgg tttttttgtt tgcaagcagc agattacgcg cagaaaaaaa ggatctcaag 9480
aagatccttt gatcttttct acggggtctg acgctcagtg gaacgaaaac tcacgttaag 9540
ggattttggt catgagatta tcaaaaagga tcttcaccta gatcctttta aattaaaaat 9600
gaagttttaa atcaatctaa agtatatatg agtaaacttg gtctgcagtt gccatgtttt 9660
acggcagtga gagcagagat agcgctgatg tccggcggtg cttttgccgt tacgcaccac 9720
cccgtcagta gctgaacagg agggacagct gatagacaca gaagccactg gagcacctca 9780
aaaacaccat catacactaa atcagtaagt tggcagcatc acccataatt gtggtttcaa 9840
aatcggctcc gtcgatacta tgttatacgc caactttgaa aacaactttg aaaaagctgt 9900
tttctggtat ttaaggtttt agaatgcaag gaacagtgaa ttggagttcg tcttgttata 9960
attagcttct tggggtatct ttaaatactg tagaaaagag gaaggaaata ataaatggct 10020
aaaatgagaa tatcaccgga attgaaaaaa ctgatcgaaa aataccgctg cgtaaaagat 10080
acggaaggaa tgtctcctgc taaggtatat aagctggtgg gagaaaatga aaacctatat 10140
ttaaaaatga cggacagccg gtataaaggg accacctatg atgtggaacg ggaaaaggac 10200
atgatgctat ggctggaagg aaagctgcct gttccaaagg tcctgcactt tgaacggcat 10260
gatggctgga gcaatctgct catgagtgag gccgatggcg tcctttgctc ggaagagtat 10320
gaagatgaac aaagccctga aaagattatc gagctgtatg cggagtgcat caggctcttt 10380
cactccatcg acatatcgga ttgtccctat acgaatagct tagacagccg cttagccgaa 10440
ttggattact tactgaataa cgatctggcc gatgtggatt gcgaaaactg ggaagaagac 10500
actccattta aagatccgcg cgagctgtat gattttttaa agacggaaaa gcccgaagag 10560
gaacttgtct tttcccacgg cgacctggga gacagcaaca tctttgtgaa agatggcaaa 10620
gtaagtggct ttattgatct tgggagaagc ggcagggcgg acaagtggta tgacattgcc 10680
ttctgcgtcc ggtcgatcag ggaggatatc ggggaagaac agtatgtcga gctatttttt 10740
gacttactgg ggatcaagcc tgattgggag aaaataaaat attatatttt actggatgaa 10800
ttgttttagt acctagatgt ggcgcaacga tgccggcgac aagcaggagc gcaccgactt 10860
cttccgcatc aagtgttttg gctctcaggc cgaggcccac ggcaagtatt tgggcaaggg 10920
gtcgctggta ttcgtgcagg gcaagattcg gaataccaag tacgagaagg acggccagac 10980
ggtctacggg accgacttca ttgccgataa ggtggattat ctggacacca aggcaccagg 11040
cgggtcaaat caggaataag ggcacattgc cccggcgtga gtcggggcaa tcccgcaagg 11100
agggtgaatg aatcggacgt ttgaccggaa ggcatacagg caagaactga tcgacgcggg 11160
gttttccgcc gaggatgccg aaaccatcgc aagccgcacc gtcatgcgtg cgccccgcga 11220
aaccttccag tccgtcggct cgatggtcca gcaagctacg gccaagatcg agcgcgacag 11280
cgtgcaactg gctccccctg ccctgcccgc gccatcggcc gccgtggagc gttcgcgtcg 11340
tctcgaacag gaggcggcag gtttggcgaa gtcgatgacc atcgacacgc gaggaactat 11400
gacgaccaag aagcgaaaaa ccgccggcga ggacctggca aaacaggtca gcgaggccaa 11460
gcaggccgcg ttgctgaaac acacgaagca gcagatcaag gaaatgcagc tttccttgtt 11520
cgatattgcg ccgtggccgg acacgatgcg agcgatgcca aacgacacgg cccgctctgc 11580
cctgttcacc acgcgcaaca agaaaatccc gcgcgaggcg ctgcaaaaca aggtcatttt 11640
ccacgtcaac aaggacgtga agatcaccta caccggcgtc gagctgcggg ccgacgatga 11700
cgaactggtg tggcagcagg tgttggagta cgcgaagcgc acccctatcg gcgagccgat 11760
caccttcacg ttctacgagc tttgccagga cctgggctgg tcgatcaatg gccggtatta 11820
cacgaaggcc gaggaatgcc tgtcgcgcct acaggcgacg gcgatgggct tcacgtccga 11880
ccgcgttggg cacctggaat cggtgtcgct gctgcaccgc ttccgcgtcc tggaccgtgg 11940
caagaaaacg tcccgttgcc aggtcctgat cgacgaggaa atcgtcgtgc tgtttgctgg 12000
cgaccactac acgaaattca tatgggagaa gtaccgcaag ctgtcgccga cggcccgacg 12060
gatgttcgac tatttcagct cgcaccggga gccgtacccg ctcaagctgg aaaccttccg 12120
cctcatgtgc ggatcggatt ccacccgcgt gaagaagtgg cgcgagcagg tcggcgaagc 12180
ctgcgaagag ttgcgaggca gcggcctggt ggaacacgcc tgggtcaatg atgacctggt 12240
gcattgcaaa cgctagggcc ttgtggggtc agttccggct gggggttcag cagccagcgc 12300
tttactggca tttcaggaac aagcgggcac tgctcgacgc acttgcttcg ctcagtatcg 12360
ctcgggacgc acggcgcgct ctacgaactg ccgataaaca gaggattaaa attgacaatt 12420
caatggcaag gactgccagc gctgccattt ttggggtgag gccgttcgcg gccgaggggc 12480
gcagcccctg gggggatggg aggcccgcgt tagcgggccg ggagggttcg agaaggggggg 12540 gcaccccccct tcggcgtgcg cggtcacgcg cacagggcgc agccctggtt aaaaacaagg 12600
tttataaata ttggtttaaa agcaggttaa aagacaggtt agcggtggcc gaaaaacggg 12660
cggaaaccct tgcaaatgct ggattttctg cctgtggaca gcccctcaaa tgtcaatagg 12720
tgcgcccctc atctgtcagc actctgcccc tcaagtgtca aggatcgcgc ccctcatctg 12780
tcagtagtcg cgcccctcaa gtgtcaatac cgcagggcac ttatccccag gcttgtccac 12840
atcatctgtg ggaaactcgc gtaaaatcag gcgttttcgc cgatttgcga ggctggccag 12900
ctccacgtcg ccggccgaaa tcgagcctgc ccctcatctg tcaacgccgc gccgggtgag 12960
tcggcccctc aagtgtcaac gtccgcccct catctgtcag tgagggccaa gttttccgcg 13020
aggtatccac aacgccggcg gccgcggtgt ctcgcacacg gcttcgacgg cgtttctggc 13080
gcgtttgcag ggccatagac ggccgccagc ccagcggcga gggcaaccag cccggtgagc 13140
gtcgcaaagg cgctcggtct tgccttgctc gtcgagatct ggggtcgatc agccggggat 13200
gcatcaggcc gacagtcgga acttcgggtc cccgacctgt accattcggt gagcaatgga 13260
taggggagtt gatatcgtca acgttcactt ctaaagaaat agcgccactc agcttcctca 13320
gcggctttat ccagcgattt cctattatgt cggcatagtt ctcaagatcg acagcctgtc 13380
acggttaagc gagaaatgaa taagaaggct gataattcgg atctctgcga gggagatgat 13440
atttgatcac aggcagcaac gctctgtcat cgttacaatc aacatgctac cctccgcgag 13500
atcatccgtg tttcaaaccc ggcagcttag ttgccgttct tccgaatagc atcggtaaca 13560
tgagcaaagt ctgccgcctt acaacggctc tcccgctgac gccgtcccgg actgatgggc 13620
tgcctgtatc gagtggtgat tttgtgccga gctgccggtc ggggagctgt tggctggctg 13680
gtggcaggat atattgtggt gtaaacaaat tgacgcttag acaacttaat aacacattgc 13740
ggacgttttt aatgtactgg ggtggttttt cttttcacca gtgagacggg caacagctga 13800
ttgcccttca ccgcctggcc ctgagagagt tgcagcaagc ggtccacgct ggtttgcccc 13860
agcaggcgaa aatcctgttt gatggtggtt ccgaaatcgg caaaatccct tataaatcaa 13920
aagaatagcc cgagataggg ttgagtgttg ttccagtttg gaacaagagt ccactattaa 13980
agaacgtgga ctccaacgtc aaagggcgaa aaaccgtcta tcagggcgat ggcccactac 14040
gtgaaccatc acccaaatca agttttttgg ggtcgaggtg ccgtaaagca ctaaatcgga 14100
accctaaagg gagcccccga tttagagctt gacggggaaa gccggcgaac gtggcgagaa 14160
aggaagggaa gaaagcgaaa ggagcgggcg ccattcaggc tgcgcaactg ttgggaaggg 14220

<210> SEQ ID NO 25
<211> LENGTH: 14232
<212> TYPE: DNA
<213> ORGANISM: Artificial Sequence
<220> FEATURE:
<223> OTHER INFORMATION: pBYKEMd-ZE3H

<400> SEQUENCE: 25
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360

-continued

```
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
```

```
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat ggctaacaag cacctctcat   3420
tgtctctctt ccttgtgctc cttggtcttt ctgcttctct tgcttctggt aagggcgtgt   3480
catactcctt gtgtaccgct gccttcacat tcaccaagat cccggctgaa acactccacg   3540
gaaccgttac cgtggaggtc caatacgccg gtacagatgg accttgcaag gttccagctc   3600
agatggcggt ggacatgcaa actcttaccc cagttggaag gttgattacc gctaaccccg   3660
ttatcactga aagcactgag aactctaaga tgatgttgga acttgatcca ccattcggtg   3720
actcttacat tgtcattggt gtgggagaga agaagatcac ccaccactgg cacaggagtg   3780
gtagcactag tggtggatca ggaggttctg gtggttctgg aggttcagga tccgatgttc   3840
agcttctcga gtctggaggt ggtcttgtgc aacctggagg ttccttgaga ctctcctgtg   3900
cagcttcagg gtttgacttc agtaggtact ggatgagttg ggttcgtcaa gctcctggga   3960
aaggactaga atggattgga gagatcaatc cagattcaag taccatcaac tatactccat   4020
ctctgaagga tcgcttcacc atttccagag acaatgccaa gaacacgttg tatcttcaga   4080
tgaacagctt gaggactgaa gacacagcct tgtactactg cacaagacag ggctatggct   4140
acaactactg ggtcaaggc accactgtca cagtgtcttc agctagcacc aaaggtccat   4200
cggtctttcc actggcacct tcttccaaga gtacttctgg aggcacagct gcactgggtt   4260
gtcttgtcaa ggactacttt ccagaacctg ttacggtttc gtggaactca ggtgctctga   4320
ccagtggagt gcacaccttt ccagctgttc ttcagtcctc aggattgtat tctcttagca   4380
gtgttgtgac tgttccatcc tcaagcttgg gcactcagac ctacatctgc aatgtgaatc   4440
acaaacccag caacaccaag gttgacaaga aagttgagcc caagtcttgt gacaagactc   4500
atacgtgtcc accgtgccca gcacctgaac ttcttggagg accgtcagtc ttcttgtttc   4560
ctccaaagcc taaggatacc ttgatgatct ccaggactcc tgaagtcaca tgtgtagttg   4620
tggatgtgag ccatgaagat cctgaggtga agttcaactg gtatgtggat ggtgtggaag   4680
tgcacaatgc caagacaaag ccgagagagg aacagtacaa cagcacgtac agggttgtct   4740
cagttctcac tgttctccat caagattggt tgaatggcaa agagtacaag tgcaaggtct   4800
ccaacaaagc cctcccagcc cccattgaga agaccatttc caaagcgaaa gggcaacccc   4860
gtgaaccaca agtgtacaca cttcctccat ctcgcgatga actgaccaag aaccaggtca   4920
gcttgacttg cctggtgaaa ggcttctatc cctctgacat agctgtagag tgggagagca   4980
atgggcaacc ggagaacaac tacaagacta cacctcccgt tctcgattct gacggctcct   5040
tcttcctcta cagcaagctc acagtggaca agagcaggtg gcaacaaggg aatgtcttct   5100
```

catgctccgt gatgcatgag gctcttcaca atcactacac acagaagagt ctctccttgt 5160
ctccgggtaa agagctcgaa gtgacatcac aaagttgaag gtaataaagc caaattaatt 5220
aagacatttt cataatgatg tcaagaatgc aaagcaaatt gcataactgc ctttatgcaa 5280
aacattaata taatataaat tataaagaac tgcgctctct gcttcttatt ttcttagctt 5340
catttattag tcactagctg ttcagaattt tcagtatctt ttgatattac taagaaccta 5400
atcacacaat gtatattctt atgcaggaaa agcagaatgc tgagctaaaa gaaaggcttt 5460
ttccattttc gagagacaat gagaaaagaa gaagaagaag aagaagaaga agaagaagaa 5520
aagagtaaat aataaagccc cacaggaggc gaagttcttg tagctccatg ttatctaagt 5580
tattgatatt gtttgcccta tattttattt ctgtcattgt gtatgttttg ttcagtttcg 5640
atctccttgc aaaatgcaga gattatgaga tgaataaact aagttatatt attatacgtg 5700
ttaatattct cctcctctct ctagctagcc ttttgttttc tctttttctt atttgatttt 5760
ctttaaatca atccatttta ggagagggcc agggagtgat ccagcaaaac atgaagatta 5820
gaagaaactt ccctcttttt tttcctgaaa acaatttaac gtcgagattt atctcttttt 5880
gtaatggaat catttctaca gttatgacga attgtacatc aacgaaaaat tagtcaaacg 5940
actaaaataa ataaatatca tgtgttatta agaaaattct cctataagaa tattttaata 6000
gatcatatgt ttgtaaaaaa aattaatttt tactaacaca tatatttact tatcaaaaat 6060
ttgacaaagt aagattaaaa taatattcat ctaacaaaaa aaaaaccaga aaatgctgaa 6120
aacccggcaa aaccgaacca atccaaaccg atatagttgg tttggtttga ttttgatata 6180
aaccgaacca actcggtcca tttgcacccc taatcataat agctttaata tttcaagata 6240
ttattaagtt aacgttgtca atatcctgga aattttgcaa aatgaatcaa gcctatatgg 6300
ctgtaatatg aatttaaaag cagctcgatg tggtggtaat atgtaattta cttgattcta 6360
aaaaaatatc ccaagtatta ataatttctg ctaggaagaa ggttagctac gatttacagc 6420
aaagccagaa tacaaagaac cataaagtga ttgaagctcg aaatatacga aggaacaaat 6480
atttttaaaa aaatacgcaa tgacttggaa caaaagaaag tgatatattt tttgttctta 6540
aacaagcatc ccctctaaag aatggcagtt ttcctttgca tgtaactatt atgctccctt 6600
cgttacaaaa attttggact actattggga acttcttctg aaaatagtgg taccgagtgt 6660
acttcaagtc agttggaaat caataaaatg attattttat gaatatattt cattgtgcaa 6720
gtagatagaa attacatatg ttacataaca cacgaaataa acaaaaaaac acaatccaaa 6780
acaaacaccc caaacaaaat aacactatat atatcctcgt atgaggagag gcacgttcag 6840
tgactcgacg attcccgagc aaaaaaagtc tccccgtcac acatatagtg ggtgacgcaa 6900
ttatcttcaa agtaatcctt ctgttgactt gtcattgata acatccagtc ttcgtcagga 6960
ttgcaaagaa ttatagaagg gatcccacct tttattttct tctttttcc atatttaggg 7020
ttgacagtga aatcagactg gcaacctatt aattgcttcc acaatgggac gaacttgaag 7080
gggatgtcgt cgatgatatt ataggtggcg tgttcatcgt agttggtgaa gtcgatggtc 7140
ccgttccagt agttgtgtcg cccgagactt ctagcccagg tggtctttcc ggtacgagtt 7200
ggtccgcaga tgtagaggct ggggtgtctg accccagtcc ttccctcatc ctggttagat 7260
cggccatcca ctcaaggtca gattgtgctt gatcgtagga gacaggatgt atgaaagtgt 7320
aggcatcgat gcttacatga tataggtgcg tctctctcca gttgtgcaga tcttcgtggc 7380
agcggagatc tgattctgtg aagggcgaca cgtactgctc aggttgtgga ggaaataatt 7440
tgttggctga atattccagc cattgaagct ttgttgccca ttcatgaggg aactcttctt 7500
tgatcatgtc aagatactcc tccttagacg ttgcagtctg gataatagtt cgccatcgtg 7560
cgtcagattt gcgaggagac accttatgat ctcggaaatc tcctctggtt ttaatatctc 7620
cgtcctttga tatgtaatca aggacttgtt tagagtttct agctggctgg atattagggt 7680
gatttccttc aaaatcgaaa aaagaaggat ccctaataca aggtttttta tcaagctgga 7740
taagagcatg atagtgggta gtgccatctt gatgaagctc agaagcaaca ccaaggaaga 7800
aaataagaaa aggtgtgagt ttctcccaga gaaactggaa taaatcatct ctttgagatg 7860
agcacttggg gtaggtaagg aaaacatatt tagattggag tctgaagttc ttgctagcag 7920
aaggcatgtt gttgtgactc cgaggggttg cctcaaactc tatcttataa ccggcgtgga 7980
ggcatggagg caagggcatt ttggtaattt aagtagttag tggaaaatga cgtcatttac 8040
ttaaagacga agtcttgcga caaggggggc ccacgccgaa ttttaatatt accggcgtgg 8100
ccccacctta tcgcgagtgc tttagcacga gcggtccaga tttaaagtag aaaagttccc 8160
gcccactagg gttaaaggtg ttcacactat aaaagcatat acgatgtgat ggtatttgat 8220
ggagcgtata ttgtatcagg tatttccgtc ggatacgaat tattcgtacg gccggaccgg 8280
tcccctaggc cggccaattc gagatcggcc gcggctgagt ggctccttca atcgttgcgg 8340
ttctgtcagt tccaaacgta aaacggcttg tcccgcgtca tcggcggggg tcataacgtg 8400
actcccttaa ttctccgctc atgatcagat tgtcgtttcc cgccttcagt ttaaactatc 8460
agtgtttgac aggatatatt ggcgggtaaa cctaagagaa aagagcgttt attagaataa 8520
tcggatattt aaaagggcgt gaaaaggttt atccgttcgt ccatttgtat gtgcatgcca 8580
accacagggt tccccagatc tggcgccggc cagcgagacg agcaagattg gccgccgccc 8640
gaaacgatcc gacagcgcgc ccagcacagg tgcgcaggca aattgcacca acgcatacag 8700
cgccagcaga atgccatagt gggcggtgac gtcgttcgag tgaaccagat cgcgcaggag 8760
gcccggcagc accggcataa tcaggccgat gccgacagcg tcgagcgcga cagtgctcag 8820
aattacgatc aggggtatgt tgggtttcac gtctggcctc cggagactgt catacgcgta 8880
aaaaggccgc gttgctggcg tttttccata ggctccgccc ccctgacgag catcacaaaa 8940
atcgacgctc aagtcagagg tggcgaaacc cgacaggact ataaagatac caggcgtttc 9000
cccctggaag ctccctcgtg cgctctcctg ttccgaccct gccgcttacc ggatacctgt 9060
ccgcctttct cccttcggga agcgtggcgc tttctcatag ctcacgctgt aggtatctca 9120
gttcggtgta ggtcgttcgc tccaagctgg gctgtgtgca cgaacccccc gttcagcccg 9180
accgctgcgc cttatccggt aactatcgtc ttgagtccaa cccggtaaga cacgacttat 9240
cgccactggc agcagccact ggtaacagga ttagcagagc gaggtatgta ggcggtgcta 9300
cagagttctt gaagtggtgg cctaactacg gctacactag aaggacagta tttggtatct 9360
gcgctctgct gaagccagtt accttcggaa aaagagttgg tagctcttga tccggcaaac 9420
aaaccaccgc tggtagcggt ggtttttttg tttgcaagca gcagattacg cgcagaaaaa 9480
aaggatctca agaagatcct ttgatctttt ctacggggtc tgacgctcag tggaacgaaa 9540
actcacgtta agggattttg gtcatgagat tatcaaaaag gatcttcacc tagatccttt 9600
taaattaaaa atgaagtttt aaatcaatct aaagtatata tgagtaaact tggtctgcag 9660
ttgccatgtt ttacggcagt gagagcagag atagcgctga tgtccggcgg tgcttttgcc 9720
gttacgcacc accccgtcag tagctgaaca ggagggacag ctgatagaca cagaagccac 9780
tggagcacct caaaaacacc atcatacact aaatcagtaa gttggcagca tcacccataa 9840
ttgtggtttc aaaatcggct ccgtcgatac tatgttatac gccaactttg aaaacaactt 9900
tgaaaaagct gttttctggt atttaaggtt ttagaatgca aggaacagtg aattggagtt 9960
cgtcttgtta taattagctt cttggggtat ctttaaatac tgtagaaaag aggaaggaaa 10020
taataaatgg ctaaaatgag aatatcaccg gaattgaaaa aactgatcga aaaataccgc 10080
tgcgtaaaag atacggaagg aatgtctcct gctaaggtat ataagctggt gggagaaaat 10140
gaaaacctat atttaaaaat gacggacagc cggtataaag ggaccaccta tgatgtggaa 10200
cgggaaaagg acatgatgct atggctggaa ggaaagctgc ctgttccaaa ggtcctgcac 10260
tttgaacggc atgatggctg gagcaatctg ctcatgagtg aggccgatgg cgtcctttgc 10320
tcggaagagt atgaagatga acaaagccct gaaaagatta tcgagctgta tgcggagtgc 10380
atcaggctct ttcactccat cgacatatcg gattgtccct atacgaatag cttagacagc 10440
cgcttagccg aattggatta cttactgaat aacgatctgg ccgatgtgga ttgcgaaaac 10500
tgggaagaag acactccatt taaagatccg cgcgagctgt atgatttttt aaagacggaa 10560
aagcccgaag aggaacttgt cttttcccac ggcgacctgg gagacagcaa catctttgtg 10620
aaagatggca aagtaagtgg ctttattgat cttgggagaa gcggcagggc ggacaagtgg 10680
tatgacattg ccttctgcgt ccggtcgatc agggaggata tcggggaaga acagtatgtc 10740
gagctatttt ttgacttact ggggatcaag cctgattggg agaaaataaa atattatatt 10800
ttactggatg aattgtttta gtacctagat gtggcgcaac gatgccggcg acaagcagga 10860
gcgcaccgac ttcttccgca tcaagtgttt tggctctcag gccgaggccc acggcaagta 10920
tttgggcaag gggtcgctgg tattcgtgca gggcaagatt cggaatacca agtacgagaa 10980
ggacggccag acggtctacg ggaccgactt cattgccgat aaggtggatt atctggacac 11040
caaggcacca ggcgggtcaa atcaggaata agggcacatt gccccggcgt gagtcggggc 11100
aatcccgcaa ggagggtgaa tgaatcggac gtttgaccgg aaggcataca ggcaagaact 11160
gatcgacgcg gggttttccg ccgaggatgc cgaaaccatc gcaagccgca ccgtcatgcg 11220
tgcgccccgc gaaaccttcc agtccgtcgg ctcgatggtc cagcaagcta cggccaagat 11280
cgagcgcgac agcgtgcaac tggctccccc tgccctgccc gcgccatcgg ccgccgtgga 11340
gcgttcgcgt cgtctcgaac aggaggcggc aggtttggcg aagtcgatga ccatcgacac 11400
gcgaggaact atgacgacca agaagcgaaa aaccgccggc gaggacctgg caaaacaggt 11460
cagcgaggcc aagcaggccg cgttgctgaa acacacgaag cagcagatca aggaaatgca 11520
gctttccttg ttcgatattg cgccgtggcc ggacacgatg cgagcgatgc caaacgacac 11580
ggcccgctct gccctgttca ccacgcgcaa caagaaaatc ccgcgcgagg cgctgcaaaa 11640
caaggtcatt ttccacgtca acaaggacgt gaagatcacc tacaccggcg tcgagctgcg 11700
ggccgacgat gacgaactgg tgtggcagca ggtgttggag tacgcgaagc gcacccctat 11760
cggcgagccg atcaccttca cgttctacga gctttgccag gacctgggct ggtcgatcaa 11820
tggccggtat tacacgaagg ccgaggaatg cctgtcgcgc ctacaggcga cggcgatggg 11880
cttcacgtcc gaccgcgttg ggcacctgga atcggtgtcg ctgctgcacc gcttccgcgt 11940
cctggaccgt ggcaagaaaa cgtcccgttg ccaggtcctg atcgacgagg aaatcgtcgt 12000
gctgtttgct ggcgaccact acacgaaatt catatgggag aagtaccgca agctgtcgcc 12060
gacggcccga cggatgttcg actatttcag ctcgcaccgg gagccgtacc cgctcaagct 12120
ggaaaccttc cgcctcatgt gcggatcgga ttccacccgc gtgaagaagt ggcgcgagca 12180
ggtcggcgaa gcctgcgaag agttgcgagg cagcggcctg gtggaacacg cctgggtcaa 12240
tgatgacctg gtgcattgca aacgctaggg ccttgtgggg tcagttccgg ctgggggttc 12300
agcagccagc gctttactgg catttcagga acaagcgggc actgctcgac gcacttgctt 12360
cgctcagtat cgctcgggac gcacggcgcg ctctacgaac tgccgataaa cagaggatta 12420
aaattgacaa ttcaatggca aggactgcca gcgctgccat ttttggggtg aggccgttcg 12480
cggccgaggg gcgcagcccc tgggggatg ggaggcccgc gttagcgggc cgggagggtt 12540
cgagaagggg gggcaccccc cttcggcgtg cgcggtcacg cgcacagggc gcagccctgg 12600
ttaaaaacaa ggtttataaa tattggttta aaagcaggtt aaaagacagg ttagcggtgg 12660
ccgaaaaacg ggcggaaacc cttgcaaatg ctggattttc tgcctgtgga cagcccctca 12720
aatgtcaata ggtgcgcccc tcatctgtca gcactctgcc cctcaagtgt caaggatcgc 12780
gcccctcatc tgtcagtagt cgcgcccctc aagtgtcaat accgcagggc acttatcccc 12840
aggcttgtcc acatcatctg tgggaaactc gcgtaaaatc aggcgttttc gccgatttgc 12900
gaggctggcc agctccacgt cgccggccga aatcgagcct gcccctcatc tgtcaacgcc 12960
gcgccgggtg agtcggcccc tcaagtgtca acgtccgccc ctcatctgtc agtgagggcc 13020
aagttttccg cgaggtatcc acaacgccgg cggccgcggt gtctcgcaca cggcttcgac 13080
ggcgtttctg gcgcgtttgc agggccatag acggccgcca gcccagcggc gagggcaacc 13140
agcccggtga gcgtcgcaaa ggcgctcggt cttgccttgc tcgtcgagat ctggggtcga 13200
tcagccgggg atgcatcagg ccgacagtcg gaacttcggg tccccgacct gtaccattcg 13260
gtgagcaatg gataggggag ttgatatcgt caacgttcac ttctaaagaa atagcgccac 13320
tcagcttcct cagcggcttt atccagcgat ttcctattat gtcggcatag ttctcaagat 13380
cgacagcctg tcacggttaa gcgagaaatg aataagaagg ctgataattc ggatctctgc 13440
gagggagatg atatttgatc acaggcagca acgctctgtc atcgttacaa tcaacatgct 13500
accctccgcg agatcatccg tgtttcaaac ccggcagctt agttgccgtt cttccgaata 13560
gcatcggtaa catgagcaaa gtctgccgcc ttacaacggc tctcccgctg acgccgtccc 13620
ggactgatgg gctgcctgta tcgagtggtg attttgtgcc gagctgccgg tcggggagct 13680
gttggctggc tggtggcagg atatattgtg gtgtaaacaa attgacgctt agacaactta 13740
ataacacatt gcggacgttt ttaatgtact ggggtggttt ttcttttcac cagtgagacg 13800
ggcaacagct gattgccctt caccgcctgg ccctgagaga gttgcagcaa gcggtccacg 13860
ctggtttgcc ccagcaggcg aaaatcctgt ttgatggtgg ttccgaaatc ggcaaaatcc 13920
cttataaatc aaaagaatag cccgagatag ggttgagtgt tgttccagtt tggaacaaga 13980
gtccactatt aaagaacgtg gactccaacg tcaaagggcg aaaaaccgtc tatcagggcg 14040
atggcccact acgtgaacca tcacccaaat caagtttttt ggggtcgagg tgccgtaaag 14100
cactaaatcg gaaccctaaa gggagccccc gatttagagc ttgacgggga aagccggcga 14160
acgtggcgag aaaggaaggg aagaaagcga aaggagcggg cgccattcag gctgcgcaac 14220
tgttgggaag gg 14232

<210> SEQ ID NO 26
<211> LENGTH: 14235
<212> TYPE: DNA
<213> ORGANISM: Artificial Sequence
<220> FEATURE:
<223> OTHER INFORMATION: pBYKEMd-ZE3Hx

<400> SEQUENCE: 26

-continued

```
cgatcggtcg attcatagaa gattagattt ttcatagtat ttttttaaag taaaccttta     60
actacggtta ggacactttt aagttaaatt taatttgaac ccttaaatta atttttaaaa    120
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
```

tcttgcgaca aggggggccc acgccgaatt ttaatattac cggcgtggcc ccaccttatc 2400
gcgagtgctt tagcacgagc ggtccagatt taaagtagaa aagttcccgc ccactagggt 2460
taaaggtgtt cacactataa aagcatatac gatgtgatgg tatttgataa agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat ggctaacaag cacctctcat 3420
tgtctctctt ccttgtgctc cttggtcttt ctgcttctct tgcttctggt aagggcgtgt 3480
catactcctt gtgtaccgct gccttcacat tcaccaagat cccggctgaa acactccacg 3540
gaaccgttac cgtggaggtc caatacgccg gtacagatgg accttgcaag gttccagctc 3600
agatggcggt ggacatgcaa actcttaccc cagttggaag gttgattacc gctaaccccg 3660
ttatcactga aagcactgag aactctaaga tgatgttgga acttgatcca ccattcggtg 3720
actcttacat tgtcattggt gtgggagaga agaagatcac ccaccactgg cacaggagtg 3780
gtagcactag tggtggatca ggaggttctg gtggttctgg aggttcagga tccgatgttc 3840
agcttcttga gtctggaggt ggtcttgtgc aacctggagg ttccttgaga ctctcctgtg 3900
cagcttcagg gtttgacttc agtaggtact ggatgagttg ggttcgtcaa gctcctggga 3960
aaggactaga atggattgga gagatcaatc cagattcaag taccatcaac tatactccat 4020
ctctgaagga tcgcttcacc atttccagag acaatgccaa gaacacgttg tatcttcaga 4080
tgaacagctt gaggactgaa gacacagcct tgtactactg cacaagacag ggctatggct 4140
acaactactg ggtcaaggc accactgtca cagtgtcttc agctagcacc aaaggtccat 4200
cggtctttcc actggcacct tcttccaaga gtacttctgg aggcacagct gcactgggtt 4260
gtcttgtcaa ggactacttt ccagaacctg ttacggtttc gtggaactca ggtgctctga 4320
ccagtggagt gcacaccttt ccagctgttc ttcagtcctc aggattgtat tctcttagca 4380
gtgttgtgac tgttccatcc tcaagcttgg gcactcagac ctacatctgc aatgtgaatc 4440
acaaacccag caacaccaag gttgacaaga aagttgagcc caagtcttgt gacaagactc 4500
atacgtgtcc accgtgccca gcacctgaac ttcttggagg accgtcagtc ttcttgtttc 4560
ctccaaagcc taaggatacc ttgatgatct ccaggactcc tgaagtcaca tgtgtagttg 4620
tggatgtgag ccatgaagat cctgaggtga agttcaactg gtatgtggat ggtgtggaag 4680
tgcacaatgc caagacaaag ccgagagagg aacagtacaa cagcacgtac agggttgtct 4740

```
cagttctcac tgttctccat caagattggt tgaatggcaa agagtacaag tgcaaggtct   4800
ccaacaaagc cctcccagct cctattgaga agaccatctc taaagccaag ggtcaaccgc   4860
gtcgtccaca agtgtacaca cttcctccat ctcgcgacga actcaccaag aatcaagtca   4920
gccttacttg tctcgttaag ggcttctatc cctccgacat cgctgttgag tgggagtcaa   4980
acggacaacc ggagaacaat tacaagacta cacctccagt tttggattcc gatggctcct   5040
tcttcctcta cagcaagctc acagtggaca aatctaggtg gcaacaaggc aacgtcttct   5100
catgctccgt gatgcatgga gcccttcaca atcactacac acagaagtac ctctccttgt   5160
ctccgggaaa gtgagagctc gaagtgacat cacaaagttg aaggtaataa agccaaatta   5220
attaagacat tttcataatg atgtcaagaa tgcaaagcaa attgcataac tgcctttatg   5280
caaaacatta atataatata aattataaag aactgcgctc tctgcttctt attttcttag   5340
cttcatttat tagtcactag ctgttcagaa ttttcagtat cttttgatat tactaagaac   5400
ctaatcacac aatgtatatt cttatgcagg aaaagcagaa tgctgagcta aaagaaaggc   5460
tttttccatt ttcgagagac aatgagaaaa gaagaagaag aagaagaaga agaagaagaa   5520
gaaaagagta aataataaag ccccacagga ggcgaagttc ttgtagctcc atgttatcta   5580
agttattgat attgtttgcc ctatatttta tttctgtcat tgtgtatgtt ttgttcagtt   5640
tcgatctcct tgcaaaatgc agagattatg agatgaataa actaagttat attattatac   5700
gtgttaatat tctcctcctc tctctagcta gccttttgtt ttctcttttt cttatttgat   5760
tttctttaaa tcaatccatt ttaggagagg gccagggagt gatccagcaa aacatgaaga   5820
ttagaagaaa cttccctctt ttttttcctg aaaacaattt aacgtcgaga tttatctctt   5880
tttgtaatgg aatcatttct acagttatga cgaattgtac atcaacgaaa aattagtcaa   5940
acgactaaaa taaataaata tcatgtgtta ttaagaaaat tctcctataa gaatatttta   6000
atagatcata tgtttgtaaa aaaaattaat ttttactaac acatatattt acttatcaaa   6060
aatttgacaa agtaagatta aaataatatt catctaacaa aaaaaaaacc agaaaatgct   6120
gaaaacccgg caaaaccgaa ccaatccaaa ccgatatagt tggtttggtt tgattttgat   6180
ataaaccgaa ccaactcggt ccatttgcac ccctaatcat aatagcttta atatttcaag   6240
atattattaa gttaacgttg tcaatatcct ggaaattttg caaaatgaat caagcctata   6300
tggctgtaat atgaatttaa aagcagctcg atgtggtggt aatatgtaat ttacttgatt   6360
ctaaaaaaat atcccaagta ttaataattt ctgctaggaa gaaggttagc tacgatttac   6420
agcaaagcca gaatacaaag aaccataaag tgattgaagc tcgaaatata cgaaggaaca   6480
aatattttta aaaaaatacg caatgacttg gaacaaaaga aagtgatata tttttgttc    6540
ttaaacaagc atcccctcta aagaatggca gttttccttt gcatgtaact attatgctcc   6600
cttcgttaca aaaattttgg actactattg ggaacttctt ctgaaaatag tggtaccgag   6660
tgtacttcaa gtcagttgga aatcaataaa atgattattt tatgaatata tttcattgtg   6720
caagtagata gaaattacat atgttacata acacacgaaa taaacaaaaa aacacaatcc   6780
aaaacaaaca ccccaaacaa aataacacta tatatatcct cgtatgagga gaggcacgtt   6840
cagtgactcg acgattcccg agcaaaaaaa gtctccccgt cacacatata gtgggtgacg   6900
caattatctt caaagtaatc cttctgttga cttgtcattg ataacatcca gtcttcgtca   6960
ggattgcaaa gaattataga agggatccca ccttttattt tcttcttttt tccatattta   7020
gggttgacag tgaaatcaga ctggcaacct attaattgct tccacaatgg gacgaacttg   7080
```

aaggggatgt cgtcgatgat attataggtg gcgtgttcat cgtagttggt gaagtcgatg 7140
gtcccgttcc agtagttgtg tcgcccgaga cttctagccc aggtggtctt tccggtacga 7200
gttggtccgc agatgtagag gctggggtgt ctgaccccag tccttccctc atcctggtta 7260
gatcggccat ccactcaagg tcagattgtg cttgatcgta ggagacagga tgtatgaaag 7320
tgtaggcatc gatgcttaca tgatataggt gcgtctctct ccagttgtgc agatcttcgt 7380
ggcagcggag atctgattct gtgaagggcg acacgtactg ctcaggttgt ggaggaaata 7440
atttgttggc tgaatattcc agccattgaa gctttgttgc ccattcatga gggaactctt 7500
ctttgatcat gtcaagatac tcctccttag acgttgcagt ctggataata gttcgccatc 7560
gtgcgtcaga tttgcgagga gacaccttat gatctcggaa atctcctctg gttttaatat 7620
ctccgtcctt tgatatgtaa tcaaggactt gtttagagtt tctagctggc tggatattag 7680
ggtgatttcc ttcaaaatcg aaaaaagaag gatccctaat acaaggtttt ttatcaagct 7740
ggataagagc atgatagtgg gtagtgccat cttgatgaag ctcagaagca acaccaagga 7800
agaaaataag aaaaggtgtg agtttctccc agagaaactg gaataaatca tctctttgag 7860
atgagcactt ggggtaggta aggaaaacat atttagattg gagtctgaag ttcttgctag 7920
cagaaggcat gttgttgtga ctccgagggg ttgcctcaaa ctctatctta taaccggcgt 7980
ggaggcatgg aggcaagggc attttggtaa tttaagtagt tagtggaaaa tgacgtcatt 8040
tacttaaaga cgaagtcttg cgacaagggg ggcccacgcc gaattttaat attaccggcg 8100
tggccccacc ttatcgcgag tgctttagca cgagcggtcc agatttaaag tagaaaagtt 8160
cccgcccact agggttaaag gtgttcacac tataaaagca tatacgatgt gatggtattt 8220
gatggagcgt atattgtatc aggtatttcc gtcggatacg aattattcgt acggccggac 8280
cggtccccta ggccggccaa ttcgagatcg gccgcggctg agtggctcct tcaatcgttg 8340
cggttctgtc agttccaaac gtaaaacggc ttgtcccgcg tcatcggcgg gggtcataac 8400
gtgactccct taattctccg ctcatgatca gattgtcgtt tcccgccttc agtttaaact 8460
atcagtgttt gacaggatat attggcgggt aaacctaaga gaaaagagcg tttattagaa 8520
taatcggata tttaaaaggg cgtgaaaagg tttatccgtt cgtccatttg tatgtgcatg 8580
ccaaccacag ggttccccag atctggcgcc ggccagcgag acgagcaaga ttggccgccg 8640
cccgaaacga tccgacagcg cgcccagcac aggtgcgcag gcaaattgca ccaacgcata 8700
cagcgccagc agaatgccat agtgggcggt gacgtcgttc gagtgaacca gatcgcgcag 8760
gaggcccggc agcaccggca taatcaggcc gatgccgaca gcgtcgagcg cgacagtgct 8820
cagaattacg atcaggggta tgttgggttt cacgtctggc ctccggagac tgtcatacgc 8880
gtaaaaaggc cgcgttgctg gcgtttttcc ataggctccg ccccccctgac gagcatcaca 8940 aaaatcgacg ctcaagtcag aggtggcgaa acccgacagg actataaaga taccaggcgt 9000
ttccccctgg aagctccctc gtgcgctctc ctgttccgac cctgccgctt accggatacc 9060
tgtccgcctt tctcccttcg ggaagcgtgg cgctttctca tagctcacgc tgtaggtatc 9120
tcagttcggt gtaggtcgtt cgctccaagc tgggctgtgt gcacgaaccc cccgttcagc 9180
ccgaccgctg cgccttatcc ggtaactatc gtcttgagtc caacccggta agacacgact 9240
tatcgccact ggcagcagcc actggtaaca ggattagcag agcgaggtat gtaggcggtg 9300
ctacagagtt cttgaagtgg tggcctaact acggctacac tagaaggaca gtatttggta 9360
tctgcgctct gctgaagcca gttaccttcg gaaaaagagt tggtagctct tgatccggca 9420
aacaaaccac cgctggtagc ggtggttttt ttgtttgcaa gcagcagatt acgcgcagaa 9480

```
aaaaaggatc tcaagaagat cctttgatct tttctacggg gtctgacgct cagtggaacg   9540
aaaactcacg ttaagggatt ttggtcatga gattatcaaa aaggatcttc acctagatcc   9600
ttttaaatta aaaatgaagt tttaaatcaa tctaaagtat atatgagtaa acttggtctg   9660
cagttgccat gttttacggc agtgagagca gagatagcgc tgatgtccgg cggtgctttt   9720
gccgttacgc accaccccgt cagtagctga acaggaggga cagctgatag acacagaagc   9780
cactggagca cctcaaaaac accatcatac actaaatcag taagttggca gcatcaccca   9840
taattgtggt ttcaaaatcg gctccgtcga tactatgtta tacgccaact ttgaaaacaa   9900
ctttgaaaaa gctgttttct ggtatttaag gttttagaat gcaaggaaca gtgaattgga   9960
gttcgtcttg ttataattag cttcttgggg tatctttaaa tactgtagaa aagaggaagg  10020
aaataataaa tggctaaaat gagaatatca ccggaattga aaaaactgat cgaaaaatac  10080
cgctgcgtaa aagatacgga aggaatgtct cctgctaagg tatataagct ggtgggagaa  10140
aatgaaaacc tatatttaaa aatgacggac agccggtata aagggaccac ctatgatgtg  10200
gaacgggaaa aggacatgat gctatggctg gaaggaaagc tgcctgttcc aaaggtcctg  10260
cactttgaac ggcatgatgg ctggagcaat ctgctcatga gtgaggccga tggcgtcctt  10320
tgctcggaag agtatgaaga tgaacaaagc cctgaaaaga ttatcgagct gtatgcggag  10380
tgcatcaggc tctttcactc catcgacata tcggattgtc cctatacgaa tagcttagac  10440
agccgcttag ccgaattgga ttacttactg aataacgatc tggccgatgt ggattgcgaa  10500
aactgggaag aagacactcc atttaaagat ccgcgcgagc tgtatgattt tttaaagacg  10560
gaaaagcccg aagaggaact tgtcttttcc cacggcgacc tgggagacag caacatcttt  10620
gtgaaagatg gcaaagtaag tggctttatt gatcttggga gaagcggcag ggcggacaag  10680
tggtatgaca ttgccttctg cgtccggtcg atcagggagg atatcgggga agaacagtat  10740
gtcgagctat tttttgactt actggggatc aagcctgatt gggagaaaat aaaatattat  10800
attttactgg atgaattgtt ttagtaccta gatgtggcgc aacgatgccg gcgacaagca  10860
ggagcgcacc gacttcttcc gcatcaagtg ttttggctct caggccgagg cccacggcaa  10920
gtatttgggc aaggggtcgc tggtattcgt gcagggcaag attcggaata ccaagtacga  10980
gaaggacggc cagacggtct acgggaccga cttcattgcc gataaggtgg attatctgga  11040
caccaaggca ccaggcgggt caaatcagga ataagggcac attgccccgg cgtgagtcgg  11100
ggcaatcccg caaggagggt gaatgaatcg gacgtttgac cggaaggcat acaggcaaga  11160
actgatcgac gcggggtttt ccgccgagga tgccgaaacc atcgcaagcc gcaccgtcat  11220
gcgtgcgccc cgcgaaacct tccagtccgt cggctcgatg gtccagcaag ctacggccaa  11280
gatcgagcgc gacagcgtgc aactggctcc ccctgccctg cccgcgccat cggccgccgt  11340
ggagcgttcg cgtcgtctcg aacaggaggc ggcaggtttg gcgaagtcga tgaccatcga  11400
cacgcgagga actatgacga ccaagaagcg aaaaaccgcc ggcgaggacc tggcaaaaca  11460
ggtcagcgag gccaagcagg ccgcgttgct gaaacacacg aagcagcaga tcaaggaaat  11520
gcagctttcc ttgttcgata ttgcgccgtg gccggacacg atgcgagcga tgccaaacga  11580
cacggcccgc tctgccctgt tcaccacgcg caacaagaaa atcccgcgcg aggcgctgca  11640
aaacaaggtc attttccacg tcaacaagga cgtgaagatc acctacaccg gcgtcgagct  11700
gcgggccgac gatgacgaac tggtgtggca gcaggtgttg gagtacgcga agcgcacccc  11760
tatcggcgag ccgatcacct tcacgttcta cgagctttgc caggacctgg gctggtcgat  11820
```

caatggccgg tattacacga aggccgagga atgcctgtcg cgcctacagg cgacggcgat 11880
gggcttcacg tccgaccgcg ttgggcacct ggaatcggtg tcgctgctgc accgcttccg 11940
cgtcctggac cgtggcaaga aaacgtcccg ttgccaggtc ctgatcgacg aggaaatcgt 12000
cgtgctgttt gctggcgacc actacacgaa attcatatgg gagaagtacc gcaagctgtc 12060
gccgacggcc cgacggatgt tcgactattt cagctcgcac cgggagccgt acccgctcaa 12120
gctggaaacc ttccgcctca tgtgcggatc ggattccacc cgcgtgaaga agtggcgcga 12180
gcaggtcggc gaagcctgcg aagagttgcg aggcagcggc ctggtggaac acgcctgggt 12240
caatgatgac ctggtgcatt gcaaacgcta gggccttgtg gggtcagttc cggctggggg 12300
ttcagcagcc agcgctttac tggcatttca ggaacaagcg ggcactgctc gacgcacttg 12360
cttcgctcag tatcgctcgg gacgcacggc gcgctctacg aactgccgat aaacagagga 12420
ttaaaattga caattcaatg gcaaggactg ccagcgctgc catttttggg gtgaggccgt 12480
tcgcggccga ggggcgcagc ccctgggggg atgggaggcc cgcgttagcg ggccgggagg 12540
gttcgagaag ggggggcacc ccccttcggc gtgcgcggtc acgcgcacag ggcgcagccc 12600
tggttaaaaa caaggtttat aaatattggt ttaaaagcag gttaaaagac aggttagcgg 12660
tggccgaaaa acgggcggaa acccttgcaa atgctggatt ttctgcctgt ggacagcccc 12720
tcaaatgtca ataggtgcgc ccctcatctg tcagcactct gcccctcaag tgtcaaggat 12780
cgcgcccctc atctgtcagt agtcgcgccc ctcaagtgtc aataccgcag ggcacttatc 12840
cccaggcttg tccacatcat ctgtgggaaa ctcgcgtaaa atcaggcgtt ttcgccgatt 12900
tgcgaggctg gccagctcca cgtcgccggc cgaaatcgag cctgcccctc atctgtcaac 12960
gccgcgccgg gtgagtcggc ccctcaagtg tcaacgtccg cccctcatct gtcagtgagg 13020
gccaagtttt ccgcgaggta tccacaacgc cggcggccgc ggtgtctcgc acacggcttc 13080
gacggcgttt ctggcgcgtt tgcagggcca tagacggccg ccagcccagc ggcgagggca 13140
accagcccgg tgagcgtcgc aaaggcgctc ggtcttgcct tgctcgtcga gatctggggt 13200
cgatcagccg gggatgcatc aggccgacag tcggaacttc gggtccccga cctgtaccat 13260
tcggtgagca atggataggg gagttgatat cgtcaacgtt cacttctaaa gaaatagcgc 13320
cactcagctt cctcagcggc tttatccagc gatttcctat tatgtcggca tagttctcaa 13380
gatcgacagc ctgtcacggt taagcgagaa atgaataaga aggctgataa ttcggatctc 13440
tgcgagggag atgatatttg atcacaggca gcaacgctct gtcatcgtta caatcaacat 13500
gctaccctcc gcgagatcat ccgtgtttca aacccggcag cttagttgcc gttcttccga 13560
atagcatcgg taacatgagc aaagtctgcc gccttacaac ggctctcccg ctgacgccgt 13620
cccggactga tgggctgcct gtatcgagtg gtgattttgt gccgagctgc cggtcgggga 13680
gctgttggct ggctggtggc aggatatatt gtggtgtaaa caaattgacg cttagacaac 13740
ttaataacac attgcggacg tttttaatgt actggggtgg tttttctttt caccagtgag 13800
acgggcaaca gctgattgcc cttcaccgcc tggccctgag agagttgcag caagcggtcc 13860
acgctggttt gccccagcag gcgaaaatcc tgtttgatgg tggttccgaa atcggcaaaa 13920
tcccttataa atcaaaagaa tagcccgaga tagggttgag tgttgttcca gtttggaaca 13980
agagtccact attaaagaac gtggactcca acgtcaaagg gcgaaaaacc gtctatcagg 14040
gcgatggccc actacgtgaa ccatcaccca aatcaagttt tttggggtcg aggtgccgta 14100
aagcactaaa tcggaaccct aaagggagcc cccgatttag agcttgacgg ggaaagccgg 14160
cgaacgtggc gagaaaggaa gggaagaaag cgaaaggagc gggcgccatt caggctgcgc 14220
aactgttggg aaggg 14235

<210> SEQ ID NO 27
<211> LENGTH: 14655
<212> TYPE: DNA
<213> ORGANISM: Artificial Sequence
<220> FEATURE:
<223> OTHER INFORMATION: pBYKEMd-HVLZe

<400> SEQUENCE: 27
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980

-continued

```
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtcaag   3780
gcaccactgt cacagtgtct tcagctacta gtggtggatc aggaggttct ggtggttctg   3840
gaggttcagg atccgatgtt ttgatgactc aaagccctct ctcacttcct gtgactcttg   3900
gacagcccgc atccatatct tgcagatcta gtcagagtat tgttcatagt aacggcaaca   3960
cctacttgga atggtatctg cagaaaccag gccagtctcc aaagcttctg atctacaagg   4020
cttccaatcg tttctctggt gtcccagaca ggtttagtgg cagtggatca gggactgact   4080
tcacattgaa gatcagcaga gttgaggctg aagatgcggg agtgtactat tgtcttcaag   4140
gttcacatgt tccgtcaacg tttggaggtg ggaccaaagt ggagatcaag gctagcacca   4200
aaggtccatc ggtctttcca ctggcacctt cttccaagag tacttctgga ggcacagctg   4260
cactgggttg tcttgtcaag gactactttc cagaacctgt tacggtttcg tggaactcag   4320
gtgctctgac cagtggagtg cacacctttc cagctgttct tcagtcctca ggattgtatt   4380
```

```
ctcttagcag tgttgtgact gttccatcct caagcttggg cactcagacc tacatctgca   4440
atgtgaatca caaacccagc aacaccaagg ttgacaagaa agttgagccc aagtcttgtg   4500
acaagactca tacgtgtcca ccgtgcccag cacctgaact tcttggagga ccgtcagtct   4560
tcttgtttcc tccaaagcct aaggatacct tgatgatctc caggactcct gaagtcacat   4620
gtgtagttgt ggatgtgagc catgaagatc ctgaggtgaa gttcaactgg tatgtggatg   4680
gtgtggaagt gcacaatgcc aagacaaagc cgagagagga acagtacaac agcacgtaca   4740
gggttgtctc agttctcact gttctccatc aagattggtt gaatggcaaa gagtacaagt   4800
gcaaggtctc caacaaagcc ctcccagccc ccattgagaa gaccatttcc aaagcgaaag   4860
ggcaaccccg tgaaccacaa gtgtacacac ttcctccatc tcgcgatgaa ctgaccaaga   4920
accaggtcag cttgacttgc ctggtgaaag gcttctatcc ctctgacata gctgtagagt   4980
gggagagcaa tgggcaaccg gagaacaact acaagactac acctcccgtt ctcgattctg   5040
acggctcctt cttcctctac agcaagctca cagtggacaa gagcaggtgg caacaaggga   5100
atgtcttctc atgctccgtg atgcatgagg ctcttcacaa tcactacaca cagaagagtc   5160
tctccttgtc tccgggtaaa ggaggtggcg gatcaggtgg aggcggttca ggcggaggtg   5220
gatccaaggg cgtgtcatac tccttgtgta ccgctgcctt cacattcacc aagatcccgg   5280
ctgaaacact ccacggaacc gttaccgtgg aggtccaata cgccggtaca gatggacctt   5340
gcaaggttcc agctcagatg gcggtggaca tgcaaactct taccccagtt ggaaggttga   5400
ttaccgctaa ccccgttatc actgaaagca ctgagaactc taagatgatg ttggaacttg   5460
atccaccatt cggtgactct tacattgtca ttggtgtggg agagaagaag atcacccacc   5520
actggcacag gagtggtagc actagtcata acactcctgt ttacaagctg gacatatctg   5580
aggcaactca ataagagctc gaagtgacat cacaaagttg aaggtaataa agccaaatta   5640
attaagacat tttcataatg atgtcaagaa tgcaaagcaa attgcataac tgcctttatg   5700
caaaacatta atataatata aattataaag aactgcgctc tctgcttctt attttcttag   5760
cttcatttat tagtcactag ctgttcagaa ttttcagtat cttttgatat tactaagaac   5820
ctaatcacac aatgtatatt cttatgcagg aaaagcagaa tgctgagcta aaagaaaggc   5880
tttttccatt ttcgagagac aatgagaaaa gaagaagaag aagaagaaga agaagaagaa   5940
gaaaagagta aataataaag ccccacagga ggcgaagttc ttgtagctcc atgttatcta   6000
agttattgat attgtttgcc ctatatttta tttctgtcat tgtgtatgtt ttgttcagtt   6060
tcgatctcct tgcaaaatgc agagattatg agatgaataa actaagttat attattatac   6120
gtgttaatat tctcctcctc tctctagcta gccttttgtt ttctcttttt cttatttgat   6180
tttctttaaa tcaatccatt ttaggagagg gccagggagt gatccagcaa aacatgaaga   6240
ttagaagaaa cttccctctt ttttttcctg aaaacaattt aacgtcgaga tttatctctt   6300
tttgtaatgg aatcatttct acagttatga cgaattgtac atcaacgaaa aattagtcaa   6360
acgactaaaa taaataaata tcatgtgtta ttaagaaaat tctcctataa gaatatttta   6420
atagatcata tgtttgtaaa aaaaattaat ttttactaac acatatattt acttatcaaa   6480
aatttgacaa agtaagatta aaataatatt catctaacaa aaaaaaaacc agaaaatgct   6540
gaaaacccgg caaaaccgaa ccaatccaaa ccgatatagt tggtttggtt tgattttgat   6600
ataaaccgaa ccaactcggt ccatttgcac ccctaatcat aatagcttta atatttcaag   6660
atattattaa gttaacgttg tcaatatcct ggaaattttg caaaatgaat caagcctata   6720
```

```
tggctgtaat atgaatttaa aagcagctcg atgtggtggt aatatgtaat ttacttgatt   6780
ctaaaaaaat atcccaagta ttaataattt ctgctaggaa gaaggttagc tacgatttac   6840
agcaaagcca gaatacaaag aaccataaag tgattgaagc tcgaaatata cgaaggaaca   6900
aatattttta aaaaaatacg caatgacttg gaacaaaaga aagtgatata ttttttgttc   6960
ttaaacaagc atcccctcta aagaatggca gttttccttt gcatgtaact attatgctcc   7020
cttcgttaca aaaattttgg actactattg ggaacttctt ctgaaaatag tggtaccgag   7080
tgtacttcaa gtcagttgga aatcaataaa atgattattt tatgaatata tttcattgtg   7140
caagtagata gaaattacat atgttacata acacacgaaa taaacaaaaa aacacaatcc   7200
aaaacaaaca ccccaaacaa aataacacta tatatatcct cgtatgagga gaggcacgtt   7260
cagtgactcg acgattcccg agcaaaaaaa gtctccccgt cacacatata gtgggtgacg   7320
caattatctt caaagtaatc cttctgttga cttgtcattg ataacatcca gtcttcgtca   7380
ggattgcaaa gaattataga agggatccca ccttttattt tcttcttttt tccatattta   7440
gggttgacag tgaaatcaga ctggcaacct attaattgct tccacaatgg gacgaacttg   7500
aaggggatgt cgtcgatgat attataggtg gcgtgttcat cgtagttggt gaagtcgatg   7560
gtcccgttcc agtagttgtg tcgcccgaga cttctagccc aggtggtctt tccggtacga   7620
gttggtccgc agatgtagag gctggggtgt ctgaccccag tccttccctc atcctggtta   7680
gatcggccat ccactcaagg tcagattgtg cttgatcgta ggagacagga tgtatgaaag   7740
tgtaggcatc gatgcttaca tgatataggt gcgtctctct ccagttgtgc agatcttcgt   7800
ggcagcggag atctgattct gtgaagggcg acacgtactg ctcaggttgt ggaggaaata   7860
atttgttggc tgaatattcc agccattgaa gctttgttgc ccattcatga gggaactctt   7920
ctttgatcat gtcaagatac tcctccttag acgttgcagt ctggataata gttcgccatc   7980
gtgcgtcaga tttgcgagga gacaccttat gatctcggaa atctcctctg gttttaatat   8040
ctccgtcctt tgatatgtaa tcaaggactt gtttagagtt tctagctggc tggatattag   8100
ggtgatttcc ttcaaaatcg aaaaaagaag gatccctaat acaaggtttt ttatcaagct   8160
ggataagagc atgatagtgg gtagtgccat cttgatgaag ctcagaagca acaccaagga   8220
agaaaataag aaaaggtgtg agtttctccc agagaaactg gaataaatca tctctttgag   8280
atgagcactt ggggtaggta aggaaaacat atttagattg gagtctgaag ttcttgctag   8340
cagaaggcat gttgttgtga ctccgagggg ttgcctcaaa ctctatctta taaccggcgt   8400
ggaggcatgg aggcaagggc attttggtaa tttaagtagt tagtggaaaa tgacgtcatt   8460
tacttaaaga cgaagtcttg cgacaagggg ggcccacgcc gaattttaat attaccggcg   8520
tggccccacc ttatcgcgag tgctttagca cgagcggtcc agatttaaag tagaaaagtt   8580
cccgcccact agggttaaag gtgttcacac tataaaagca tatacgatgt gatggtattt   8640
gatggagcgt atattgtatc aggtatttcc gtcggatacg aattattcgt acggccggac   8700
cggtccccta ggccggccaa ttcgagatcg gccgcggctg agtggctcct tcaatcgttg   8760
cggttctgtc agttccaaac gtaaaacggc ttgtcccgcg tcatcggcgg gggtcataac   8820
gtgactccct taattctccg ctcatgatca gattgtcgtt tcccgccttc agtttaaact   8880
atcagtgttt gacaggatat attggcgggt aaacctaaga gaaaagagcg tttattagaa   8940
taatcggata tttaaaaggg cgtgaaaagg tttatccgtt cgtccatttg tatgtgcatg   9000
ccaaccacag ggttccccag atctggcgcc ggccagcgag acgagcaaga ttggccgccg   9060
cccgaaacga tccgacagcg cgcccagcac aggtgcgcag gcaaattgca ccaacgcata   9120
```

```
cagcgccagc agaatgccat agtgggcggt gacgtcgttc gagtgaacca gatcgcgcag   9180
gaggcccggc agcaccggca taatcaggcc gatgccgaca gcgtcgagcg cgacagtgct   9240
cagaattacg atcaggggta tgttgggttt cacgtctggc ctccggagac tgtcatacgc   9300
gtaaaaaggc cgcgttgctg gcgtttttcc ataggctccg ccccctgac gagcatcaca   9360
aaaatcgacg ctcaagtcag aggtggcgaa acccgacagg actataaaga taccaggcgt   9420
ttccccctgg aagctccctc gtgcgctctc ctgttccgac cctgccgctt accggatacc   9480
tgtccgcctt tctcccttcg ggaagcgtgg cgctttctca tagctcacgc tgtaggtatc   9540
tcagttcggt gtaggtcgtt cgctccaagc tgggctgtgt gcacgaaccc cccgttcagc   9600
ccgaccgctg cgccttatcc ggtaactatc gtcttgagtc caacccggta agacacgact   9660
tatcgccact ggcagcagcc actggtaaca ggattagcag agcgaggtat gtaggcggtg   9720
ctacagagtt cttgaagtgg tggcctaact acggctacac tagaaggaca gtatttggta   9780
tctgcgctct gctgaagcca gttaccttcg gaaaaagagt tggtagctct tgatccggca   9840
aacaaaccac cgctggtagc ggtggttttt ttgtttgcaa gcagcagatt acgcgcagaa   9900
aaaaaggatc tcaagaagat cctttgatct tttctacggg gtctgacgct cagtggaacg   9960
aaaactcacg ttaagggatt ttggtcatga gattatcaaa aaggatcttc acctagatcc  10020
ttttaaatta aaaatgaagt tttaaatcaa tctaaagtat atatgagtaa acttggtctg  10080
cagttgccat gttttacggc agtgagagca gagatagcgc tgatgtccgg cggtgctttt  10140
gccgttacgc accaccccgt cagtagctga acaggaggga cagctgatag acacagaagc  10200
cactggagca cctcaaaaac accatcatac actaaatcag taagttggca gcatcaccca  10260
taattgtggt ttcaaaatcg gctccgtcga tactatgtta tacgccaact ttgaaaacaa  10320
ctttgaaaaa gctgttttct ggtatttaag gttttagaat gcaaggaaca gtgaattgga  10380
gttcgtcttg ttataattag cttcttgggg tatctttaaa tactgtagaa aagaggaagg  10440
aaataataaa tggctaaaat gagaatatca ccggaattga aaaaactgat cgaaaaatac  10500
cgctgcgtaa aagatacgga aggaatgtct cctgctaagg tatataagct ggtgggagaa  10560
aatgaaaacc tatatttaaa aatgacggac agccggtata aagggaccac ctatgatgtg  10620
gaacgggaaa aggacatgat gctatggctg gaaggaaagc tgcctgttcc aaaggtcctg  10680
cactttgaac ggcatgatgg ctggagcaat ctgctcatga gtgaggccga tggcgtcctt  10740
tgctcggaag agtatgaaga tgaacaaagc cctgaaaaga ttatcgagct gtatgcggag  10800
tgcatcaggc tctttcactc catcgacata tcggattgtc cctatacgaa tagcttagac  10860
agccgcttag ccgaattgga ttacttactg aataacgatc tggccgatgt ggattgcgaa  10920
aactgggaag aagacactcc atttaaagat ccgcgcgagc tgtatgattt tttaaagacg  10980
gaaaagcccg aagaggaact tgtcttttcc cacggcgacc tgggagacag caacatcttt  11040
gtgaaagatg gcaaagtaag tggctttatt gatcttggga gaagcggcag ggcggacaag  11100
tggtatgaca ttgccttctg cgtccggtcg atcagggagg atatcgggga agaacagtat  11160
gtcgagctat tttttgactt actggggatc aagcctgatt gggagaaaat aaaatattat  11220
attttactgg atgaattgtt ttagtaccta gatgtggcgc aacgatgccg gcgacaagca  11280
ggagcgcacc gacttcttcc gcatcaagtg ttttggctct caggccgagg cccacggcaa  11340
gtatttgggc aaggggtcgc tggtattcgt gcagggcaag attcggaata ccaagtacga  11400
gaaggacggc cagacggtct acgggaccga cttcattgcc gataaggtgg attatctgga  11460
```

-continued

```
caccaaggca ccaggcgggt caaatcagga ataagggcac attgccccgg cgtgagtcgg  11520
ggcaatcccg caaggagggt gaatgaatcg gacgtttgac cggaaggcat acaggcaaga  11580
actgatcgac gcggggtttt ccgccgagga tgccgaaacc atcgcaagcc gcaccgtcat  11640
gcgtgcgccc cgcgaaacct tccagtccgt cggctcgatg gtccagcaag ctacggccaa  11700
gatcgagcgc gacagcgtgc aactggctcc ccctgccctg cccgcgccat cggccgccgt  11760
ggagcgttcg cgtcgtctcg aacaggaggc ggcaggtttg gcgaagtcga tgaccatcga  11820
cacgcgagga actatgacga ccaagaagcg aaaaaccgcc ggcgaggacc tggcaaaaca  11880
ggtcagcgag gccaagcagg ccgcgttgct gaaacacacg aagcagcaga tcaaggaaat  11940
gcagctttcc ttgttcgata ttgcgccgtg gccggacacg atgcgagcga tgccaaacga  12000
cacggcccgc tctgccctgt tcaccacgcg caacaagaaa atcccgcgcg aggcgctgca  12060
aaacaaggtc attttccacg tcaacaagga cgtgaagatc acctacaccg gcgtcgagct  12120
gcgggccgac gatgacgaac tggtgtggca gcaggtgttg gagtacgcga agcgcacccc  12180
tatcggcgag ccgatcacct tcacgttcta cgagctttgc caggacctgg gctggtcgat  12240
caatggccgg tattacacga aggccgagga atgcctgtcg cgcctacagg cgacggcgat  12300
gggcttcacg tccgaccgcg ttgggcacct ggaatcggtg tcgctgctgc accgcttccg  12360
cgtcctggac cgtggcaaga aaacgtcccg ttgccaggtc ctgatcgacg aggaaatcgt  12420
cgtgctgttt gctggcgacc actacacgaa attcatatgg gagaagtacc gcaagctgtc  12480
gccgacggcc cgacggatgt tcgactattt cagctcgcac cgggagccgt acccgctcaa  12540
gctggaaacc ttccgcctca tgtgcggatc ggattccacc cgcgtgaaga agtggcgcga  12600
gcaggtcggc gaagcctgcg aagagttgcg aggcagcggc ctggtggaac acgcctgggt  12660
caatgatgac ctggtgcatt gcaaacgcta gggccttgtg gggtcagttc cggctggggg  12720
ttcagcagcc agcgctttac tggcatttca ggaacaagcg ggcactgctc gacgcacttg  12780
cttcgctcag tatcgctcgg gacgcacggc gcgctctacg aactgccgat aaacagagga  12840
ttaaaattga caattcaatg gcaaggactg ccagcgctgc catttttggg gtgaggccgt  12900
tcgcggccga ggggcgcagc ccctgggggg atgggaggcc cgcgttagcg ggccgggagg  12960
gttcgagaag ggggggcacc ccccttcggc gtgcgcggtc acgcgcacag ggcgcagccc  13020
tggttaaaaa caaggtttat aaatattggt ttaaaagcag gttaaaagac aggttagcgg  13080
tggccgaaaa acgggcggaa acccttgcaa atgctggatt ttctgcctgt ggacagcccc  13140
tcaaatgtca ataggtgcgc ccctcatctg tcagcactct gcccctcaag tgtcaaggat  13200
cgcgcccctc atctgtcagt agtcgcgccc ctcaagtgtc aataccgcag ggcacttatc  13260
cccaggcttg tccacatcat ctgtgggaaa ctcgcgtaaa atcaggcgtt ttcgccgatt  13320
tgcgaggctg gccagctcca cgtcgccggc cgaaatcgag cctgcccctc atctgtcaac  13380
gccgcgccgg gtgagtcggc ccctcaagtg tcaacgtccg cccctcatct gtcagtgagg  13440
gccaagtttt ccgcgaggta tccacaacgc cggcggccgc ggtgtctcgc acacggcttc  13500
gacggcgttt ctggcgcgtt tgcagggcca tagacggccg ccagcccagc ggcgagggca  13560
accagcccgg tgagcgtcgc aaaggcgctc ggtcttgcct tgctcgtcga gatctggggt  13620
cgatcagccg gggatgcatc aggccgacag tcggaacttc gggtccccga cctgtaccat  13680
tcggtgagca atggataggg gagttgatat cgtcaacgtt cacttctaaa gaaatagcgc  13740
cactcagctt cctcagcggc tttatccagc gatttcctat tatgtcggca tagttctcaa  13800
gatcgacagc ctgtcacggt taagcgagaa atgaataaga aggctgataa ttcggatctc  13860
```

tgcgagggag atgatatttg atcacaggca gcaacgctct gtcatcgtta caatcaacat 13920
gctaccctcc gcgagatcat ccgtgtttca aacccggcag cttagttgcc gttcttccga 13980
atagcatcgg taacatgagc aaagtctgcc gccttacaac ggctctcccg ctgacgccgt 14040
cccggactga tgggctgcct gtatcgagtg gtgattttgt gccgagctgc cggtcgggga 14100
gctgttggct ggctggtggc aggatatatt gtggtgtaaa caaattgacg cttagacaac 14160
ttaataacac attgcggacg tttttaatgt actggggtgg tttttctttt caccagtgag 14220
acgggcaaca gctgattgcc cttcaccgcc tggccctgag agagttgcag caagcggtcc 14280
acgctggttt gccccagcag gcgaaaatcc tgtttgatgg tggttccgaa atcggcaaaa 14340
tcccttataa atcaaaagaa tagcccgaga tagggttgag tgttgttcca gtttggaaca 14400
agagtccact attaaagaac gtggactcca acgtcaaagg gcgaaaaacc gtctatcagg 14460
gcgatggccc actacgtgaa ccatcaccca aatcaagttt tttggggtcg aggtgccgta 14520
aagcactaaa tcggaaccct aaagggagcc cccgatttag agcttgacgg ggaaagccgg 14580
cgaacgtggc gagaaaggaa gggaagaaag cgaaaggagc gggcgccatt caggctgcgc 14640
aactgttggg aaggg 14655

<210> SEQ ID NO 28
<211> LENGTH: 14244
<212> TYPE: DNA
<213> ORGANISM: Artificial Sequence
<220> FEATURE:
<223> OTHER INFORMATION: pBYKEMd2-HVL-Hx

<400> SEQUENCE: 28
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200

-continued ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980
gctgtccata aaaccgccca gtctagctat cgccatgtaa gcccactgca agctacctgc 2040
tttctctttg cgcttgcgtt ttcccttgtc cagatagccc agtagctgac attcatccgg 2100
ggtcagcacc gtttctgcgg actggctttc tacgtgttcc gcttccttta gcagcccttg 2160
cgccctgagt gcttgcggca gcgtgaagct ggcgcgccgc tctagcagaa ggcatgttgt 2220
tgtgactccg aggggttgcc tcaaactcta tcttataacc ggcgtggagg catggaggca 2280
agggcatttt ggtaatttaa gtagttagtg gaaaatgacg tcatttactt aaagacgaag 2340
tcttgcgaca agggggggcc acgccgaatt ttaatattac cggcgtggcc ccaccttatc 2400
gcgagtgctt tagcacgagc ggtccagatt taaagtagaa aagttcccgc ccactagggt 2460
taaaggtgtt cacactataa aagcatatac gatgtgatgg tatttgataa agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat gggatggtct tgcatcatac 3420
tctttcttgt tgcaactgct acaggtgtcc actctgatgt tcagcttctc gagtctggag 3480
gtggtcttgt gcaacctgga ggttccttga gactctcctg tgcagcttca gggtttgact 3540
tcagtaggta ctggatgagt tgggttcgtc aagctcctgg gaaaggacta gaatggattg 3600
gagagatcaa tccagattca agtaccatca actatactcc atctctgaag gatcgcttca 3660
ccatttccag agacaatgcc aagaacacgt tgtatcttca gatgaacagc ttgaggactg 3720
aagacacagc cttgtactac tgcacaagac agggctatgg ctacaactac tggggtcaag 3780
gcaccactgt cacagtgtct tcagctacta gtggtggatc aggaggttct ggtggttctg 3840
gaggttcagg atccgatgtt ttgatgactc aaagccctct ctcacttcct gtgactcttg 3900
gacagcccgc atccatatct tgcagatcta gtcagagtat tgttcatagt aacggcaaca 3960
cctacttgga atggtatctg cagaaaccag gccagtctcc aaagcttctg atctacaagg 4020
cttccaatcg tttctctggt gtcccagaca ggtttagtgg cagtggatca gggactgact 4080
tcacattgaa gatcagcaga gttgaggctg aagatgcggg agtgtactat tgtcttcaag 4140
gttcacatgt tccgtcaacg tttggaggtg ggaccaaagt ggagatcaag gctagcacca 4200
aaggtccatc ggtctttcca ctggcacctt cttccaagag tacttctgga ggcacagctg 4260
cactgggttg tcttgtcaag gactactttc cagaacctgt tacggtttcg tggaactcag 4320
gtgctctgac cagtggagtg cacacctttc cagctgttct tcagtcctca ggattgtatt 4380
ctcttagcag tgttgtgact gttccatcct caagcttggg cactcagacc tacatctgca 4440
atgtgaatca caaacccagc aacaccaagg ttgacaagaa agttgagccc aagtcttgtg 4500
acaagactca tacgtgtcca ccgtgcccag cacctgaact tcttggagga ccgtcagtct 4560
tcttgtttcc tccaaagcct aaggatacct tgatgatctc caggactcct gaagtcacat 4620
gtgtagttgt ggatgtgagc catgaagatc ctgaggtgaa gttcaactgg tatgtggatg 4680
gtgtggaagt gcacaatgcc aagacaaagc cgagagagga acagtacaac agcacgtaca 4740
gggttgtctc agttctcact gttctccatc aagattggtt gaatggcaaa gagtacaagt 4800
gcaaggtctc caacaaagcc ctcccagctc ctattgagaa gaccatctct aaagccaagg 4860
gtcaaccgcg tcgtccacaa gtgtacacac ttcctccatc tcgcgacgaa ctcaccaaga 4920
atcaagtcag ccttacttgt ctcgttaagg gcttctatcc ctccgacatc gctgttgagt 4980
gggagtcaaa cggacaaccg gagaacaatt acaagactac acctccagtt ttggattccg 5040
atggctcctt cttcctctac agcaagctca cagtggacaa atctaggtgg caacaaggca 5100
acgtcttctc atgctccgtg atgcatggag cccttcacaa tcactacaca cagaagtacc 5160
tctccttgtc tccgggaaag tgagagctcg aagtgacatc acaaagttga aggtaataaa 5220
gccaaattaa ttaagacatt ttcataatga tgtcaagaat gcaaagcaaa ttgcataact 5280
gcctttatgc aaaacattaa tataatataa attataaaga actgcgctct ctgcttctta 5340
ttttcttagc ttcatttatt agtcactagc tgttcagaat tttcagtatc ttttgatatt 5400
actaagaacc taatcacaca atgtatattc ttatgcagga aaagcagaat gctgagctaa 5460
aagaaaggct tttttccattt tcgagagaca atgagaaaag aagaagaaga agaagaagaa 5520
gaagaagaag aaaagagtaa ataataaagc cccacaggag gcgaagttct tgtagctcca 5580
tgttatctaa gttattgata ttgtttgccc tatattttat ttctgtcatt gtgtatgttt 5640
tgttcagttt cgatctcctt gcaaaatgca gagattatga gatgaataaa ctaagttata 5700
ttattatacg tgttaatatt ctcctcctct ctctagctag ccttttgttt tctctttttc 5760
ttatttgatt ttctttaaat caatccattt taggagaggg ccagggagtg atccagcaaa 5820
acatgaagat tagaagaaac ttccctcttt tttttcctga aaacaattta acgtcgagat 5880
ttatctcttt ttgtaatgga atcatttcta cagttatgac gaattgtaca tcaacgaaaa 5940
attagtcaaa cgactaaaat aaataaatat catgtgttat taagaaaatt ctcctataag 6000
aatattttaa tagatcatat gtttgtaaaa aaaattaatt tttactaaca catatattta 6060
cttatcaaaa atttgacaaa gtaagattaa aataatattc atctaacaaa aaaaaaacca 6120
gaaaatgctg aaaacccggc aaaaccgaac caatccaaac cgatatagtt ggtttggttt 6180
gattttgata taaaccgaac caactcggtc catttgcacc cctaatcata atagctttaa 6240
tatttcaaga tattattaag ttaacgttgt caatatcctg gaaattttgc aaaatgaatc 6300
aagcctatat ggctgtaata tgaatttaaa agcagctcga tgtggtggta atatgtaatt 6360
tacttgattc taaaaaaata tcccaagtat taataatttc tgctaggaag aaggttagct 6420
acgatttaca gcaaagccag aatacaaaga accataaagt gattgaagct cgaaatatac 6480
gaaggaacaa atatttttaa aaaaatacgc aatgacttgg aacaaaagaa agtgatatat 6540
tttttgttct taaacaagca tcccctctaa agaatggcag ttttcctttg catgtaacta 6600
ttatgctccc ttcgttacaa aaattttgga ctactattgg gaacttcttc tgaaaatagt 6660
ggtaccgagt gtacttcaag tcagttggaa atcaataaaa tgattatttt atgaatatat 6720
ttcattgtgc aagtagatag aaattacata tgttacataa cacacgaaat aaacaaaaaa 6780
acacaatcca aaacaaacac cccaaacaaa ataacactat atatatcctc gtatgaggag 6840
aggcacgttc agtgactcga cgattcccga gcaaaaaaag tctccccgtc acacatatag 6900
tgggtgacgc aattatcttc aaagtaatcc ttctgttgac ttgtcattga taacatccag 6960
tcttcgtcag gattgcaaag aattatagaa gggatcccac cttttatttt cttctttttt 7020
ccatatttag ggttgacagt gaaatcagac tggcaaccta ttaattgctt ccacaatggg 7080
acgaacttga aggggatgtc gtcgatgata ttataggtgg cgtgttcatc gtagttggtg 7140
aagtcgatgg tcccgttcca gtagttgtgt cgcccgagac ttctagccca ggtggtcttt 7200
ccggtacgag ttggtccgca gatgtagagg ctggggtgtc tgaccccagt ccttccctca 7260
tcctggttag atcggccatc cactcaaggt cagattgtgc ttgatcgtag gagacaggat 7320
gtatgaaagt gtaggcatcg atgcttacat gatataggtg cgtctctctc cagttgtgca 7380
gatcttcgtg gcagcggaga tctgattctg tgaagggcga cacgtactgc tcaggttgtg 7440
gaggaaataa tttgttggct gaatattcca gccattgaag ctttgttgcc cattcatgag 7500
ggaactcttc tttgatcatg tcaagatact cctccttaga cgttgcagtc tggataatag 7560
ttcgccatcg tgcgtcagat ttgcgaggag acaccttatg atctcggaaa tctcctctgg 7620
ttttaatatc tccgtccttt gatatgtaat caaggacttg tttagagttt ctagctggct 7680
ggatattagg gtgatttcct tcaaaatcga aaaaagaagg atccctaata caaggttttt 7740
tatcaagctg gataagagca tgatagtggg tagtgccatc ttgatgaagc tcagaagcaa 7800
caccaaggaa gaaaataaga aaaggtgtga gtttctccca gagaaactgg aataaatcat 7860
ctctttgaga tgagcacttg gggtaggtaa ggaaaacata tttagattgg agtctgaagt 7920
tcttgctagc agaaggcatg ttgttgtgac tccgaggggt tgcctcaaac tctatcttat 7980
aaccggcgtg gaggcatgga ggcaagggca ttttggtaat ttaagtagtt agtggaaaat 8040
gacgtcattt acttaaagac gaagtcttgc gacaaggggg gcccacgccg aattttaata 8100
ttaccggcgt ggccccacct tatcgcgagt gctttagcac gagcggtcca gatttaaagt 8160
agaaaagttc ccgcccacta gggttaaagg tgttcacact ataaaagcat atacgatgtg 8220
atggtatttg atggagcgta tattgtatca ggtatttccg tcggatacga attattcgta 8280
cggccggacc ggtcccctag gccggccaat tcgagatcgg ccgcggctga gtggctcctt 8340
caatcgttgc ggttctgtca gttccaaacg taaaacggct tgtcccgcgt catcggcggg 8400
ggtcataacg tgactccctt aattctccgc tcatgatcag attgtcgttt cccgccttca 8460
gtttaaacta tcagtgtttg acaggatata ttggcgggta aacctaagag aaaagagcgt 8520
ttattagaat aatcggatat ttaaaagggc gtgaaaaggt ttatccgttc gtccatttgt 8580
atgtgcatgc caaccacagg gttccccaga tctggcgccg gccagcgaga cgagcaagat 8640
tggccgccgc ccgaaacgat ccgacagcgc gcccagcaca ggtgcgcagg caaattgcac 8700
caacgcatac agcgccagca gaatgccata gtgggcggtg acgtcgttcg agtgaaccag 8760
atcgcgcagg aggcccggca gcaccggcat aatcaggccg atgccgacag cgtcgagcgc 8820
gacagtgctc agaattacga tcaggggtat gttgggtttc acgtctggcc tccggagact 8880
gtcatacgcg taaaaaggcc gcgttgctgg cgtttttcca taggctccgc ccccctgacg 8940
agcatcacaa aaatcgacgc tcaagtcaga ggtggcgaaa cccgacagga ctataaagat 9000
accaggcgtt tccccctgga agctccctcg tgcgctctcc tgttccgacc ctgccgctta 9060
ccggatacct gtccgccttt ctcccttcgg gaagcgtggc gctttctcat agctcacgct 9120
gtaggtatct cagttcggtg taggtcgttc gctccaagct gggctgtgtg cacgaacccc 9180
ccgttcagcc cgaccgctgc gccttatccg gtaactatcg tcttgagtcc aacccggtaa 9240
gacacgactt atcgccactg gcagcagcca ctggtaacag gattagcaga gcgaggtatg 9300
taggcggtgc tacagagttc ttgaagtggt ggcctaacta cggctacact agaaggacag 9360
tatttggtat ctgcgctctg ctgaagccag ttaccttcgg aaaaagagtt ggtagctctt 9420
gatccggcaa acaaaccacc gctggtagcg gtggtttttt tgtttgcaag cagcagatta 9480
cgcgcagaaa aaaaggatct caagaagatc ctttgatctt ttctacgggg tctgacgctc 9540
agtggaacga aaactcacgt taagggattt tggtcatgag attatcaaaa aggatcttca 9600
cctagatcct tttaaattaa aaatgaagtt ttaaatcaat ctaaagtata tatgagtaaa 9660
cttggtctgc agttgccatg ttttacggca gtgagagcag agatagcgct gatgtccggc 9720
ggtgcttttg ccgttacgca ccaccccgtc agtagctgaa caggagggac agctgataga 9780
cacagaagcc actggagcac ctcaaaaaca ccatcataca ctaaatcagt aagttggcag 9840
catcacccat aattgtggtt tcaaaatcgg ctccgtcgat actatgttat acgccaactt 9900
tgaaaacaac tttgaaaaag ctgttttctg gtatttaagg ttttagaatg caaggaacag 9960
tgaattggag ttcgtcttgt tataattagc ttcttggggt atctttaaat actgtagaaa 10020
agaggaagga aataataaat ggctaaaatg agaatatcac cggaattgaa aaaactgatc 10080
gaaaaatacc gctgcgtaaa agatacggaa ggaatgtctc ctgctaaggt atataagctg 10140
gtgggagaaa atgaaaacct atatttaaaa atgacggaca gccggtataa agggaccacc 10200
tatgatgtgg aacgggaaaa ggacatgatg ctatggctgg aaggaaagct gcctgttcca 10260
aaggtcctgc actttgaacg gcatgatggc tggagcaatc tgctcatgag tgaggccgat 10320
ggcgtccttt gctcggaaga gtatgaagat gaacaaagcc ctgaaaagat tatcgagctg 10380
tatgcggagt gcatcaggct ctttcactcc atcgacatat cggattgtcc ctatacgaat 10440
agcttagaca gccgcttagc cgaattggat tacttactga ataacgatct ggccgatgtg 10500
gattgcgaaa actgggaaga agacactcca tttaaagatc cgcgcgagct gtatgatttt 10560
ttaaagacgg aaaagcccga agaggaactt gtcttttccc acggcgacct gggagacagc 10620
aacatctttg tgaaagatgg caaagtaagt ggctttattg atcttgggag aagcggcagg 10680

```
gcggacaagt ggtatgacat tgccttctgc gtccggtcga tcagggagga tatcggggaa  10740
gaacagtatg tcgagctatt ttttgactta ctggggatca agcctgattg ggagaaaata  10800
aaatattata ttttactgga tgaattgttt tagtacctag atgtggcgca acgatgccgg  10860
cgacaagcag gagcgcaccg acttcttccg catcaagtgt tttggctctc aggccgaggc  10920
ccacggcaag tatttgggca aggggtcgct ggtattcgtg cagggcaaga ttcggaatac  10980
caagtacgag aaggacggcc agacggtcta cgggaccgac ttcattgccg ataaggtgga  11040
ttatctggac accaaggcac caggcgggtc aaatcaggaa taagggcaca ttgccccggc  11100
gtgagtcggg gcaatcccgc aaggagggtg aatgaatcgg acgtttgacc ggaaggcata  11160
caggcaagaa ctgatcgacg cggggttttc cgccgaggat gccgaaacca tcgcaagccg  11220
caccgtcatg cgtgcgcccc gcgaaacctt ccagtccgtc ggctcgatgg tccagcaagc  11280
tacggccaag atcgagcgcg acagcgtgca actggctccc cctgccctgc ccgcgccatc  11340
ggccgccgtg gagcgttcgc gtcgtctcga acaggaggcg gcaggtttgg cgaagtcgat  11400
gaccatcgac acgcgaggaa ctatgacgac caagaagcga aaaaccgccg gcgaggacct  11460
ggcaaaacag gtcagcgagg ccaagcaggc cgcgttgctg aaacacacga agcagcagat  11520
caaggaaatg cagctttcct tgttcgatat tgcgccgtgg ccggacacga tgcgagcgat  11580
gccaaacgac acggcccgct ctgccctgtt caccacgcgc aacaagaaaa tcccgcgcga  11640
ggcgctgcaa aacaaggtca ttttccacgt caacaaggac gtgaagatca cctacaccgg  11700
cgtcgagctg cgggccgacg atgacgaact ggtgtggcag caggtgttgg agtacgcgaa  11760
gcgcacccct atcggcgagc cgatcacctt cacgttctac gagctttgcc aggacctggg  11820
ctggtcgatc aatggccggt attacacgaa ggccgaggaa tgcctgtcgc gcctacaggc  11880
gacggcgatg ggcttcacgt ccgaccgcgt tgggcacctg gaatcggtgt cgctgctgca  11940
ccgcttccgc gtcctggacc gtggcaagaa aacgtcccgt tgccaggtcc tgatcgacga  12000
ggaaatcgtc gtgctgtttg ctggcgacca ctacacgaaa ttcatatggg agaagtaccg  12060
caagctgtcg ccgacggccc gacggatgtt cgactatttc agctcgcacc gggagccgta  12120
cccgctcaag ctggaaacct tccgcctcat gtgcggatcg gattccaccc gcgtgaagaa  12180
gtggcgcgag caggtcggcg aagcctgcga agagttgcga ggcagcggcc tggtggaaca  12240
cgcctgggtc aatgatgacc tggtgcattg caaacgctag ggccttgtgg ggtcagttcc  12300
ggctgggggt tcagcagcca gcgctttact ggcatttcag gaacaagcgg gcactgctcg  12360
acgcacttgc ttcgctcagt atcgctcggg acgcacggcg cgctctacga actgccgata  12420
aacagaggat taaaattgac aattcaatgg caaggactgc cagcgctgcc atttttgggg  12480
tgaggccgtt cgcggccgag gggcgcagcc cctgggggga tgggaggccc gcgttagcgg  12540
gccgggaggg ttcgagaagg gggggcaccc cccttcggcg tgcgcggtca cgcgcacagg  12600
gcgcagccct ggttaaaaac aaggtttata aatattggtt taaaagcagg ttaaaagaca  12660
ggttagcggt ggccgaaaaa cgggcggaaa cccttgcaaa tgctggattt tctgcctgtg  12720
gacagcccct caaatgtcaa taggtgcgcc cctcatctgt cagcactctg cccctcaagt  12780
gtcaaggatc gcgcccctca tctgtcagta gtcgcgcccc tcaagtgtca ataccgcagg  12840
gcacttatcc ccaggcttgt ccacatcatc tgtgggaaac tcgcgtaaaa tcaggcgttt  12900
tcgccgattt gcgaggctgg ccagctccac gtcgccggcc gaaatcgagc ctgcccctca  12960
tctgtcaacg ccgcgccggg tgagtcggcc cctcaagtgt caacgtccgc ccctcatctg  13020
tcagtgaggg ccaagttttc cgcgaggtat ccacaacgcc ggcggccgcg gtgtctcgca  13080
```

cacggcttcg acggcgtttc tggcgcgttt gcagggccat agacggccgc cagcccagcg 13140
gcgagggcaa ccagcccggt gagcgtcgca aaggcgctcg gtcttgcctt gctcgtcgag 13200
atctggggtc gatcagccgg ggatgcatca ggccgacagt cggaacttcg ggtccccgac 13260
ctgtaccatt cggtgagcaa tggatagggg agttgatatc gtcaacgttc acttctaaag 13320
aaatagcgcc actcagcttc ctcagcggct ttatccagcg atttcctatt atgtcggcat 13380
agttctcaag atcgacagcc tgtcacggtt aagcgagaaa tgaataagaa ggctgataat 13440
tcggatctct gcgagggaga tgatatttga tcacaggcag caacgctctg tcatcgttac 13500
aatcaacatg ctaccctccg cgagatcatc cgtgtttcaa acccggcagc ttagttgccg 13560
ttcttccgaa tagcatcggt aacatgagca aagtctgccg ccttacaacg gctctcccgc 13620
tgacgccgtc ccggactgat gggctgcctg tatcgagtgg tgattttgtg ccgagctgcc 13680
ggtcggggag ctgttggctg gctggtggca ggatatattg tggtgtaaac aaattgacgc 13740
ttagacaact taataacaca ttgcggacgt ttttaatgta ctggggtggt ttttcttttc 13800
accagtgaga cgggcaacag ctgattgccc ttcaccgcct ggccctgaga gagttgcagc 13860
aagcggtcca cgctggtttg ccccagcagg cgaaaatcct gtttgatggt ggttccgaaa 13920
tcggcaaaat cccttataaa tcaaaagaat agcccgagat agggttgagt gttgttccag 13980
tttggaacaa gagtccacta ttaaagaacg tggactccaa cgtcaaaggg cgaaaaaccg 14040
tctatcaggg cgatggccca ctacgtgaac catcacccaa atcaagtttt ttggggtcga 14100
ggtgccgtaa agcactaaat cggaacccta aagggagccc ccgatttaga gcttgacggg 14160
gaaagccggc gaacgtggcg agaaaggaag ggaagaaagc gaaaggagcg ggcgccattc 14220
aggctgcgca actgttggga aggg 14244

<210> SEQ ID NO 29
<211> LENGTH: 14607
<212> TYPE: DNA
<213> ORGANISM: Artificial Sequence
<220> FEATURE:
<223> OTHER INFORMATION: pBYKEMd2-HVLZnt

<400> SEQUENCE: 29
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840

```
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatcccttta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
```

taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat gggatggtct tgcatcatac 3420
tctttcttgt tgcaactgct acaggtgtcc actctgatgt tcagcttctc gagtctggag 3480
gtggtcttgt gcaacctgga ggttccttga gactctcctg tgcagcttca gggtttgact 3540
tcagtaggta ctggatgagt tgggttcgtc aagctcctgg gaaaggacta gaatggattg 3600
gagagatcaa tccagattca agtaccatca actatactcc atctctgaag gatcgcttca 3660
ccatttccag agacaatgcc aagaacacgt tgtatcttca gatgaacagc ttgaggactg 3720
aagacacagc cttgtactac tgcacaagac agggctatgg ctacaactac tggggtcaag 3780
gcaccactgt cacagtgtct tcagctacta gtggtggatc aggaggttct ggtggttctg 3840
gaggttcagg atccgatgtt ttgatgactc aaagccctct ctcacttcct gtgactcttg 3900
gacagcccgc atccatatct tgcagatcta gtcagagtat tgttcatagt aacggcaaca 3960
cctacttgga atggtatctg cagaaaccag gccagtctcc aaagcttctg atctacaagg 4020
cttccaatcg tttctctggt gtcccagaca ggtttagtgg cagtggatca gggactgact 4080
tcacattgaa gatcagcaga gttgaggctg aagatgcggg agtgtactat tgtcttcaag 4140
gttcacatgt tccgtcaacg tttggaggtg ggaccaaagt ggagatcaag gctagcacca 4200
aaggtccatc ggtctttcca ctggcacctt cttccaagag tacttctgga ggcacagctg 4260
cactgggttg tcttgtcaag gactactttc cagaacctgt tacggtttcg tggaactcag 4320
gtgctctgac cagtggagtg cacacctttc cagctgttct tcagtcctca ggattgtatt 4380
ctcttagcag tgttgtgact gttccatcct caagcttggg cactcagacc tacatctgca 4440
atgtgaatca caaacccagc aacaccaagg ttgacaagaa agttgagccc aagtcttgtg 4500
acaagactca tacgtgtcca ccgtgcccag cacctgaact tcttggagga ccgtcagtct 4560
tcttgtttcc tccaaagcct aaggatacct tgatgatctc caggactcct gaagtcacat 4620
gtgtagttgt ggatgtgagc catgaagatc ctgaggtgaa gttcaactgg tatgtggatg 4680
gtgtggaagt gcacaatgcc aagacaaagc cgagagagga acagtacaac agcacgtaca 4740
gggttgtctc agttctcact gttctccatc aagattggtt gaatggcaaa gagtacaagt 4800
gcaaggtctc caacaaagcc ctcccagccc ccattgagaa gaccatttcc aaagcgaaag 4860
ggcaaccccg tgaaccacaa gtgtacacac ttcctccatc tcgcgatgaa ctgaccaaga 4920
accaggtcag cttgacttgc ctggtgaaag gcttctatcc ctctgacata gctgtagagt 4980
gggagagcaa tgggcaaccg gagaacaact acaagactac acctcccgtt ctcgattctg 5040
acggctcctt cttcctctac agcaagctca cagtggacaa gagcaggtgg caacaaggga 5100
atgtcttctc atgctccgtg atgcatgagg ctcttcacaa tcactacaca cagaagagtc 5160
tctccttgtc tccgggtaaa ggaggtggcg gatcaggtgg aggcggttca ggcggaggtg 5220
gatccaaggg cgtgtcatac tccttgtgta ccgctgcctt cacattcacc aagatcccgg 5280
ctgaaacact ccacggaacc gttaccgtgg aggtccaata cgccggtaca gatggacctt 5340
gcaaggttcc agctcagatg gcggtggaca tgcaaactct taccccagtt ggaaggttga 5400
ttaccgctaa ccccgttatc actgaaagca ctgagaactc taagatgatg ttggaacttg 5460
atccaccatt cggtgactct tacattgtca ttggtgtggg agagaagaag atcacccacc 5520
actggcacag gagtggtagc acttaagagc tcgaagtgac atcacaaagt tgaaggtaat 5580
aaagccaaat taattaagac attttcataa tgatgtcaag aatgcaaagc aaattgcata 5640
actgccttta tgcaaaacat taatataata taaattataa agaactgcgc tctctgcttc 5700
ttattttctt agcttcattt attagtcact agctgttcag aattttcagt atcttttgat 5760
attactaaga acctaatcac acaatgtata ttcttatgca ggaaaagcag aatgctgagc 5820
taaaagaaag gctttttcca ttttcgagag acaatgagaa aagaagaaga agaagaagaa 5880
gaagaagaag aagaaaagag taaataataa agccccacag gaggcgaagt tcttgtagct 5940
ccatgttatc taagttattg atattgtttg ccctatattt tatttctgtc attgtgtatg 6000
ttttgttcag tttcgatctc cttgcaaaat gcagagatta tgagatgaat aaactaagtt 6060
atattattat acgtgttaat attctcctcc tctctctagc tagccttttg ttttctcttt 6120
ttcttatttg attttcttta aatcaatcca ttttaggaga gggccaggga gtgatccagc 6180
aaaacatgaa gattagaaga aacttccctc tttttttcc tgaaaacaat ttaacgtcga 6240
gatttatctc tttttgtaat ggaatcattt ctacagttat gacgaattgt acatcaacga 6300
aaaattagtc aaacgactaa aataaataaa tatcatgtgt tattaagaaa attctcctat 6360
aagaatattt taatagatca tatgtttgta aaaaaaatta atttttacta acacatatat 6420
ttacttatca aaaatttgac aaagtaagat taaaataata ttcatctaac aaaaaaaaaa 6480
ccagaaaatg ctgaaaaccc ggcaaaaccg aaccaatcca aaccgatata gttggtttgg 6540
tttgattttg atataaaccg aaccaactcg gtccatttgc acccctaatc ataatagctt 6600
taatatttca agatattatt aagttaacgt tgtcaatatc ctggaaattt tgcaaaatga 6660
atcaagccta tatggctgta atatgaattt aaaagcagct cgatgtggtg gtaatatgta 6720
atttacttga ttctaaaaaa atatcccaag tattaataat ttctgctagg aagaaggtta 6780
gctacgattt acagcaaagc cagaatacaa agaaccataa agtgattgaa gctcgaaata 6840
tacgaaggaa caaatatttt taaaaaaata cgcaatgact tggaacaaaa gaaagtgata 6900
tattttttgt tcttaaacaa gcatcccctc taaagaatgg cagttttcct ttgcatgtaa 6960
ctattatgct cccttcgtta caaaaatttt ggactactat tgggaacttc ttctgaaaat 7020
agtggtaccg agtgtacttc aagtcagttg gaaatcaata aaatgattat tttatgaata 7080
tatttcattg tgcaagtaga tagaaattac atatgttaca taacacacga aataaacaaa 7140
aaaacacaat ccaaaacaaa caccccaaac aaaataacac tatatatatc ctcgtatgag 7200
gagaggcacg ttcagtgact cgacgattcc cgagcaaaaa aagtctcccc gtcacacata 7260
tagtgggtga cgcaattatc ttcaaagtaa tccttctgtt gacttgtcat tgataacatc 7320
cagtcttcgt caggattgca aagaattata gaagggatcc caccttttat tttcttcttt 7380
tttccatatt tagggttgac agtgaaatca gactggcaac ctattaattg cttccacaat 7440
gggacgaact tgaaggggat gtcgtcgatg atattatagg tggcgtgttc atcgtagttg 7500
gtgaagtcga tggtcccgtt ccagtagttg tgtcgcccga gacttctagc ccaggtggtc 7560
tttccggtac gagttggtcc gcagatgtag aggctggggt gtctgacccc agtccttccc 7620
tcatcctggt tagatcggcc atccactcaa ggtcagattg tgcttgatcg taggagacag 7680
gatgtatgaa agtgtaggca tcgatgctta catgatatag gtgcgtctct ctccagttgt 7740
gcagatcttc gtggcagcgg agatctgatt ctgtgaaggg cgacacgtac tgctcaggtt 7800
gtggaggaaa taatttgttg gctgaatatt ccagccattg aagctttgtt gcccattcat 7860
gagggaactc ttctttgatc atgtcaagat actcctcctt agacgttgca gtctggataa 7920
tagttcgcca tcgtgcgtca gatttgcgag gagacacctt atgatctcgg aaatctcctc 7980
tggttttaat atctccgtcc tttgatatgt aatcaaggac ttgtttagag tttctagctg 8040
gctggatatt agggtgattt ccttcaaaat cgaaaaaaga aggatcccta atacaaggtt 8100
ttttatcaag ctggataaga gcatgatagt gggtagtgcc atcttgatga agctcagaag 8160
caacaccaag gaagaaaata agaaaaggtg tgagtttctc ccagagaaac tggaataaat 8220
catctctttg agatgagcac ttggggtagg taaggaaaac atatttagat tggagtctga 8280
agttcttgct agcagaaggc atgttgttgt gactccgagg ggttgcctca aactctatct 8340
tataaccggc gtggaggcat ggaggcaagg gcattttggt aatttaagta gttagtggaa 8400
aatgacgtca tttacttaaa gacgaagtct tgcgacaagg ggggcccacg ccgaatttta 8460
atattaccgg cgtggcccca ccttatcgcg agtgctttag cacgagcggt ccagatttaa 8520
agtagaaaag ttcccgccca ctagggttaa aggtgttcac actataaaag catatacgat 8580
gtgatggtat ttgatggagc gtatattgta tcaggtattt ccgtcggata cgaattattc 8640
gtacggccgg accggtcccc taggccggcc aattcgagat cggccgcggc tgagtggctc 8700
cttcaatcgt tgcggttctg tcagttccaa acgtaaaacg gcttgtcccg cgtcatcggc 8760
gggggtcata acgtgactcc cttaattctc cgctcatgat cagattgtcg tttcccgcct 8820
tcagtttaaa ctatcagtgt ttgacaggat atattggcgg gtaaacctaa gagaaaagag 8880
cgtttattag aataatcgga tatttaaaag ggcgtgaaaa ggtttatccg ttcgtccatt 8940
tgtatgtgca tgccaaccac agggttcccc agatctggcg ccggccagcg agacgagcaa 9000
gattggccgc cgcccgaaac gatccgacag cgcgcccagc acaggtgcgc aggcaaattg 9060
caccaacgca tacagcgcca gcagaatgcc atagtgggcg gtgacgtcgt tcgagtgaac 9120
cagatcgcgc aggaggcccg gcagcaccgg cataatcagg ccgatgccga cagcgtcgag 9180
cgcgacagtg ctcagaatta cgatcagggg tatgttgggt ttcacgtctg gcctccggag 9240
actgtcatac gcgtaaaaag gccgcgttgc tggcgttttt ccataggctc cgcccccctg 9300
acgagcatca caaaaatcga cgctcaagtc agaggtggcg aaacccgaca ggactataaa 9360
gataccaggc gtttccccct ggaagctccc tcgtgcgctc tcctgttccg accctgccgc 9420
ttaccggata cctgtccgcc tttctccctt cgggaagcgt ggcgctttct catagctcac 9480
gctgtaggta tctcagttcg gtgtaggtcg ttcgctccaa gctgggctgt gtgcacgaac 9540
cccccgttca gcccgaccgc tgcgccttat ccggtaacta tcgtcttgag tccaacccgg 9600
taagacacga cttatcgcca ctggcagcag ccactggtaa caggattagc agagcgaggt 9660
atgtaggcgg tgctacagag ttcttgaagt ggtggcctaa ctacggctac actagaagga 9720
cagtatttgg tatctgcgct ctgctgaagc cagttacctt cggaaaaaga gttggtagct 9780
cttgatccgg caaacaaacc accgctggta gcggtggttt ttttgtttgc aagcagcaga 9840
ttacgcgcag aaaaaaagga tctcaagaag atcctttgat cttttctacg gggtctgacg 9900
ctcagtggaa cgaaaactca cgttaaggga ttttggtcat gagattatca aaaaggatct 9960
tcacctagat ccttttaaat taaaaatgaa gttttaaatc aatctaaagt atatatgagt 10020
aaacttggtc tgcagttgcc atgttttacg gcagtgagag cagagatagc gctgatgtcc 10080
ggcggtgctt ttgccgttac gcaccacccc gtcagtagct gaacaggagg gacagctgat 10140
agacacagaa gccactggag cacctcaaaa acaccatcat acactaaatc agtaagttgg 10200
cagcatcacc cataattgtg gtttcaaaat cggctccgtc gatactatgt tatacgccaa 10260
ctttgaaaac aactttgaaa aagctgtttt ctggtattta aggttttaga atgcaaggaa 10320
cagtgaattg gagttcgtct tgttataatt agcttcttgg ggtatcttta aatactgtag 10380
aaaagaggaa ggaaataata aatggctaaa atgagaatat caccggaatt gaaaaaactg 10440
atcgaaaaat accgctgcgt aaaagatacg gaaggaatgt ctcctgctaa ggtatataag 10500
ctggtgggag aaaatgaaaa cctatattta aaaatgacgg acagccggta taaagggacc 10560
acctatgatg tggaacggga aaaggacatg atgctatggc tggaaggaaa gctgcctgtt 10620
ccaaaggtcc tgcactttga acggcatgat ggctggagca atctgctcat gagtgaggcc 10680
gatggcgtcc tttgctcgga agagtatgaa gatgaacaaa gccctgaaaa gattatcgag 10740
ctgtatgcgg agtgcatcag gctctttcac tccatcgaca tatcggattg tccctatacg 10800
aatagcttag acagccgctt agccgaattg gattacttac tgaataacga tctggccgat 10860
gtggattgcg aaaactggga agaagacact ccatttaaag atccgcgcga gctgtatgat 10920
tttttaaaga cggaaaagcc cgaagaggaa cttgtctttt cccacggcga cctgggagac 10980
agcaacatct ttgtgaaaga tggcaaagta agtggcttta ttgatcttgg gagaagcggc 11040
agggcggaca agtggtatga cattgccttc tgcgtccggt cgatcaggga ggatatcggg 11100
gaagaacagt atgtcgagct atttttttgac ttactgggga tcaagcctga ttgggagaaa 11160
ataaaatatt atattttact ggatgaattg ttttagtacc tagatgtggc gcaacgatgc 11220
cggcgacaag caggagcgca ccgacttctt ccgcatcaag tgttttggct ctcaggccga 11280
ggcccacggc aagtatttgg gcaaggggtc gctggtattc gtgcagggca agattcggaa 11340
taccaagtac gagaaggacg gccagacggt ctacgggacc gacttcattg ccgataaggt 11400
ggattatctg gacaccaagg caccaggcgg gtcaaatcag gaataagggc acattgcccc 11460
ggcgtgagtc ggggcaatcc cgcaaggagg gtgaatgaat cggacgtttg accggaaggc 11520
atacaggcaa gaactgatcg acgcggggtt ttccgccgag gatgccgaaa ccatcgcaag 11580
ccgcaccgtc atgcgtgcgc cccgcgaaac cttccagtcc gtcggctcga tggtccagca 11640
agctacggcc aagatcgagc gcgacagcgt gcaactggct ccccctgccc tgcccgcgcc 11700
atcggccgcc gtggagcgtt cgcgtcgtct cgaacaggag gcggcaggtt tggcgaagtc 11760
gatgaccatc gacacgcgag gaactatgac gaccaagaag cgaaaaaccg ccggcgagga 11820
cctggcaaaa caggtcagcg aggccaagca ggccgcgttg ctgaaacaca cgaagcagca 11880
gatcaaggaa atgcagcttt ccttgttcga tattgcgccg tggccggaca cgatgcgagc 11940
gatgccaaac gacacggccc gctctgccct gttcaccacg cgcaacaaga aaatcccgcg 12000
cgaggcgctg caaaacaagg tcattttcca cgtcaacaag gacgtgaaga tcacctacac 12060
cggcgtcgag ctgcgggccg acgatgacga actggtgtgg cagcaggtgt tggagtacgc 12120
gaagcgcacc cctatcggcg agccgatcac cttcacgttc tacgagcttt gccaggacct 12180
gggctggtcg atcaatggcc ggtattacac gaaggccgag gaatgcctgt cgcgcctaca 12240
ggcgacggcg atgggcttca cgtccgaccg cgttgggcac ctggaatcgg tgtcgctgct 12300
gcaccgcttc cgcgtcctgg accgtggcaa gaaaacgtcc cgttgccagg tcctgatcga 12360
cgaggaaatc gtcgtgctgt ttgctggcga ccactacacg aaattcatat gggagaagta 12420
ccgcaagctg tcgccgacgg cccgacggat gttcgactat ttcagctcgc accgggagcc 12480
gtacccgctc aagctggaaa ccttccgcct catgtgcgga tcggattcca cccgcgtgaa 12540
gaagtggcgc gagcaggtcg gcgaagcctg cgaagagttg cgaggcagcg gcctggtgga 12600
acacgcctgg gtcaatgatg acctggtgca ttgcaaacgc tagggccttg tggggtcagt 12660
tccggctggg ggttcagcag ccagcgcttt actggcattt caggaacaag cgggcactgc 12720
tcgacgcact tgcttcgctc agtatcgctc gggacgcacg gcgcgctcta cgaactgccg 12780
ataaacagag gattaaaatt gacaattcaa tggcaaggac tgccagcgct gccatttttg 12840
gggtgaggcc gttcgcggcc gaggggcgca gcccctgggg ggatgggagg cccgcgttag 12900
cgggccggga gggttcgaga aggggggca cccccttcg gcgtgcgcgg tcacgcgcac 12960
agggcgcagc cctggttaaa aacaaggttt ataaatattg gtttaaaagc aggttaaaag 13020
acaggttagc ggtggccgaa aaacgggcgg aaacccttgc aaatgctgga ttttctgcct 13080
gtggacagcc cctcaaatgt caataggtgc gcccctcatc tgtcagcact ctgcccctca 13140
agtgtcaagg atcgcgcccc tcatctgtca gtagtcgcgc ccctcaagtg tcaataccgc 13200
agggcactta tccccaggct tgtccacatc atctgtggga aactcgcgta aaatcaggcg 13260
ttttcgccga tttgcgaggc tggccagctc cacgtcgccg gccgaaatcg agcctgcccc 13320
tcatctgtca acgccgcgcc gggtgagtcg gcccctcaag tgtcaacgtc cgcccctcat 13380
ctgtcagtga gggccaagtt ttccgcgagg tatccacaac gccggcggcc gcggtgtctc 13440
gcacacggct tcgacggcgt ttctggcgcg tttgcagggc catagacggc cgccagccca 13500
gcggcgaggg caaccagccc ggtgagcgtc gcaaaggcgc tcggtcttgc cttgctcgtc 13560
gagatctggg gtcgatcagc cggggatgca tcaggccgac agtcggaact tcgggtcccc 13620
gacctgtacc attcggtgag caatggatag gggagttgat atcgtcaacg ttcacttcta 13680
aagaaatagc gccactcagc ttcctcagcg gctttatcca gcgatttcct attatgtcgg 13740
catagttctc aagatcgaca gcctgtcacg gttaagcgag aaatgaataa gaaggctgat 13800
aattcggatc tctgcgaggg agatgatatt tgatcacagg cagcaacgct ctgtcatcgt 13860
tacaatcaac atgctaccct ccgcgagatc atccgtgttt caaacccggc agcttagttg 13920
ccgttcttcc gaatagcatc ggtaacatga gcaaagtctg ccgccttaca acggctctcc 13980
cgctgacgcc gtcccggact gatgggctgc ctgtatcgag tggtgatttt gtgccgagct 14040
gccggtcggg gagctgttgg ctggctggtg gcaggatata ttgtggtgta aacaaattga 14100
cgcttagaca acttaataac acattgcgga cgtttttaat gtactggggt ggtttttctt 14160
ttcaccagtg agacgggcaa cagctgattg cccttcaccg cctggccctg agagagttgc 14220
agcaagcggt ccacgctggt ttgccccagc aggcgaaaat cctgtttgat ggtggttccg 14280
aaatcggcaa aatcccttat aaatcaaaag aatagcccga gatagggttg agtgttgttc 14340
cagtttggaa caagagtcca ctattaaaga acgtggactc caacgtcaaa gggcgaaaaa 14400
ccgtctatca gggcgatggc ccactacgtg aaccatcacc caaatcaagt tttttggggt 14460
cgaggtgccg taaagcacta aatcggaacc ctaaagggag cccccgattt agagcttgac 14520
ggggaaagcc ggcgaacgtg gcgagaaagg aagggaagaa agcgaaagga gcgggcgcca 14580
ttcaggctgc gcaactgttg ggaaggg 14607

<210> SEQ ID NO 30
<211> LENGTH: 14622
<212> TYPE: DNA
<213> ORGANISM: Artificial Sequence
<220> FEATURE:
<223> OTHER INFORMATION: pBYKEMd2-ZHVLnt

<400> SEQUENCE: 30
cgatcggtcg attcatagaa gattagattt ttcatagtat ttttttaaag taaaccttta 60
actacggtta ggacactttt aagttaaatt taatttgaac ccttaaatta atttttaaaa 120

-continued

```
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
```

gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat ggctaacaag cacctctcat 3420
tgtctctctt ccttgtgctc cttggtcttt ctgcttctct tgcttctggt aagggcgtgt 3480
catactcctt gtgtaccgct gccttcacat tcaccaagat cccggctgaa acactccacg 3540
gaaccgttac cgtggaggtc caatacgccg gtacagatgg accttgcaag gttccagctc 3600
agatggcggt ggacatgcaa actcttaccc cagttggaag gttgattacc gctaaccccg 3660
ttatcactga aagcactgag aactctaaga tgatgttgga acttgatcca ccattcggtg 3720
actcttacat tgtcattggt gtgggagaga agaagatcac ccaccactgg cacaggagtg 3780
gtagcactag tggtggatca ggaggttctg gtggttctgg aggttcagga tccgatgttc 3840
agcttctcga gtctggaggt ggtcttgtgc aacctggagg ttccttgaga ctctcctgtg 3900
cagcttcagg gtttgacttc agtaggtact ggatgagttg ggttcgtcaa gctcctggga 3960
aaggactaga atggattgga gagatcaatc cagattcaag taccatcaac tatactccat 4020
ctctgaagga tcgcttcacc atttccagag acaatgccaa gaacacgttg tatcttcaga 4080
tgaacagctt gaggactgaa gacacagcct tgtactactg cacaagacag ggctatggct 4140
acaactactg gggtcaaggc accactgtca cagtgtcttc agctactagt ggtggatcag 4200
gaggttctgg tggttctgga ggttcaggat ccgatgtttt gatgactcaa agccctctct 4260
cacttcctgt gactcttgga cagcccgcat ccatatcttg cagatctagt cagagtattg 4320
ttcatagtaa cggcaacacc tacttggaat ggtatctgca gaaaccaggc cagtctccaa 4380
agcttctgat ctacaaggct tccaatcgtt tctctggtgt cccagacagg tttagtggca 4440
gtggatcagg gactgacttc acattgaaga tcagcagagt tgaggctgaa gatgcgggag 4500
tgtactattg tcttcaaggt tcacatgttc cgtcaacgtt tggaggtggg accaaagtgg 4560
agatcaaggc tagcaccaaa ggtccatcgg tctttccact ggcaccttct tccaagagta 4620
cttctggagg cacagctgca ctgggttgtc ttgtcaagga ctactttcca gaacctgtta 4680
cggtttcgtg gaactcaggt gctctgacca gtggagtgca cacctttcca gctgttcttc 4740
agtcctcagg attgtattct cttagcagtg ttgtgactgt tccatcctca agcttgggca 4800
ctcagaccta catctgcaat gtgaatcaca aacccagcaa caccaaggtt gacaagaaag 4860
ttgagcccaa gtcttgtgac aagactcata cgtgtccacc gtgcccagca cctgaacttc 4920
ttggaggacc gtcagtcttc ttgtttcctc caaagcctaa ggataccttg atgatctcca 4980
ggactcctga agtcacatgt gtagttgtgg atgtgagcca tgaagatcct gaggtgaagt 5040
tcaactggta tgtggatggt gtggaagtgc acaatgccaa gacaaagccg agagaggaac 5100
agtacaacag cacgtacagg gttgtctcag ttctcactgt tctccatcaa gattggttga 5160
atggcaaaga gtacaagtgc aaggtctcca acaaagccct cccagccccc attgagaaga 5220
ccatttccaa agcgaaaggg caaccccgtg aaccacaagt gtacacactt cctccatctc 5280
gcgatgaact gaccaagaac caggtcagct tgacttgcct ggtgaaaggc ttctatccct 5340
ctgacatagc tgtagagtgg gagagcaatg ggcaaccgga gaacaactac aagactacac 5400
ctcccgttct cgattctgac ggctccttct tcctctacag caagctcaca gtggacaaga 5460
gcaggtggca acaagggaat gtcttctcat gctccgtgat gcatgaggct cttcacaatc 5520
actacacaca gaagagtctc tccttgtctc cgggtaaata agagctcgaa gtgacatcac 5580
aaagttgaag gtaataaagc caaattaatt aagacatttt cataatgatg tcaagaatgc 5640
aaagcaaatt gcataactgc ctttatgcaa aacattaata taatataaat tataaagaac 5700
tgcgctctct gcttcttatt ttcttagctt catttattag tcactagctg ttcagaattt 5760
tcagtatctt ttgatattac taagaaccta atcacacaat gtatattctt atgcaggaaa 5820
agcagaatgc tgagctaaaa gaaaggcttt ttccattttc gagagacaat gagaaaagaa 5880
gaagaagaag aagaagaaga agaagaagaa aagagtaaat aataaagccc cacaggaggc 5940
gaagttcttg tagctccatg ttatctaagt tattgatatt gtttgcccta tattttattt 6000
ctgtcattgt gtatgttttg ttcagtttcg atctccttgc aaaatgcaga gattatgaga 6060
tgaataaact aagttatatt attatacgtg ttaatattct cctcctctct ctagctagcc 6120
ttttgtttc tctttttctt atttgatttt ctttaaatca atccatttta ggagagggcc 6180
agggagtgat ccagcaaaac atgaagatta gaagaaactt ccctcttttt tttcctgaaa 6240
acaatttaac gtcgagattt atctcttttt gtaatggaat catttctaca gttatgacga 6300
attgtacatc aacgaaaaat tagtcaaacg actaaaataa ataaatatca tgtgttatta 6360
agaaaattct cctataagaa tattttaata gatcatatgt ttgtaaaaaa aattaatttt 6420
tactaacaca tatatttact tatcaaaaat ttgacaaagt aagattaaaa taatattcat 6480
ctaacaaaaa aaaaaccaga aaatgctgaa aacccggcaa aaccgaacca atccaaaccg 6540
atatagttgg tttggtttga ttttgatata aaccgaacca actcggtcca tttgcacccc 6600
taatcataat agctttaata tttcaagata ttattaagtt aacgttgtca atatcctgga 6660
aattttgcaa aatgaatcaa gcctatatgg ctgtaatatg aatttaaaag cagctcgatg 6720
tggtggtaat atgtaattta cttgattcta aaaaaatatc ccaagtatta ataatttctg 6780
ctaggaagaa ggttagctac gatttacagc aaagccagaa tacaaagaac cataaagtga 6840
ttgaagctcg aaatatacga aggaacaaat atttttaaaa aaatacgcaa tgacttggaa 6900
caaaagaaag tgatatattt tttgttctta aacaagcatc ccctctaaag aatggcagtt 6960
ttcctttgca tgtaactatt atgctccctt cgttacaaaa attttggact actattggga 7020
acttcttctg aaaatagtgg taccgagtgt acttcaagtc agttggaaat caataaaatg 7080
attattttat gaatatattt cattgtgcaa gtagatagaa attacatatg ttacataaca 7140
cacgaaataa acaaaaaaac acaatccaaa acaaacaccc caaacaaaat aacactatat 7200
atatcctcgt atgaggagag gcacgttcag tgactcgacg attcccgagc aaaaaaagtc 7260
tccccgtcac acatatagtg ggtgacgcaa ttatcttcaa agtaatcctt ctgttgactt 7320
gtcattgata acatccagtc ttcgtcagga ttgcaaagaa ttatagaagg gatcccacct 7380
tttattttct tcttttttcc atatttaggg ttgacagtga aatcagactg gcaacctatt 7440
aattgcttcc acaatgggac gaacttgaag ggatgtcgt cgatgatatt ataggtggcg 7500
tgttcatcgt agttggtgaa gtcgatggtc ccgttccagt agttgtgtcg cccgagactt 7560
ctagcccagg tggtctttcc ggtacgagtt ggtccgcaga tgtagaggct ggggtgtctg 7620
accccagtcc ttccctcatc ctggttagat cggccatcca ctcaaggtca gattgtgctt 7680
gatcgtagga gacaggatgt atgaaagtgt aggcatcgat gcttacatga tataggtgcg 7740
tctctctcca gttgtgcaga tcttcgtggc agcggagatc tgattctgtg aagggcgaca 7800
cgtactgctc aggttgtgga ggaaataatt tgttggctga atattccagc cattgaagct 7860
ttgttgccca ttcatgaggg aactcttctt tgatcatgtc aagatactcc tccttagacg 7920
ttgcagtctg gataatagtt cgccatcgtg cgtcagattt gcgaggagac accttatgat 7980
ctcggaaatc tcctctggtt ttaatatctc cgtcctttga tatgtaatca aggacttgtt 8040
tagagtttct agctggctgg atattagggt gatttccttc aaaatcgaaa aaagaaggat 8100
ccctaataca aggtttttta tcaagctgga taagagcatg atagtgggta gtgccatctt 8160
gatgaagctc agaagcaaca ccaaggaaga aaataagaaa aggtgtgagt ttctcccaga 8220
gaaactggaa taaatcatct ctttgagatg agcacttggg gtaggtaagg aaaacatatt 8280
tagattggag tctgaagttc ttgctagcag aaggcatgtt gttgtgactc cgaggggttg 8340
cctcaaactc tatcttataa ccggcgtgga ggcatggagg caagggcatt ttggtaattt 8400
aagtagttag tggaaaatga cgtcatttac ttaaagacga agtcttgcga caaggggggc 8460
ccacgccgaa ttttaatatt accggcgtgg ccccacctta tcgcgagtgc tttagcacga 8520
gcggtccaga tttaaagtag aaaagttccc gcccactagg gttaaaggtg ttcacactat 8580
aaaagcatat acgatgtgat ggtatttgat ggagcgtata ttgtatcagg tatttccgtc 8640
ggatacgaat tattcgtacg gccggaccgg tcccctaggc cggccaattc gagatcggcc 8700
gcggctgagt ggctccttca atcgttgcgg ttctgtcagt tccaaacgta aaacggcttg 8760
tcccgcgtca tcggcggggg tcataacgtg actcccttaa ttctccgctc atgatcagat 8820
tgtcgtttcc cgccttcagt ttaaactatc agtgtttgac aggatatatt ggcgggtaaa 8880
cctaagagaa aagagcgttt attagaataa tcggatattt aaaagggcgt gaaaaggttt 8940
atccgttcgt ccatttgtat gtgcatgcca accacagggt tccccagatc tggcgccggc 9000
cagcgagacg agcaagattg gccgccgccc gaaacgatcc gacagcgcgc ccagcacagg 9060
tgcgcaggca aattgcacca acgcatacag cgccagcaga atgccatagt gggcggtgac 9120
gtcgttcgag tgaaccagat cgcgcaggag gcccggcagc accggcataa tcaggccgat 9180
gccgacagcg tcgagcgcga cagtgctcag aattacgatc aggggtatgt tgggtttcac 9240
gtctggcctc cggagactgt catacgcgta aaaaggccgc gttgctggcg tttttccata 9300
ggctccgccc ccctgacgag catcacaaaa atcgacgctc aagtcagagg tggcgaaacc 9360
cgacaggact ataaagatac caggcgtttc cccctggaag ctccctcgtg cgctctcctg 9420
ttccgaccct gccgcttacc ggatacctgt ccgcctttct cccttcggga agcgtggcgc 9480
tttctcatag ctcacgctgt aggtatctca gttcggtgta ggtcgttcgc tccaagctgg 9540
gctgtgtgca cgaacccccc gttcagcccg accgctgcgc cttatccggt aactatcgtc 9600

```
ttgagtccaa cccggtaaga cacgacttat cgccactggc agcagccact ggtaacagga   9660
ttagcagagc gaggtatgta ggcggtgcta cagagttctt gaagtggtgg cctaactacg   9720
gctacactag aaggacagta tttggtatct gcgctctgct gaagccagtt accttcggaa   9780
aaagagttgg tagctcttga tccggcaaac aaaccaccgc tggtagcggt ggtttttttg   9840
tttgcaagca gcagattacg cgcagaaaaa aaggatctca agaagatcct ttgatctttt   9900
ctacggggtc tgacgctcag tggaacgaaa actcacgtta agggattttg gtcatgagat   9960
tatcaaaaag gatcttcacc tagatccttt taaattaaaa atgaagtttt aaatcaatct  10020
aaagtatata tgagtaaact tggtctgcag ttgccatgtt ttacggcagt gagagcagag  10080
atagcgctga tgtccggcgg tgcttttgcc gttacgcacc accccgtcag tagctgaaca  10140
ggagggacag ctgatagaca cagaagccac tggagcacct caaaaacacc atcatacact  10200
aaatcagtaa gttggcagca tcacccataa ttgtggtttc aaaatcggct ccgtcgatac  10260
tatgttatac gccaactttg aaaacaactt tgaaaaagct gttttctggt atttaaggtt  10320
ttagaatgca aggaacagtg aattggagtt cgtcttgtta taattagctt cttggggtat  10380
ctttaaatac tgtagaaaag aggaaggaaa taataaatgg ctaaaatgag aatatcaccg  10440
gaattgaaaa aactgatcga aaaataccgc tgcgtaaaag atacggaagg aatgtctcct  10500
gctaaggtat ataagctggt gggagaaaat gaaaacctat atttaaaaat gacggacagc  10560
cggtataaag ggaccaccta tgatgtggaa cgggaaaagg acatgatgct atggctggaa  10620
ggaaagctgc ctgttccaaa ggtcctgcac tttgaacggc atgatggctg gagcaatctg  10680
ctcatgagtg aggccgatgg cgtcctttgc tcggaagagt atgaagatga acaaagccct  10740
gaaaagatta tcgagctgta tgcggagtgc atcaggctct ttcactccat cgacatatcg  10800
gattgtccct atacgaatag cttagacagc cgcttagccg aattggatta cttactgaat  10860
aacgatctgg ccgatgtgga ttgcgaaaac tgggaagaag acactccatt taaagatccg  10920
cgcgagctgt atgatttttt aaagacggaa aagcccgaag aggaacttgt cttttcccac  10980
ggcgacctgg gagacagcaa catctttgtg aaagatggca aagtaagtgg ctttattgat  11040
cttgggagaa gcggcagggc ggacaagtgg tatgacattg ccttctgcgt ccggtcgatc  11100
agggaggata tcggggaaga acagtatgtc gagctatttt ttgacttact ggggatcaag  11160
cctgattggg agaaaataaa atattatatt ttactggatg aattgtttta gtacctagat  11220
gtggcgcaac gatgccggcg acaagcagga gcgcaccgac ttcttccgca tcaagtgttt  11280
tggctctcag gccgaggccc acggcaagta tttgggcaag gggtcgctgg tattcgtgca  11340
gggcaagatt cggaatacca agtacgagaa ggacggccag acggtctacg ggaccgactt  11400
cattgccgat aaggtggatt atctggacac caaggcacca ggcgggtcaa atcaggaata  11460
agggcacatt gccccggcgt gagtcggggc aatcccgcaa ggagggtgaa tgaatcggac  11520
gtttgaccgg aaggcataca ggcaagaact gatcgacgcg gggttttccg ccgaggatgc  11580
cgaaaccatc gcaagccgca ccgtcatgcg tgcgccccgc gaaaccttcc agtccgtcgg  11640
ctcgatggtc cagcaagcta cggccaagat cgagcgcgac agcgtgcaac tggctccccc  11700
tgccctgccc gcgccatcgg ccgccgtgga gcgttcgcgt cgtctcgaac aggaggcggc  11760
aggtttggcg aagtcgatga ccatcgacac gcgaggaact atgacgacca agaagcgaaa  11820
aaccgccggc gaggacctgg caaaacaggt cagcgaggcc aagcaggccg cgttgctgaa  11880
acacacgaag cagcagatca aggaaatgca gctttccttg ttcgatattg cgccgtggcc  11940
ggacacgatg cgagcgatgc caaacgacac ggcccgctct gccctgttca ccacgcgcaa  12000
```

caagaaaatc ccgcgcgagg cgctgcaaaa caaggtcatt ttccacgtca acaaggacgt 12060
gaagatcacc tacaccggcg tcgagctgcg ggccgacgat gacgaactgg tgtggcagca 12120
ggtgttggag tacgcgaagc gcacccctat cggcgagccg atcaccttca cgttctacga 12180
gctttgccag gacctgggct ggtcgatcaa tggccggtat tacacgaagg ccgaggaatg 12240
cctgtcgcgc ctacaggcga cggcgatggg cttcacgtcc gaccgcgttg ggcacctgga 12300
atcggtgtcg ctgctgcacc gcttccgcgt cctggaccgt ggcaagaaaa cgtcccgttg 12360
ccaggtcctg atcgacgagg aaatcgtcgt gctgtttgct ggcgaccact acacgaaatt 12420
catatgggag aagtaccgca agctgtcgcc gacggcccga cggatgttcg actatttcag 12480
ctcgcaccgg gagccgtacc cgctcaagct ggaaaccttc cgcctcatgt gcggatcgga 12540
ttccacccgc gtgaagaagt ggcgcgagca ggtcggcgaa gcctgcgaag agttgcgagg 12600
cagcggcctg gtggaacacg cctgggtcaa tgatgacctg gtgcattgca aacgctaggg 12660
ccttgtgggg tcagttccgg ctgggggttc agcagccagc gctttactgg catttcagga 12720
acaagcgggc actgctcgac gcacttgctt cgctcagtat cgctcgggac gcacggcgcg 12780
ctctacgaac tgccgataaa cagaggatta aaattgacaa ttcaatggca aggactgcca 12840
gcgctgccat ttttggggtg aggccgttcg cggccgaggg gcgcagcccc tggggggatg 12900
ggaggcccgc gttagcgggc cgggagggtt cgagaagggg gggcaccccc cttcggcgtg 12960
cgcggtcacg cgcacagggc gcagccctgg ttaaaaacaa ggtttataaa tattggttta 13020
aaagcaggtt aaaagacagg ttagcggtgg ccgaaaaacg ggcggaaacc cttgcaaatg 13080
ctggattttc tgcctgtgga cagcccctca aatgtcaata ggtgcgcccc tcatctgtca 13140
gcactctgcc cctcaagtgt caaggatcgc gcccctcatc tgtcagtagt cgcgcccctc 13200
aagtgtcaat accgcagggc acttatcccc aggcttgtcc acatcatctg tgggaaactc 13260
gcgtaaaatc aggcgttttc gccgatttgc gaggctggcc agctccacgt cgccggccga 13320
aatcgagcct gcccctcatc tgtcaacgcc gcgccgggtg agtcggcccc tcaagtgtca 13380
acgtccgccc ctcatctgtc agtgagggcc aagttttccg cgaggtatcc acaacgccgg 13440
cggccgcggt gtctcgcaca cggcttcgac ggcgtttctg gcgcgtttgc agggccatag 13500
acggccgcca gcccagcggc gagggcaacc agcccggtga gcgtcgcaaa ggcgctcggt 13560
cttgccttgc tcgtcgagat ctggggtcga tcagccgggg atgcatcagg ccgacagtcg 13620
gaacttcggg tccccgacct gtaccattcg gtgagcaatg gataggggag ttgatatcgt 13680
caacgttcac ttctaaagaa atagcgccac tcagcttcct cagcggcttt atccagcgat 13740
ttcctattat gtcggcatag ttctcaagat cgacagcctg tcacggttaa gcgagaaatg 13800
aataagaagg ctgataattc ggatctctgc gagggagatg atatttgatc acaggcagca 13860
acgctctgtc atcgttacaa tcaacatgct accctccgcg agatcatccg tgtttcaaac 13920
ccggcagctt agttgccgtt cttccgaata gcatcggtaa catgagcaaa gtctgccgcc 13980
ttacaacggc tctcccgctg acgccgtccc ggactgatgg gctgcctgta tcgagtggtg 14040
attttgtgcc gagctgccgg tcggggagct gttggctggc tggtggcagg atatattgtg 14100
gtgtaaacaa attgacgctt agacaactta ataacacatt gcggacgttt ttaatgtact 14160
ggggtggttt ttcttttcac cagtgagacg ggcaacagct gattgccctt caccgcctgg 14220
ccctgagaga gttgcagcaa gcggtccacg ctggtttgcc ccagcaggcg aaaatcctgt 14280
ttgatggtgg ttccgaaatc ggcaaaatcc cttataaatc aaaagaatag cccgagatag 14340
ggttgagtgt tgttccagtt tggaacaaga gtccactatt aaagaacgtg gactccaacg 14400
tcaaagggcg aaaaaccgtc tatcagggcg atggcccact acgtgaacca tcacccaaat 14460
caagtttttt ggggtcgagg tgccgtaaag cactaaatcg gaaccctaaa gggagccccc 14520
gatttagagc ttgacgggga aagccggcga acgtggcgag aaaggaaggg aagaaagcga 14580
aaggagcggg cgccattcag gctgcgcaac tgttgggaag gg 14622

<210> SEQ ID NO 31
<211> LENGTH: 14712
<212> TYPE: DNA
<213> ORGANISM: Artificial Sequence
<220> FEATURE:
<223> OTHER INFORMATION: pBYKEMd2-ZHVLe

<400> SEQUENCE: 31
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980
gctgtccata aaaccgccca gtctagctat cgccatgtaa gcccactgca agctacctgc 2040
tttctctttg cgcttgcgtt ttcccttgtc cagatagccc agtagctgac attcatccgg 2100
ggtcagcacc gtttctgcgg actggctttc tacgtgttcc gcttccttta gcagcccttg 2160
cgccctgagt gcttgcggca gcgtgaagct ggcgcgccgc tctagcagaa ggcatgttgt 2220
tgtgactccg aggggttgcc tcaaactcta tcttataacc ggcgtggagg catggaggca 2280
agggcatttt ggtaatttaa gtagttagtg gaaaatgacg tcatttactt aaagacgaag 2340
tcttgcgaca aggggggccc acgccgaatt ttaatattac cggcgtggcc ccaccttatc 2400
gcgagtgctt tagcacgagc ggtccagatt taaagtagaa aagttcccgc ccactagggt 2460
taaaggtgtt cacactataa aagcatatac gatgtgatgg tatttgataa agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat ggctaacaag cacctctcat 3420
tgtctctctt ccttgtgctc cttggtcttt ctgcttctct tgcttctggt aagggcgtgt 3480
catactcctt gtgtaccgct gccttcacat tcaccaagat cccggctgaa acactccacg 3540
gaaccgttac cgtggaggtc caatacgccg gtacagatgg accttgcaag gttccagctc 3600
agatggcggt ggacatgcaa actcttaccc cagttggaag gttgattacc gctaaccccg 3660
ttatcactga aagcactgag aactctaaga tgatgttgga acttgatcca ccattcggtg 3720
actcttacat tgtcattggt gtgggagaga agaagatcac ccaccactgg cacaggagtg 3780
gtagcactag tggtggatca ggaggttctg gtggttctgg aggttcagga tccgatgttc 3840
agcttctcga gtctggaggt ggtcttgtgc aacctggagg ttccttgaga ctctcctgtg 3900
cagcttcagg gtttgacttc agtaggtact ggatgagttg ggttcgtcaa gctcctggga 3960
aaggactaga atggattgga gagatcaatc cagattcaag taccatcaac tatactccat 4020
ctctgaagga tcgcttcacc atttccagag acaatgccaa gaacacgttg tatcttcaga 4080
tgaacagctt gaggactgaa gacacagcct tgtactactg cacaagacag ggctatggct 4140

```
acaactactg gggtcaaggc accactgtca cagtgtcttc agctactagt ggtggatcag   4200
gaggttctgg tggttctgga ggttcaggat ccgatgtttt gatgactcaa agccctctct   4260
cacttcctgt gactcttgga cagcccgcat ccatatcttg cagatctagt cagagtattg   4320
ttcatagtaa cggcaacacc tacttggaat ggtatctgca gaaaccaggc cagtctccaa   4380
agcttctgat ctacaaggct tccaatcgtt tctctggtgt cccagacagg tttagtggca   4440
gtggatcagg gactgacttc acattgaaga tcagcagagt tgaggctgaa gatgcgggag   4500
tgtactattg tcttcaaggt tcacatgttc cgtcaacgtt tggaggtggg accaaagtgg   4560
agatcaaggc tagcaccaaa ggtccatcgg tctttccact ggcaccttct tccaagagta   4620
cttctggagg cacagctgca ctgggttgtc ttgtcaagga ctactttcca gaacctgtta   4680
cggtttcgtg gaactcaggt gctctgacca gtggagtgca cacctttcca gctgttcttc   4740
agtcctcagg attgtattct cttagcagtg ttgtgactgt tccatcctca agcttgggca   4800
ctcagaccta catctgcaat gtgaatcaca aacccagcaa caccaaggtt gacaagaaag   4860
ttgagcccaa gtcttgtgac aagactcata cgtgtccacc gtgcccagca cctgaacttc   4920
ttggaggacc gtcagtcttc ttgtttcctc caaagcctaa ggataccttg atgatctcca   4980
ggactcctga agtcacatgt gtagttgtgg atgtgagcca tgaagatcct gaggtgaagt   5040
tcaactggta tgtggatggt gtggaagtgc acaatgccaa gacaaagccg agagaggaac   5100
agtacaacag cacgtacagg gttgtctcag ttctcactgt tctccatcaa gattggttga   5160
atggcaaaga gtacaagtgc aaggtctcca acaaagccct cccagccccc attgagaaga   5220
ccatttccaa agcgaaaggg caaccccgtg aaccacaagt gtacacactt cctccatctc   5280
gcgatgaact gaccaagaac caggtcagct tgacttgcct ggtgaaaggc ttctatccct   5340
ctgacatagc tgtagagtgg gagagcaatg ggcaaccgga gaacaactac aagactacac   5400
ctcccgttct cgattctgac ggctccttct tcctctacag caagctcaca gtggacaaga   5460
gcaggtggca acaagggaat gtcttctcat gctccgtgat gcatgaggct cttcacaatc   5520
actacacaca gaagagtctc tccttgtctc cgggtaaagg aggtggcgga tcaggtggag   5580
gcggttcagg cggaggtgga tcccataaca ctcctgttta caagctggac atatctgagg   5640
caactcaata agagctcgaa gtgacatcac aaagttgaag gtaataaagc caaattaatt   5700
aagacatttt cataatgatg tcaagaatgc aaagcaaatt gcataactgc ctttatgcaa   5760
aacattaata taatataaat tataaagaac tgcgctctct gcttcttatt ttcttagctt   5820
catttattag tcactagctg ttcagaattt tcagtatctt ttgatattac taagaaccta   5880
atcacacaat gtatattctt atgcaggaaa agcagaatgc tgagctaaaa gaaaggcttt   5940
ttccatttc gagagacaat gagaaaagaa gaagaagaag aagaagaaga agaagaagaa   6000
aagagtaaat aataaagccc cacaggaggc gaagttcttg tagctccatg ttatctaagt   6060
tattgatatt gtttgcccta tattttattt ctgtcattgt gtatgttttg ttcagtttcg   6120
atctccttgc aaaatgcaga gattatgaga tgaataaact aagttatatt attatacgtg   6180
ttaatattct cctcctctct ctagctagcc ttttgttttc tctttttctt atttgatttt   6240
ctttaaatca atccatttta ggagagggcc agggagtgat ccagcaaaac atgaagatta   6300
gaagaaactt ccctcttttt tttcctgaaa acaatttaac gtcgagattt atctcttttt   6360
gtaatggaat catttctaca gttatgacga attgtacatc aacgaaaaat tagtcaaacg   6420
actaaaataa ataaatatca tgtgttatta agaaaattct cctataagaa tattttaata   6480
gatcatatgt ttgtaaaaaa aattaatttt tactaacaca tatatttact tatcaaaaat   6540
```

```
ttgacaaagt aagattaaaa taatattcat ctaacaaaaa aaaaaccaga aaatgctgaa   6600
aacccggcaa aaccgaacca atccaaaccg atatagttgg tttggtttga ttttgatata   6660
aaccgaacca actcggtcca tttgcacccc taatcataat agctttaata tttcaagata   6720
ttattaagtt aacgttgtca atatcctgga aattttgcaa aatgaatcaa gcctatatgg   6780
ctgtaatatg aatttaaaag cagctcgatg tggtggtaat atgtaattta cttgattcta   6840
aaaaaatatc ccaagtatta ataatttctg ctaggaagaa ggttagctac gatttacagc   6900
aaagccagaa tacaaagaac cataaagtga ttgaagctcg aaatatacga aggaacaaat   6960
atttttaaaa aaatacgcaa tgacttggaa caaaagaaag tgatatattt tttgttctta   7020
aacaagcatc ccctctaaag aatggcagtt ttcctttgca tgtaactatt atgctccctt   7080
cgttacaaaa attttggact actattggga acttcttctg aaaatagtgg taccgagtgt   7140
acttcaagtc agttggaaat caataaaatg attattttat gaatatattt cattgtgcaa   7200
gtagatagaa attacatatg ttacataaca cacgaaataa acaaaaaaac acaatccaaa   7260
acaaacaccc caaacaaaat aacactatat atatcctcgt atgaggagag gcacgttcag   7320
tgactcgacg attcccgagc aaaaaaagtc tccccgtcac acatatagtg ggtgacgcaa   7380
ttatcttcaa agtaatcctt ctgttgactt gtcattgata acatccagtc ttcgtcagga   7440
ttgcaaagaa ttatagaagg gatcccacct tttattttct tctttttcc atatttaggg   7500
ttgacagtga aatcagactg gcaacctatt aattgcttcc acaatgggac gaacttgaag   7560
gggatgtcgt cgatgatatt ataggtggcg tgttcatcgt agttggtgaa gtcgatggtc   7620
ccgttccagt agttgtgtcg cccgagactt ctagcccagg tggtctttcc ggtacgagtt   7680
ggtccgcaga tgtagaggct ggggtgtctg accccagtcc ttccctcatc ctggttagat   7740
cggccatcca ctcaaggtca gattgtgctt gatcgtagga gacaggatgt atgaaagtgt   7800
aggcatcgat gcttacatga tataggtgcg tctctctcca gttgtgcaga tcttcgtggc   7860
agcggagatc tgattctgtg aagggcgaca cgtactgctc aggttgtgga ggaaataatt   7920
tgttggctga atattccagc cattgaagct ttgttgccca ttcatgaggg aactcttctt   7980
tgatcatgtc aagatactcc tccttagacg ttgcagtctg gataatagtt cgccatcgtg   8040
cgtcagattt gcgaggagac accttatgat ctcggaaatc tcctctggtt ttaatatctc   8100
cgtcctttga tatgtaatca aggacttgtt tagagtttct agctggctgg atattagggt   8160
gatttccttc aaaatcgaaa aaagaaggat ccctaataca aggtttttta tcaagctgga   8220
taagagcatg atagtgggta gtgccatctt gatgaagctc agaagcaaca ccaaggaaga   8280
aaataagaaa aggtgtgagt ttctcccaga gaaactggaa taaatcatct ctttgagatg   8340
agcacttggg gtaggtaagg aaaacatatt tagattggag tctgaagttc ttgctagcag   8400
aaggcatgtt gttgtgactc cgaggggttg cctcaaactc tatcttataa ccggcgtgga   8460
ggcatggagg caagggcatt ttggtaattt aagtagttag tggaaaatga cgtcatttac   8520
ttaaagacga agtcttgcga caaggggggc ccacgccgaa ttttaatatt accggcgtgg   8580
ccccacctta tcgcgagtgc tttagcacga gcggtccaga tttaaagtag aaaagttccc   8640
gcccactagg gttaaaggtg ttcacactat aaaagcatat acgatgtgat ggtatttgat   8700
ggagcgtata ttgtatcagg tatttccgtc ggatacgaat tattcgtacg gccggaccgg   8760
tcccctaggc cggccaattc gagatcggcc gcggctgagt ggctccttca atcgttgcgg   8820
ttctgtcagt tccaaacgta aaacggcttg tcccgcgtca tcggcggggg tcataacgtg   8880
```

```
actcccttaa ttctccgctc atgatcagat tgtcgtttcc cgccttcagt ttaaactatc   8940
agtgtttgac aggatatatt ggcgggtaaa cctaagagaa aagagcgttt attagaataa   9000
tcggatattt aaaagggcgt gaaaaggttt atccgttcgt ccatttgtat gtgcatgcca   9060
accacagggt tccccagatc tggcgccggc cagcgagacg agcaagattg gccgccgccc   9120
gaaacgatcc gacagcgcgc ccagcacagg tgcgcaggca aattgcacca acgcatacag   9180
cgccagcaga atgccatagt gggcggtgac gtcgttcgag tgaaccagat cgcgcaggag   9240
gcccggcagc accggcataa tcaggccgat gccgacagcg tcgagcgcga cagtgctcag   9300
aattacgatc aggggtatgt tgggtttcac gtctggcctc cggagactgt catacgcgta   9360
aaaaggccgc gttgctggcg tttttccata ggctccgccc ccctgacgag catcacaaaa   9420
atcgacgctc aagtcagagg tggcgaaacc cgacaggact ataaagatac caggcgtttc   9480
cccctggaag ctccctcgtg cgctctcctg ttccgaccct gccgcttacc ggatacctgt   9540
ccgcctttct cccttcggga agcgtggcgc tttctcatag ctcacgctgt aggtatctca   9600
gttcggtgta ggtcgttcgc tccaagctgg gctgtgtgca cgaacccccc gttcagcccg   9660
accgctgcgc cttatccggt aactatcgtc ttgagtccaa cccggtaaga cacgacttat   9720
cgccactggc agcagccact ggtaacagga ttagcagagc gaggtatgta ggcggtgcta   9780
cagagttctt gaagtggtgg cctaactacg gctacactag aaggacagta tttggtatct   9840
gcgctctgct gaagccagtt accttcggaa aaagagttgg tagctcttga tccggcaaac   9900
aaaccaccgc tggtagcggt ggtttttttg tttgcaagca gcagattacg cgcagaaaaa   9960
aaggatctca agaagatcct ttgatctttt ctacggggtc tgacgctcag tggaacgaaa  10020
actcacgtta agggattttg gtcatgagat tatcaaaaag gatcttcacc tagatccttt  10080
taaattaaaa atgaagtttt aaatcaatct aaagtatata tgagtaaact tggtctgcag  10140
ttgccatgtt ttacggcagt gagagcagag atagcgctga tgtccggcgg tgcttttgcc  10200
gttacgcacc accccgtcag tagctgaaca ggagggacag ctgatagaca cagaagccac  10260
tggagcacct caaaaacacc atcatacact aaatcagtaa gttggcagca tcacccataa  10320
ttgtggtttc aaaatcggct ccgtcgatac tatgttatac gccaactttg aaaacaactt  10380
tgaaaaagct gttttctggt atttaaggtt ttagaatgca aggaacagtg aattggagtt  10440
cgtcttgtta taattagctt cttggggtat ctttaaatac tgtagaaaag aggaaggaaa  10500
taataaatgg ctaaaatgag aatatcaccg gaattgaaaa aactgatcga aaaataccgc  10560
tgcgtaaaag atacggaagg aatgtctcct gctaaggtat ataagctggt gggagaaaat  10620
gaaaacctat atttaaaaat gacggacagc cggtataaag ggaccaccta tgatgtggaa  10680
cgggaaaagg acatgatgct atggctggaa ggaaagctgc ctgttccaaa ggtcctgcac  10740
tttgaacggc atgatggctg gagcaatctg ctcatgagtg aggccgatgg cgtcctttgc  10800
tcggaagagt atgaagatga acaaagccct gaaaagatta tcgagctgta tgcggagtgc  10860
atcaggctct ttcactccat cgacatatcg gattgtccct atacgaatag cttagacagc  10920
cgcttagccg aattggatta cttactgaat aacgatctgg ccgatgtgga ttgcgaaaac  10980
tgggaagaag acactccatt taaagatccg cgcgagctgt atgatttttt aaagacggaa  11040
aagcccgaag aggaacttgt cttttcccac ggcgacctgg gagacagcaa catctttgtg  11100
aaagatggca aagtaagtgg ctttattgat cttgggagaa gcggcagggc ggacaagtgg  11160
tatgacattg ccttctgcgt ccggtcgatc agggaggata tcggggaaga acagtatgtc  11220
gagctatttt ttgacttact ggggatcaag cctgattggg agaaaataaa atattatatt  11280
```

```
ttactggatg aattgtttta gtacctagat gtggcgcaac gatgccggcg acaagcagga  11340
gcgcaccgac ttcttccgca tcaagtgttt tggctctcag gccgaggccc acggcaagta  11400
tttgggcaag ggtcgctgg tattcgtgca gggcaagatt cggaatacca agtacgagaa  11460
ggacggccag acggtctacg ggaccgactt cattgccgat aaggtggatt atctggacac  11520
caaggcacca ggcgggtcaa atcaggaata agggcacatt gccccggcgt gagtcggggc  11580
aatcccgcaa ggagggtgaa tgaatcggac gtttgaccgg aaggcataca ggcaagaact  11640
gatcgacgcg gggttttccg ccgaggatgc cgaaaccatc gcaagccgca ccgtcatgcg  11700
tgcgccccgc gaaaccttcc agtccgtcgg ctcgatggtc cagcaagcta cggccaagat  11760
cgagcgcgac agcgtgcaac tggctccccc tgccctgccc gcgccatcgg ccgccgtgga  11820
gcgttcgcgt cgtctcgaac aggaggcggc aggtttggcg aagtcgatga ccatcgacac  11880
gcgaggaact atgacgacca agaagcgaaa aaccgccggc gaggacctgg caaaacaggt  11940
cagcgaggcc aagcaggccg cgttgctgaa acacacgaag cagcagatca aggaaatgca  12000
gctttccttg ttcgatattg cgccgtggcc ggacacgatg cgagcgatgc caaacgacac  12060
ggcccgctct gccctgttca ccacgcgcaa caagaaaatc ccgcgcgagg cgctgcaaaa  12120
caaggtcatt ttccacgtca acaaggacgt gaagatcacc tacaccggcg tcgagctgcg  12180
ggccgacgat gacgaactgg tgtggcagca ggtgttggag tacgcgaagc gcacccctat  12240
cggcgagccg atcaccttca cgttctacga gctttgccag gacctgggct ggtcgatcaa  12300
tggccggtat tacacgaagg ccgaggaatg cctgtcgcgc ctacaggcga cggcgatggg  12360
cttcacgtcc gaccgcgttg ggcacctgga atcggtgtcg ctgctgcacc gcttccgcgt  12420
cctggaccgt ggcaagaaaa cgtcccgttg ccaggtcctg atcgacgagg aaatcgtcgt  12480
gctgtttgct ggcgaccact acacgaaatt catatgggag aagtaccgca agctgtcgcc  12540
gacggcccga cggatgttcg actatttcag ctcgcaccgg gagccgtacc cgctcaagct  12600
ggaaaccttc cgcctcatgt gcggatcgga ttccacccgc gtgaagaagt ggcgcgagca  12660
ggtcggcgaa gcctgcgaag agttgcgagg cagcggcctg gtggaacacg cctgggtcaa  12720
tgatgacctg gtgcattgca aacgctaggg ccttgtgggg tcagttccgg ctgggggttc  12780
agcagccagc gctttactgg catttcagga acaagcgggc actgctcgac gcacttgctt  12840
cgctcagtat cgctcgggac gcacggcgcg ctctacgaac tgccgataaa cagaggatta  12900
aaattgacaa ttcaatggca aggactgcca gcgctgccat ttttggggtg aggccgttcg  12960
cggccgaggg gcgcagcccc tggggggatg ggaggcccgc gttagcgggc cgggagggtt  13020
cgagaagggg gggcaccccc cttcggcgtg cgcggtcacg cgcacagggc gcagccctgg  13080
ttaaaaacaa ggtttataaa tattggttta aaagcaggtt aaaagacagg ttagcggtgg  13140
ccgaaaaacg ggcggaaacc cttgcaaatg ctggattttc tgcctgtgga cagcccctca  13200
aatgtcaata ggtgcgcccc tcatctgtca gcactctgcc cctcaagtgt caaggatcgc  13260
gcccctcatc tgtcagtagt cgcgcccctc aagtgtcaat accgcagggc acttatcccc  13320
aggcttgtcc acatcatctg tgggaaactc gcgtaaaatc aggcgttttc gccgatttgc  13380
gaggctggcc agctccacgt cgccggccga aatcgagcct gcccctcatc tgtcaacgcc  13440
gcgccgggtg agtcggcccc tcaagtgtca acgtccgccc ctcatctgtc agtgagggcc  13500
aagttttccg cgaggtatcc acaacgccgg cggccgcggt gtctcgcaca cggcttcgac  13560
ggcgtttctg gcgcgtttgc agggccatag acggccgcca gcccagcggc gagggcaacc  13620
```

agcccggtga gcgtcgcaaa ggcgctcggt cttgccttgc tcgtcgagat ctggggtcga 13680
tcagccgggg atgcatcagg ccgacagtcg gaacttcggg tccccgacct gtaccattcg 13740
gtgagcaatg gataggggag ttgatatcgt caacgttcac ttctaaagaa atagcgccac 13800
tcagcttcct cagcggcttt atccagcgat ttcctattat gtcggcatag ttctcaagat 13860
cgacagcctg tcacggttaa gcgagaaatg aataagaagg ctgataattc ggatctctgc 13920
gagggagatg atatttgatc acaggcagca acgctctgtc atcgttacaa tcaacatgct 13980
accctccgcg agatcatccg tgtttcaaac ccggcagctt agttgccgtt cttccgaata 14040
gcatcggtaa catgagcaaa gtctgccgcc ttacaacggc tctcccgctg acgccgtccc 14100
ggactgatgg gctgcctgta tcgagtggtg attttgtgcc gagctgccgg tcggggagct 14160
gttggctggc tggtggcagg atatattgtg gtgtaaacaa attgacgctt agacaactta 14220
ataacacatt gcggacgttt ttaatgtact ggggtggttt ttcttttcac cagtgagacg 14280
ggcaacagct gattgccctt caccgcctgg ccctgagaga gttgcagcaa gcggtccacg 14340
ctggtttgcc ccagcaggcg aaaatcctgt ttgatggtgg ttccgaaatc ggcaaaatcc 14400
cttataaatc aaaagaatag cccgagatag ggttgagtgt tgttccagtt tggaacaaga 14460
gtccactatt aaagaacgtg gactccaacg tcaaagggcg aaaaaccgtc tatcagggcg 14520
atggcccact acgtgaacca tcacccaaat caagtttttt ggggtcgagg tgccgtaaag 14580
cactaaatcg gaaccctaaa gggagccccc gatttagagc ttgacgggga aagccggcga 14640
acgtggcgag aaaggaaggg aagaaagcga aaggagcggg cgccattcag gctgcgcaac 14700
tgttgggaag gg 14712

<210> SEQ ID NO 32
<211> LENGTH: 14622
<212> TYPE: DNA
<213> ORGANISM: Artificial Sequence
<220> FEATURE:
<223> OTHER INFORMATION: pBYKEMd2- ZHVLhx

<400> SEQUENCE: 32
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960

```
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
```

```
catttcattt ggagaggacc tcgagaaaca aacaaaatca acaaatatag aaaataacgc   3360
atttccaatt ctttgaaatt tctgcaacat ctagaacaat ggctaacaag cacctctcat   3420
tgtctctctt ccttgtgctc cttggtcttt ctgcttctct tgcttctggt aagggcgtgt   3480
catactcctt gtgtaccgct gccttcacat tcaccaagat cccggctgaa acactccacg   3540
gaaccgttac cgtggaggtc caatacgccg gtacagatgg accttgcaag gttccagctc   3600
agatggcggt ggacatgcaa actcttaccc cagttggaag gttgattacc gctaaccccg   3660
ttatcactga aagcactgag aactctaaga tgatgttgga acttgatcca ccattcggtg   3720
actcttacat tgtcattggt gtgggagaga agaagatcac ccaccactgg cacaggagtg   3780
gtagcactag tggtggatca ggaggttctg gtggttctgg aggttcagga tccgatgttc   3840
agcttctcga gtctggaggt ggtcttgtgc aacctggagg ttccttgaga ctctcctgtg   3900
cagcttcagg gtttgacttc agtaggtact ggatgagttg ggttcgtcaa gctcctggga   3960
aaggactaga atggattgga gagatcaatc cagattcaag taccatcaac tatactccat   4020
ctctgaagga tcgcttcacc atttccagag acaatgccaa gaacacgttg tatcttcaga   4080
tgaacagctt gaggactgaa gacacagcct tgtactactg cacaagacag ggctatggct   4140
acaactactg gggtcaaggc accactgtca cagtgtcttc agctactagt ggtggatcag   4200
gaggttctgg tggttctgga ggttcaggat ccgatgtttt gatgactcaa agccctctct   4260
cacttcctgt gactcttgga cagcccgcat ccatatcttg cagatctagt cagagtattg   4320
ttcatagtaa cggcaacacc tacttggaat ggtatctgca gaaaccaggc cagtctccaa   4380
agcttctgat ctacaaggct tccaatcgtt tctctggtgt cccagacagg tttagtggca   4440
gtggatcagg gactgacttc acattgaaga tcagcagagt tgaggctgaa gatgcgggag   4500
tgtactattg tcttcaaggt tcacatgttc cgtcaacgtt tggaggtggg accaaagtgg   4560
agatcaaggc tagcaccaaa ggtccatcgg tctttccact ggcaccttct tccaagagta   4620
cttctggagg cacagctgca ctgggttgtc ttgtcaagga ctactttcca gaacctgtta   4680
cggtttcgtg gaactcaggt gctctgacca gtggagtgca cacctttcca gctgttcttc   4740
agtcctcagg attgtattct cttagcagtg ttgtgactgt tccatcctca agcttgggca   4800
ctcagaccta catctgcaat gtgaatcaca aacccagcaa caccaaggtt gacaagaaag   4860
ttgagcccaa gtcttgtgac aagactcata cgtgtccacc gtgcccagca cctgaacttc   4920
ttggaggacc gtcagtcttc ttgtttcctc caaagcctaa ggataccttg atgatctcca   4980
ggactcctga agtcacatgt gtagttgtgg atgtgagcca tgaagatcct gaggtgaagt   5040
tcaactggta tgtggatggt gtggaagtgc acaatgccaa gacaaagccg agagaggaac   5100
agtacaacag cacgtacagg gttgtctcag ttctcactgt tctccatcaa gattggttga   5160
atggcaaaga gtacaagtgc aaggtctcca acaaagccct cccagctcct attgagaaga   5220
ccatctctaa agccaagggt caaccgcgtc gtccacaagt gtacacactt cctccatctc   5280
gcgacgaact caccaagaat caagtcagcc ttacttgtct cgttaagggc ttctatccct   5340
ccgacatcgc tgttgagtgg gagtcaaacg gacaaccgga gaacaattac aagactacac   5400
ctccagtttt ggattccgat ggctccttct tcctctacag caagctcaca gtggacaaat   5460
ctaggtggca acaaggcaac gtcttctcat gctccgtgat gcatggagcc cttcacaatc   5520
actacacaca gaagtacctc tccttgtctc cgggaaagtg agagctcgaa gtgacatcac   5580
aaagttgaag gtaataaagc caaattaatt aagacatttt cataatgatg tcaagaatgc   5640
aaagcaaatt gcataactgc ctttatgcaa aacattaata taatataaat tataaagaac   5700
```

```
tgcgctctct gcttcttatt ttcttagctt catttattag tcactagctg ttcagaattt   5760
tcagtatctt ttgatattac taagaaccta atcacacaat gtatattctt atgcaggaaa   5820
agcagaatgc tgagctaaaa gaaaggcttt ttccattttc gagagacaat gagaaaagaa   5880
gaagaagaag aagaagaaga agaagaagaa aagagtaaat aataaagccc cacaggaggc   5940
gaagttcttg tagctccatg ttatctaagt tattgatatt gtttgcccta tattttattt   6000
ctgtcattgt gtatgttttg ttcagtttcg atctccttgc aaaatgcaga gattatgaga   6060
tgaataaact aagttatatt attatacgtg ttaatattct cctcctctct ctagctagcc   6120
ttttgttttc tctttttctt atttgatttt ctttaaatca atccatttta ggagagggcc   6180
agggagtgat ccagcaaaac atgaagatta gaagaaactt ccctcttttt tttcctgaaa   6240
acaatttaac gtcgagattt atctcttttt gtaatggaat catttctaca gttatgacga   6300
attgtacatc aacgaaaaat tagtcaaacg actaaaataa ataaatatca tgtgttatta   6360
agaaaattct cctataagaa tattttaata gatcatatgt ttgtaaaaaa aattaatttt   6420
tactaacaca tatatttact tatcaaaaat ttgacaaagt aagattaaaa taatattcat   6480
ctaacaaaaa aaaaaccaga aaatgctgaa aacccggcaa aaccgaacca atccaaaccg   6540
atatagttgg tttggtttga ttttgatata aaccgaacca actcggtcca tttgcacccc   6600
taatcataat agctttaata tttcaagata ttattaagtt aacgttgtca atatcctgga   6660
aattttgcaa aatgaatcaa gcctatatgg ctgtaatatg aatttaaaag cagctcgatg   6720
tggtggtaat atgtaattta cttgattcta aaaaaatatc ccaagtatta ataatttctg   6780
ctaggaagaa ggttagctac gatttacagc aaagccagaa tacaaagaac cataaagtga   6840
ttgaagctcg aaatatacga aggaacaaat atttttaaaa aaatacgcaa tgacttggaa   6900
caaaagaaag tgatatattt tttgttctta aacaagcatc ccctctaaag aatggcagtt   6960
ttcctttgca tgtaactatt atgctccctt cgttacaaaa attttggact actattggga   7020
acttcttctg aaaatagtgg taccgagtgt acttcaagtc agttggaaat caataaaatg   7080
attattttat gaatatattt cattgtgcaa gtagatagaa attacatatg ttacataaca   7140
cacgaaataa acaaaaaaac acaatccaaa acaaacaccc caaacaaaat aacactatat   7200
atatcctcgt atgaggagag gcacgttcag tgactcgacg attcccgagc aaaaaaagtc   7260
tccccgtcac acatatagtg ggtgacgcaa ttatcttcaa agtaatcctt ctgttgactt   7320
gtcattgata acatccagtc ttcgtcagga ttgcaaagaa ttatagaagg gatcccacct   7380
tttattttct tctttttcc atatttaggg ttgacagtga aatcagactg gcaacctatt   7440
aattgcttcc acaatgggac gaacttgaag gggatgtcgt cgatgatatt ataggtggcg   7500
tgttcatcgt agttggtgaa gtcgatggtc ccgttccagt agttgtgtcg cccgagactt   7560
ctagcccagg tggtctttcc ggtacgagtt ggtccgcaga tgtagaggct ggggtgtctg   7620
accccagtcc ttccctcatc ctggttagat cggccatcca ctcaaggtca gattgtgctt   7680
gatcgtagga gacaggatgt atgaaagtgt aggcatcgat gcttacatga tataggtgcg   7740
tctctctcca gttgtgcaga tcttcgtggc agcggagatc tgattctgtg aagggcgaca   7800
cgtactgctc aggttgtgga ggaaataatt tgttggctga atattccagc cattgaagct   7860
ttgttgccca ttcatgaggg aactcttctt tgatcatgtc aagatactcc tccttagacg   7920
ttgcagtctg gataatagtt cgccatcgtg cgtcagattt gcgaggagac accttatgat   7980
ctcggaaatc tcctctggtt ttaatatctc cgtcctttga tatgtaatca aggacttgtt   8040
```

```
tagagtttct agctggctgg atattagggt gatttccttc aaaatcgaaa aaagaaggat   8100
ccctaataca aggtttttta tcaagctgga taagagcatg atagtgggta gtgccatctt   8160
gatgaagctc agaagcaaca ccaaggaaga aaataagaaa aggtgtgagt ttctcccaga   8220
gaaactggaa taaatcatct ctttgagatg agcacttggg gtaggtaagg aaaacatatt   8280
tagattggag tctgaagttc ttgctagcag aaggcatgtt gttgtgactc cgaggggttg   8340
cctcaaactc tatcttataa ccggcgtgga ggcatggagg caagggcatt ttggtaattt   8400
aagtagttag tggaaaatga cgtcatttac ttaaagacga agtcttgcga caagggggc   8460
ccacgccgaa ttttaatatt accggcgtgg ccccacctta tcgcgagtgc tttagcacga   8520
gcggtccaga tttaaagtag aaaagttccc gcccactagg gttaaaggtg ttcacactat   8580
aaaagcatat acgatgtgat ggtatttgat ggagcgtata ttgtatcagg tatttccgtc   8640
ggatacgaat tattcgtacg gccggaccgg tcccctaggc cggccaattc gagatcggcc   8700
gcggctgagt ggctccttca atcgttgcgg ttctgtcagt tccaaacgta aaacggcttg   8760
tcccgcgtca tcggcggggg tcataacgtg actcccttaa ttctccgctc atgatcagat   8820
tgtcgtttcc cgccttcagt ttaaactatc agtgtttgac aggatatatt ggcgggtaaa   8880
cctaagagaa aagagcgttt attagaataa tcggatattt aaaagggcgt gaaaaggttt   8940
atccgttcgt ccatttgtat gtgcatgcca accacagggt tccccagatc tggcgccggc   9000
cagcgagacg agcaagattg gccgccgccc gaaacgatcc gacagcgcgc ccagcacagg   9060
tgcgcaggca aattgcacca acgcatacag cgccagcaga atgccatagt gggcggtgac   9120
gtcgttcgag tgaaccagat cgcgcaggag gcccggcagc accggcataa tcaggccgat   9180
gccgacagcg tcgagcgcga cagtgctcag aattacgatc aggggtatgt tgggtttcac   9240
gtctggcctc cggagactgt catacgcgta aaaaggccgc gttgctggcg tttttccata   9300
ggctccgccc ccctgacgag catcacaaaa atcgacgctc aagtcagagg tggcgaaacc   9360
cgacaggact ataaagatac caggcgtttc cccctggaag ctccctcgtg cgctctcctg   9420
ttccgaccct gccgcttacc ggatacctgt ccgcctttct cccttcggga agcgtggcgc   9480
tttctcatag ctcacgctgt aggtatctca gttcggtgta ggtcgttcgc tccaagctgg   9540
gctgtgtgca cgaacccccc gttcagcccg accgctgcgc cttatccggt aactatcgtc   9600
ttgagtccaa cccggtaaga cacgacttat cgccactggc agcagccact ggtaacagga   9660
ttagcagagc gaggtatgta ggcggtgcta cagagttctt gaagtggtgg cctaactacg   9720
gctacactag aaggacagta tttggtatct gcgctctgct gaagccagtt accttcggaa   9780
aaagagttgg tagctcttga tccggcaaac aaaccaccgc tggtagcggt ggtttttttg   9840
tttgcaagca gcagattacg cgcagaaaaa aaggatctca agaagatcct ttgatctttt   9900
ctacggggtc tgacgctcag tggaacgaaa actcacgtta agggattttg gtcatgagat   9960
tatcaaaaag gatcttcacc tagatccttt taaattaaaa atgaagtttt aaatcaatct  10020
aaagtatata tgagtaaact tggtctgcag ttgccatgtt ttacggcagt gagagcagag  10080
atagcgctga tgtccggcgg tgcttttgcc gttacgcacc accccgtcag tagctgaaca  10140
ggagggacag ctgatagaca cagaagccac tggagcacct caaaaacacc atcatacact  10200
aaatcagtaa gttggcagca tcacccataa ttgtggtttc aaaatcggct ccgtcgatac  10260
tatgttatac gccaactttg aaaacaactt tgaaaaagct gttttctggt atttaaggtt  10320
ttagaatgca aggaacagtg aattggagtt cgtcttgtta taattagctt cttggggtat  10380
ctttaaatac tgtagaaaag aggaaggaaa taataaatgg ctaaaatgag aatatcaccg  10440
```

```
gaattgaaaa aactgatcga aaaataccgc tgcgtaaaag atacggaagg aatgtctcct  10500
gctaaggtat ataagctggt gggagaaaat gaaaacctat atttaaaaat gacggacagc  10560
cggtataaag ggaccaccta tgatgtggaa cgggaaaagg acatgatgct atggctggaa  10620
ggaaagctgc ctgttccaaa ggtcctgcac tttgaacggc atgatggctg gagcaatctg  10680
ctcatgagtg aggccgatgg cgtcctttgc tcggaagagt atgaagatga acaaagccct  10740
gaaaagatta tcgagctgta tgcggagtgc atcaggctct ttcactccat cgacatatcg  10800
gattgtccct atacgaatag cttagacagc cgcttagccg aattggatta cttactgaat  10860
aacgatctgg ccgatgtgga ttgcgaaaac tgggaagaag acactccatt taaagatccg  10920
cgcgagctgt atgatttttt aaagacggaa aagcccgaag aggaacttgt cttttcccac  10980
ggcgacctgg gagacagcaa catctttgtg aaagatggca aagtaagtgg ctttattgat  11040
cttgggagaa gcggcagggc ggacaagtgg tatgacattg ccttctgcgt ccggtcgatc  11100
agggaggata tcggggaaga acagtatgtc gagctatttt ttgacttact ggggatcaag  11160
cctgattggg agaaaataaa atattatatt ttactggatg aattgtttta gtacctagat  11220
gtggcgcaac gatgccggcg acaagcagga gcgcaccgac ttcttccgca tcaagtgttt  11280
tggctctcag gccgaggccc acggcaagta tttgggcaag gggtcgctgg tattcgtgca  11340
gggcaagatt cggaatacca agtacgagaa ggacggccag acggtctacg ggaccgactt  11400
cattgccgat aaggtggatt atctggacac caaggcacca ggcgggtcaa atcaggaata  11460
agggcacatt gccccggcgt gagtcggggc aatcccgcaa ggagggtgaa tgaatcggac  11520
gtttgaccgg aaggcataca ggcaagaact gatcgacgcg gggttttccg ccgaggatgc  11580
cgaaaccatc gcaagccgca ccgtcatgcg tgcgccccgc gaaaccttcc agtccgtcgg  11640
ctcgatggtc cagcaagcta cggccaagat cgagcgcgac agcgtgcaac tggctccccc  11700
tgccctgccc gcgccatcgg ccgccgtgga gcgttcgcgt cgtctcgaac aggaggcggc  11760
aggtttggcg aagtcgatga ccatcgacac gcgaggaact atgacgacca agaagcgaaa  11820
aaccgccggc gaggacctgg caaaacaggt cagcgaggcc aagcaggccg cgttgctgaa  11880
acacacgaag cagcagatca aggaaatgca gctttccttg ttcgatattg cgccgtggcc  11940
ggacacgatg cgagcgatgc caaacgacac ggcccgctct gccctgttca ccacgcgcaa  12000
caagaaaatc ccgcgcgagg cgctgcaaaa caaggtcatt ttccacgtca acaaggacgt  12060
gaagatcacc tacaccggcg tcgagctgcg ggccgacgat gacgaactgg tgtggcagca  12120
ggtgttggag tacgcgaagc gcacccctat cggcgagccg atcaccttca cgttctacga  12180
gctttgccag gacctgggct ggtcgatcaa tggccggtat tacacgaagg ccgaggaatg  12240
cctgtcgcgc ctacaggcga cggcgatggg cttcacgtcc gaccgcgttg ggcacctgga  12300
atcggtgtcg ctgctgcacc gcttccgcgt cctggaccgt ggcaagaaaa cgtcccgttg  12360
ccaggtcctg atcgacgagg aaatcgtcgt gctgtttgct ggcgaccact acacgaaatt  12420
catatgggag aagtaccgca agctgtcgcc gacggcccga cggatgttcg actatttcag  12480
ctcgcaccgg gagccgtacc cgctcaagct ggaaaccttc cgcctcatgt gcggatcgga  12540
ttccacccgc gtgaagaagt ggcgcgagca ggtcggcgaa gcctgcgaag agttgcgagg  12600
cagcggcctg gtggaacacg cctgggtcaa tgatgacctg gtgcattgca aacgctaggg  12660
ccttgtgggg tcagttccgg ctgggggttc agcagccagc gctttactgg catttcagga  12720
acaagcgggc actgctcgac gcacttgctt cgctcagtat cgctcgggac gcacggcgcg  12780
```

ctctacgaac tgccgataaa cagaggatta aaattgacaa ttcaatggca aggactgcca 12840
gcgctgccat ttttggggtg aggccgttcg cggccgaggg gcgcagcccc tgggggggatg 12900 ggaggcccgc gttagcgggc cgggagggtt cgagaagggg gggcaccccc cttcggcgtg 12960
cgcggtcacg cgcacagggc gcagccctgg ttaaaaacaa ggtttataaa tattggttta 13020
aaagcaggtt aaaagacagg ttagcggtgg ccgaaaaacg ggcggaaacc cttgcaaatg 13080
ctggattttc tgcctgtgga cagcccctca aatgtcaata ggtgcgcccc tcatctgtca 13140
gcactctgcc cctcaagtgt caaggatcgc gcccctcatc tgtcagtagt cgcgcccctc 13200
aagtgtcaat accgcagggc acttatcccc aggcttgtcc acatcatctg tgggaaactc 13260
gcgtaaaatc aggcgttttc gccgatttgc gaggctggcc agctccacgt cgccggccga 13320
aatcgagcct gcccctcatc tgtcaacgcc gcgccgggtg agtcggcccc tcaagtgtca 13380
acgtccgccc ctcatctgtc agtgagggcc aagttttccg cgaggtatcc acaacgccgg 13440
cggccgcggt gtctcgcaca cggcttcgac ggcgtttctg gcgcgtttgc agggccatag 13500
acggccgcca gcccagcggc gagggcaacc agcccggtga gcgtcgcaaa ggcgctcggt 13560
cttgccttgc tcgtcgagat ctggggtcga tcagccgggg atgcatcagg ccgacagtcg 13620
gaacttcggg tccccgacct gtaccattcg gtgagcaatg gataggggag ttgatatcgt 13680
caacgttcac ttctaaagaa atagcgccac tcagcttcct cagcggcttt atccagcgat 13740
ttcctattat gtcggcatag ttctcaagat cgacagcctg tcacggttaa gcgagaaatg 13800
aataagaagg ctgataattc ggatctctgc gagggagatg atatttgatc acaggcagca 13860
acgctctgtc atcgttacaa tcaacatgct accctccgcg agatcatccg tgtttcaaac 13920
ccggcagctt agttgccgtt cttccgaata gcatcggtaa catgagcaaa gtctgccgcc 13980
ttacaacggc tctcccgctg acgccgtccc ggactgatgg gctgcctgta tcgagtggtg 14040
attttgtgcc gagctgccgg tcggggagct gttggctggc tggtggcagg atatattgtg 14100
gtgtaaacaa attgacgctt agacaactta ataacacatt gcggacgttt ttaatgtact 14160
ggggtggttt ttcttttcac cagtgagacg ggcaacagct gattgccctt caccgcctgg 14220
ccctgagaga gttgcagcaa gcggtccacg ctggtttgcc ccagcaggcg aaaatcctgt 14280
ttgatggtgg ttccgaaatc ggcaaaatcc cttataaatc aaaagaatag cccgagatag 14340
ggttgagtgt tgttccagtt tggaacaaga gtccactatt aaagaacgtg gactccaacg 14400
tcaaagggcg aaaaaccgtc tatcagggcg atggcccact acgtgaacca tcacccaaat 14460
caagtttttt ggggtcgagg tgccgtaaag cactaaatcg gaaccctaaa gggagccccc 14520
gatttagagc ttgacgggga aagccggcga acgtggcgag aaaggaaggg aagaaagcga 14580
aaggagcggg cgccattcag gctgcgcaac tgttgggaag gg 14622

<210> SEQ ID NO 33
<211> LENGTH: 13178
<212> TYPE: DNA
<213> ORGANISM: Artificial Sequence
<220> FEATURE:
<223> OTHER INFORMATION: pBYKEMd-6D8K

<400> SEQUENCE: 33
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240

```
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
```

-continued

```
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcattc   3420
tcttcttggt agccacagct acaggtgtcc actccgatgt tttgatgact caaagccctc   3480
tctcacttcc tgtgactctt ggacagcccg catccatatc ttgcagatct agtcagagta   3540
ttgttcatag taacggcaac acctacttgg aatggtatct gcagaaacca ggccagtctc   3600
caaagcttct gatctacaag gcttccaatc gtttctctgg tgtcccagac aggtttagtg   3660
gcagtggatc agggactgac ttcacattga agatcagcag agttgaggct gaagatgcgg   3720
gagtgtacta ttgtcttcaa ggttcacatg ttccgtcaac gtttggaggt gggaccaaag   3780
tggagatcaa gactgttgcg gcgccatctg tcttcatctt tcctccatct gatgaacaac   3840
tcaagtctgg aactgcttct gttgtgtgcc ttctgaacaa cttctatcct agagaagcca   3900
aagtacagtg gaaggttgac aatgctcttc aatcaggtaa ctcccaggag agtgtcacag   3960
agcaagattc caaggattcc acctacagcc tctcaagtac cttgacgttg agcaaggcag   4020
actatgagaa acacaaagtg tacgcatgcg aagtcactca tcagggcctg tcatcacccg   4080
tgacaaagag cttcaacagg ggagagtgtt aggtaccgag ctcgaagtga catcacaaag   4140
ttgaaggtaa taaagccaaa ttaattaaga cattttcata atgatgtcaa gaatgcaaag   4200
caaattgcat aactgccttt atgcaaaaca ttaatataat ataaattata aagaactgcg   4260
ctctctgctt cttatttct tagcttcatt tattagtcac tagctgttca gaattttcag   4320
tatcttttga tattactaag aacctaatca cacaatgtat attcttatgc aggaaaagca   4380
gaatgctgag ctaaaagaaa ggctttttcc attttcgaga gacaatgaga aaagaagaag   4440
aagaagaaga agaagaagaa gaagaaaaga gtaaataata aagccccaca ggaggcgaag   4500
ttcttgtagc tccatgttat ctaagttatt gatattgttt gccctatatt ttatttctgt   4560
cattgtgtat gttttgttca gtttcgatct ccttgcaaaa tgcagagatt atgagatgaa   4620
taaactaagt tatattatta tacgtgttaa tattctcctc ctctctctag ctagcctttt   4680
gttttctctt tttcttattt gattttcttt aaatcaatcc attttaggag agggccaggg   4740
agtgatccag caaaacatga agattagaag aaacttccct ctttttttc ctgaaaacaa   4800
tttaacgtcg agatttatct ctttttgtaa tggaatcatt tctacagtta tgacgaattg   4860
tacatcaacg aaaaattagt caaacgacta aaataaataa atatcatgtg ttattaagaa   4920
aattctccta taagaatatt ttaatagatc atatgtttgt aaaaaaaatt aatttttact   4980
```

aacacatata tttacttatc aaaaatttga caaagtaaga ttaaaataat attcatctaa 5040
caaaaaaaaa accagaaaat gctgaaaacc cggcaaaacc gaaccaatcc aaaccgatat 5100
agttggtttg gtttgatttt gatataaacc gaaccaactc ggtccatttg cacccctaat 5160
cataatagct ttaatatttc aagatattat taagttaacg ttgtcaatat cctggaaatt 5220
ttgcaaaatg aatcaagcct atatggctgt aatatgaatt taaaagcagc tcgatgtggt 5280
ggtaatatgt aatttacttg attctaaaaa aatatcccaa gtattaataa tttctgctag 5340
gaagaaggtt agctacgatt tacagcaaag ccagaataca aagaaccata aagtgattga 5400
agctcgaaat atacgaagga acaaatattt ttaaaaaaat acgcaatgac ttggaacaaa 5460
agaaagtgat atatttttg ttcttaaaca agcatcccct ctaaagaatg gcagttttcc 5520
tttgcatgta actattatgc tcccttcgtt acaaaaattt tggactacta ttgggaactt 5580
cttctgaaaa tagtggtacc gagtgtactt caagtcagtt ggaaatcaat aaaatgatta 5640
ttttatgaat atatttcatt gtgcaagtag atagaaatta catatgttac ataacacacg 5700
aaataaacaa aaaaacacaa tccaaaacaa acaccccaaa caaaataaca ctatatatat 5760
cctcgtatga ggagaggcac gttcagtgac tcgacgattc ccgagcaaaa aaagtctccc 5820
cgtcacacat atagtgggtg acgcaattat cttcaaagta atccttctgt tgacttgtca 5880
ttgataacat ccagtcttcg tcaggattgc aaagaattat agaagggatc ccacctttta 5940
ttttcttctt ttttccatat ttagggttga cagtgaaatc agactggcaa cctattaatt 6000
gcttccacaa tgggacgaac ttgaagggga tgtcgtcgat gatattatag gtggcgtgtt 6060
catcgtagtt ggtgaagtcg atggtcccgt tccagtagtt gtgtcgcccg agacttctag 6120
cccaggtggt ctttccggta cgagttggtc cgcagatgta gaggctgggg tgtctgaccc 6180
cagtccttcc ctcatcctgg ttagatcggc catccactca aggtcagatt gtgcttgatc 6240
gtaggagaca ggatgtatga aagtgtaggc atcgatgctt acatgatata ggtgcgtctc 6300
tctccagttg tgcagatctt cgtggcagcg gagatctgat tctgtgaagg gcgacacgta 6360
ctgctcaggt tgtggaggaa ataatttgtt ggctgaatat tccagccatt gaagctttgt 6420
tgcccattca tgagggaact cttctttgat catgtcaaga tactcctcct tagacgttgc 6480
agtctggata atagttcgcc atcgtgcgtc agatttgcga ggagacacct tatgatctcg 6540
gaaatctcct ctggttttaa tatctccgtc ctttgatatg taatcaagga cttgtttaga 6600
gtttctagct ggctggatat tagggtgatt tccttcaaaa tcgaaaaaag aaggatccct 6660
aatacaaggt tttttatcaa gctggataag agcatgatag tgggtagtgc catcttgatg 6720
aagctcagaa gcaacaccaa ggaagaaaat aagaaaaggt gtgagtttct cccagagaaa 6780
ctggaataaa tcatctcttt gagatgagca cttggggtag gtaaggaaaa catatttaga 6840
ttggagtctg aagttcttgc tagcagaagg catgttgttg tgactccgag gggttgcctc 6900
aaactctatc ttataaccgg cgtggaggca tggaggcaag ggcattttgg taatttaagt 6960
agttagtgga aaatgacgtc atttacttaa agacgaagtc ttgcgacaag gggggcccac 7020
gccgaatttt aatattaccg gcgtggcccc accttatcgc gagtgcttta gcacgagcgg 7080
tccagattta aagtagaaaa gttcccgccc actagggtta aaggtgttca cactataaaa 7140
gcatatacga tgtgatggta tttgatggag cgtatattgt atcaggtatt tccgtcggat 7200
acgaattatt cgtacggccg gaccggtccc ctaggccggc caattcgaga tcggccgcgg 7260
ctgagtggct ccttcaatcg ttgcggttct gtcagttcca aacgtaaaac ggcttgtccc 7320

-continued gcgtcatcgg cgggggtcat aacgtgactc ccttaattct ccgctcatga tcagattgtc 7380
gtttcccgcc ttcagtttaa actatcagtg tttgacagga tatattggcg ggtaaaccta 7440
agagaaaaga gcgtttatta gaataatcgg atatttaaaa gggcgtgaaa aggtttatcc 7500
gttcgtccat ttgtatgtgc atgccaacca cagggttccc cagatctggc gccggccagc 7560
gagacgagca agattggccg ccgcccgaaa cgatccgaca gcgcgcccag cacaggtgcg 7620
caggcaaatt gcaccaacgc atacagcgcc agcagaatgc catagtgggc ggtgacgtcg 7680
ttcgagtgaa ccagatcgcg caggaggccc ggcagcaccg gcataatcag gccgatgccg 7740
acagcgtcga gcgcgacagt gctcagaatt acgatcaggg gtatgttggg tttcacgtct 7800
ggcctccgga gactgtcata cgcgtaaaaa ggccgcgttg ctggcgtttt tccataggct 7860
ccgcccccct gacgagcatc acaaaaatcg acgctcaagt cagaggtggc gaaacccgac 7920
aggactataa agataccagg cgtttccccc tggaagctcc ctcgtgcgct ctcctgttcc 7980
gaccctgccg cttaccggat acctgtccgc ctttctccct tcgggaagcg tggcgctttc 8040
tcatagctca cgctgtaggt atctcagttc ggtgtaggtc gttcgctcca agctgggctg 8100
tgtgcacgaa ccccccgttc agcccgaccg ctgcgcctta tccggtaact atcgtcttga 8160
gtccaacccg gtaagacacg acttatcgcc actggcagca gccactggta acaggattag 8220
cagagcgagg tatgtaggcg gtgctacaga gttcttgaag tggtggccta actacggcta 8280
cactagaagg acagtatttg gtatctgcgc tctgctgaag ccagttacct tcggaaaaag 8340
agttggtagc tcttgatccg gcaaacaaac caccgctggt agcggtggtt tttttgtttg 8400
caagcagcag attacgcgca gaaaaaaagg atctcaagaa gatcctttga tcttttctac 8460
ggggtctgac gctcagtgga acgaaaactc acgttaaggg attttggtca tgagattatc 8520
aaaaaggatc ttcacctaga tccttttaaa ttaaaaatga agttttaaat caatctaaag 8580
tatatatgag taaacttggt ctgcagttgc catgttttac ggcagtgaga gcagagatag 8640
cgctgatgtc cggcggtgct tttgccgtta cgcaccaccc cgtcagtagc tgaacaggag 8700
ggacagctga tagacacaga agccactgga gcacctcaaa aacaccatca tacactaaat 8760
cagtaagttg gcagcatcac ccataattgt ggtttcaaaa tcggctccgt cgatactatg 8820
ttatacgcca actttgaaaa caactttgaa aaagctgttt tctggtattt aaggttttag 8880
aatgcaagga acagtgaatt ggagttcgtc ttgttataat tagcttcttg gggtatcttt 8940
aaatactgta gaaaagagga aggaaataat aaatggctaa aatgagaata tcaccggaat 9000
tgaaaaaact gatcgaaaaa taccgctgcg taaaagatac ggaaggaatg tctcctgcta 9060
aggtatataa gctggtggga gaaaatgaaa acctatattt aaaaatgacg gacagccggt 9120
ataaagggac cacctatgat gtggaacggg aaaaggacat gatgctatgg ctggaaggaa 9180
agctgcctgt tccaaaggtc ctgcactttg aacggcatga tggctggagc aatctgctca 9240
tgagtgaggc cgatggcgtc ctttgctcgg aagagtatga agatgaacaa agccctgaaa 9300
agattatcga gctgtatgcg gagtgcatca ggctctttca ctccatcgac atatcggatt 9360
gtccctatac gaatagctta gacagccgct tagccgaatt ggattactta ctgaataacg 9420
atctggccga tgtggattgc gaaaactggg aagaagacac tccatttaaa gatccgcgcg 9480
agctgtatga tttttaaag acggaaaagc ccgaagagga acttgtcttt tcccacggcg 9540
acctgggaga cagcaacatc tttgtgaaag atggcaaagt aagtggcttt attgatcttg 9600
ggagaagcgg cagggcggac aagtggtatg acattgcctt ctgcgtccgg tcgatcaggg 9660
aggatatcgg ggaagaacag tatgtcgagc tattttttga cttactgggg atcaagcctg 9720

```
attgggagaa aataaaatat tatattttac tggatgaatt gttttagtac ctagatgtgg   9780
cgcaacgatg ccggcgacaa gcaggagcgc accgacttct tccgcatcaa gtgttttggc   9840
tctcaggccg aggcccacgg caagtatttg ggcaaggggt cgctggtatt cgtgcagggc   9900
aagattcgga ataccaagta cgagaaggac ggccagacgg tctacgggac cgacttcatt   9960
gccgataagg tggattatct ggacaccaag gcaccaggcg ggtcaaatca ggaataaggg  10020
cacattgccc cggcgtgagt cggggcaatc ccgcaaggag ggtgaatgaa tcggacgttt  10080
gaccggaagg catacaggca agaactgatc gacgcggggt tttccgccga ggatgccgaa  10140
accatcgcaa gccgcaccgt catgcgtgcg ccccgcgaaa ccttccagtc cgtcggctcg  10200
atggtccagc aagctacggc caagatcgag cgcgacagcg tgcaactggc tccccctgcc  10260
ctgcccgcgc catcggccgc cgtggagcgt tcgcgtcgtc tcgaacagga ggcggcaggt  10320
ttggcgaagt cgatgaccat cgacacgcga ggaactatga cgaccaagaa gcgaaaaacc  10380
gccggcgagg acctggcaaa acaggtcagc gaggccaagc aggccgcgtt gctgaaacac  10440
acgaagcagc agatcaagga aatgcagctt tccttgttcg atattgcgcc gtggccggac  10500
acgatgcgag cgatgccaaa cgacacggcc cgctctgccc tgttcaccac gcgcaacaag  10560
aaaatcccgc gcgaggcgct gcaaaacaag gtcattttcc acgtcaacaa ggacgtgaag  10620
atcacctaca ccggcgtcga gctgcgggcc gacgatgacg aactggtgtg gcagcaggtg  10680
ttggagtacg cgaagcgcac ccctatcggc gagccgatca ccttcacgtt ctacgagctt  10740
tgccaggacc tgggctggtc gatcaatggc cggtattaca cgaaggccga ggaatgcctg  10800
tcgcgcctac aggcgacggc gatgggcttc acgtccgacc gcgttgggca cctggaatcg  10860
gtgtcgctgc tgcaccgctt ccgcgtcctg gaccgtggca agaaaacgtc ccgttgccag  10920
gtcctgatcg acgaggaaat cgtcgtgctg tttgctggcg accactacac gaaattcata  10980
tgggagaagt accgcaagct gtcgccgacg gcccgacgga tgttcgacta tttcagctcg  11040
caccgggagc cgtacccgct caagctggaa accttccgcc tcatgtgcgg atcggattcc  11100
acccgcgtga agaagtggcg cgagcaggtc ggcgaagcct gcgaagagtt gcgaggcagc  11160
ggcctggtgg aacacgcctg ggtcaatgat gacctggtgc attgcaaacg ctagggcctt  11220
gtggggtcag ttccggctgg gggttcagca gccagcgctt tactggcatt tcaggaacaa  11280
gcgggcactg ctcgacgcac ttgcttcgct cagtatcgct cgggacgcac ggcgcgctct  11340
acgaactgcc gataaacaga ggattaaaat tgacaattca atggcaagga ctgccagcgc  11400
tgccattttt ggggtgaggc cgttcgcggc cgaggggcgc agcccctggg gggatgggag  11460
gcccgcgtta gcgggccggg agggttcgag aagggggggc acccccccttc ggcgtgcgcg  11520
gtcacgcgca cagggcgcag ccctggttaa aaacaaggtt tataaatatt ggtttaaaag  11580
caggttaaaa gacaggttag cggtggccga aaaacgggcg gaaacccttg caaatgctgg  11640
attttctgcc tgtggacagc ccctcaaatg tcaataggtg cgcccctcat ctgtcagcac  11700
tctgcccctc aagtgtcaag gatcgcgccc ctcatctgtc agtagtcgcg cccctcaagt  11760
gtcaataccg cagggcactt atccccaggc ttgtccacat catctgtggg aaactcgcgt  11820
aaaatcaggc gttttcgccg atttgcgagg ctggccagct ccacgtcgcc ggccgaaatc  11880
gagcctgccc ctcatctgtc aacgccgcgc cgggtgagtc ggcccctcaa gtgtcaacgt  11940
ccgcccctca tctgtcagtg agggccaagt tttccgcgag gtatccacaa cgccggcggc  12000
cgcggtgtct cgcacacggc ttcgacggcg tttctggcgc gtttgcaggg ccatagacgg  12060
```

```
ccgccagccc agcggcgagg gcaaccagcc cggtgagcgt cgcaaaggcg ctcggtcttg  12120

ccttgctcgt cgagatctgg ggtcgatcag ccggggatgc atcaggccga cagtcggaac  12180

ttcgggtccc cgacctgtac cattcggtga gcaatggata ggggagttga tatcgtcaac  12240

gttcacttct aaagaaatag cgccactcag cttcctcagc ggctttatcc agcgatttcc  12300

tattatgtcg gcatagttct caagatcgac agcctgtcac ggttaagcga gaaatgaata  12360

agaaggctga taattcggat ctctgcgagg gagatgatat ttgatcacag gcagcaacgc  12420

tctgtcatcg ttacaatcaa catgctaccc tccgcgagat catccgtgtt tcaaacccgg  12480

cagcttagtt gccgttcttc cgaatagcat cggtaacatg agcaaagtct gccgccttac  12540

aacggctctc ccgctgacgc cgtcccggac tgatgggctg cctgtatcga gtggtgattt  12600

tgtgccgagc tgccggtcgg ggagctgttg gctggctggt ggcaggatat attgtggtgt  12660

aaacaaattg acgcttagac aacttaataa cacattgcgg acgtttttaa tgtactgggg  12720

tggtttttct tttcaccagt gagacgggca acagctgatt gcccttcacc gcctggccct  12780

gagagagttg cagcaagcgg tccacgctgg tttgccccag caggcgaaaa tcctgtttga  12840

tggtggttcc gaaatcggca aaatccctta taaatcaaaa gaatagcccg agatagggtt  12900

gagtgttgtt ccagtttgga acaagagtcc actattaaag aacgtggact ccaacgtcaa  12960

agggcgaaaa accgtctatc agggcgatgg cccactacgt gaaccatcac ccaaatcaag  13020

ttttttgggg tcgaggtgcc gtaaagcact aaatcggaac cctaaaggga gcccccgatt  13080

tagagcttga cggggaaagc cggcgaacgt ggcgagaaag gaagggaaga aagcgaaagg  13140

agcgggcgcc attcaggctg cgcaactgtt gggaaggg                          13178
```

```
<210> SEQ ID NO 34
<211> LENGTH: 16
<212> TYPE: PRT
<213> ORGANISM: Norovirus

<400> SEQUENCE: 34

Leu Pro Gln Glu Trp Val Gln Tyr Phe Tyr Gln Glu Ala Ala Pro Ala
1               5                   10                  15


<210> SEQ ID NO 35
<211> LENGTH: 20
<212> TYPE: PRT
<213> ORGANISM: Norovirus

<400> SEQUENCE: 35

Leu Pro Gln Glu Trp Val Gln Tyr Phe Tyr Gln Glu Ala Ala Pro Ala
1               5                   10                  15

Gln Ser Val Ala
            20


<210> SEQ ID NO 36
<211> LENGTH: 20
<212> TYPE: PRT
<213> ORGANISM: Norovirus

<400> SEQUENCE: 36

Leu Pro Gln Glu Phe Val Ser Trp Phe Ala Ser Asn Ala Phe Thr Val
1               5                   10                  15

Gln Ser Glu Ala
            20


<210> SEQ ID NO 37
```

<211> LENGTH: 16
<212> TYPE: PRT
<213> ORGANISM: Norovirus

<400> SEQUENCE: 37

Ala Leu Leu Arg Phe Val Asn Pro Asp Thr Gly Arg Val Leu Phe Glu
1 5 10 15

<210> SEQ ID NO 38
<211> LENGTH: 16
<212> TYPE: PRT
<213> ORGANISM: Norovirus

<400> SEQUENCE: 38

Ala Leu Leu His Tyr Val Asp Pro Asp Thr Asn Arg Asn Leu Gly Glu
1 5 10 15

<210> SEQ ID NO 39
<211> LENGTH: 16
<212> TYPE: PRT
<213> ORGANISM: Norovirus

<400> SEQUENCE: 39

Leu Leu Leu Arg Tyr Arg Asn Thr Leu Thr Gly Gln Leu Leu Phe Glu
1 5 10 15

<210> SEQ ID NO 40
<211> LENGTH: 12
<212> TYPE: PRT
<213> ORGANISM: Norovirus

<400> SEQUENCE: 40

Val Ser Trp Val Ser Arg Phe Tyr Gln Leu Lys Pro
1 5 10

<210> SEQ ID NO 41
<211> LENGTH: 12
<212> TYPE: PRT
<213> ORGANISM: Norovirus

<400> SEQUENCE: 41

Asp Ser Trp Val Asn Gln Phe Tyr Thr Leu Ala Pro
1 5 10

<210> SEQ ID NO 42
<211> LENGTH: 12
<212> TYPE: PRT
<213> ORGANISM: Norovirus

<400> SEQUENCE: 42

Val Ser Trp Val Pro Arg Leu Tyr Gln Leu Ala Ser
1 5 10

<210> SEQ ID NO 43
<211> LENGTH: 20
<212> TYPE: PRT
<213> ORGANISM: Norovirus

<400> SEQUENCE: 43

Leu Pro Gln Glu Tyr Ile Thr His Phe Val Ser Glu Gln Ala Pro Thr
1 5 10 15

Val Gly Glu Ala
20

<210> SEQ ID NO 44
<211> LENGTH: 9
<212> TYPE: PRT
<213> ORGANISM: Norovirus

<400> SEQUENCE: 44

Ser Trp Val Ser Arg Phe Tyr Gln Leu
1 5

<210> SEQ ID NO 45
<211> LENGTH: 12
<212> TYPE: PRT
<213> ORGANISM: Norovirus

<400> SEQUENCE: 45

Gln Asn Val Ile Asp Pro Trp Ile Arg Asn Asn Phe
1 5 10

<210> SEQ ID NO 46
<211> LENGTH: 17
<212> TYPE: PRT
<213> ORGANISM: Norovirus

<400> SEQUENCE: 46

Gln Ala Pro Gly Gly Glu Phe Thr Val Ser Pro Arg Asn Ala Pro Gly
1 5 10 15

Glu

<210> SEQ ID NO 47
<211> LENGTH: 9
<212> TYPE: PRT
<213> ORGANISM: Norovirus

<400> SEQUENCE: 47

Lys Val Ile Phe Ala Ala Val Pro Pro
1 5

<210> SEQ ID NO 48
<211> LENGTH: 9
<212> TYPE: PRT
<213> ORGANISM: Norovirus

<400> SEQUENCE: 48

Lys Val Val Val Ala Leu Val Pro Pro
1 5

<210> SEQ ID NO 49
<211> LENGTH: 9
<212> TYPE: PRT
<213> ORGANISM: Norovirus

<400> SEQUENCE: 49

Lys Ile Ile Val Cys Cys Val Pro Pro
1 5

<210> SEQ ID NO 50
<211> LENGTH: 12
<212> TYPE: PRT
<213> ORGANISM: Norovirus

<400> SEQUENCE: 50

Val Asn Met Ile Asp Pro Trp Ile Val Asn Asn Phe
1 5 10

<210> SEQ ID NO 51
<211> LENGTH: 12
<212> TYPE: PRT
<213> ORGANISM: Norovirus

<400> SEQUENCE: 51

Ile Asn Gln Ile Asp Pro Trp Ile Phe Gln Asn Phe
1 5 10

<210> SEQ ID NO 52
<211> LENGTH: 17
<212> TYPE: PRT
<213> ORGANISM: Norovirus

<400> SEQUENCE: 52

Gln Ser Pro Gln Gly Glu Phe Thr Ile Ser Pro Asn Asn Thr Pro Gly
1 5 10 15

Asp

<210> SEQ ID NO 53
<211> LENGTH: 17
<212> TYPE: PRT
<213> ORGANISM: Norovirus

<400> SEQUENCE: 53

Gln Cys Pro Leu Gly Glu Phe Ser Ile Ser Pro Arg Asn Thr Pro Gly
1 5 10 15

Glu

<210> SEQ ID NO 54
<211> LENGTH: 10
<212> TYPE: PRT
<213> ORGANISM: Norovirus

<400> SEQUENCE: 54

Thr Met Phe Pro His Ile Ile Val Asp Val
1 5 10

<210> SEQ ID NO 55
<211> LENGTH: 131
<212> TYPE: PRT
<213> ORGANISM: Norovirus

<400> SEQUENCE: 55

Met Arg Met Ala Thr Pro Ser Ser Ala Pro Ser Val Arg Asn Thr Glu
1 5 10 15

Lys Arg Lys Asn Lys Lys Ala Ser Ser Lys Ala Ser Val Ser Phe Gly
20 25 30

Ala Pro Ser Pro Leu Ser Ser Glu Ser Glu Asp Glu Ile Asn Tyr Met
35 40 45

Thr Pro Pro Glu Gln Glu Ala Gln Pro Gly Ala Leu Ala Ala Leu His
50 55 60

Ala Glu Gly Pro Leu Ala Gly Leu Pro Val Thr Arg Ser Asp Ala Arg
65 70 75 80

Val Leu Ile Phe Asn Glu Trp Glu Glu Arg Lys Lys Ser Asp Pro Trp
85 90 95

Leu Arg Leu Asp Met Ser Asp Lys Ala Ile Phe Arg Arg Tyr Pro His
100 105 110

Leu Arg Pro Lys Glu Asp Arg Pro Asp Ala Pro Ser His Ala Glu Asp
115 120 125

```
Ala Met Asp
    130


<210> SEQ ID NO 56
<211> LENGTH: 134
<212> TYPE: PRT
<213> ORGANISM: Norovirus

<400> SEQUENCE: 56

Met Lys Met Ala Ser Asn Asp Ala Ser Ala Ala Ala Val Ala Asn Ser
1               5                   10                  15

Asn Asn Asp Ile Ala Lys Ser Ser Ser Asp Gly Val Leu Ser Asn Met
            20                  25                  30

Ala Val Thr Phe Lys Arg Ala Leu Gly Ala Arg Pro Lys Gln Pro Pro
        35                  40                  45

Pro Lys Glu Ile Pro Pro Arg Pro Pro Arg Pro Pro Thr Pro Glu Leu
    50                  55                  60

Val Lys Lys Ile Pro Pro Pro Pro Pro Asn Gly Glu Asp Glu Leu Val
65                  70                  75                  80

Val Ser Tyr Ser Ala Lys Asp Gly Val Ser Gly Leu Pro Glu Leu Thr
                85                  90                  95

Thr Val Arg Gln Pro Glu Glu Thr Asn Thr Ala Phe Ser Val Pro Pro
            100                 105                 110

Leu Asn Gln Arg Glu Ser Arg Asp Ala Lys Glu Pro Leu Thr Gly Thr
        115                 120                 125

Ile Ile Glu Met Trp Asp
    130


<210> SEQ ID NO 57
<211> LENGTH: 169
<212> TYPE: PRT
<213> ORGANISM: Norovirus

<400> SEQUENCE: 57

Met Met Met Ala Ser Asn Asp Ala Ile Ala Val Ala Asp Val Ser Asn
1               5                   10                  15

Asn Asn Ala Asn Thr Asn Asn Asp Asn Ile Gly Ser Arg Leu Met Ala
            20                  25                  30

Arg Ile Arg Gly Arg Ile Gly Pro Gln Arg Gly Glu Thr Thr Thr Lys
        35                  40                  45

Ile Lys Asp Ala Asn Met Ala Leu Asp Leu Leu Arg Arg Ser Gln Thr
    50                  55                  60

Pro Ser Pro Ser Arg Gln Glu Ser Pro Pro Lys Ser Gln Arg Asp Arg
65                  70                  75                  80

Pro Pro Arg Thr Ala Ser Glu Val Lys Lys Val Met Gly Trp Asp Ala
                85                  90                  95

Glu Pro Glu His Gln Glu Ser Thr Ala Lys Ala Trp Ser Asp Leu Ala
            100                 105                 110

Gln Glu Glu Lys Glu Glu Ile Met Arg Asn Asn Glu Lys Leu Phe Asp
        115                 120                 125

Ala Gly Gly Ile Thr Pro Ser Thr Leu Pro Ser Thr Phe Glu Arg Ala
    130                 135                 140

Asp Pro Ile Asp Ser Pro Ser Glu Gln Gln Pro Val Ile Trp Ser Ala
145                 150                 155                 160

Ser Gly Gly Val Asp Ile Gly Val Asn
                165
```

<210> SEQ ID NO 58
<211> LENGTH: 10
<212> TYPE: PRT
<213> ORGANISM: Norovirus

<400> SEQUENCE: 58

Thr Leu Phe Pro His Val Ile Ala Asp Val
1               5                   10

<210> SEQ ID NO 59
<211> LENGTH: 10
<212> TYPE: PRT
<213> ORGANISM: Norovirus

<400> SEQUENCE: 59

Thr Met Phe Pro His Ile Ile Val Asp Val
1               5                   10

<210> SEQ ID NO 60
<211> LENGTH: 10
<212> TYPE: PRT
<213> ORGANISM: Norovirus

<400> SEQUENCE: 60

Thr Cys Phe Pro His Val Met Cys Asp Val
1               5                   10

<210> SEQ ID NO 61
<211> LENGTH: 12
<212> TYPE: PRT
<213> ORGANISM: Norovirus

<400> SEQUENCE: 61

Leu Gln Leu Gly Pro His Leu Asn Pro Phe Leu Ser
1               5                   10

<210> SEQ ID NO 62
<211> LENGTH: 12
<212> TYPE: PRT
<213> ORGANISM: Norovirus

<400> SEQUENCE: 62

Ala Pro Leu Gly Pro Asp Leu Asn Pro Tyr Leu Ser
1               5                   10

<210> SEQ ID NO 63
<211> LENGTH: 12
<212> TYPE: PRT
<213> ORGANISM: Norovirus

<400> SEQUENCE: 63

Leu Ala Leu Gly Pro Gly Leu Asn Pro Tyr Leu Ala
1               5                   10

<210> SEQ ID NO 64
<211> LENGTH: 9
<212> TYPE: PRT
<213> ORGANISM: Norovirus

<400> SEQUENCE: 64

Ser Trp Val Ser Arg Phe Tyr Gln Leu
1               5

<210> SEQ ID NO 65

<211> LENGTH: 9
<212> TYPE: PRT
<213> ORGANISM: Norovirus

<400> SEQUENCE: 65

Ser Trp Val Asn Gln Phe Tyr Thr Leu
1 5

<210> SEQ ID NO 66
<211> LENGTH: 9
<212> TYPE: PRT
<213> ORGANISM: Norovirus

<400> SEQUENCE: 66

Ser Trp Val Pro Arg Leu Tyr Gln Leu
1 5

<210> SEQ ID NO 67
<211> LENGTH: 14
<212> TYPE: PRT
<213> ORGANISM: Norovirus

<400> SEQUENCE: 67

Phe Val Ser Glu Gln Ala Pro Thr Met Gly Asp Ala Ala Leu
1 5 10

<210> SEQ ID NO 68
<211> LENGTH: 14
<212> TYPE: PRT
<213> ORGANISM: Norovirus

<400> SEQUENCE: 68

Phe Tyr Gln Glu Ala Ala Pro Ala Gln Ser Asp Val Ala Leu
1 5 10

<210> SEQ ID NO 69
<211> LENGTH: 14
<212> TYPE: PRT
<213> ORGANISM: Norovirus

<400> SEQUENCE: 69

Phe Ala Ser Asn Ala Phe Thr Val Gln Ser Glu Ala Leu Leu
1 5 10

<210> SEQ ID NO 70
<211> LENGTH: 10
<212> TYPE: PRT
<213> ORGANISM: Norovirus

<400> SEQUENCE: 70

Ser Pro Ala Pro Val Gly Phe Pro Asp Phe
1 5 10

<210> SEQ ID NO 71
<211> LENGTH: 10
<212> TYPE: PRT
<213> ORGANISM: Norovirus

<400> SEQUENCE: 71

Ile Pro Ala Pro Leu Gly Thr Pro Asp Phe
1 5 10

<210> SEQ ID NO 72
<211> LENGTH: 10
<212> TYPE: PRT

<213> ORGANISM: Norovirus

<400> SEQUENCE: 72

Arg Ala Ala Pro Leu Gly Tyr Pro Asp Phe
1 5 10

<210> SEQ ID NO 73
<211> LENGTH: 16323
<212> TYPE: DNA
<213> ORGANISM: Artificial Sequence
<220> FEATURE:
<223> OTHER INFORMATION: vector sequence encoding recombinant immune complex

<400> SEQUENCE: 73
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980
gctgtccata aaaccgccca gtctagctat cgccatgtaa gcccactgca agctacctgc 2040
tttctctttg cgcttgcgtt ttcccttgtc cagatagccc agtagctgac attcatccgg 2100
ggtcagcacc gtttctgcgg actggctttc tacgtgttcc gcttccttta gcagcccttg 2160
cgccctgagt gcttgcggca gcgtgaagct ggcgcgccgc tctagcagaa ggcatgttgt 2220
tgtgactccg aggggttgcc tcaaactcta tcttataacc ggcgtggagg catggaggca 2280
agggcatttt ggtaatttaa gtagttagtg gaaaatgacg tcatttactt aaagacgaag 2340
tcttgcgaca aggggggccc acgccgaatt ttaatattac cggcgtggcc ccaccttatc 2400
gcgagtgctt tagcacgagc ggtccagatt taaagtagaa aagttcccgc ccactagggt 2460
taaaggtgtt cacactataa aagcatatac gatgtgatgg tatttgatgg agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat ggctaacaag cacctctcat 3420
tgtctctctt ccttgtgctc cttggtcttt ctgcttctct tgcttctggt atgaggatgg 3480
ctacaccttc ttccgctccc tcagttagaa acactgagaa gaggaagaac aagaaagcgt 3540
catccaaggc ttctgtttct ttcggggcac cttccccact ttcttctgag tctgaggacg 3600
agatcaacta catgactcct ccagaacaag aggcgcagcc tggtgccttg gctgctttgc 3660
acgccgaggg accattggcc ggacttccag ttactaggtc agatgccaga gtacttatct 3720
tcaacgagtg ggaagaaaga aagaagtccg atccctggct cagattagac atgtccgaca 3780
aagccatctt cagacgttat cctcaccttc gtcctaagga ggacagacca gacgcaccat 3840
cacacgccga ggacgccatg gacggtggat ctggagggtc tggaggagga ggatctggag 3900
gctctggagg atctatgaag atggcctcca atgatgcttc tgctgctgct gtcgcgaatt 3960
ccaacaatga catcgcaaaa tcttcctccg acggcgtttt gtccaacatg gctgttactt 4020
tcaagcgtgc tttgggagct agaccaaaac agccaccacc taaggagatc ccaccaagac 4080
ctcctcgtcc gcccactcca gagttggtta agaaaatccc acctccacca ccgaacggag 4140
aggatgagct tgtcgtttct tactctgcta aggacggagt ttctggactt ccagagctta 4200

```
ctacagttcg tcagccagaa gagaccaaca ctgccttctc tgttccacca ttgaaccaga   4260
gggagtccag agacgccaag gagcctctta ctggaactat catcgagatg tgggacggag   4320
gctctggtgg atctggcgga ggcggctctg gaggatctgg tggatctatg atgatggctt   4380
ccaacgacgc gatcgcagta gcggacgttt ccaacaataa cgcaaacacc aacaatgata   4440
acatcggttc tcgtctcatg gctagaatca gagggagaat cggaccacag agaggagaga   4500
ctaccactaa gatcaaggac gcaaacatgg ccttggatct cttgcgtaga agccaaacac   4560
catccccatc ccgtcaagag tccccaccca agtctcaaag agacagacct cccagaactg   4620
cctctgaagt taagaaggtt atgggttggg acgctgagcc ggaacatcaa gaatctactg   4680
ccaaggcttg gtccgatctt gcacaagaag agaaggagga gatcatgaga aacaacgaga   4740
aacttttcga cgccggagga attactccat ctactcttcc atctactttt gaaagagccg   4800
atcctatcga ctcaccatct gagcaacagc ctgttatttg gtctgcctcc ggaggtgtgg   4860
acatcggagt caacactagt ggtggatcag gaggttctgg tggttctgga ggttcaggat   4920
ccgatgttca gcttcttgag tctggaggtg gtcttgtgca acctggaggt tccttgagac   4980
tctcctgtgc agcttcaggg tttgacttca gtaggtactg gatgagttgg gttcgtcaag   5040
ctcctgggaa aggactagaa tggattggag agatcaatcc agattcaagt accatcaact   5100
atactccatc tctgaaggat cgcttcacca tttccagaga caatgccaag aacacgttgt   5160
atcttcagat gaacagcttg aggactgaag acacagcctt gtactactgc acaagacagg   5220
gctatggcta caactactgg ggtcaaggca ccactgtcac agtgtcttca gctagcacca   5280
aaggtccatc ggtctttcca ctggcacctt cttccaagag tacttctgga ggcacagctg   5340
cactgggttg tcttgtcaag gactactttc cagaacctgt tacggtttcg tggaactcag   5400
gtgctctgac cagtggagtg cacacctttc cagctgttct tcagtcctca ggattgtatt   5460
ctcttagcag tgttgtgact gttccatcct caagcttggg cactcagacc tacatctgca   5520
atgtgaatca caaacccagc aacaccaagg ttgacaagaa agttgagccc aagtcttgtg   5580
acaagactca tacgtgtcca ccgtgcccag cacctgaact tcttggagga ccgtcagtct   5640
tcttgtttcc tccaaagcct aaggatacct tgatgatctc caggactcct gaagtcacat   5700
gtgtagttgt ggatgtgagc catgaagatc ctgaggtgaa gttcaactgg tatgtggatg   5760
gtgtggaagt gcacaatgcc aagacaaagc cgagagagga acagtacaac agcacgtaca   5820
gggttgtctc agttctcact gttctccatc aagattggtt gaatggcaaa gagtacaagt   5880
gcaaggtttc caacaaggcc ctcccagccc ccattgagaa gaccatttcc aaagcgaaag   5940
ggcaaccccg tgaaccacaa gtgtacacac ttcctccatc tcgcgatgaa ctgaccaaga   6000
accaggtcag cttgacttgc ctggtgaaag gcttctatcc ctctgacata gctgtagagt   6060
gggagagcaa tgggcaaccg gagaacaact acaagactac acctcccgtt ctcgattctg   6120
acggctcctt cttcctctac agcaagctca cagtggacaa gagcaggtgg caacaaggga   6180
atgtcttctc atgctccgtg atgcatgagg ctcttcacaa tcactacaca cagaagagtc   6240
tctccttgtc tccgggtaaa ggaggtggcg gatcaggtgg aggcggttca ggcggaggtg   6300
gatcttacaa gctggacata tcttaagagc tcaaagcaga atgctgagct aaaagaaagg   6360
ctttttccat tttcgagaga caatgagaaa agaagaagaa gaagaagaag aagaagaaga   6420
agaaaagagt aaataataaa gccccacagg aggcgaagtt cttgtagctc catgttatct   6480
aagttattga tattgtttgc cctatatttt atttctgtca ttgtgtatgt tttgttcagt   6540
ttcgatctcc ttgcaaaatg cagagattat gagatgaata aactaagtta tattattata   6600
```

cgtgttaata ttctcctcct ctctctagct agccttttgt tttctctttt tcttatttga 6660
ttttctttaa atcaatccat tttaggagag ggccagggag tgatccagca aaacatgaag 6720
attagaagaa acttccctct ttttttcct gaaaacaatt taacgtcgag atttatctct 6780
ttttgtaatg gaatcatttc tacagttatg acgctcatac agcattccca gaaagagaaa 6840
cagaagaaat atacaaactt tcattttgag agcagcacct cgtctattga ttgcagataa 6900
tatgcttctc atttgtattt ccttttgatt atttttgttt ctatcccttt gtttgagtca 6960
atctcaaata ttcggtcatt gttggtatga aaaatcaagc agttcatgtt aagagtcaat 7020
ttaaaattaa tatttttata tagagttgta tgtgaaatga tgttgtgatt tggtatatat 7080
ggataaagag cttgtcagtt cattttggtc tgattttttt ggtatccaaa taagaaacac 7140
aaaagggata tgtccctcta ctatcaaata ttagttataa gtattcatgt tatactattc 7200
gatattttct accccaatcg ttacctattt aaaagtattt acccctccat ctatcaaacc 7260
cctggaccca gctttcctat tacatgtggc ttcatcttaa gcccccaaac ctttttctta 7320
tttttgattt ttaaaggctc atcttaaaat ttattactca aattaatacc tcttaataac 7380
ccacctcaag gacccagtaa ttaaatatcc aattagctcc agtaattggg gttcatatta 7440
gctccagtct taaattttaa aggcgatgat cgtattcctc cacttggttc atttatactc 7500
aaagaatact caatgtcttt agtgtttaga taactttttg taaatcatat agattgtttt 7560
aacaaaaaac aattcaatag tagattttca catgaaagtt acataaaaat tctttaaaat 7620
tactttctca aaaaattgtt ccaaacatat tatcccacaa ttaaactcaa tctgtttttc 7680
gaaacctaaa tcaaaaccaa tccaactacc ttatataata tataatcaat acattgtaaa 7740
gaactgcatg ttcttttaaa ttttgggggc aaagttattc cgtacgttca cacatgtact 7800
aataggaggt aataaatgat atgtgaaaca atcgaggtgt aaacaagcta gcatgaattc 7860
tcgattaaaa atcccaatta tatttggtct aatttagttt ggtattgagt aaaacaaatt 7920
cgaaccaaac caaaatataa atatatagtt tttatatata tgcctttaag actttttata 7980
gaattttctt taaaaaatat ctaggtacat caacgaaaaa ttagtcaaac gactaaaata 8040
aataaatatc atgtgttatt aagaaaattc tcctataaga atattttaat agatcatatg 8100
tttgtaaaaa aaattaattt ttactaacac atatatttac ttatcaaaaa tttgacaaag 8160
taagattaaa ataatattca tctaacaaaa aaaaaaccag aaaatgctga aaacccggca 8220
aaaccgaacc aatccaaacc gatatagttg gtttggtttg attttgatat aaaccgaacc 8280
aactcggtcc atttgcaccc ctaatcataa tagctttaat atttcaagat attattaagt 8340
taacgttgtc aatatcctgg aaattttgca aaatgaatca agcctatatg gctgtaatat 8400
gaatttaaaa gcagctcgat gtggtggtaa tatgtaattt acttgattct aaaaaaatat 8460
cccaagtatt aataatttct gctaggaaga aggttagcta cgatttacag caaagccaga 8520
atacaaagaa ccataaagtg attgaagctc gaaatatacg aaggaacaaa tatttttaaa 8580
aaaatacgca atgacttgga acaaaagaaa gtgatatatt ttttgttctt aaacaagcat 8640
cccctctaaa gaatggcagt tttcctttgc atgtaactat tatgctccct tcgttacaaa 8700
aattttggac tactattggg aacttcttct gaaaatagtg gtaccgagtg tacttcaagt 8760
cagttggaaa tcaataaaat gattatttta tgaatatatt tcattgtgca agtagataga 8820
aattacatat gttacataac acacgaaata aacaaaaaaa cacaatccaa aacaaacacc 8880
ccaaacaaaa taacactata tatatcctcg tatgaggaga ggcacgttca gtgactcgac 8940
gattcccgag caaaaaaagt ctccccgtca cacatatagt gggtgacgca attatcttca 9000
aagtaatcct tctgttgact tgtcattgat aacatccagt cttcgtcagg attgcaaaga 9060
attatagaag ggattccacc ttttattttc ttctttttc catatttagg gttgacagtg 9120
aaatcagact ggcaacctat taattgcttc cacaatggga cgaacttgaa ggggatgtcg 9180
tcgatgatat tataggtggc gtgttcatcg tagttggtga agtcgatggt cccgttccag 9240
tagttgtgtc gcccgagact tctagcccag gtggtctttc cggtacgagt tggtccgcag 9300
atgtagaggc tggggtgtct gaccccagtc cttccctcat cctggttaga tcggccatcc 9360
actcaaggtc agattgtgct tgatcgtagg agacaggatg tatgaaagtg taggcatcga 9420
tgcttacatg atataggtgc gtctctctcc agttgtgcag atcttcgtgg cagcggagat 9480
ctgattctgt gaagggcgac acgtactgct caggttgtgg aggaaataat ttgttggctg 9540
aatattccag ccattgaagc tttgttgccc attcatgagg gaactcttct ttgatcatgt 9600
caagatactc ctccttagac gttgcagtct ggataatagt tcgccatcgt gcgtcagatt 9660
tgcgaggaga caccttatga tctcggaaat ctcctctggt tttaatatct ccgtcctttg 9720
atatgtaatc aaggacttgt ttagagtttc tagctggctg gatattaggg tgatttcctt 9780
caaaatcgaa aaaagaagga tctctaatac aaggtttttt atcaagctgg ataagagcat 9840
gatagtgggt agtgccatct tgatgaagct cagaagcaac accaaggaag aaaataagaa 9900
aaggtgtgag tttctcccag agaaactgga ataaatcatc tctttgagat gagcacttgg 9960
ggtaggtaag gaaaacatat ttagattgga gtctgaagtt cttgctagca gaaggcatgt 10020
tgttgtgact ccgaggggtt gcctcaaact ctatcttata accggcgtgg aggcatggag 10080
gcaagggcat tttggtaatt taagtagtta gtggaaaatg acgtcattta cttaaagacg 10140
aagtcttgcg acaagggggg cccacgccga attttaatat taccggcgtg gccccacctt 10200
atcgcgagtg ctttagcacg agcggtccag atttaaagta gaaaagttcc cgcccactag 10260
ggttaaaggt gttcacacta taaaagcata tacgatgtga tggtatttga tggagcgtat 10320
attgtatcag gtatttccgt cggatacgaa ttattcgtac ggccggaccg gtcccctagg 10380
ccggccaatt cgagatcggc cgcggctgag tggctccttc aatcgttgcg gttctgtcag 10440
ttccaaacgt aaaacggctt gtcccgcgtc atcggcgggg gtcataacgt gactccctta 10500
attctccgct catgatcaga ttgtcgtttc ccgccttcag tttaaactat cagtgtttga 10560
caggatatat tggcgggtaa acctaagaga aaagagcgtt tattagaata atcggatatt 10620
taaaagggcg tgaaaaggtt tatccgttcg tccatttgta tgtgcatgcc aaccacaggg 10680
ttccccagat ctggcgccgg ccagcgagac gagcaagatt ggccgccgcc cgaaacgatc 10740
cgacagcgcg cccagcacag gtgcgcaggc aaattgcacc aacgcataca gcgccagcag 10800
aatgccatag tgggcggtga cgtcgttcga gtgaaccaga tcgcgcagga ggcccggcag 10860
caccggcata atcaggccga tgccgacagc gtcgagcgcg acagtgctca gaattacgat 10920
caggggtatg ttgggtttca cgtctggcct ccggagactg tcatacgcgt aaaaaggccg 10980
cgttgctggc gtttttccat aggctccgcc cccctgacga gcatcacaaa aatcgacgct 11040
caagtcagag gtggcgaaac ccgacaggac tataaagata ccaggcgttt ccccctggaa 11100
gctccctcgt gcgctctcct gttccgaccc tgccgcttac cggatacctg tccgcctttc 11160
tcccttcggg aagcgtggcg ctttctcata gctcacgctg taggtatctc agttcggtgt 11220
aggtcgttcg ctccaagctg ggctgtgtgc acgaaccccc cgttcagccc gaccgctgcg 11280
ccttatccgg taactatcgt cttgagtcca acccggtaag acacgactta tcgccactgg 11340

```
cagcagccac tggtaacagg attagcagag cgaggtatgt aggcggtgct acagagttct  11400
tgaagtggtg gcctaactac ggctacacta gaaggacagt atttggtatc tgcgctctgc  11460
tgaagccagt taccttcgga aaaagagttg gtagctcttg atccggcaaa caaaccaccg  11520
ctggtagcgg tggttttttt gtttgcaagc agcagattac gcgcagaaaa aaaggatctc  11580
aagaagatcc tttgatcttt tctacggggt ctgacgctca gtggaacgaa aactcacgtt  11640
aagggatttt ggtcatgaga ttatcaaaaa ggatcttcac ctagatcctt ttaaattaaa  11700
aatgaagttt taaatcaatc taaagtatat atgagtaaac ttggtctgca gttgccatgt  11760
tttacggcag tgagagcaga gatagcgctg atgtccggcg gtgcttttgc cgttacgcac  11820
caccccgtca gtagctgaac aggagggaca gctgatagac acagaagcca ctggagcacc  11880
tcaaaaacac catcatacac taaatcagta agttggcagc atcacccata attgtggttt  11940
caaaatcggc tccgtcgata ctatgttata cgccaacttt gaaaacaact ttgaaaaagc  12000
tgttttctgg tatttaaggt tttagaatgc aaggaacagt gaattggagt tcgtcttgtt  12060
ataattagct tcttggggta tctttaaata ctgtagaaaa gaggaaggaa ataataaatg  12120
gctaaaatga gaatatcacc ggaattgaaa aaactgatcg aaaaataccg ctgcgtaaaa  12180
gatacggaag gaatgtctcc tgctaaggta tataagctgg tgggagaaaa tgaaaaccta  12240
tatttaaaaa tgacggacag ccggtataaa gggaccacct atgatgtgga acgggaaaag  12300
gacatgatgc tatggctgga aggaaagctg cctgttccaa aggtcctgca ctttgaacgg  12360
catgatggct ggagcaatct gctcatgagt gaggccgatg gcgtcctttg ctcggaagag  12420
tatgaagatg aacaaagccc tgaaaagatt atcgagctgt atgcggagtg catcaggctc  12480
tttcactcca tcgacatatc ggattgtccc tatacgaata gcttagacag ccgcttagcc  12540
gaattggatt acttactgaa taacgatctg gccgatgtgg attgcgaaaa ctgggaagaa  12600
gacactccat ttaaagatcc gcgcgagctg tatgattttt taaagacgga aaagcccgaa  12660
gaggaacttg tcttttccca cggcgacctg ggagacagca acatctttgt gaaagatggc  12720
aaagtaagtg gctttattga tcttgggaga agcggcaggg cggacaagtg gtatgacatt  12780
gccttctgcg tccggtcgat cagggaggat atcggggaag aacagtatgt cgagctattt  12840
tttgacttac tggggatcaa gcctgattgg gagaaaataa aatattatat tttactggat  12900
gaattgtttt agtacctaga tgtggcgcaa cgatgccggc gacaagcagg agcgcaccga  12960
cttcttccgc atcaagtgtt ttggctctca ggccgaggcc cacggcaagt atttgggcaa  13020
ggggtcgctg gtattcgtgc agggcaagat tcggaatacc aagtacgaga aggacggcca  13080
gacggtctac gggaccgact tcattgccga taaggtggat tatctggaca ccaaggcacc  13140
aggcgggtca aatcaggaat aagggcacat tgccccggcg tgagtcgggg caatcccgca  13200
aggagggtga atgaatcgga cgtttgaccg gaaggcatac aggcaagaac tgatcgacgc  13260
ggggttttcc gccgaggatg ccgaaaccat cgcaagccgc accgtcatgc gtgcgccccg  13320
cgaaaccttc cagtccgtcg gctcgatggt ccagcaagct acggccaaga tcgagcgcga  13380
cagcgtgcaa ctggctcccc ctgccctgcc cgcgccatcg gccgccgtgg agcgttcgcg  13440
tcgtctcgaa caggaggcgg caggtttggc gaagtcgatg accatcgaca cgcgaggaac  13500
tatgacgacc aagaagcgaa aaaccgccgg cgaggacctg gcaaaacagg tcagcgaggc  13560
caagcaggcc gcgttgctga aacacacgaa gcagcagatc aaggaaatgc agctttcctt  13620
gttcgatatt gcgccgtggc cggacacgat gcgagcgatg ccaaacgaca cggcccgctc  13680
```

tgccctgttc accacgcgca acaagaaaat cccgcgcgag gcgctgcaaa acaaggtcat 13740
tttccacgtc aacaaggacg tgaagatcac ctacaccggc gtcgagctgc gggccgacga 13800
tgacgaactg gtgtggcagc aggtgttgga gtacgcgaag cgcaccccta tcggcgagcc 13860
gatcaccttc acgttctacg agctttgcca ggacctgggc tggtcgatca atggccggta 13920
ttacacgaag gccgaggaat gcctgtcgcg cctacaggcg acggcgatgg gcttcacgtc 13980
cgaccgcgtt gggcacctgg aatcggtgtc gctgctgcac cgcttccgcg tcctggaccg 14040
tggcaagaaa acgtcccgtt gccaggtcct gatcgacgag gaaatcgtcg tgctgtttgc 14100
tggcgaccac tacacgaaat tcatatggga gaagtaccgc aagctgtcgc cgacggcccg 14160
acggatgttc gactatttca gctcgcaccg ggagccgtac ccgctcaagc tggaaacctt 14220
ccgcctcatg tgcggatcgg attccacccg cgtgaagaag tggcgcgagc aggtcggcga 14280
agcctgcgaa gagttgcgag gcagcggcct ggtggaacac gcctgggtca atgatgacct 14340
ggtgcattgc aaacgctagg gccttgtggg gtcagttccg gctgggggtt cagcagccag 14400
cgctttactg gcatttcagg aacaagcggg cactgctcga cgcacttgct tcgctcagta 14460
tcgctcggga cgcacggcgc gctctacgaa ctgccgataa acagaggatt aaaattgaca 14520
attcaatggc aaggactgcc agcgctgcca tttttggggt gaggccgttc gcggccgagg 14580
ggcgcagccc ctgggggat gggaggcccg cgttagcggg ccgggagggt tcgagaaggg 14640
ggggcacccc ccttcggcgt gcgcggtcac gcgcacaggg cgcagccctg gttaaaaaca 14700
aggtttataa atattggttt aaaagcaggt taaaagacag gttagcggtg gccgaaaaac 14760
gggcggaaac ccttgcaaat gctggatttt ctgcctgtgg acagcccctc aaatgtcaat 14820
aggtgcgccc ctcatctgtc agcactctgc ccctcaagtg tcaaggatcg cgcccctcat 14880
ctgtcagtag tcgcgcccct caagtgtcaa taccgcaggg cacttatccc caggcttgtc 14940
cacatcatct gtgggaaact cgcgtaaaat caggcgtttt cgccgatttg cgaggctggc 15000
cagctccacg tcgccggccg aaatcgagcc tgcccctcat ctgtcaacgc cgcgccgggt 15060
gagtcggccc ctcaagtgtc aacgtccgcc cctcatctgt cagtgagggc caagttttcc 15120
gcgaggtatc cacaacgccg gcggccgcgg tgtctcgcac acggcttcga cggcgtttct 15180
ggcgcgtttg cagggccata gacggccgcc agcccagcgg cgagggcaac cagcccggtg 15240
agcgtcgcaa aggcgctcgg tcttgccttg ctcgtcgaga tctggggtcg atcagccggg 15300
gatgcatcag gccgacagtc ggaacttcgg gtccccgacc tgtaccattc ggtgagcaat 15360
ggatagggga gttgatatcg tcaacgttca cttctaaaga aatagcgcca ctcagcttcc 15420
tcagcggctt tatccagcga tttcctatta tgtcggcata gttctcaaga tcgacagcct 15480
gtcacggtta agcgagaaat gaataagaag gctgataatt cggatctctg cgagggagat 15540
gatatttgat cacaggcagc aacgctctgt catcgttaca atcaacatgc taccctccgc 15600
gagatcatcc gtgtttcaaa cccggcagct tagttgccgt tcttccgaat agcatcggta 15660
acatgagcaa agtctgccgc cttacaacgg ctctcccgct gacgccgtcc cggactgatg 15720
ggctgcctgt atcgagtggt gattttgtgc cgagctgccg gtcggggagc tgttggctgg 15780
ctggtggcag gatatattgt ggtgtaaaca aattgacgct tagacaactt aataacacat 15840
tgcggacgtt tttaatgtac tggggtggtt tttctttttca ccagtgagac gggcaacagc 15900
tgattgccct tcaccgcctg gccctgagag agttgcagca agcggtccac gctggtttgc 15960
cccagcaggc gaaaatcctg tttgatggtg gttccgaaat cggcaaaatc ccttataaat 16020
caaaagaata gcccgagata gggttgagtg ttgttccagt ttggaacaag agtccactat 16080
taaagaacgt ggactccaac gtcaaagggc gaaaaaccgt ctatcagggc gatggcccac 16140
tacgtgaacc atcacccaaa tcaagttttt tggggtcgag gtgccgtaaa gcactaaatc 16200
ggaaccctaa agggagcccc cgatttagag cttgacgggg aaagccggcg aacgtggcga 16260
gaaaggaagg gaagaaagcg aaaggagcgg gcgccattca ggctgcgcaa ctgttgggaa 16320
ggg 16323

<210> SEQ ID NO 74
<211> LENGTH: 15495
<212> TYPE: DNA
<213> ORGANISM: Artificial Sequence
<220> FEATURE:
<223> OTHER INFORMATION: binary vector sequence encoding immunoglobin G variant

<400> SEQUENCE: 74
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740

```
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat ggctaacaag cacctctcat   3420
tgtctctctt ccttgtgctc cttggtcttt ctgcttctct tgcttctggt ttgcctcaag   3480
agtatattac tcattttgtt tctgaacaag cccctaccgt tggtgaagct ggcggttccg   3540
gtggaagcct tccacaagaa tgggttcagt acttttacca agaggctgcc ccagctcaat   3600
cagtggccgg gggatctggt ggcagccttc ctcaagagtt cgtttcttgg tttgcttcca   3660
atgccttcac agtgcagtct gaggctggag gctccggtgg atcagcattg ttgcactacg   3720
tagacccaga caccaatcgt aaccttggag aaggtggatc tggaggttct gcgttgttgc   3780
gttttgtgaa tccagacact ggaagagtgc ttttcgaggg agggtctgga ggttcccttt   3840
tgttgagata cagaaacact cttactggac aattattgtt tgagggagga tctggaggtt   3900
cagtgtcttg ggtttctagg ttttatcagt tgaagcctgg cggctctggt ggatcagact   3960
cctgggtgaa tcagttttac actcttgcac ctggaggctc tggtggctct gtctcttggg   4020
ttccaagatt gtaccaatta gcttcaacta gtggtggatc aggaggttct ggtggttctg   4080
```

gaggttcagg atccgatgtt cagcttcttg agtctggagg tggtcttgtg caacctggag 4140
gttccttgag actctcctgt gcagcttcag ggtttgactt cagtaggtac tggatgagtt 4200
gggttcgtca agctcctggg aaaggactag aatggattgg agagatcaat ccagattcaa 4260
gtaccatcaa ctatactcca tctctgaagg atcgcttcac catttccaga gacaatgcca 4320
agaacacgtt gtatcttcag atgaacagct tgaggactga agacacagcc ttgtactact 4380
gcacaagaca gggctatggc tacaactact ggggtcaagg caccactgtc acagtgtctt 4440
cagctagcac caaaggtcca tcggtctttc cactggcacc ttcttccaag agtacttctg 4500
gaggcacagc tgcactgggt tgtcttgtca aggactactt tccagaacct gttacggttt 4560
cgtggaactc aggtgctctg accagtggag tgcacacctt tccagctgtt cttcagtcct 4620
caggattgta ttctcttagc agtgttgtga ctgttccatc ctcaagcttg ggcactcaga 4680
cctacatctg caatgtgaat cacaaaccca gcaacaccaa ggttgacaag aaagttgagc 4740
ccaagtcttg tgacaagact catacgtgtc caccgtgccc agcacctgaa cttcttggag 4800
gaccgtcagt cttcttgttt cctccaaagc ctaaggatac cttgatgatc tccaggactc 4860
ctgaagtcac atgtgtagtt gtggatgtga gccatgaaga tcctgaggtg aagttcaact 4920
ggtatgtgga tggtgtggaa gtgcacaatg ccaagacaaa gccgagagag gaacagtaca 4980
acagcacgta cagggttgtc tcagttctca ctgttctcca tcaagattgg ttgaatggca 5040
aagagtacaa gtgcaaggtt tccaacaagg ccctcccagc ccccattgag aagaccattt 5100
ccaaagcgaa agggcaaccc cgtgaaccac aagtgtacac acttcctcca tctcgcgatg 5160
aactgaccaa gaaccaggtc agcttgactt gcctggtgaa aggcttctat ccctctgaca 5220
tagctgtaga gtgggagagc aatgggcaac cggagaacaa ctacaagact acacctcccg 5280
ttctcgattc tgacggctcc ttcttcctct acagcaagct cacagtggac aagagcaggt 5340
ggcaacaagg gaatgtcttc tcatgctccg tgatgcatga ggctcttcac aatcactaca 5400
cacagaagag tctctccttg tctccgggta aaggaggtgg cggatcaggt ggaggcggtt 5460
caggcggagg tggatcatac aagctggaca tatcttaaga gctcaaagca gaatgctgag 5520
ctaaaagaaa ggctttttcc attttcgaga gacaatgaga aaagaagaag aagaagaaga 5580
agaagaagaa gaagaaaaga gtaaataata aagccccaca ggaggcgaag ttcttgtagc 5640
tccatgttat ctaagttatt gatattgttt gccctatatt ttatttctgt cattgtgtat 5700
gttttgttca gtttcgatct ccttgcaaaa tgcagagatt atgagatgaa taaactaagt 5760
tatattatta tacgtgttaa tattctcctc ctctctctag ctagcctttt gttttctctt 5820
tttcttattt gattttcttt aaatcaatcc attttaggag agggccaggg agtgatccag 5880
caaaacatga agattagaag aaacttccct cttttttttc ctgaaaacaa tttaacgtcg 5940
agatttatct ctttttgtaa tggaatcatt tctacagtta tgacgctcat acagcattcc 6000
cagaaagaga aacagaagaa atatacaaac tttcattttg agagcagcac ctcgtctatt 6060
gattgcagat aatatgcttc tcatttgtat ttccttttga ttatttttgt ttctatccct 6120
ttgtttgagt caatctcaaa tattcggtca ttgttggtat gaaaaatcaa gcagttcatg 6180
ttaagagtca atttaaaatt aatattttta tatagagttg tatgtgaaat gatgttgtga 6240
tttggtatat atggataaag agcttgtcag ttcattttgg tctgattttt ttggtatcca 6300
aataagaaac acaaaaggga tatgtccctc tactatcaaa tattagttat aagtattcat 6360
gttatactat tcgatatttt ctaccccaat cgttacctat ttaaaagtat ttacccctcc 6420
atctatcaaa cccctggacc cagctttcct attacatgtg gcttcatctt aagcccccaa 6480
acctttttct tatttttgat ttttaaaggc tcatcttaaa atttattact caaattaata 6540
cctcttaata acccacctca aggacccagt aattaaatat ccaattagct ccagtaattg 6600
gggttcatat tagctccagt cttaaatttt aaaggcgatg atcgtattcc tccacttggt 6660
tcatttatac tcaaagaata ctcaatgtct ttagtgttta gataactttt tgtaaatcat 6720
atagattgtt ttaacaaaaa acaattcaat agtagatttt cacatgaaag ttacataaaa 6780
attctttaaa attactttct caaaaaattg ttccaaacat attatcccac aattaaactc 6840
aatctgtttt tcgaaaccta aatcaaaacc aatccaacta ccttatataa tatataatca 6900
atacattgta aagaactgca tgttctttta aattttgggg gcaaagttat tccgtacgtt 6960
cacacatgta ctaataggag gtaataaatg atatgtgaaa caatcgaggt gtaaacaagc 7020
tagcatgaat tctcgattaa aaatcccaat tatatttggt ctaatttagt ttggtattga 7080
gtaaaacaaa ttcgaaccaa accaaaatat aaatatatag tttttatata tatgccttta 7140
agacttttta tagaattttc tttaaaaaat atctaggtac atcaacgaaa aattagtcaa 7200
acgactaaaa taaataaata tcatgtgtta ttaagaaaat tctcctataa gaatatttta 7260
atagatcata tgtttgtaaa aaaaattaat ttttactaac acatatattt acttatcaaa 7320
aatttgacaa agtaagatta aaataatatt catctaacaa aaaaaaaacc agaaaatgct 7380
gaaaacccgg caaaaccgaa ccaatccaaa ccgatatagt tggtttggtt tgattttgat 7440
ataaaccgaa ccaactcggt ccatttgcac ccctaatcat aatagcttta atatttcaag 7500
atattattaa gttaacgttg tcaatatcct ggaaattttg caaaatgaat caagcctata 7560
tggctgtaat atgaatttaa aagcagctcg atgtggtggt aatatgtaat ttacttgatt 7620
ctaaaaaaat atcccaagta ttaataattt ctgctaggaa gaaggttagc tacgatttac 7680
agcaaagcca gaatacaaag aaccataaag tgattgaagc tcgaaatata cgaaggaaca 7740
aatattttta aaaaaatacg caatgacttg gaacaaaaga aagtgatata ttttttgttc 7800
ttaaacaagc atcccctcta aagaatggca gttttccttt gcatgtaact attatgctcc 7860
cttcgttaca aaaattttgg actactattg ggaacttctt ctgaaaatag tggtaccgag 7920
tgtacttcaa gtcagttgga aatcaataaa atgattattt tatgaatata tttcattgtg 7980
caagtagata gaaattacat atgttacata acacacgaaa taaacaaaaa aacacaatcc 8040
aaaacaaaca ccccaaacaa aataacacta tatatatcct cgtatgagga gaggcacgtt 8100
cagtgactcg acgattcccg agcaaaaaaa gtctccccgt cacacatata gtgggtgacg 8160
caattatctt caaagtaatc cttctgttga cttgtcattg ataacatcca gtcttcgtca 8220
ggattgcaaa gaattataga agggattcca ccttttattt tcttcttttt tccatattta 8280
gggttgacag tgaaatcaga ctggcaacct attaattgct tccacaatgg gacgaacttg 8340
aaggggatgt cgtcgatgat attataggtg gcgtgttcat cgtagttggt gaagtcgatg 8400
gtcccgttcc agtagttgtg tcgcccgaga cttctagccc aggtggtctt tccggtacga 8460
gttggtccgc agatgtagag gctggggtgt ctgaccccag tccttccctc atcctggtta 8520
gatcggccat ccactcaagg tcagattgtg cttgatcgta ggagacagga tgtatgaaag 8580
tgtaggcatc gatgcttaca tgatataggt gcgtctctct ccagttgtgc agatcttcgt 8640
ggcagcggag atctgattct gtgaagggcg acacgtactg ctcaggttgt ggaggaaata 8700
atttgttggc tgaatattcc agccattgaa gctttgttgc ccattcatga gggaactctt 8760
ctttgatcat gtcaagatac tcctccttag acgttgcagt ctggataata gttcgccatc 8820
gtgcgtcaga tttgcgagga gacaccttat gatctcggaa atctcctctg gttttaatat 8880
ctccgtcctt tgatatgtaa tcaaggactt gtttagagtt tctagctggc tggatattag 8940
ggtgatttcc ttcaaaatcg aaaaaagaag gatctctaat acaaggtttt ttatcaagct 9000
ggataagagc atgatagtgg gtagtgccat cttgatgaag ctcagaagca acaccaagga 9060
agaaaataag aaaaggtgtg agtttctccc agagaaactg gaataaatca tctctttgag 9120
atgagcactt ggggtaggta aggaaaacat atttagattg gagtctgaag ttcttgctag 9180
cagaaggcat gttgttgtga ctccgagggg ttgcctcaaa ctctatctta taaccggcgt 9240
ggaggcatgg aggcaagggc attttggtaa tttaagtagt tagtggaaaa tgacgtcatt 9300
tacttaaaga cgaagtcttg cgacaagggg ggcccacgcc gaattttaat attaccggcg 9360
tggccccacc ttatcgcgag tgctttagca cgagcggtcc agatttaaag tagaaaagtt 9420
cccgcccact agggttaaag gtgttcacac tataaaagca tatacgatgt gatggtattt 9480
gatggagcgt atattgtatc aggtatttcc gtcggatacg aattattcgt acggccggac 9540
cggtccccta ggccggccaa ttcgagatcg gccgcggctg agtggctcct tcaatcgttg 9600
cggttctgtc agttccaaac gtaaaacggc ttgtcccgcg tcatcggcgg gggtcataac 9660
gtgactccct taattctccg ctcatgatca gattgtcgtt tcccgccttc agtttaaact 9720
atcagtgttt gacaggatat attggcgggt aaacctaaga gaaaagagcg tttattagaa 9780
taatcggata tttaaaaggg cgtgaaaagg tttatccgtt cgtccatttg tatgtgcatg 9840
ccaaccacag ggttccccag atctggcgcc ggccagcgag acgagcaaga ttggccgccg 9900
cccgaaacga tccgacagcg cgcccagcac aggtgcgcag gcaaattgca ccaacgcata 9960
cagcgccagc agaatgccat agtgggcggt gacgtcgttc gagtgaacca gatcgcgcag 10020
gaggcccggc agcaccggca taatcaggcc gatgccgaca gcgtcgagcg cgacagtgct 10080
cagaattacg atcaggggta tgttgggttt cacgtctggc ctccggagac tgtcatacgc 10140
gtaaaaaggc cgcgttgctg gcgtttttcc ataggctccg cccccctgac gagcatcaca 10200
aaaatcgacg ctcaagtcag aggtggcgaa acccgacagg actataaaga taccaggcgt 10260
ttccccctgg aagctccctc gtgcgctctc ctgttccgac cctgccgctt accggatacc 10320
tgtccgcctt tctcccttcg ggaagcgtgg cgctttctca tagctcacgc tgtaggtatc 10380
tcagttcggt gtaggtcgtt cgctccaagc tgggctgtgt gcacgaaccc cccgttcagc 10440
ccgaccgctg cgccttatcc ggtaactatc gtcttgagtc caacccggta agacacgact 10500
tatcgccact ggcagcagcc actggtaaca ggattagcag agcgaggtat gtaggcggtg 10560
ctacagagtt cttgaagtgg tggcctaact acggctacac tagaaggaca gtatttggta 10620
tctgcgctct gctgaagcca gttaccttcg gaaaaagagt tggtagctct tgatccggca 10680
aacaaaccac cgctggtagc ggtggttttt ttgtttgcaa gcagcagatt acgcgcagaa 10740
aaaaaggatc tcaagaagat cctttgatct tttctacggg gtctgacgct cagtggaacg 10800
aaaactcacg ttaagggatt ttggtcatga gattatcaaa aaggatcttc acctagatcc 10860
ttttaaatta aaaatgaagt tttaaatcaa tctaaagtat atatgagtaa acttggtctg 10920
cagttgccat gttttacggc agtgagagca gagatagcgc tgatgtccgg cggtgctttt 10980
gccgttacgc accaccccgt cagtagctga acaggaggga cagctgatag acacagaagc 11040
cactggagca cctcaaaaac accatcatac actaaatcag taagttggca gcatcaccca 11100
taattgtggt ttcaaaatcg gctccgtcga tactatgtta tacgccaact ttgaaaacaa 11160
ctttgaaaaa gctgttttct ggtatttaag gttttagaat gcaaggaaca gtgaattgga 11220
gttcgtcttg ttataattag cttcttgggg tatctttaaa tactgtagaa aagaggaagg 11280
aaataataaa tggctaaaat gagaatatca ccggaattga aaaaactgat cgaaaaatac 11340
cgctgcgtaa aagatacgga aggaatgtct cctgctaagg tatataagct ggtgggagaa 11400
aatgaaaacc tatatttaaa aatgacggac agccggtata aagggaccac ctatgatgtg 11460
gaacgggaaa aggacatgat gctatggctg gaaggaaagc tgcctgttcc aaaggtcctg 11520
cactttgaac ggcatgatgg ctggagcaat ctgctcatga gtgaggccga tggcgtcctt 11580
tgctcggaag agtatgaaga tgaacaaagc cctgaaaaga ttatcgagct gtatgcggag 11640
tgcatcaggc tctttcactc catcgacata tcggattgtc cctatacgaa tagcttagac 11700
agccgcttag ccgaattgga ttacttactg aataacgatc tggccgatgt ggattgcgaa 11760
aactgggaag aagacactcc atttaaagat ccgcgcgagc tgtatgattt tttaaagacg 11820
gaaaagcccg aagaggaact tgtcttttcc cacggcgacc tgggagacag caacatcttt 11880
gtgaaagatg gcaaagtaag tggctttatt gatcttggga gaagcggcag ggcggacaag 11940
tggtatgaca ttgccttctg cgtccggtcg atcagggagg atatcgggga agaacagtat 12000
gtcgagctat tttttgactt actggggatc aagcctgatt gggagaaaat aaaatattat 12060
attttactgg atgaattgtt ttagtaccta gatgtggcgc aacgatgccg gcgacaagca 12120
ggagcgcacc gacttcttcc gcatcaagtg ttttggctct caggccgagg cccacggcaa 12180
gtatttgggc aaggggtcgc tggtattcgt gcagggcaag attcggaata ccaagtacga 12240
gaaggacggc cagacggtct acgggaccga cttcattgcc gataaggtgg attatctgga 12300
caccaaggca ccaggcgggt caaatcagga ataagggcac attgccccgg cgtgagtcgg 12360
ggcaatcccg caaggagggt gaatgaatcg gacgtttgac cggaaggcat acaggcaaga 12420
actgatcgac gcggggtttt ccgccgagga tgccgaaacc atcgcaagcc gcaccgtcat 12480
gcgtgcgccc cgcgaaacct tccagtccgt cggctcgatg gtccagcaag ctacggccaa 12540
gatcgagcgc gacagcgtgc aactggctcc ccctgccctg cccgcgccat cggccgccgt 12600
ggagcgttcg cgtcgtctcg aacaggaggc ggcaggtttg gcgaagtcga tgaccatcga 12660
cacgcgagga actatgacga ccaagaagcg aaaaaccgcc ggcgaggacc tggcaaaaca 12720
ggtcagcgag gccaagcagg ccgcgttgct gaaacacacg aagcagcaga tcaaggaaat 12780
gcagctttcc ttgttcgata ttgcgccgtg gccggacacg atgcgagcga tgccaaacga 12840
cacggcccgc tctgccctgt tcaccacgcg caacaagaaa atcccgcgcg aggcgctgca 12900
aaacaaggtc attttccacg tcaacaagga cgtgaagatc acctacaccg gcgtcgagct 12960
gcgggccgac gatgacgaac tggtgtggca gcaggtgttg gagtacgcga agcgcacccc 13020
tatcggcgag ccgatcacct tcacgttcta cgagctttgc caggacctgg gctggtcgat 13080
caatggccgg tattacacga aggccgagga atgcctgtcg cgcctacagg cgacggcgat 13140
gggcttcacg tccgaccgcg ttgggcacct ggaatcggtg tcgctgctgc accgcttccg 13200
cgtcctggac cgtggcaaga aaacgtcccg ttgccaggtc ctgatcgacg aggaaatcgt 13260
cgtgctgttt gctggcgacc actacacgaa attcatatgg gagaagtacc gcaagctgtc 13320
gccgacggcc cgacggatgt tcgactattt cagctcgcac cgggagccgt acccgctcaa 13380
gctggaaacc ttccgcctca tgtgcggatc ggattccacc cgcgtgaaga agtggcgcga 13440
gcaggtcggc gaagcctgcg aagagttgcg aggcagcggc ctggtggaac acgcctgggt 13500
caatgatgac ctggtgcatt gcaaacgcta gggccttgtg gggtcagttc cggctggggg 13560

```
ttcagcagcc agcgctttac tggcatttca ggaacaagcg ggcactgctc gacgcacttg  13620

cttcgctcag tatcgctcgg gacgcacggc gcgctctacg aactgccgat aaacagagga  13680

ttaaaattga caattcaatg gcaaggactg ccagcgctgc catttttggg gtgaggccgt  13740

tcgcggccga ggggcgcagc ccctgggggg atgggaggcc cgcgttagcg ggccgggagg  13800

gttcgagaag ggggggcacc ccccttcggc gtgcgcggtc acgcgcacag ggcgcagccc  13860

tggttaaaaa caaggtttat aaatattggt ttaaaagcag gttaaaagac aggttagcgg  13920

tggccgaaaa acgggcggaa acccttgcaa atgctggatt ttctgcctgt ggacagcccc  13980

tcaaatgtca ataggtgcgc ccctcatctg tcagcactct gcccctcaag tgtcaaggat  14040

cgcgcccctc atctgtcagt agtcgcgccc ctcaagtgtc aataccgcag ggcacttatc  14100

cccaggcttg tccacatcat ctgtgggaaa ctcgcgtaaa atcaggcgtt ttcgccgatt  14160

tgcgaggctg gccagctcca cgtcgccggc cgaaatcgag cctgcccctc atctgtcaac  14220

gccgcgccgg gtgagtcggc ccctcaagtg tcaacgtccg cccctcatct gtcagtgagg  14280

gccaagtttt ccgcgaggta tccacaacgc cggcggccgc ggtgtctcgc acacggcttc  14340

gacggcgttt ctggcgcgtt tgcagggcca tagacggccg ccagcccagc ggcgagggca  14400

accagcccgg tgagcgtcgc aaaggcgctc ggtcttgcct tgctcgtcga gatctggggt  14460

cgatcagccg gggatgcatc aggccgacag tcggaacttc gggtccccga cctgtaccat  14520

tcggtgagca atggataggg gagttgatat cgtcaacgtt cacttctaaa gaaatagcgc  14580

cactcagctt cctcagcggc tttatccagc gatttcctat tatgtcggca tagttctcaa  14640

gatcgacagc ctgtcacggt taagcgagaa atgaataaga aggctgataa ttcggatctc  14700

tgcgagggag atgatatttg atcacaggca gcaacgctct gtcatcgtta caatcaacat  14760

gctaccctcc gcgagatcat ccgtgtttca aacccggcag cttagttgcc gttcttccga  14820

atagcatcgg taacatgagc aaagtctgcc gccttacaac ggctctcccg ctgacgccgt  14880

cccggactga tgggctgcct gtatcgagtg gtgattttgt gccgagctgc cggtcgggga  14940

gctgttggct ggctggtggc aggatatatt gtggtgtaaa caaattgacg cttagacaac  15000

ttaataacac attgcggacg tttttaatgt actggggtgg tttttctttt caccagtgag  15060

acgggcaaca gctgattgcc cttcaccgcc tggccctgag agagttgcag caagcggtcc  15120

acgctggttt gccccagcag gcgaaaatcc tgtttgatgg tggttccgaa atcggcaaaa  15180

tcccttataa atcaaaagaa tagcccgaga tagggttgag tgttgttcca gtttggaaca  15240

agagtccact attaaagaac gtggactcca acgtcaaagg gcgaaaaacc gtctatcagg  15300

gcgatggccc actacgtgaa ccatcaccca aatcaagttt tttggggtcg aggtgccgta  15360

aagcactaaa tcggaaccct aaagggagcc cccgatttag agcttgacgg ggaaagccgg  15420

cgaacgtggc gagaaaggaa gggaagaaag cgaaaggagc gggcgccatt caggctgcgc  15480

aactgttggg aaggg                                                    15495
```

<210> SEQ ID NO 75
<211> LENGTH: 15404
<212> TYPE: DNA
<213> ORGANISM: Artificial Sequence
<220> FEATURE:
<223> OTHER INFORMATION: vector sequence encoding recombinant immune complex

<400> SEQUENCE: 75

```
cgatcggtcg attcatagaa gattagattt ttcatagtat ttttttaaag taaaccttta     60
```

```
actacggtta ggacactttt aagttaaatt taatttgaac ccttaaatta atttttaaaa    120
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
```

taaaggtgtt cacactataa aagcatatac gatgtgatgg tatttgatgg agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat ggctaacaag cacctctcat 3420
tgtctctctt ccttgtgctc cttggtcttt ctgcttctct tgcttctggt gtaaacatga 3480
tagacccgtg gattgtgaac aacttcggag gctctggtgg aagccagaac gtcatcgacc 3540
cttggataag aaacaatttt ggaggatctg gtggcagcat caaccagatc gacccgtgga 3600
tatttcagaa ttttgggggt tctggtggat cacagtctcc acaaggggaa ttcaccatct 3660
caccaaacaa cactcctgga gatggtggct ccggaggttc ccaagcccct ggtggagagt 3720
tcactgtttc tccaagaaac gctcctggtg agggcggatc tggtgggagt cagtgcccct 3780
tgggtgaatt ttctatctct ccaagaaata ctcctggaga aggagggagt ggtggatcaa 3840
agatcatcgt ttgttgtgtg ccacctggag ggtccggtgg ctctaaggtt atctttgctg 3900
ctgttccacc cggaggctcc ggtggatcta aggttgtcgt agctttggtt cctccaacta 3960
gtggtggatc aggaggttct ggtggttctg gaggttcagg atccgatgtt cagcttcttg 4020
agtctggagg tggtcttgtg caacctggag gttccttgag actctcctgt gcagcttcag 4080
ggtttgactt cagtaggtac tggatgagtt gggttcgtca agctcctggg aaaggactag 4140
aatggattgg agagatcaat ccagattcaa gtaccatcaa ctatactcca tctctgaagg 4200
atcgcttcac catttccaga gacaatgcca agaacacgtt gtatcttcag atgaacagct 4260
tgaggactga agacacagcc ttgtactact gcacaagaca gggctatggc tacaactact 4320
ggggtcaagg caccactgtc acagtgtctt cagctagcac caaaggtcca tcggtctttc 4380
cactggcacc ttcttccaag agtacttctg gaggcacagc tgcactgggt tgtcttgtca 4440
aggactactt tccagaacct gttacggttt cgtggaactc aggtgctctg accagtggag 4500
tgcacacctt tccagctgtt cttcagtcct caggattgta ttctcttagc agtgttgtga 4560
ctgttccatc ctcaagcttg ggcactcaga cctacatctg caatgtgaat cacaaaccca 4620
gcaacaccaa ggttgacaag aaagttgagc ccaagtcttg tgacaagact catacgtgtc 4680
caccgtgccc agcacctgaa cttcttggag gaccgtcagt cttcttgttt cctccaaagc 4740
ctaaggatac cttgatgatc tccaggactc ctgaagtcac atgtgtagtt gtggatgtga 4800
gccatgaaga tcctgaggtg aagttcaact ggtatgtgga tggtgtggaa gtgcacaatg 4860
ccaagacaaa gccgagagag gaacagtaca acagcacgta cagggttgtc tcagttctca 4920
ctgttctcca tcaagattgg ttgaatggca aagagtacaa gtgcaaggtt tccaacaagg 4980
ccctcccagc ccccattgag aagaccattt ccaaagcgaa agggcaaccc cgtgaaccac 5040
aagtgtacac acttcctcca tctcgcgatg aactgaccaa gaaccaggtc agcttgactt 5100
gcctggtgaa aggcttctat ccctctgaca tagctgtaga gtgggagagc aatgggcaac 5160
cggagaacaa ctacaagact acacctcccg ttctcgattc tgacggctcc ttcttcctct 5220
acagcaagct cacagtggac aagagcaggt ggcaacaagg gaatgtcttc tcatgctccg 5280
tgatgcatga ggctcttcac aatcactaca cacagaagag tctctccttg tctccgggta 5340
aaggaggtgg cggatcaggt ggaggcggtt caggcggagg tggatctaca agctggacat 5400
atcttaagag ctcaaagcag aatgctgagc taaaagaaag gcttttttcca ttttcgagag 5460
acaatgagaa aagaagaaga agaagaagaa gaagaagaag aagaaaagag taaataataa 5520
agccccacag gaggcgaagt tcttgtagct ccatgttatc taagttattg atattgtttg 5580
ccctatattt tatttctgtc attgtgtatg ttttgttcag tttcgatctc cttgcaaaat 5640
gcagagatta tgagatgaat aaactaagtt atattattat acgtgttaat attctcctcc 5700
tctctctagc tagccttttg ttttctcttt ttcttatttg attttcttta aatcaatcca 5760
ttttaggaga gggccaggga gtgatccagc aaaacatgaa gattagaaga aacttccctc 5820
ttttttttcc tgaaaacaat ttaacgtcga gatttatctc tttttgtaat ggaatcattt 5880
ctacagttat gacgctcata cagcattccc agaaagagaa acagaagaaa tatacaaact 5940
ttcattttga gagcagcacc tcgtctattg attgcagata atatgcttct catttgtatt 6000
tccttttgat tatttttgtt tctatccctt tgtttgagtc aatctcaaat attcggtcat 6060
tgttggtatg aaaaatcaag cagttcatgt taagagtcaa tttaaaatta atatttttat 6120
atagagttgt atgtgaaatg atgttgtgat ttggtatata tggataaaga gcttgtcagt 6180
tcattttggt ctgatttttt tggtatccaa ataagaaaca caaaagggat atgtccctct 6240
actatcaaat attagttata agtattcatg ttatactatt cgatattttc taccccaatc 6300
gttacctatt taaaagtatt taccccctcca tctatcaaac ccctggaccc agctttccta 6360
ttacatgtgg cttcatctta agcccccaaa cctttttctt atttttgatt tttaaaggct 6420
catcttaaaa tttattactc aaattaatac ctcttaataa cccacctcaa ggacccagta 6480
attaaatatc caattagctc cagtaattgg ggttcatatt agctccagtc ttaaatttta 6540
aaggcgatga tcgtattcct ccacttggtt catttatact caaagaatac tcaatgtctt 6600
tagtgtttag ataacttttt gtaaatcata tagattgttt taacaaaaaa caattcaata 6660
gtagattttc acatgaaagt tacataaaaa ttctttaaaa ttactttctc aaaaaattgt 6720
tccaaacata ttatcccaca attaaactca atctgttttt cgaaacctaa atcaaaacca 6780
atccaactac cttatataat atataatcaa tacattgtaa agaactgcat gttcttttaa 6840
attttggggg caaagttatt ccgtacgttc acacatgtac taataggagg taataaatga 6900
tatgtgaaac aatcgaggtg taaacaagct agcatgaatt ctcgattaaa aatcccaatt 6960
atatttggtc taatttagtt tggtattgag taaaacaaat tcgaaccaaa ccaaaatata 7020
aatatatagt ttttatatat atgcctttaa gactttttat agaattttct ttaaaaaata 7080
tctaggtaca tcaacgaaaa attagtcaaa cgactaaaat aaataaatat catgtgttat 7140
taagaaaatt ctcctataag aatattttaa tagatcatat gtttgtaaaa aaaattaatt 7200

```
tttactaaca catatattta cttatcaaaa atttgacaaa gtaagattaa aataatattc   7260
atctaacaaa aaaaaaacca gaaaatgctg aaaacccggc aaaaccgaac caatccaaac   7320
cgatatagtt ggtttggttt gattttgata taaaccgaac caactcggtc catttgcacc   7380
cctaatcata atagctttaa tatttcaaga tattattaag ttaacgttgt caatatcctg   7440
gaaattttgc aaaatgaatc aagcctatat ggctgtaata tgaatttaaa agcagctcga   7500
tgtggtggta atatgtaatt tacttgattc taaaaaaata tcccaagtat taataatttc   7560
tgctaggaag aaggttagct acgatttaca gcaaagccag aatacaaaga accataaagt   7620
gattgaagct cgaaatatac gaaggaacaa atatttttaa aaaaatacgc aatgacttgg   7680
aacaaaagaa agtgatatat tttttgttct taaacaagca tcccctctaa agaatggcag   7740
ttttcctttg catgtaacta ttatgctccc ttcgttacaa aaattttgga ctactattgg   7800
gaacttcttc tgaaaatagt ggtaccgagt gtacttcaag tcagttggaa atcaataaaa   7860
tgattatttt atgaatatat ttcattgtgc aagtagatag aaattacata tgttacataa   7920
cacacgaaat aaacaaaaaa acacaatcca aaacaaacac cccaaacaaa ataacactat   7980
atatatcctc gtatgaggag aggcacgttc agtgactcga cgattcccga gcaaaaaaag   8040
tctccccgtc acacatatag tgggtgacgc aattatcttc aaagtaatcc ttctgttgac   8100
ttgtcattga taacatccag tcttcgtcag gattgcaaag aattatagaa gggattccac   8160
cttttatttt cttctttttt ccatatttag ggttgacagt gaaatcagac tggcaaccta   8220
ttaattgctt ccacaatggg acgaacttga aggggatgtc gtcgatgata ttataggtgg   8280
cgtgttcatc gtagttggtg aagtcgatgg tcccgttcca gtagttgtgt cgcccgagac   8340
ttctagccca ggtggtcttt ccggtacgag ttggtccgca gatgtagagg ctggggtgtc   8400
tgaccccagt ccttccctca tcctggttag atcggccatc cactcaaggt cagattgtgc   8460
ttgatcgtag gagacaggat gtatgaaagt gtaggcatcg atgcttacat gatataggtg   8520
cgtctctctc cagttgtgca gatcttcgtg gcagcggaga tctgattctg tgaagggcga   8580
cacgtactgc tcaggttgtg gaggaaataa tttgttggct gaatattcca gccattgaag   8640
ctttgttgcc cattcatgag ggaactcttc tttgatcatg tcaagatact cctccttaga   8700
cgttgcagtc tggataatag ttcgccatcg tgcgtcagat ttgcgaggag acaccttatg   8760
atctcggaaa tctcctctgg ttttaatatc tccgtccttt gatatgtaat caaggacttg   8820
tttagagttt ctagctggct ggatattagg gtgatttcct tcaaaatcga aaaaagaagg   8880
atctctaata caaggttttt tatcaagctg gataagagca tgatagtggg tagtgccatc   8940
ttgatgaagc tcagaagcaa caccaaggaa gaaaataaga aaaggtgtga gtttctccca   9000
gagaaactgg aataaatcat ctctttgaga tgagcacttg ggtaggtaa ggaaaacata   9060
tttagattgg agtctgaagt tcttgctagc agaaggcatg ttgttgtgac tccgaggggt   9120
tgcctcaaac tctatcttat aaccggcgtg gaggcatgga ggcaagggca ttttggtaat   9180
ttaagtagtt agtggaaaat gacgtcattt acttaaagac gaagtcttgc gacaaggggg   9240
gcccacgccg aattttaata ttaccggcgt ggccccacct tatcgcgagt gctttagcac   9300
gagcggtcca gatttaaagt agaaaagttc ccgcccacta gggttaaagg tgttcacact   9360
ataaaagcat atacgatgtg atggtatttg atggagcgta tattgtatca ggtatttccg   9420
tcggatacga attattcgta cggccggacc ggtcccctag gccggccaat tcgagatcgg   9480
ccgcggctga gtggctcctt caatcgttgc ggttctgtca gttccaaacg taaaacggct   9540
```

tgtcccgcgt catcggcggg ggtcataacg tgactccctt aattctccgc tcatgatcag 9600
attgtcgttt cccgccttca gtttaaacta tcagtgtttg acaggatata ttggcgggta 9660
aacctaagag aaaagagcgt ttattagaat aatcggatat ttaaaagggc gtgaaaaggt 9720
ttatccgttc gtccatttgt atgtgcatgc caaccacagg gttccccaga tctggcgccg 9780
gccagcgaga cgagcaagat tggccgccgc ccgaaacgat ccgacagcgc gcccagcaca 9840
ggtgcgcagg caaattgcac caacgcatac agcgccagca gaatgccata gtgggcggtg 9900
acgtcgttcg agtgaaccag atcgcgcagg aggcccggca gcaccggcat aatcaggccg 9960
atgccgacag cgtcgagcgc gacagtgctc agaattacga tcaggggtat gttgggtttc 10020
acgtctggcc tccggagact gtcatacgcg taaaaaggcc gcgttgctgg cgtttttcca 10080
taggctccgc ccccctgacg agcatcacaa aaatcgacgc tcaagtcaga ggtggcgaaa 10140
cccgacagga ctataaagat accaggcgtt tccccctgga agctccctcg tgcgctctcc 10200
tgttccgacc ctgccgctta ccggatacct gtccgccttt ctcccttcgg gaagcgtggc 10260
gctttctcat agctcacgct gtaggtatct cagttcggtg taggtcgttc gctccaagct 10320
gggctgtgtg cacgaacccc ccgttcagcc cgaccgctgc gccttatccg gtaactatcg 10380
tcttgagtcc aacccggtaa gacacgactt atcgccactg gcagcagcca ctggtaacag 10440
gattagcaga gcgaggtatg taggcggtgc tacagagttc ttgaagtggt ggcctaacta 10500
cggctacact agaaggacag tatttggtat ctgcgctctg ctgaagccag ttaccttcgg 10560
aaaaagagtt ggtagctctt gatccggcaa acaaaccacc gctggtagcg gtggtttttt 10620
tgtttgcaag cagcagatta cgcgcagaaa aaaaggatct caagaagatc ctttgatctt 10680
ttctacgggg tctgacgctc agtggaacga aaactcacgt taagggattt tggtcatgag 10740
attatcaaaa aggatcttca cctagatcct tttaaattaa aaatgaagtt ttaaatcaat 10800
ctaaagtata tatgagtaaa cttggtctgc agttgccatg ttttacggca gtgagagcag 10860
agatagcgct gatgtccggc ggtgcttttg ccgttacgca ccaccccgtc agtagctgaa 10920
caggagggac agctgataga cacagaagcc actggagcac ctcaaaaaca ccatcataca 10980
ctaaatcagt aagttggcag catcacccat aattgtggtt tcaaaatcgg ctccgtcgat 11040
actatgttat acgccaactt tgaaaacaac tttgaaaaag ctgttttctg gtatttaagg 11100
ttttagaatg caaggaacag tgaattggag ttcgtcttgt tataattagc ttcttggggt 11160
atctttaaat actgtagaaa agaggaagga aataataaat ggctaaaatg agaatatcac 11220
cggaattgaa aaaactgatc gaaaaatacc gctgcgtaaa agatacggaa ggaatgtctc 11280
ctgctaaggt atataagctg gtgggagaaa atgaaaacct atatttaaaa atgacggaca 11340
gccggtataa agggaccacc tatgatgtgg aacgggaaaa ggacatgatg ctatggctgg 11400
aaggaaagct gcctgttcca aaggtcctgc actttgaacg gcatgatggc tggagcaatc 11460
tgctcatgag tgaggccgat ggcgtccttt gctcggaaga gtatgaagat gaacaaagcc 11520
ctgaaaagat tatcgagctg tatgcggagt gcatcaggct ctttcactcc atcgacatat 11580
cggattgtcc ctatacgaat agcttagaca gccgcttagc cgaattggat tacttactga 11640
ataacgatct ggccgatgtg gattgcgaaa actgggaaga agacactcca tttaaagatc 11700
cgcgcgagct gtatgatttt ttaaagacgg aaaagcccga agaggaactt gtcttttccc 11760
acggcgacct gggagacagc aacatctttg tgaaagatgg caaagtaagt ggctttattg 11820
atcttgggag aagcggcagg gcggacaagt ggtatgacat tgccttctgc gtccggtcga 11880
tcagggagga tatcggggaa gaacagtatg tcgagctatt ttttgactta ctggggatca 11940
agcctgattg ggagaaaata aaatattata ttttactgga tgaattgttt tagtacctag 12000
atgtggcgca acgatgccgg cgacaagcag gagcgcaccg acttcttccg catcaagtgt 12060
tttggctctc aggccgaggc ccacggcaag tatttgggca aggggtcgct ggtattcgtg 12120
cagggcaaga ttcggaatac caagtacgag aaggacggcc agacggtcta cgggaccgac 12180
ttcattgccg ataaggtgga ttatctggac accaaggcac caggcgggtc aaatcaggaa 12240
taagggcaca ttgccccggc gtgagtcggg gcaatcccgc aaggagggtg aatgaatcgg 12300
acgtttgacc ggaaggcata caggcaagaa ctgatcgacg cggggttttc cgccgaggat 12360
gccgaaacca tcgcaagccg caccgtcatg cgtgcgcccc gcgaaacctt ccagtccgtc 12420
ggctcgatgg tccagcaagc tacggccaag atcgagcgcg acagcgtgca actggctccc 12480
cctgccctgc ccgcgccatc ggccgccgtg gagcgttcgc gtcgtctcga acaggaggcg 12540
gcaggtttgg cgaagtcgat gaccatcgac acgcgaggaa ctatgacgac caagaagcga 12600
aaaaccgccg gcgaggacct ggcaaaacag gtcagcgagg ccaagcaggc cgcgttgctg 12660
aaacacacga agcagcagat caaggaaatg cagctttcct tgttcgatat tgcgccgtgg 12720
ccggacacga tgcgagcgat gccaaacgac acggcccgct ctgccctgtt caccacgcgc 12780
aacaagaaaa tcccgcgcga ggcgctgcaa aacaaggtca ttttccacgt caacaaggac 12840
gtgaagatca cctacaccgg cgtcgagctg cgggccgacg atgacgaact ggtgtggcag 12900
caggtgttgg agtacgcgaa gcgcacccct atcggcgagc cgatcacctt cacgttctac 12960
gagctttgcc aggacctggg ctggtcgatc aatggccggt attacacgaa ggccgaggaa 13020
tgcctgtcgc gcctacaggc gacggcgatg ggcttcacgt ccgaccgcgt tgggcacctg 13080
gaatcggtgt cgctgctgca ccgcttccgc gtcctggacc gtggcaagaa aacgtcccgt 13140
tgccaggtcc tgatcgacga ggaaatcgtc gtgctgtttg ctggcgacca ctacacgaaa 13200
ttcatatggg agaagtaccg caagctgtcg ccgacggccc gacggatgtt cgactatttc 13260
agctcgcacc gggagccgta cccgctcaag ctggaaacct tccgcctcat gtgcggatcg 13320
gattccaccc gcgtgaagaa gtggcgcgag caggtcggcg aagcctgcga agagttgcga 13380
ggcagcggcc tggtggaaca cgcctgggtc aatgatgacc tggtgcattg caaacgctag 13440
ggccttgtgg ggtcagttcc ggctgggggt tcagcagcca gcgctttact ggcatttcag 13500
gaacaagcgg gcactgctcg acgcacttgc ttcgctcagt atcgctcggg acgcacggcg 13560
cgctctacga actgccgata aacagaggat taaaattgac aattcaatgg caaggactgc 13620
cagcgctgcc atttttgggg tgaggccgtt cgcggccgag gggcgcagcc cctgggggga 13680
tgggaggccc gcgttagcgg gccgggaggg ttcgagaagg gggggcaccc cccttcggcg 13740
tgcgcggtca cgcgcacagg gcgcagccct ggttaaaaac aaggtttata aatattggtt 13800
taaaagcagg ttaaaagaca ggttagcggt ggccgaaaaa cgggcggaaa cccttgcaaa 13860
tgctggattt tctgcctgtg gacagcccct caaatgtcaa taggtgcgcc cctcatctgt 13920
cagcactctg cccctcaagt gtcaaggatc gcgcccctca tctgtcagta gtcgcgcccc 13980
tcaagtgtca ataccgcagg gcacttatcc ccaggcttgt ccacatcatc tgtgggaaac 14040
tcgcgtaaaa tcaggcgttt tcgccgattt gcgaggctgg ccagctccac gtcgccggcc 14100
gaaatcgagc ctgcccctca tctgtcaacg ccgcgccggg tgagtcggcc cctcaagtgt 14160
caacgtccgc ccctcatctg tcagtgaggg ccaagttttc cgcgaggtat ccacaacgcc 14220
ggcggccgcg gtgtctcgca cacggcttcg acggcgtttc tggcgcgttt gcagggccat 14280
agacggccgc cagcccagcg gcgagggcaa ccagcccggt gagcgtcgca aaggcgctcg 14340
gtcttgcctt gctcgtcgag atctggggtc gatcagccgg ggatgcatca ggccgacagt 14400
cggaacttcg ggtccccgac ctgtaccatt cggtgagcaa tggatagggg agttgatatc 14460
gtcaacgttc acttctaaag aaatagcgcc actcagcttc ctcagcggct ttatccagcg 14520
atttcctatt atgtcggcat agttctcaag atcgacagcc tgtcacggtt aagcgagaaa 14580
tgaataagaa ggctgataat tcggatctct gcgagggaga tgatatttga tcacaggcag 14640
caacgctctg tcatcgttac aatcaacatg ctaccctccg cgagatcatc cgtgtttcaa 14700
acccggcagc ttagttgccg ttcttccgaa tagcatcggt aacatgagca aagtctgccg 14760
ccttacaacg gctctcccgc tgacgccgtc ccggactgat gggctgcctg tatcgagtgg 14820
tgattttgtg ccgagctgcc ggtcggggag ctgttggctg gctggtggca ggatatattg 14880
tggtgtaaac aaattgacgc ttagacaact taataacaca ttgcggacgt ttttaatgta 14940
ctggggtggt ttttcttttc accagtgaga cgggcaacag ctgattgccc ttcaccgcct 15000
ggccctgaga gagttgcagc aagcggtcca cgctggtttg ccccagcagg cgaaaatcct 15060
gtttgatggt ggttccgaaa tcggcaaaat cccttataaa tcaaaagaat agcccgagat 15120
agggttgagt gttgttccag tttggaacaa gagtccacta ttaaagaacg tggactccaa 15180
cgtcaaaggg cgaaaaaccg tctatcaggg cgatggccca ctacgtgaac catcacccaa 15240
atcaagtttt ttggggtcga ggtgccgtaa agcactaaat cggaacccta aagggagccc 15300
ccgatttaga gcttgacggg gaaagccggc gaacgtggcg agaaaggaag ggaagaaagc 15360
gaaaggagcg ggcgccattc aggctgcgca actgttggga aggg 15404

<210> SEQ ID NO 76
<211> LENGTH: 15665
<212> TYPE: DNA
<213> ORGANISM: Artificial Sequence
<220> FEATURE:
<223> OTHER INFORMATION: vector sequence encoding recombinant immune complex

<400> SEQUENCE: 76
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900

```
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggcc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
```

catttcattt ggagaggacc tcgagaaaca aacaaaatca acaaatatag aaaataacgc 3360
atttccaatt ctttgaaatt tctgcaacat ctagaacaat ggctaacaag cacctctcat 3420
tgtctctctt ccttgtgctc cttggtcttt ctgcttctct tgcttctggt actttgttcc 3480
cgcatgttat cgccgacgtg ggtggaagtg gagggtcaac aatgttccca catatcatcg 3540
tagacgttgg cggatctggt ggatctactt gttttccaca cgttatgtgc gatgttggag 3600
ggtctggcgg atctttgcag cttgggccac acttgaatcc cttccttagt gggggatctg 3660
gaggttctgc gccgcttgga ccagacctca atccgtactt gtctggaggt tccggtggat 3720
ctttggcttt gggacctggc ttaaatcctt acttagccgg aggttctgga ggttcttctt 3780
gggtttcaag gttctatcag ctcggaggat ctggaggctc ctcttgggtg aaccagtttt 3840
acacccttgg agggtctgga ggttcttcat gggttccaag attgtaccaa ctcggtggat 3900
ctggaggatc ttttgtatcc gagcaagccc ctactatggg tgatgccgct cttggcggtt 3960
ctggcggatc tttctaccaa gaggctgctc ctgctcagtc agatgttgct ttgggtggct 4020
ctggagggtc ttttgcttcc aacgctttca ctgttcaatc tgaggctctt cttggaggat 4080
ctggagggtc ttctccagcg cccgttggat ttccagattt cggaggctct ggagggtcca 4140
tcccagcccc acttggaact ccagacttcg gagggtctgg tggttcccgt gcggctcctc 4200
tcggataccc ggacttcact agtggtggat caggaggttc tggtggttct ggaggttcag 4260
gatccgatgt tcagcttctt gagtctggag gtggtcttgt gcaacctgga ggttccttga 4320
gactctcctg tgcagcttca gggtttgact tcagtaggta ctggatgagt tgggttcgtc 4380
aagctcctgg gaaaggacta gaatggattg gagagatcaa tccagattca agtaccatca 4440
actatactcc atctctgaag gatcgcttca ccatttccag agacaatgcc aagaacacgt 4500
tgtatcttca gatgaacagc ttgaggactg aagacacagc cttgtactac tgcacaagac 4560
agggctatgg ctacaactac tggggtcaag gcaccactgt cacagtgtct tcagctagca 4620
ccaaaggtcc atcggtcttt ccactggcac cttcttccaa gagtacttct ggaggcacag 4680
ctgcactggg ttgtcttgtc aaggactact ttccagaacc tgttacggtt tcgtggaact 4740
caggtgctct gaccagtgga gtgcacacct ttccagctgt tcttcagtcc tcaggattgt 4800
attctcttag cagtgttgtg actgttccat cctcaagctt gggcactcag acctacatct 4860
gcaatgtgaa tcacaaaccc agcaacacca aggttgacaa gaaagttgag cccaagtctt 4920
gtgacaagac tcatacgtgt ccaccgtgcc cagcacctga acttcttgga ggaccgtcag 4980
tcttcttgtt tcctccaaag cctaaggata ccttgatgat ctccaggact cctgaagtca 5040
catgtgtagt tgtggatgtg agccatgaag atcctgaggt gaagttcaac tggtatgtgg 5100
atggtgtgga agtgcacaat gccaagacaa agccgagaga ggaacagtac aacagcacgt 5160
acagggttgt ctcagttctc actgttctcc atcaagattg gttgaatggc aaagagtaca 5220
agtgcaaggt ttccaacaag gccctcccag cccccattga gaagaccatt tccaaagcga 5280
aagggcaacc ccgtgaacca caagtgtaca cacttcctcc atctcgcgat gaactgacca 5340
agaaccaggt cagcttgact tgcctggtga aaggcttcta tccctctgac atagctgtag 5400
agtgggagag caatgggcaa ccggagaaca actacaagac tacacctccc gttctcgatt 5460
ctgacggctc cttcttcctc tacagcaagc tcacagtgga caagagcagg tggcaacaag 5520
ggaatgtctt ctcatgctcc gtgatgcatg aggctcttca caatcactac acacagaaga 5580
gtctctcctt gtctccgggt aaaggaggtg gcggatcagg tggaggcggt tcaggcggag 5640

```
gtggatctac aagctggaca tatcttaaga gctcaaagca gaatgctgag ctaaaagaaa   5700
ggctttttcc attttcgaga gacaatgaga aaagaagaag aagaagaaga agaagaagaa   5760
gaagaaaaga gtaaataata aagccccaca ggaggcgaag ttcttgtagc tccatgttat   5820
ctaagttatt gatattgttt gccctatatt ttatttctgt cattgtgtat gttttgttca   5880
gtttcgatct ccttgcaaaa tgcagagatt atgagatgaa taaactaagt tatattatta   5940
tacgtgttaa tattctcctc ctctctctag ctagcctttt gttttctctt tttcttattt   6000
gattttcttt aaatcaatcc attttaggag agggccaggg agtgatccag caaaacatga   6060
agattagaag aaacttccct ctttttttc ctgaaaacaa tttaacgtcg agatttatct   6120
ctttttgtaa tggaatcatt tctacagtta tgacgctcat acagcattcc cagaaagaga   6180
aacagaagaa atatacaaac tttcattttg agagcagcac ctcgtctatt gattgcagat   6240
aatatgcttc tcatttgtat ttccttttga ttatttttgt ttctatccct ttgtttgagt   6300
caatctcaaa tattcggtca ttgttggtat gaaaaatcaa gcagttcatg ttaagagtca   6360
atttaaaatt aatattttta tatagagttg tatgtgaaat gatgttgtga tttggtatat   6420
atggataaag agcttgtcag ttcattttgg tctgattttt ttggtatcca aataagaaac   6480
acaaaaggga tatgtccctc tactatcaaa tattagttat aagtattcat gttatactat   6540
tcgatatttt ctaccccaat cgttacctat ttaaaagtat ttacccctcc atctatcaaa   6600
cccctggacc cagctttcct attacatgtg gcttcatctt aagcccccaa accttttttct   6660
tatttttgat ttttaaaggc tcatcttaaa atttattact caaattaata cctcttaata   6720
acccacctca aggacccagt aattaaatat ccaattagct ccagtaattg gggttcatat   6780
tagctccagt cttaaatttt aaaggcgatg atcgtattcc tccacttggt tcatttatac   6840
tcaaagaata ctcaatgtct ttagtgttta gataactttt tgtaaatcat atagattgtt   6900
ttaacaaaaa acaattcaat agtagatttt cacatgaaag ttacataaaa attctttaaa   6960
attactttct caaaaaattg ttccaaacat attatcccac aattaaactc aatctgtttt   7020
tcgaaaccta aatcaaaacc aatccaacta ccttatataa tatataatca atacattgta   7080
aagaactgca tgttctttta aattttgggg gcaaagttat tccgtacgtt cacacatgta   7140
ctaataggag gtaataaatg atatgtgaaa caatcgaggt gtaaacaagc tagcatgaat   7200
tctcgattaa aaatcccaat tatatttggt ctaatttagt ttggtattga gtaaaacaaa   7260
ttcgaaccaa accaaaatat aaatatatag tttttatata tatgccttta agacttttta   7320
tagaattttc tttaaaaaat atctaggtac atcaacgaaa aattagtcaa acgactaaaa   7380
taaataaata tcatgtgtta ttaagaaaat tctcctataa gaatatttta atagatcata   7440
tgtttgtaaa aaaaattaat ttttactaac acatatattt acttatcaaa aatttgacaa   7500
agtaagatta aaataatatt catctaacaa aaaaaaaacc agaaaatgct gaaaacccgg   7560
caaaaccgaa ccaatccaaa ccgatatagt tggtttggtt tgattttgat ataaaccgaa   7620
ccaactcggt ccatttgcac ccctaatcat aatagcttta atatttcaag atattattaa   7680
gttaacgttg tcaatatcct ggaaattttg caaaatgaat caagcctata tggctgtaat   7740
atgaatttaa aagcagctcg atgtggtggt aatatgtaat ttacttgatt ctaaaaaaat   7800
atcccaagta ttaataattt ctgctaggaa gaaggttagc tacgatttac agcaaagcca   7860
gaatacaaag aaccataaag tgattgaagc tcgaaatata cgaaggaaca aatattttta   7920
aaaaaatacg caatgacttg gaacaaaaga aagtgatata ttttttgttc ttaaacaagc   7980
atcccctcta aagaatggca gttttccttt gcatgtaact attatgctcc cttcgttaca   8040
```

```
aaaattttgg actactattg ggaacttctt ctgaaaatag tggtaccgag tgtacttcaa   8100
gtcagttgga aatcaataaa atgattattt tatgaatata tttcattgtg caagtagata   8160
gaaattacat atgttacata acacacgaaa taaacaaaaa aacacaatcc aaaacaaaca   8220
ccccaaacaa aataacacta tatatatcct cgtatgagga gaggcacgtt cagtgactcg   8280
acgattcccg agcaaaaaaa gtctccccgt cacacatata gtgggtgacg caattatctt   8340
caaagtaatc cttctgttga cttgtcattg ataacatcca gtcttcgtca ggattgcaaa   8400
gaattataga agggattcca ccttttattt tcttcttttt tccatattta gggttgacag   8460
tgaaatcaga ctggcaacct attaattgct tccacaatgg gacgaacttg aaggggatgt   8520
cgtcgatgat attataggtg gcgtgttcat cgtagttggt gaagtcgatg gtcccgttcc   8580
agtagttgtg tcgcccgaga cttctagccc aggtggtctt tccggtacga gttggtccgc   8640
agatgtagag gctggggtgt ctgaccccag tccttccctc atcctggtta gatcggccat   8700
ccactcaagg tcagattgtg cttgatcgta ggagacagga tgtatgaaag tgtaggcatc   8760
gatgcttaca tgatataggt gcgtctctct ccagttgtgc agatcttcgt ggcagcggag   8820
atctgattct gtgaagggcg acacgtactg ctcaggttgt ggaggaaata atttgttggc   8880
tgaatattcc agccattgaa gctttgttgc ccattcatga gggaactctt ctttgatcat   8940
gtcaagatac tcctccttag acgttgcagt ctggataata gttcgccatc gtgcgtcaga   9000
tttgcgagga gacaccttat gatctcggaa atctcctctg gttttaatat ctccgtcctt   9060
tgatatgtaa tcaaggactt gtttagagtt tctagctggc tggatattag ggtgatttcc   9120
ttcaaaatcg aaaaaagaag gatctctaat acaaggtttt ttatcaagct ggataagagc   9180
atgatagtgg gtagtgccat cttgatgaag ctcagaagca acaccaagga agaaaataag   9240
aaaaggtgtg agtttctccc agagaaactg gaataaatca tctctttgag atgagcactt   9300
ggggtaggta aggaaaacat atttagattg gagtctgaag ttcttgctag cagaaggcat   9360
gttgttgtga ctccgagggg ttgcctcaaa ctctatctta taaccggcgt ggaggcatgg   9420
aggcaagggc attttggtaa tttaagtagt tagtggaaaa tgacgtcatt tacttaaaga   9480
cgaagtcttg cgacaagggg ggcccacgcc gaattttaat attaccggcg tggccccacc   9540
ttatcgcgag tgctttagca cgagcggtcc agatttaaag tagaaaagtt cccgcccact   9600
agggttaaag gtgttcacac tataaaagca tatacgatgt gatggtattt gatggagcgt   9660
atattgtatc aggtatttcc gtcggatacg aattattcgt acggccggac cggtccccta   9720
ggccggccaa ttcgagatcg gccgcggctg agtggctcct tcaatcgttg cggttctgtc   9780
agttccaaac gtaaaacggc ttgtcccgcg tcatcggcgg gggtcataac gtgactccct   9840
taattctccg ctcatgatca gattgtcgtt tcccgccttc agtttaaact atcagtgttt   9900
gacaggatat attggcgggt aaacctaaga gaaaagagcg tttattagaa taatcggata   9960
tttaaaaggg cgtgaaaagg tttatccgtt cgtccatttg tatgtgcatg ccaaccacag  10020
ggttccccag atctggcgcc ggccagcgag acgagcaaga ttggccgccg cccgaaacga  10080
tccgacagcg cgcccagcac aggtgcgcag gcaaattgca ccaacgcata cagcgccagc  10140
agaatgccat agtgggcggt gacgtcgttc gagtgaacca gatcgcgcag gaggcccggc  10200
agcaccggca taatcaggcc gatgccgaca gcgtcgagcg cgacagtgct cagaattacg  10260
atcaggggta tgttgggttt cacgtctggc ctccggagac tgtcatacgc gtaaaaaggc  10320
cgcgttgctg gcgtttttcc ataggctccg ccccccctgac gagcatcaca aaaatcgacg  10380
```

ctcaagtcag aggtggcgaa acccgacagg actataaaga taccaggcgt ttccccctgg 10440
aagctccctc gtgcgctctc ctgttccgac cctgccgctt accggatacc tgtccgcctt 10500
tctcccttcg ggaagcgtgg cgctttctca tagctcacgc tgtaggtatc tcagttcggt 10560
gtaggtcgtt cgctccaagc tgggctgtgt gcacgaaccc cccgttcagc ccgaccgctg 10620
cgccttatcc ggtaactatc gtcttgagtc caacccggta agacacgact tatcgccact 10680
ggcagcagcc actggtaaca ggattagcag agcgaggtat gtaggcggtg ctacagagtt 10740
cttgaagtgg tggcctaact acggctacac tagaaggaca gtatttggta tctgcgctct 10800
gctgaagcca gttaccttcg gaaaaagagt tggtagctct tgatccggca aacaaaccac 10860
cgctggtagc ggtggttttt ttgtttgcaa gcagcagatt acgcgcagaa aaaaaggatc 10920
tcaagaagat cctttgatct tttctacggg gtctgacgct cagtggaacg aaaactcacg 10980
ttaagggatt ttggtcatga gattatcaaa aaggatcttc acctagatcc ttttaaatta 11040
aaaatgaagt tttaaatcaa tctaaagtat atatgagtaa acttggtctg cagttgccat 11100
gttttacggc agtgagagca gagatagcgc tgatgtccgg cggtgctttt gccgttacgc 11160
accaccccgt cagtagctga acaggaggga cagctgatag acacagaagc cactggagca 11220
cctcaaaaac accatcatac actaaatcag taagttggca gcatcaccca taattgtggt 11280
ttcaaaatcg gctccgtcga tactatgtta tacgccaact ttgaaaacaa ctttgaaaaa 11340
gctgttttct ggtatttaag gttttagaat gcaaggaaca gtgaattgga gttcgtcttg 11400
ttataattag cttcttgggg tatctttaaa tactgtagaa aagaggaagg aaataataaa 11460
tggctaaaat gagaatatca ccggaattga aaaaactgat cgaaaaatac cgctgcgtaa 11520
aagatacgga aggaatgtct cctgctaagg tatataagct ggtgggagaa aatgaaaacc 11580
tatatttaaa aatgacggac agccggtata aagggaccac ctatgatgtg gaacgggaaa 11640
aggacatgat gctatggctg gaaggaaagc tgcctgttcc aaaggtcctg cactttgaac 11700
ggcatgatgg ctggagcaat ctgctcatga gtgaggccga tggcgtcctt tgctcggaag 11760
agtatgaaga tgaacaaagc cctgaaaaga ttatcgagct gtatgcggag tgcatcaggc 11820
tctttcactc catcgacata tcggattgtc cctatacgaa tagcttagac agccgcttag 11880
ccgaattgga ttacttactg aataacgatc tggccgatgt ggattgcgaa aactgggaag 11940
aagacactcc atttaaagat ccgcgcgagc tgtatgattt tttaaagacg gaaaagcccg 12000
aagaggaact tgtcttttcc cacggcgacc tgggagacag caacatcttt gtgaaagatg 12060
gcaaagtaag tggctttatt gatcttggga gaagcggcag ggcggacaag tggtatgaca 12120
ttgccttctg cgtccggtcg atcagggagg atatcgggga agaacagtat gtcgagctat 12180
tttttgactt actggggatc aagcctgatt gggagaaaat aaaatattat attttactgg 12240
atgaattgtt ttagtaccta gatgtggcgc aacgatgccg gcgacaagca ggagcgcacc 12300
gacttcttcc gcatcaagtg ttttggctct caggccgagg cccacggcaa gtatttgggc 12360
aaggggtcgc tggtattcgt gcagggcaag attcggaata ccaagtacga gaaggacggc 12420
cagacggtct acgggaccga cttcattgcc gataaggtgg attatctgga caccaaggca 12480
ccaggcgggt caaatcagga ataagggcac attgccccgg cgtgagtcgg ggcaatcccg 12540
caaggagggt gaatgaatcg gacgtttgac cggaaggcat acaggcaaga actgatcgac 12600
gcggggtttt ccgccgagga tgccgaaacc atcgcaagcc gcaccgtcat gcgtgcgccc 12660
cgcgaaacct tccagtccgt cggctcgatg gtccagcaag ctacggccaa gatcgagcgc 12720
gacagcgtgc aactggctcc ccctgccctg cccgcgccat cggccgccgt ggagcgttcg 12780
cgtcgtctcg aacaggaggc ggcaggtttg gcgaagtcga tgaccatcga cacgcgagga 12840
actatgacga ccaagaagcg aaaaaccgcc ggcgaggacc tggcaaaaca ggtcagcgag 12900
gccaagcagg ccgcgttgct gaaacacacg aagcagcaga tcaaggaaat gcagctttcc 12960
ttgttcgata ttgcgccgtg gccggacacg atgcgagcga tgccaaacga cacggcccgc 13020
tctgccctgt tcaccacgcg caacaagaaa atcccgcgcg aggcgctgca aaacaaggtc 13080
attttccacg tcaacaagga cgtgaagatc acctacaccg gcgtcgagct gcgggccgac 13140
gatgacgaac tggtgtggca gcaggtgttg gagtacgcga agcgcacccc tatcggcgag 13200
ccgatcacct tcacgttcta cgagctttgc caggacctgg gctggtcgat caatggccgg 13260
tattacacga aggccgagga atgcctgtcg cgcctacagg cgacggcgat gggcttcacg 13320
tccgaccgcg ttgggcacct ggaatcggtg tcgctgctgc accgcttccg cgtcctggac 13380
cgtggcaaga aaacgtcccg ttgccaggtc ctgatcgacg aggaaatcgt cgtgctgttt 13440
gctggcgacc actacacgaa attcatatgg gagaagtacc gcaagctgtc gccgacggcc 13500
cgacggatgt tcgactattt cagctcgcac cgggagccgt acccgctcaa gctggaaacc 13560
ttccgcctca tgtgcggatc ggattccacc cgcgtgaaga agtggcgcga gcaggtcggc 13620
gaagcctgcg aagagttgcg aggcagcggc ctggtggaac acgcctgggt caatgatgac 13680
ctggtgcatt gcaaacgcta gggccttgtg gggtcagttc cggctggggg ttcagcagcc 13740
agcgctttac tggcatttca ggaacaagcg ggcactgctc gacgcacttg cttcgctcag 13800
tatcgctcgg gacgcacggc gcgctctacg aactgccgat aaacagagga ttaaaattga 13860
caattcaatg gcaaggactg ccagcgctgc catttttggg gtgaggccgt tcgcggccga 13920
ggggcgcagc ccctgggggg atgggaggcc cgcgttagcg ggccgggagg gttcgagaag 13980
ggggggcacc ccccttcggc gtgcgcggtc acgcgcacag ggcgcagccc tggttaaaaa 14040
caaggtttat aaatattggt ttaaaagcag gttaaaagac aggttagcgg tggccgaaaa 14100
acgggcggaa acccttgcaa atgctggatt ttctgcctgt ggacagcccc tcaaatgtca 14160
ataggtgcgc ccctcatctg tcagcactct gcccctcaag tgtcaaggat cgcgcccctc 14220
atctgtcagt agtcgcgccc ctcaagtgtc aataccgcag ggcacttatc cccaggcttg 14280
tccacatcat ctgtgggaaa ctcgcgtaaa atcaggcgtt ttcgccgatt tgcgaggctg 14340
gccagctcca cgtcgccggc cgaaatcgag cctgcccctc atctgtcaac gccgcgccgg 14400
gtgagtcggc ccctcaagtg tcaacgtccg cccctcatct gtcagtgagg gccaagtttt 14460
ccgcgaggta tccacaacgc cggcggccgc ggtgtctcgc acacggcttc gacggcgttt 14520
ctggcgcgtt tgcagggcca tagacggccg ccagcccagc ggcgagggca accagcccgg 14580
tgagcgtcgc aaaggcgctc ggtcttgcct tgctcgtcga gatctggggt cgatcagccg 14640
gggatgcatc aggccgacag tcggaacttc gggtccccga cctgtaccat tcggtgagca 14700
atggataggg gagttgatat cgtcaacgtt cacttctaaa gaaatagcgc cactcagctt 14760
cctcagcggc tttatccagc gatttcctat tatgtcggca tagttctcaa gatcgacagc 14820
ctgtcacggt taagcgagaa atgaataaga aggctgataa ttcggatctc tgcgagggag 14880
atgatatttg atcacaggca gcaacgctct gtcatcgtta caatcaacat gctaccctcc 14940
gcgagatcat ccgtgtttca aacccggcag cttagttgcc gttcttccga atagcatcgg 15000
taacatgagc aaagtctgcc gccttacaac ggctctcccg ctgacgccgt cccggactga 15060
tgggctgcct gtatcgagtg gtgattttgt gccgagctgc cggtcgggga gctgttggct 15120
ggctggtggc aggatatatt gtggtgtaaa caaattgacg cttagacaac ttaataacac 15180
attgcggacg tttttaatgt actggggtgg tttttctttt caccagtgag acgggcaaca 15240
gctgattgcc cttcaccgcc tggccctgag agagttgcag caagcggtcc acgctggttt 15300
gccccagcag gcgaaaatcc tgtttgatgg tggttccgaa atcggcaaaa tcccttataa 15360
atcaaaagaa tagcccgaga tagggttgag tgttgttcca gtttggaaca agagtccact 15420
attaaagaac gtggactcca acgtcaaagg gcgaaaaacc gtctatcagg gcgatggccc 15480
actacgtgaa ccatcaccca aatcaagttt tttggggtcg aggtgccgta aagcactaaa 15540
tcggaaccct aaagggagcc cccgatttag agcttgacgg ggaaagccgg cgaacgtggc 15600
gagaaaggaa gggaagaaag cgaaaggagc gggcgccatt caggctgcgc aactgttggg 15660
aaggg 15665

<210> SEQ ID NO 77
<211> LENGTH: 15131
<212> TYPE: DNA
<213> ORGANISM: Artificial Sequence
<220> FEATURE:
<223> OTHER INFORMATION: vector sequence encoding recombinant immune complex

<400> SEQUENCE: 77
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440

```
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggcc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtcaag   3780
gcaccactgt cacagtgtct tcagctagca ccaaaggtcc atcggtcttt ccactggcac   3840
```

cttcttccaa gagtacttct ggaggcacag ctgcactggg ttgtcttgtc aaggactact 3900
ttccagaacc tgttacggtt tcgtggaact caggtgctct gaccagtgga gtgcacacct 3960
ttccagctgt tcttcagtcc tcaggattgt attctcttag cagtgttgtg actgttccat 4020
cctcaagctt gggcactcag acctacatct gcaatgtgaa tcacaaaccc agcaacacca 4080
aggttgacaa gaaagttgag cccaagtctt gtgacaagac tcatacgtgt ccaccgtgcc 4140
cagcacctga acttcttgga ggaccgtcag tcttcttgtt tcctccaaag cctaaggata 4200
ccttgatgat ctccaggact cctgaagtca catgtgtagt tgtggatgtg agccatgaag 4260
atcctgaggt gaagttcaac tggtatgtgg atggtgtgga agtgcacaat gccaagacaa 4320
agccgagaga ggaacagtac aacagcacgt acagggttgt ctcagttctc actgttctcc 4380
atcaagattg gttgaatggc aaagagtaca agtgcaaggt ctccaacaaa gccctcccag 4440
cccccattga gaagaccatt tccaaagcga aagggcaacc ccgtgaacca caagtgtaca 4500
cacttcctcc atctcgcgat gaactgacca agaaccaggt cagcttgact tgcctggtga 4560
aaggcttcta tccctctgac atagctgtag agtgggagag caatgggcaa ccggagaaca 4620
actacaagac tacacctccc gttctcgatt ctgacggctc cttcttcctc tacagcaagc 4680
tcacagtgga caagagcagg tggcaacaag ggaatgtctt ctcatgctcc gtgatgcatg 4740
aggctcttca caatcactac acacagaaga gtctctcctt gtctccgggt aaaggaggtg 4800
gcggatcagg tggaggcggt tcaggcggag gtggatcctt gcctcaagag tatattactc 4860
attttgtttc tgaacaagcc cctaccgttg gtgaagctgg cggttccggt ggaagccttc 4920
cacaagaatg ggttcagtac ttttaccaag aggctgcccc agctcaatca gtggccgggg 4980
gatctggtgg cagccttcct caagagttcg tttcttggtt tgcttccaat gccttcacag 5040
tgcagtctga ggctggaggc tccggtggat cagcattgtt gcactacgta gacccagaca 5100
ccaatcgtaa ccttggagaa ggtggatctg gaggttctgc gttgttgcgt tttgtgaatc 5160
cagacactgg aagagtgctt ttcgagggag ggtctggagg ttccctttttg ttgagataca 5220
gaaacactct tactggacaa ttattgtttg agggaggatc tggaggttca gtgtcttggg 5280
tttctaggtt ttatcagttg aagcctggcg gctctggtgg atcagactcc tgggtgaatc 5340
agttttacac tcttgcacct ggaggctctg gtggctctgt ctcttgggtt ccaagattgt 5400
accaattagc ttcaactagt tacaagctgg acatatctta agagctcaaa gcagaatgct 5460
gagctaaaag aaaggctttt tccattttcg agagacaatg agaaaagaag aagaagaaga 5520
agaagaagaa gaagaagaaa agagtaaata ataaagcccc acaggaggcg aagttcttgt 5580
agctccatgt tatctaagtt attgatattg tttgccctat attttatttc tgtcattgtg 5640
tatgttttgt tcagtttcga tctccttgca aaatgcagag attatgagat gaataaacta 5700
agttatatta ttatacgtgt taatattctc ctcctctctc tagctagcct tttgttttct 5760
ctttttctta tttgatttc tttaaatcaa tccattttag gagagggcca gggagtgatc 5820
cagcaaaaca tgaagattag aagaaacttc cctctttttt ttcctgaaaa caatttaacg 5880
tcgagattta tctcttttg taatggaatc atttctacag ttatgacggc tcactgagga 5940
aatatataga caaattaagt ttggttctat gagttctaat ttggacttaa gagttgtttg 6000
aaattctatt ttatagtgat gcttataatg tatttggact gttttctgct gtgtgtaaga 6060
ccttttggtc tgtgaactgg aaacatacat gaataaattt ctttgaattt actggaattt 6120
ttgcatcaac aaaagaaaaa ttgaagttac taacttgtaa atggaacaat tgtaatgtta 6180 aggatataa atatcttaat atagtgcgat acgaatcaca cgaatgcaag actttctctc 6240
tctgctcccg ctcatgctct cggtgcatgt tagctaaata tacatcggtg catccatggc 6300
aggagcatga ggacggggat gaggaaggga gtgaggaggg ccaaaagaag tacacatagt 6360
ttcctttggg agcgaattct cgattaaaaa tcccaattat atttggtcta atttagtttg 6420
gtattgagta aaacaaattc gaaccaaacc aaaatataaa tatatagttt ttatatatat 6480
gcctttaaga ctttttatag aattttcttt aaaaaatatc tagaaatatt tgcgactctt 6540
ctggcatgta atatttcgtt aaatatgaag tgctccattt ttattaactt taaataattg 6600
gttgtacgat cactttctta tcaagtgtta ctaaaatgcg tcaatctctt tgttcttcca 6660
tattcatatg tcaaaatcta tcaaaattct tatatatctt tttcgaattt gaagtgaaat 6720
ttcgataatt taaaattaaa tagaacatat cattatttag gtatcatatt gatttttata 6780
cttaattact aaatttggtt aactttgaaa gtgtacatca acgaaaaatt agtcaaacga 6840
ctaaaataaa taaatatcat gtgttattaa gaaaattctc ctataagaat attttaatag 6900
atcatatgtt tgtaaaaaaa attaattttt actaacacat atatttactt atcaaaaatt 6960
tgacaaagta agattaaaat aatattcatc taacaaaaaa aaaaccagaa aatgctgaaa 7020
acccggcaaa accgaaccaa tccaaaccga tatagttggt ttggtttgat tttgatataa 7080
accgaaccaa ctcggtccat ttgcacccct aatcataata gctttaatat ttcaagatat 7140
tattaagtta acgttgtcaa tatcctggaa attttgcaaa atgaatcaag cctatatggc 7200
tgtaatatga atttaaaagc agctcgatgt ggtggtaata tgtaatttac ttgattctaa 7260
aaaaatatcc caagtattaa taatttctgc taggaagaag gttagctacg atttacagca 7320
aagccagaat acaaagaacc ataaagtgat tgaagctcga aatatacgaa ggaacaaata 7380
tttttaaaaa aatacgcaat gacttggaac aaaagaaagt gatatatttt ttgttcttaa 7440
acaagcatcc cctctaaaga atggcagttt tcctttgcat gtaactatta tgctcccttc 7500
gttacaaaaa ttttggacta ctattgggaa cttcttctga aaatagtggt accgagtgta 7560
cttcaagtca gttggaaatc aataaaatga ttattttatg aatatatttc attgtgcaag 7620
tagatagaaa ttacatatgt tacataacac acgaaataaa caaaaaaaca caatccaaaa 7680
caaacacccc aaacaaaata acactatata tatcctcgta tgaggagagg cacgttcagt 7740
gactcgacga ttcccgagca aaaaaagtct ccccgtcaca catatagtgg gtgacgcaat 7800
tatcttcaaa gtaatccttc tgttgacttg tcattgataa catccagtct tcgtcaggat 7860
tgcaaagaat tatagaaggg attccacctt ttattttctt ctttttttcca tatttagggt 7920
tgacagtgaa atcagactgg caacctatta attgcttcca caatgggacg aacttgaagg 7980
ggatgtcgtc gatgatatta taggtggcgt gttcatcgta gttggtgaag tcgatggtcc 8040
cgttccagta gttgtgtcgc ccgagacttc tagcccaggt ggtctttccg gtacgagttg 8100
gtccgcagat gtagaggctg gggtgtctga ccccagtcct tccctcatcc tggttagatc 8160
ggccatccac tcaaggtcag attgtgcttg atcgtaggag acaggatgta tgaaagtgta 8220
ggcatcgatg cttacatgat ataggtgcgt ctctctccag ttgtgcagat cttcgtggca 8280
gcggagatct gattctgtga agggcgacac gtactgctca ggttgtggag gaaataattt 8340
gttggctgaa tattccagcc attgaagctt tgttgcccat tcatgaggga actcttcttt 8400
gatcatgtca agatactcct ccttagacgt tgcagtctgg ataatagttc gccatcgtgc 8460
gtcagatttg cgaggagaca ccttatgatc tcggaaatct cctctggttt taatatctcc 8520
gtcctttgat atgtaatcaa ggacttgttt agagtttcta gctggctgga tattagggtg 8580

```
atttccttca aaatcgaaaa aagaaggatc tctaatacaa ggttttttat caagctggat   8640
aagagcatga tagtgggtag tgccatcttg atgaagctca gaagcaacac caaggaagaa   8700
aataagaaaa ggtgtgagtt tctcccagag aaactggaat aaatcatctc tttgagatga   8760
gcacttgggg taggtaagga aaacatattt agattggagt ctgaagttct tgctagcaga   8820
aggcatgttg ttgtgactcc gaggggttgc ctcaaactct atcttataac cggcgtggag   8880
gcatggaggc aagggcattt tggtaattta agtagttagt ggaaaatgac gtcatttact   8940
taaagacgaa gtcttgcgac aaggggggcc cacgccgaat tttaatatta ccggcgtggc   9000
cccaccttat cgcgagtgct ttagcacgag cggtccagat ttaaagtaga aaagttcccg   9060
cccactaggg ttaaaggtgt tcacactata aaagcatata cgatgtgatg gtatttgatg   9120
gagcgtatat tgtatcaggt atttccgtcg gatacgaatt attcgtacgg ccggaccggt   9180
cccctaggcc ggccaattcg agatcggccg cggctgagtg gctccttcaa tcgttgcggt   9240
tctgtcagtt ccaaacgtaa aacggcttgt cccgcgtcat cggcgggggt cataacgtga   9300
ctcccttaat tctccgctca tgatcagatt gtcgtttccc gccttcagtt taaactatca   9360
gtgtttgaca ggatatattg gcgggtaaac ctaagagaaa agagcgttta ttagaataat   9420
cggatattta aaagggcgtg aaaaggttta tccgttcgtc catttgtatg tgcatgccaa   9480
ccacagggtt ccccagatct ggcgccggcc agcgagacga gcaagattgg ccgccgcccg   9540
aaacgatccg acagcgcgcc cagcacaggt gcgcaggcaa attgcaccaa cgcatacagc   9600
gccagcagaa tgccatagtg ggcggtgacg tcgttcgagt gaaccagatc gcgcaggagg   9660
cccggcagca ccggcataat caggccgatg ccgacagcgt cgagcgcgac agtgctcaga   9720
attacgatca ggggtatgtt gggtttcacg tctggcctcc ggagactgtc atacgcgtaa   9780
aaaggccgcg ttgctggcgt ttttccatag gctccgcccc cctgacgagc atcacaaaaa   9840
tcgacgctca agtcagaggt ggcgaaaccc gacaggacta taaagatacc aggcgtttcc   9900
ccctggaagc tccctcgtgc gctctcctgt tccgaccctg ccgcttaccg gatacctgtc   9960
cgcctttctc ccttcgggaa gcgtggcgct ttctcatagc tcacgctgta ggtatctcag  10020
ttcggtgtag gtcgttcgct ccaagctggg ctgtgtgcac gaaccccccg ttcagcccga  10080
ccgctgcgcc ttatccggta actatcgtct tgagtccaac ccggtaagac acgacttatc  10140
gccactggca gcagccactg gtaacaggat tagcagagcg aggtatgtag gcggtgctac  10200
agagttcttg aagtggtggc ctaactacgg ctacactaga aggacagtat ttggtatctg  10260
cgctctgctg aagccagtta ccttcggaaa aagagttggt agctcttgat ccggcaaaca  10320
aaccaccgct ggtagcggtg gtttttttgt ttgcaagcag cagattacgc gcagaaaaaa  10380
aggatctcaa gaagatcctt tgatcttttc tacggggtct gacgctcagt ggaacgaaaa  10440
ctcacgttaa gggattttgg tcatgagatt atcaaaaagg atcttcacct agatcctttt  10500
aaattaaaaa tgaagtttta aatcaatcta aagtatatat gagtaaactt ggtctgcagt  10560
tgccatgttt tacggcagtg agagcagaga tagcgctgat gtccggcggt gcttttgccg  10620
ttacgcacca ccccgtcagt agctgaacag gagggacagc tgatagacac agaagccact  10680
ggagcacctc aaaaacacca tcatacacta aatcagtaag ttggcagcat cacccataat  10740
tgtggtttca aaatcggctc cgtcgatact atgttatacg ccaactttga aaacaacttt  10800
gaaaaagctg ttttctggta tttaaggttt tagaatgcaa ggaacagtga attggagttc  10860
gtcttgttat aattagcttc ttggggtatc tttaaatact gtagaaaaga ggaaggaaat  10920
```

```
aataaatggc taaaatgaga atatcaccgg aattgaaaaa actgatcgaa aaataccgct  10980
gcgtaaaaga tacggaagga atgtctcctg ctaaggtata taagctggtg ggagaaaatg  11040
aaaacctata tttaaaaatg acggacagcc ggtataaagg gaccacctat gatgtggaac  11100
gggaaaagga catgatgcta tggctggaag gaaagctgcc tgttccaaag gtcctgcact  11160
ttgaacggca tgatggctgg agcaatctgc tcatgagtga ggccgatggc gtcctttgct  11220
cggaagagta tgaagatgaa caaagccctg aaaagattat cgagctgtat gcggagtgca  11280
tcaggctctt tcactccatc gacatatcgg attgtcccta tacgaatagc ttagacagcc  11340
gcttagccga attggattac ttactgaata acgatctggc cgatgtggat tgcgaaaact  11400
gggaagaaga cactccattt aaagatccgc gcgagctgta tgattttttta aagacggaaa  11460
agcccgaaga ggaacttgtc ttttcccacg gcgacctggg agacagcaac atctttgtga  11520
aagatggcaa agtaagtggc tttattgatc ttgggagaag cggcagggcg gacaagtggt  11580
atgacattgc cttctgcgtc cggtcgatca gggaggatat cggggaagaa cagtatgtcg  11640
agctattttt tgacttactg gggatcaagc ctgattggga gaaaataaaa tattatattt  11700
tactggatga attgttttag tacctagatg tggcgcaacg atgccggcga caagcaggag  11760
cgcaccgact tcttccgcat caagtgtttt ggctctcagg ccgaggccca cggcaagtat  11820
ttgggcaagg ggtcgctggt attcgtgcag ggcaagattc ggaataccaa gtacgagaag  11880
gacggccaga cggtctacgg gaccgacttc attgccgata aggtggatta tctggacacc  11940
aaggcaccag gcgggtcaaa tcaggaataa gggcacattg ccccggcgtg agtcggggca  12000
atcccgcaag gagggtgaat gaatcggacg tttgaccgga aggcatacag gcaagaactg  12060
atcgacgcgg ggttttccgc cgaggatgcc gaaaccatcg caagccgcac cgtcatgcgt  12120
gcgccccgcg aaaccttcca gtccgtcggc tcgatggtcc agcaagctac ggccaagatc  12180
gagcgcgaca gcgtgcaact ggctccccct gccctgcccg cgccatcggc cgccgtggag  12240
cgttcgcgtc gtctcgaaca ggaggcggca ggtttggcga agtcgatgac catcgacacg  12300
cgaggaacta tgacgaccaa gaagcgaaaa accgccggcg aggacctggc aaaacaggtc  12360
agcgaggcca agcaggccgc gttgctgaaa cacacgaagc agcagatcaa ggaaatgcag  12420
ctttccttgt tcgatattgc gccgtggccg gacacgatgc gagcgatgcc aaacgacacg  12480
gcccgctctg ccctgttcac cacgcgcaac aagaaaatcc cgcgcgaggc gctgcaaaac  12540
aaggtcattt tccacgtcaa caaggacgtg aagatcacct acaccggcgt cgagctgcgg  12600
gccgacgatg acgaactggt gtggcagcag gtgttggagt acgcgaagcg cacccctatc  12660
ggcgagccga tcaccttcac gttctacgag ctttgccagg acctgggctg gtcgatcaat  12720
ggccggtatt acacgaaggc cgaggaatgc ctgtcgcgcc tacaggcgac ggcgatgggc  12780
ttcacgtccg accgcgttgg gcacctggaa tcggtgtcgc tgctgcaccg cttccgcgtc  12840
ctggaccgtg gcaagaaaac gtcccgttgc caggtcctga tcgacgagga aatcgtcgtg  12900
ctgtttgctg gcgaccacta cacgaaattc atatgggaga agtaccgcaa gctgtcgccg  12960
acggcccgac ggatgttcga ctatttcagc tcgcaccggg agccgtaccc gctcaagctg  13020
gaaaccttcc gcctcatgtg cggatcggat tccacccgcg tgaagaagtg gcgcgagcag  13080
gtcggcgaag cctgcgaaga gttgcgaggc agcggcctgg tggaacacgc ctgggtcaat  13140
gatgacctgg tgcattgcaa acgctagggc cttgtggggt cagttccggc tgggggttca  13200
gcagccagcg ctttactggc atttcaggaa caagcgggca ctgctcgacg cacttgcttc  13260
gctcagtatc gctcgggacg cacggcgcgc tctacgaact gccgataaac agaggattaa  13320
```

aattgacaat tcaatggcaa ggactgccag cgctgccatt tttggggtga ggccgttcgc 13380
ggccgagggg cgcagcccct ggggggatgg gaggcccgcg ttagcgggcc gggagggttc 13440
gagaaggggg ggcacccccc ttcggcgtgc gcggtcacgc gcacagggcg cagccctggt 13500
taaaaacaag gtttataaat attggtttaa aagcaggtta aaagacaggt tagcggtggc 13560
cgaaaaacgg gcggaaaccc ttgcaaatgc tggattttct gcctgtggac agcccctcaa 13620
atgtcaatag gtgcgcccct catctgtcag cactctgccc ctcaagtgtc aaggatcgcg 13680
cccctcatct gtcagtagtc gcgcccctca agtgtcaata ccgcagggca cttatcccca 13740
ggcttgtcca catcatctgt gggaaactcg cgtaaaatca ggcgttttcg ccgatttgcg 13800
aggctggcca gctccacgtc gccggccgaa atcgagcctg cccctcatct gtcaacgccg 13860
cgccgggtga gtcggcccct caagtgtcaa cgtccgcccc tcatctgtca gtgagggcca 13920
agttttccgc gaggtatcca caacgccggc ggccgcggtg tctcgcacac ggcttcgacg 13980
gcgtttctgg cgcgtttgca gggccataga cggccgccag cccagcggcg agggcaacca 14040
gcccggtgag cgtcgcaaag gcgctcggtc ttgccttgct cgtcgagatc tggggtcgat 14100
cagccgggga tgcatcaggc cgacagtcgg aacttcgggt ccccgacctg taccattcgg 14160
tgagcaatgg ataggggagt tgatatcgtc aacgttcact tctaaagaaa tagcgccact 14220
cagcttcctc agcggcttta tccagcgatt tcctattatg tcggcatagt tctcaagatc 14280
gacagcctgt cacggttaag cgagaaatga ataagaaggc tgataattcg gatctctgcg 14340
agggagatga tatttgatca caggcagcaa cgctctgtca tcgttacaat caacatgcta 14400
ccctccgcga gatcatccgt gtttcaaacc cggcagctta gttgccgttc ttccgaatag 14460
catcggtaac atgagcaaag tctgccgcct tacaacggct ctcccgctga cgccgtcccg 14520
gactgatggg ctgcctgtat cgagtggtga ttttgtgccg agctgccggt cggggagctg 14580
ttggctggct ggtggcagga tatattgtgg tgtaaacaaa ttgacgctta gacaacttaa 14640
taacacattg cggacgtttt taatgtactg gggtggtttt tcttttcacc agtgagacgg 14700
gcaacagctg attgcccttc accgcctggc cctgagagag ttgcagcaag cggtccacgc 14760
tggtttgccc cagcaggcga aaatcctgtt tgatggtggt tccgaaatcg gcaaaatccc 14820
ttataaatca aaagaatagc ccgagatagg gttgagtgtt gttccagttt ggaacaagag 14880
tccactatta aagaacgtgg actccaacgt caaagggcga aaaaccgtct atcagggcga 14940
tggcccacta cgtgaaccat cacccaaatc aagttttttg gggtcgaggt gccgtaaagc 15000
actaaatcgg aaccctaaag ggagcccccg atttagagct tgacggggaa agccggcgaa 15060
cgtggcgaga aaggaaggga agaaagcgaa aggagcgggc gccattcagg ctgcgcaact 15120
gttgggaagg g 15131

<210> SEQ ID NO 78
<211> LENGTH: 15041
<212> TYPE: DNA
<213> ORGANISM: Artificial Sequence
<220> FEATURE:
<223> OTHER INFORMATION: vector sequence encoding recombinant immune complex

<400> SEQUENCE: 78
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180

```
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
ctttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
```

-continued

```
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtcaag   3780
gcaccactgt cacagtgtct tcagctagca ccaaaggtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgctct gaccagtgga gtgcacacct   3960
ttccagctgt tcttcagtcc tcaggattgt attctcttag cagtgttgtg actgttccat   4020
cctcaagctt gggcactcag acctacatct gcaatgtgaa tcacaaaccc agcaacacca   4080
aggttgacaa gaaagttgag cccaagtctt gtgacaagac tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtgga agtgcacaat gccaagacaa   4320
agccgagaga ggaacagtac aacagcacgt acagggttgt ctcagttctc actgttctcc   4380
atcaagattg gttgaatggc aaagagtaca agtgcaaggt ctccaacaaa gccctcccag   4440
cccccattga gaagaccatt tccaaagcga aagggcaacc ccgtgaacca caagtgtaca   4500
cacttcctcc atctcgcgat gaactgacca agaaccaggt cagcttgact tgcctggtga   4560
aaggcttcta tccctctgac atagctgtag agtgggagag caatgggcaa ccggagaaca   4620
actacaagac tacacctccc gttctcgatt ctgacggctc cttcttcctc tacagcaagc   4680
tcacagtgga caagagcagg tggcaacaag ggaatgtctt ctcatgctcc gtgatgcatg   4740
aggctcttca caatcactac acacagaaga gtctctcctt gtctccgggt aaaggaggtg   4800
gcggatcagg tggaggcggt tcaggcggag gtggatccgt aaacatgata gacccgtgga   4860
ttgtgaacaa cttcggaggc tctggtggaa gccagaacgt catcgaccct tggataagaa   4920
```

```
acaattttgg aggatctggt ggcagcatca accagatcga cccgtggata tttcagaatt   4980
ttgggggttc tggtggatca cagtctccac aaggggaatt caccatctca ccaaacaaca   5040
ctcctggaga tggtggctcc ggaggttccc aagcccctgg tggagagttc actgtttctc   5100
caagaaacgc tcctggtgag ggcggatctg gtgggagtca gtgccccttg ggtgaatttt   5160
ctatctctcc aagaaatact cctggagaag gagggagtgg tggatcaaag atcatcgttt   5220
gttgtgtgcc acctggaggg tccggtggct ctaaggttat ctttgctgct gttccacccg   5280
gaggctccgg tggatctaag gttgtcgtag ctttggttcc tccaactagt tacaagctgg   5340
acatatctta agagctcaaa gcagaatgct gagctaaaag aaaggctttt tccattttcg   5400
agagacaatg agaaaagaag aagaagaaga agaagaagaa gaagaagaaa agagtaaata   5460
ataaagcccc acaggaggcg aagttcttgt agctccatgt tatctaagtt attgatattg   5520
tttgccctat attttatttc tgtcattgtg tatgttttgt tcagtttcga tctccttgca   5580
aaatgcagag attatgagat gaataaacta agttatatta ttatacgtgt taatattctc   5640
ctcctctctc tagctagcct tttgttttct ctttttctta tttgattttc tttaaatcaa   5700
tccattttag gagagggcca gggagtgatc cagcaaaaca tgaagattag aagaaacttc   5760
cctctttttt ttcctgaaaa caatttaacg tcgagattta tctcttttttg taatggaatc   5820
atttctacag ttatgacggc tcactgagga aatatataga caaattaagt ttggttctat   5880
gagttctaat ttggacttaa gagttgtttg aaattctatt ttatagtgat gcttataatg   5940
tatttggact gttttctgct gtgtgtaaga ccttttggtc tgtgaactgg aaacatacat   6000
gaataaattt ctttgaattt actggaattt ttgcatcaac aaaagaaaaa ttgaagttac   6060
taacttgtaa atggaacaat tgtaatgtta aaggatataa atatcttaat atagtgcgat   6120
acgaatcaca cgaatgcaag actttctctc tctgctcccg ctcatgctct cggtgcatgt   6180
tagctaaata tacatcggtg catccatggc aggagcatga ggacggggat gaggaaggga   6240
gtgaggaggg ccaaaagaag tacacatagt ttcctttggg agcgaattct cgattaaaaa   6300
tcccaattat atttggtcta atttagtttg gtattgagta aaacaaattc gaaccaaacc   6360
aaaatataaa tatatagttt ttatatatat gcctttaaga ctttttatag aattttcttt   6420
aaaaaatatc tagaaatatt tgcgactctt ctggcatgta atatttcgtt aaatatgaag   6480
tgctccattt ttattaactt taaataattg gttgtacgat cactttctta tcaagtgtta   6540
ctaaaatgcg tcaatctctt tgttcttcca tattcatatg tcaaaatcta tcaaaattct   6600
tatatatctt tttcgaattt gaagtgaaat ttcgataatt taaaattaaa tagaacatat   6660
cattatttag gtatcatatt gatttttata cttaattact aaatttggtt aactttgaaa   6720
gtgtacatca acgaaaaatt agtcaaacga ctaaaataaa taaatatcat gtgttattaa   6780
gaaaattctc ctataagaat attttaatag atcatatgtt tgtaaaaaaa attaattttt   6840
actaacacat atatttactt atcaaaaatt tgacaaagta agattaaaat aatattcatc   6900
taacaaaaaa aaaaccagaa aatgctgaaa acccggcaaa accgaaccaa tccaaaccga   6960
tatagttggt ttggtttgat tttgatataa accgaaccaa ctcggtccat ttgcacccct   7020
aatcataata gctttaatat ttcaagatat tattaagtta acgttgtcaa tatcctggaa   7080
attttgcaaa atgaatcaag cctatatggc tgtaatatga atttaaaagc agctcgatgt   7140
ggtggtaata tgtaatttac ttgattctaa aaaaatatcc caagtattaa taatttctgc   7200
taggaagaag gttagctacg atttacagca aagccagaat acaaagaacc ataaagtgat   7260
```

tgaagctcga aatatacgaa ggaacaaata tttttaaaaa aatacgcaat gacttggaac 7320
aaaagaaagt gatatatttt ttgttcttaa acaagcatcc cctctaaaga atggcagttt 7380
tcctttgcat gtaactatta tgctcccttc gttacaaaaa ttttggacta ctattgggaa 7440
cttcttctga aaatagtggt accgagtgta cttcaagtca gttggaaatc aataaaatga 7500
ttattttatg aatatatttc attgtgcaag tagatagaaa ttacatatgt tacataacac 7560
acgaaataaa caaaaaaaca caatccaaaa caaacacccc aaacaaaata acactatata 7620
tatcctcgta tgaggagagg cacgttcagt gactcgacga ttcccgagca aaaaaagtct 7680
ccccgtcaca catatagtgg gtgacgcaat tatcttcaaa gtaatccttc tgttgacttg 7740
tcattgataa catccagtct tcgtcaggat tgcaaagaat tatagaaggg attccacctt 7800
ttattttctt ctttttttcca tatttagggt tgacagtgaa atcagactgg caacctatta 7860
attgcttcca caatgggacg aacttgaagg ggatgtcgtc gatgatatta taggtggcgt 7920
gttcatcgta gttggtgaag tcgatggtcc cgttccagta gttgtgtcgc ccgagacttc 7980
tagcccaggt ggtctttccg gtacgagttg gtccgcagat gtagaggctg ggtgtctga 8040
ccccagtcct tccctcatcc tggttagatc ggccatccac tcaaggtcag attgtgcttg 8100
atcgtaggag acaggatgta tgaaagtgta ggcatcgatg cttacatgat ataggtgcgt 8160
ctctctccag ttgtgcagat cttcgtggca gcggagatct gattctgtga agggcgacac 8220
gtactgctca ggttgtggag gaaataattt gttggctgaa tattccagcc attgaagctt 8280
tgttgcccat tcatgaggga actcttcttt gatcatgtca agatactcct ccttagacgt 8340
tgcagtctgg ataatagttc gccatcgtgc gtcagatttg cgaggagaca ccttatgatc 8400
tcggaaatct cctctggttt taatatctcc gtcctttgat atgtaatcaa ggacttgttt 8460
agagtttcta gctggctgga tattagggtg atttccttca aaatcgaaaa aagaaggatc 8520
tctaatacaa ggttttttat caagctggat aagagcatga tagtgggtag tgccatcttg 8580
atgaagctca gaagcaacac caaggaagaa aataagaaaa ggtgtgagtt tctcccagag 8640
aaactggaat aaatcatctc tttgagatga gcacttgggg taggtaagga aaacatattt 8700
agattggagt ctgaagttct tgctagcaga aggcatgttg ttgtgactcc gaggggttgc 8760
ctcaaactct atcttataac cggcgtggag gcatggaggc aagggcattt tggtaattta 8820
agtagttagt ggaaaatgac gtcatttact taaagacgaa gtcttgcgac aagggggggcc 8880
cacgccgaat tttaatatta ccggcgtggc cccaccttat cgcgagtgct ttagcacgag 8940
cggtccagat ttaaagtaga aaagttcccg cccactaggg ttaaaggtgt tcacactata 9000
aaagcatata cgatgtgatg gtatttgatg gagcgtatat tgtatcaggt atttccgtcg 9060
gatacgaatt attcgtacgg ccggaccggt cccctaggcc ggccaattcg agatcggccg 9120
cggctgagtg gctccttcaa tcgttgcggt tctgtcagtt ccaaacgtaa aacggcttgt 9180
cccgcgtcat cggcgggggt cataacgtga ctcccttaat tctccgctca tgatcagatt 9240
gtcgtttccc gccttcagtt taaactatca gtgtttgaca ggatatattg gcgggtaaac 9300
ctaagagaaa agagcgttta ttagaataat cggatattta aaagggcgtg aaaaggttta 9360
tccgttcgtc catttgtatg tgcatgccaa ccacagggtt ccccagatct ggcgccggcc 9420
agcgagacga gcaagattgg ccgccgcccg aaacgatccg acagcgcgcc cagcacaggt 9480
gcgcaggcaa attgcaccaa cgcatacagc gccagcagaa tgccatagtg ggcggtgacg 9540
tcgttcgagt gaaccagatc gcgcaggagg cccggcagca ccggcataat caggccgatg 9600
ccgacagcgt cgagcgcgac agtgctcaga attacgatca ggggtatgtt gggtttcacg 9660
tctggcctcc ggagactgtc atacgcgtaa aaaggccgcg ttgctggcgt ttttccatag 9720
gctccgcccc cctgacgagc atcacaaaaa tcgacgctca agtcagaggt ggcgaaaccc 9780
gacaggacta taaagatacc aggcgtttcc ccctggaagc tccctcgtgc gctctcctgt 9840
tccgaccctg ccgcttaccg gatacctgtc cgcctttctc ccttcgggaa gcgtggcgct 9900
ttctcatagc tcacgctgta ggtatctcag ttcggtgtag gtcgttcgct ccaagctggg 9960
ctgtgtgcac gaaccccccg ttcagcccga ccgctgcgcc ttatccggta actatcgtct 10020
tgagtccaac ccggtaagac acgacttatc gccactggca gcagccactg gtaacaggat 10080
tagcagagcg aggtatgtag gcggtgctac agagttcttg aagtggtggc ctaactacgg 10140
ctacactaga aggacagtat ttggtatctg cgctctgctg aagccagtta ccttcggaaa 10200
aagagttggt agctcttgat ccggcaaaca aaccaccgct ggtagcggtg gtttttttgt 10260
ttgcaagcag cagattacgc gcagaaaaaa aggatctcaa gaagatcctt tgatcttttc 10320
tacggggtct gacgctcagt ggaacgaaaa ctcacgttaa gggattttgg tcatgagatt 10380
atcaaaaagg atcttcacct agatcctttt aaattaaaaa tgaagtttta aatcaatcta 10440
aagtatatat gagtaaactt ggtctgcagt tgccatgttt tacggcagtg agagcagaga 10500
tagcgctgat gtccggcggt gcttttgccg ttacgcacca ccccgtcagt agctgaacag 10560
gagggacagc tgatagacac agaagccact ggagcacctc aaaaacacca tcatacacta 10620
aatcagtaag ttggcagcat cacccataat tgtggtttca aaatcggctc cgtcgatact 10680
atgttatacg ccaactttga aaacaacttt gaaaaagctg ttttctggta tttaaggttt 10740
tagaatgcaa ggaacagtga attggagttc gtcttgttat aattagcttc ttggggtatc 10800
tttaaatact gtagaaaaga ggaaggaaat aataaatggc taaaatgaga atatcaccgg 10860
aattgaaaaa actgatcgaa aaataccgct gcgtaaaaga tacggaagga atgtctcctg 10920
ctaaggtata taagctggtg ggagaaaatg aaaacctata tttaaaaatg acggacagcc 10980
ggtataaagg gaccacctat gatgtggaac gggaaaagga catgatgcta tggctggaag 11040
gaaagctgcc tgttccaaag gtcctgcact ttgaacggca tgatggctgg agcaatctgc 11100
tcatgagtga ggccgatggc gtcctttgct cggaagagta tgaagatgaa caaagccctg 11160
aaaagattat cgagctgtat gcggagtgca tcaggctctt tcactccatc gacatatcgg 11220
attgtcccta tacgaatagc ttagacagcc gcttagccga attggattac ttactgaata 11280
acgatctggc cgatgtggat tgcgaaaact gggaagaaga cactccattt aaagatccgc 11340
gcgagctgta tgatttttta aagacggaaa agcccgaaga ggaacttgtc ttttcccacg 11400
gcgacctggg agacagcaac atctttgtga aagatggcaa agtaagtggc tttattgatc 11460
ttgggagaag cggcagggcg gacaagtggt atgacattgc cttctgcgtc cggtcgatca 11520
gggaggatat cggggaagaa cagtatgtcg agctattttt tgacttactg gggatcaagc 11580
ctgattggga gaaaataaaa tattatattt tactggatga attgttttag tacctagatg 11640
tggcgcaacg atgccggcga caagcaggag cgcaccgact tcttccgcat caagtgtttt 11700
ggctctcagg ccgaggccca cggcaagtat ttgggcaagg ggtcgctggt attcgtgcag 11760
ggcaagattc ggaataccaa gtacgagaag gacggccaga cggtctacgg gaccgacttc 11820
attgccgata aggtggatta tctggacacc aaggcaccag gcgggtcaaa tcaggaataa 11880
gggcacattg ccccggcgtg agtcggggca atcccgcaag gagggtgaat gaatcggacg 11940
tttgaccgga aggcatacag gcaagaactg atcgacgcgg ggttttccgc cgaggatgcc 12000
gaaaccatcg caagccgcac cgtcatgcgt gcgccccgcg aaaccttcca gtccgtcggc 12060
tcgatggtcc agcaagctac ggccaagatc gagcgcgaca gcgtgcaact ggctccccct 12120
gccctgcccg cgccatcggc cgccgtggag cgttcgcgtc gtctcgaaca ggaggcggca 12180
ggtttggcga agtcgatgac catcgacacg cgaggaacta tgacgaccaa gaagcgaaaa 12240
accgccggcg aggacctggc aaaacaggtc agcgaggcca agcaggccgc gttgctgaaa 12300
cacacgaagc agcagatcaa ggaaatgcag ctttccttgt tcgatattgc gccgtggccg 12360
gacacgatgc gagcgatgcc aaacgacacg gcccgctctg ccctgttcac cacgcgcaac 12420
aagaaaatcc cgcgcgaggc gctgcaaaac aaggtcattt tccacgtcaa caaggacgtg 12480
aagatcacct acaccggcgt cgagctgcgg gccgacgatg acgaactggt gtggcagcag 12540
gtgttggagt acgcgaagcg cacccctatc ggcgagccga tcaccttcac gttctacgag 12600
ctttgccagg acctgggctg gtcgatcaat ggccggtatt acacgaaggc cgaggaatgc 12660
ctgtcgcgcc tacaggcgac ggcgatgggc ttcacgtccg accgcgttgg gcacctggaa 12720
tcggtgtcgc tgctgcaccg cttccgcgtc ctggaccgtg gcaagaaaac gtcccgttgc 12780
caggtcctga tcgacgagga aatcgtcgtg ctgtttgctg gcgaccacta cacgaaattc 12840
atatgggaga agtaccgcaa gctgtcgccg acggcccgac ggatgttcga ctatttcagc 12900
tcgcaccggg agccgtaccc gctcaagctg gaaaccttcc gcctcatgtg cggatcggat 12960
tccacccgcg tgaagaagtg gcgcgagcag gtcggcgaag cctgcgaaga gttgcgaggc 13020
agcggcctgg tggaacacgc ctgggtcaat gatgacctgg tgcattgcaa acgctagggc 13080
cttgtggggt cagttccggc tgggggttca gcagccagcg ctttactggc atttcaggaa 13140
caagcgggca ctgctcgacg cacttgcttc gctcagtatc gctcgggacg cacggcgcgc 13200
tctacgaact gccgataaac agaggattaa aattgacaat tcaatggcaa ggactgccag 13260
cgctgccatt tttggggtga ggccgttcgc ggccgagggg cgcagcccct ggggggatgg 13320
gaggcccgcg ttagcgggcc gggagggttc gagaaggggg ggcacccccc ttcggcgtgc 13380
gcggtcacgc gcacagggcg cagccctggt taaaaacaag gtttataaat attggtttaa 13440
aagcaggtta aaagacaggt tagcggtggc cgaaaaacgg gcggaaaccc ttgcaaatgc 13500
tggattttct gcctgtggac agcccctcaa atgtcaatag gtgcgcccct catctgtcag 13560
cactctgccc ctcaagtgtc aaggatcgcg cccctcatct gtcagtagtc gcgcccctca 13620
agtgtcaata ccgcagggca cttatcccca ggcttgtcca catcatctgt gggaaactcg 13680
cgtaaaatca ggcgttttcg ccgatttgcg aggctggcca gctccacgtc gccggccgaa 13740
atcgagcctg cccctcatct gtcaacgccg cgccgggtga gtcggcccct caagtgtcaa 13800
cgtccgcccc tcatctgtca gtgagggcca agttttccgc gaggtatcca caacgccggc 13860
ggccgcggtg tctcgcacac ggcttcgacg gcgtttctgg cgcgtttgca gggccataga 13920
cggccgccag cccagcggcg agggcaacca gcccggtgag cgtcgcaaag gcgctcggtc 13980
ttgccttgct cgtcgagatc tggggtcgat cagccgggga tgcatcaggc cgacagtcgg 14040
aacttcgggt ccccgacctg taccattcgg tgagcaatgg ataggggagt tgatatcgtc 14100
aacgttcact tctaaagaaa tagcgccact cagcttcctc agcggcttta tccagcgatt 14160
tcctattatg tcggcatagt tctcaagatc gacagcctgt cacggttaag cgagaaatga 14220
ataagaaggc tgataattcg gatctctgcg agggagatga tatttgatca caggcagcaa 14280
cgctctgtca tcgttacaat caacatgcta ccctccgcga gatcatccgt gtttcaaacc 14340
cggcagctta gttgccgttc ttccgaatag catcggtaac atgagcaaag tctgccgcct 14400
tacaacggct ctcccgctga cgccgtcccg gactgatggg ctgcctgtat cgagtggtga 14460
ttttgtgccg agctgccggt cggggagctg ttggctggct ggtggcagga tatattgtgg 14520
tgtaaacaaa ttgacgctta gacaacttaa taacacattg cggacgtttt taatgtactg 14580
gggtggtttt tcttttcacc agtgagacgg gcaacagctg attgcccttc accgcctggc 14640
cctgagagag ttgcagcaag cggtccacgc tggtttgccc cagcaggcga aaatcctgtt 14700
tgatggtggt tccgaaatcg gcaaaatccc ttataaatca aaagaatagc ccgagatagg 14760
gttgagtgtt gttccagttt ggaacaagag tccactatta aagaacgtgg actccaacgt 14820
caaagggcga aaaaccgtct atcagggcga tggcccacta cgtgaaccat cacccaaatc 14880
aagttttttg gggtcgaggt gccgtaaagc actaaatcgg aaccctaaag ggagcccccg 14940
atttagagct tgacggggaa agccggcgaa cgtggcgaga aaggaaggga agaaagcgaa 15000
aggagcgggc gccattcagg ctgcgcaact gttgggaagg g 15041

<210> SEQ ID NO 79
<211> LENGTH: 15302
<212> TYPE: DNA
<213> ORGANISM: Artificial Sequence
<220> FEATURE:
<223> OTHER INFORMATION: vector sequence encoding recombinant immune complex

<400> SEQUENCE: 79
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380

-continued gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860
atattaccct ttgttgaaaa gtctcaattg ccctttggtc ttctgagact gtatctttga 1920
tatttttgga gtagacaagt gtgtcgtgct ccaccatgtt ctggcaattc cggttcgctt 1980
gctgtccata aaaccgccca gtctagctat cgccatgtaa gcccactgca agctacctgc 2040
tttctctttg cgcttgcgtt ttcccttgtc cagatagccc agtagctgac attcatccgg 2100
ggtcagcacc gtttctgcgg actggctttc tacgtgttcc gcttccttta gcagcccttg 2160
cgccctgagt gcttgcggca gcgtgaagct ggcgcgccgc tctagcagaa ggcatgttgt 2220
tgtgactccg aggggttgcc tcaaactcta tcttataacc ggcgtggagg catggaggca 2280
agggcatttt ggtaatttaa gtagttagtg gaaaatgacg tcatttactt aaagacgaag 2340
tcttgcgaca aggggggccc acgccgaatt ttaatattac cggcgtggcc ccaccttatc 2400
gcgagtgctt tagcacgagc ggtccagatt taaagtagaa aagttcccgc ccactagggt 2460
taaaggtgtt cacactataa aagcatatac gatgtgatgg tatttgatgg agcgtatatt 2520
gtatcaggta tttccgtcgg atacgaatta ttcgtacgac cctcctgcag gtcaacatgg 2580
tggagcacga cacacttgtc tactccaaaa atatcaaaga tacagtctca gaagaccaaa 2640
gggcaattga gacttttcaa caaagggtaa tatccggaaa cctcctcgga ttccattgcc 2700
cagctatctg tcactttatt gtgaagatag tggaaaagga aggtggctcc tacaaatgcc 2760
atcattgcga taaaggaaag gccatcgttg aagatgcctc tgccgacagt ggtcccaaag 2820
atggaccccc acccacgagg agcatcgtgg aaaaagaaga cgttccaacc acgtcttcaa 2880
agcaagtgga ttgatgtgat aacatggtgg agcacgacac acttgtctac tccaaaaata 2940
tcaaagatac agtctcagaa gaccaaaggg caattgagac ttttcaacaa agggtaatat 3000
ccggaaacct cctcggattc cattgcccag ctatctgtca ctttattgtg aagatagtgg 3060
aaaaggaagg tggctcctac aaatgccatc attgcgataa aggaaaggcc atcgttgaag 3120
atgcctctgc cgacagtggt cccaaagatg gacccccacc cacgaggagc atcgtggaaa 3180
aagaagacgt tccaaccacg tcttcaaagc aagtggattg atgtgatatc tccactgacg 3240
taagggatga cgcacaatcc cactatcctt cgcaagaccc ttcctctata taaggaagtt 3300
catttcattt ggagaggacc tcgagaaaca aacaaaatca acaaatatag aaaataacgc 3360
atttccaatt ctttgaaatt tctgcaacat ctagaacaat gggatggtct tgcatcatac 3420
tctttcttgt tgcaactgct acaggtgtcc actctgatgt tcagcttctc gagtctggag 3480
gtggtcttgt gcaacctgga ggttccttga gactctcctg tgcagcttca gggtttgact 3540
tcagtaggta ctggatgagt tgggttcgtc aagctcctgg gaaaggacta gaatggattg 3600
gagagatcaa tccagattca agtaccatca actatactcc atctctgaag gatcgcttca 3660
ccatttccag agacaatgcc aagaacacgt tgtatcttca gatgaacagc ttgaggactg 3720

```
aagacacagc cttgtactac tgcacaagac agggctatgg ctacaactac tggggtcaag   3780
gcaccactgt cacagtgtct tcagctagca ccaaaggtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgctct gaccagtgga gtgcacacct   3960
ttccagctgt tcttcagtcc tcaggattgt attctcttag cagtgttgtg actgttccat   4020
cctcaagctt gggcactcag acctacatct gcaatgtgaa tcacaaaccc agcaacacca   4080
aggttgacaa gaaagttgag cccaagtctt gtgacaagac tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtgga agtgcacaat gccaagacaa   4320
agccgagaga ggaacagtac aacagcacgt acagggttgt ctcagttctc actgttctcc   4380
atcaagattg gttgaatggc aaagagtaca agtgcaaggt ctccaacaaa gccctcccag   4440
cccccattga gaagaccatt tccaaagcga aagggcaacc ccgtgaacca caagtgtaca   4500
cacttcctcc atctcgcgat gaactgacca agaaccaggt cagcttgact tgcctggtga   4560
aaggcttcta tccctctgac atagctgtag agtgggagag caatgggcaa ccggagaaca   4620
actacaagac tacacctccc gttctcgatt ctgacggctc cttcttcctc tacagcaagc   4680
tcacagtgga caagagcagg tggcaacaag ggaatgtctt ctcatgctcc gtgatgcatg   4740
aggctcttca caatcactac acacagaaga gtctctcctt gtctccgggt aaaggaggtg   4800
gcggatcagg tggaggcggt tcaggcggag gtggatccac tttgttcccg catgttatcg   4860
ccgacgtggg tggaagtgga gggtcaacaa tgttcccaca tatcatcgta gacgttggcg   4920
gatctggtgg atctacttgt tttccacacg ttatgtgcga tgttggaggg tctggcggat   4980
ctttgcagct tgggccacac ttgaatccct tccttagtgg gggatctgga ggttctgcgc   5040
cgcttggacc agacctcaat ccgtacttgt ctggaggttc cggtggatct ttggctttgg   5100
gacctggctt aaatccttac ttagccggag gttctggagg ttcttcttgg gtttcaaggt   5160
tctatcagct cggaggatct ggaggctcct cttgggtgaa ccagttttac acccttggag   5220
ggtctggagg ttcttcatgg gttccaagat tgtaccaact cggtggatct ggaggatctt   5280
ttgtatccga gcaagcccct actatgggtg atgccgctct tggcggttct ggcggatctt   5340
tctaccaaga ggctgctcct gctcagtcag atgttgcttt gggtggctct ggagggtctt   5400
ttgcttccaa cgctttcact gttcaatctg aggctcttct tggaggatct ggagggtctt   5460
ctccagcgcc cgttggattt ccagatttcg gaggctctgg agggtccatc ccagccccac   5520
ttggaactcc agacttcgga gggtctggtg gttcccgtgc ggctcctctc ggatacccgg   5580
acttcactag ttacaagctg gacatatctt aagagctcaa agcagaatgc tgagctaaaa   5640
gaaaggcttt ttccattttc gagagacaat gagaaaagaa gaagaagaag aagaagaaga   5700
agaagaagaa aagagtaaat aataaagccc cacaggaggc gaagttcttg tagctccatg   5760
ttatctaagt tattgatatt gtttgcccta tattttattt ctgtcattgt gtatgttttg   5820
ttcagtttcg atctccttgc aaaatgcaga gattatgaga tgaataaact aagttatatt   5880
attatacgtg ttaatattct cctcctctct ctagctagcc ttttgttttc tctttttctt   5940
atttgatttt ctttaaatca atccatttta ggagagggcc agggagtgat ccagcaaaac   6000
atgaagatta gaagaaactt ccctcttttt tttcctgaaa acaatttaac gtcgagattt   6060
atctcttttt gtaatggaat catttctaca gttatgacgg ctcactgagg aaatatatag   6120
```

acaaattaag tttggttcta tgagttctaa tttggactta agagttgttt gaaattctat 6180
tttatagtga tgcttataat gtatttggac tgttttctgc tgtgtgtaag accttttggt 6240
ctgtgaactg gaaacataca tgaataaatt tctttgaatt tactggaatt tttgcatcaa 6300
caaaagaaaa attgaagtta ctaacttgta aatggaacaa ttgtaatgtt aaaggatata 6360
aatatcttaa tatagtgcga tacgaatcac acgaatgcaa gactttctct ctctgctccc 6420
gctcatgctc tcggtgcatg ttagctaaat atacatcggt gcatccatgg caggagcatg 6480
aggacgggga tgaggaaggg agtgaggagg gccaaaagaa gtacacatag tttcctttgg 6540
gagcgaattc tcgattaaaa atcccaatta tatttggtct aatttagttt ggtattgagt 6600
aaaacaaatt cgaaccaaac caaaatataa atatatagtt tttatatata tgcctttaag 6660
actttttata gaattttctt taaaaaatat ctagaaatat ttgcgactct tctggcatgt 6720
aatatttcgt taaatatgaa gtgctccatt tttattaact ttaaataatt ggttgtacga 6780
tcactttctt atcaagtgtt actaaaatgc gtcaatctct ttgttcttcc atattcatat 6840
gtcaaaatct atcaaaattc ttatatatct ttttcgaatt tgaagtgaaa tttcgataat 6900
ttaaaattaa atagaacata tcattattta ggtatcatat tgatttttat acttaattac 6960
taaatttggt taactttgaa agtgtacatc aacgaaaaat tagtcaaacg actaaaataa 7020
ataaatatca tgtgttatta agaaaattct cctataagaa tattttaata gatcatatgt 7080
ttgtaaaaaa aattaatttt tactaacaca tatatttact tatcaaaaat ttgacaaagt 7140
aagattaaaa taatattcat ctaacaaaaa aaaaaccaga aaatgctgaa aacccggcaa 7200
aaccgaacca atccaaaccg atatagttgg tttggtttga ttttgatata aaccgaacca 7260
actcggtcca tttgcacccc taatcataat agctttaata tttcaagata ttattaagtt 7320
aacgttgtca atatcctgga aattttgcaa aatgaatcaa gcctatatgg ctgtaatatg 7380
aatttaaaag cagctcgatg tggtggtaat atgtaattta cttgattcta aaaaaatatc 7440
ccaagtatta ataatttctg ctaggaagaa ggttagctac gatttacagc aaagccagaa 7500
tacaaagaac cataaagtga ttgaagctcg aaatatacga aggaacaaat atttttaaaa 7560
aaatacgcaa tgacttggaa caaaagaaag tgatatattt tttgttctta aacaagcatc 7620
ccctctaaag aatggcagtt ttcctttgca tgtaactatt atgctccctt cgttacaaaa 7680
attttggact actattggga acttcttctg aaaatagtgg taccgagtgt acttcaagtc 7740
agttggaaat caataaaatg attattttat gaatatattt cattgtgcaa gtagatagaa 7800
attacatatg ttacataaca cacgaaataa acaaaaaaac acaatccaaa acaaacaccc 7860
caaacaaaat aacactatat atatcctcgt atgaggagag gcacgttcag tgactcgacg 7920
attcccgagc aaaaaaagtc tccccgtcac acatatagtg ggtgacgcaa ttatcttcaa 7980
agtaatcctt ctgttgactt gtcattgata acatccagtc ttcgtcagga ttgcaaagaa 8040
ttatagaagg gattccacct tttattttct tcttttttcc atatttaggg ttgacagtga 8100
aatcagactg gcaacctatt aattgcttcc acaatgggac gaacttgaag gggatgtcgt 8160
cgatgatatt ataggtggcg tgttcatcgt agttggtgaa gtcgatggtc ccgttccagt 8220
agttgtgtcg cccgagactt ctagcccagg tggtctttcc ggtacgagtt ggtccgcaga 8280
tgtagaggct ggggtgtctg accccagtcc ttccctcatc ctggttagat cggccatcca 8340
ctcaaggtca gattgtgctt gatcgtagga gacaggatgt atgaaagtgt aggcatcgat 8400
gcttacatga tataggtgcg tctctctcca gttgtgcaga tcttcgtggc agcggagatc 8460

```
tgattctgtg aagggcgaca cgtactgctc aggttgtgga ggaaataatt tgttggctga   8520
atattccagc cattgaagct ttgttgccca ttcatgaggg aactcttctt tgatcatgtc   8580
aagatactcc tccttagacg ttgcagtctg gataatagtt cgccatcgtg cgtcagattt   8640
gcgaggagac accttatgat ctcggaaatc tcctctggtt ttaatatctc cgtcctttga   8700
tatgtaatca aggacttgtt tagagtttct agctggctgg atattagggt gatttccttc   8760
aaaatcgaaa aaagaaggat ctctaataca aggtttttta tcaagctgga taagagcatg   8820
atagtgggta gtgccatctt gatgaagctc agaagcaaca ccaaggaaga aaataagaaa   8880
aggtgtgagt ttctcccaga gaaactggaa taaatcatct ctttgagatg agcacttggg   8940
gtaggtaagg aaaacatatt tagattggag tctgaagttc ttgctagcag aaggcatgtt   9000
gttgtgactc cgaggggttg cctcaaactc tatcttataa ccggcgtgga ggcatggagg   9060
caagggcatt ttggtaattt aagtagttag tggaaaatga cgtcatttac ttaaagacga   9120
agtcttgcga caagggggc ccacgccgaa ttttaatatt accggcgtgg ccccacctta   9180
tcgcgagtgc tttagcacga gcggtccaga tttaaagtag aaaagttccc gcccactagg   9240
gttaaaggtg ttcacactat aaaagcatat acgatgtgat ggtatttgat ggagcgtata   9300
ttgtatcagg tatttccgtc ggatacgaat tattcgtacg gccggaccgg tcccctaggc   9360
cggccaattc gagatcggcc gcggctgagt ggctccttca atcgttgcgg ttctgtcagt   9420
tccaaacgta aaacggcttg tcccgcgtca tcggcggggg tcataacgtg actcccttaa   9480
ttctccgctc atgatcagat tgtcgtttcc cgccttcagt ttaaactatc agtgtttgac   9540
aggatatatt ggcgggtaaa cctaagagaa aagagcgttt attagaataa tcggatattt   9600
aaaagggcgt gaaaaggttt atccgttcgt ccatttgtat gtgcatgcca accacagggt   9660
tccccagatc tggcgccggc cagcgagacg agcaagattg gccgccgccc gaaacgatcc   9720
gacagcgcgc ccagcacagg tgcgcaggca aattgcacca acgcatacag cgccagcaga   9780
atgccatagt gggcggtgac gtcgttcgag tgaaccagat cgcgcaggag gcccggcagc   9840
accggcataa tcaggccgat gccgacagcg tcgagcgcga cagtgctcag aattacgatc   9900
aggggtatgt tgggtttcac gtctggcctc cggagactgt catacgcgta aaaaggccgc   9960
gttgctggcg tttttccata ggctccgccc ccctgacgag catcacaaaa atcgacgctc  10020
aagtcagagg tggcgaaacc cgacaggact ataaagatac caggcgtttc cccctggaag  10080
ctccctcgtg cgctctcctg ttccgaccct gccgcttacc ggatacctgt ccgcctttct  10140
cccttcggga agcgtggcgc tttctcatag ctcacgctgt aggtatctca gttcggtgta  10200
ggtcgttcgc tccaagctgg gctgtgtgca cgaacccccc gttcagcccg accgctgcgc  10260
cttatccggt aactatcgtc ttgagtccaa cccggtaaga cacgacttat cgccactggc  10320
agcagccact ggtaacagga ttagcagagc gaggtatgta ggcggtgcta cagagttctt  10380
gaagtggtgg cctaactacg gctacactag aaggacagta tttggtatct gcgctctgct  10440
gaagccagtt accttcggaa aaagagttgg tagctcttga tccggcaaac aaaccaccgc  10500
tggtagcggt ggtttttttg tttgcaagca gcagattacg cgcagaaaaa aaggatctca  10560
agaagatcct ttgatctttt ctacggggtc tgacgctcag tggaacgaaa actcacgtta  10620
agggattttg gtcatgagat tatcaaaaag gatcttcacc tagatccttt taaattaaaa  10680
atgaagtttt aaatcaatct aaagtatata tgagtaaact tggtctgcag ttgccatgtt  10740
ttacggcagt gagagcagag atagcgctga tgtccggcgg tgcttttgcc gttacgcacc  10800
accccgtcag tagctgaaca ggagggacag ctgatagaca cagaagccac tggagcacct  10860
```

caaaaacacc atcatacact aaatcagtaa gttggcagca tcacccataa ttgtggtttc 10920
aaaatcggct ccgtcgatac tatgttatac gccaactttg aaaacaactt tgaaaaagct 10980
gttttctggt atttaaggtt ttagaatgca aggaacagtg aattggagtt cgtcttgtta 11040
taattagctt cttggggtat ctttaaatac tgtagaaaag aggaaggaaa taataaatgg 11100
ctaaaatgag aatatcaccg gaattgaaaa aactgatcga aaaataccgc tgcgtaaaag 11160
atacggaagg aatgtctcct gctaaggtat ataagctggt gggagaaaat gaaaacctat 11220
atttaaaaat gacggacagc cggtataaag ggaccaccta tgatgtggaa cgggaaaagg 11280
acatgatgct atggctggaa ggaaagctgc ctgttccaaa ggtcctgcac tttgaacggc 11340
atgatggctg gagcaatctg ctcatgagtg aggccgatgg cgtcctttgc tcggaagagt 11400
atgaagatga acaaagccct gaaaagatta tcgagctgta tgcggagtgc atcaggctct 11460
ttcactccat cgacatatcg gattgtccct atacgaatag cttagacagc cgcttagccg 11520
aattggatta cttactgaat aacgatctgg ccgatgtgga ttgcgaaaac tgggaagaag 11580
acactccatt taaagatccg cgcgagctgt atgatttttt aaagacggaa aagcccgaag 11640
aggaacttgt cttttcccac ggcgacctgg gagacagcaa catctttgtg aaagatggca 11700
aagtaagtgg ctttattgat cttgggagaa gcggcagggc ggacaagtgg tatgacattg 11760
ccttctgcgt ccggtcgatc agggaggata tcggggaaga acagtatgtc gagctatttt 11820
ttgacttact ggggatcaag cctgattggg agaaaataaa atattatatt ttactggatg 11880
aattgtttta gtacctagat gtggcgcaac gatgccggcg acaagcagga gcgcaccgac 11940
ttcttccgca tcaagtgttt tggctctcag gccgaggccc acggcaagta tttgggcaag 12000
gggtcgctgg tattcgtgca gggcaagatt cggaatacca agtacgagaa ggacggccag 12060
acggtctacg ggaccgactt cattgccgat aaggtggatt atctggacac caaggcacca 12120
ggcgggtcaa atcaggaata agggcacatt gccccggcgt gagtcggggc aatcccgcaa 12180
ggagggtgaa tgaatcggac gtttgaccgg aaggcataca ggcaagaact gatcgacgcg 12240
gggttttccg ccgaggatgc cgaaaccatc gcaagccgca ccgtcatgcg tgcgccccgc 12300
gaaaccttcc agtccgtcgg ctcgatggtc cagcaagcta cggccaagat cgagcgcgac 12360
agcgtgcaac tggctccccc tgccctgccc gcgccatcgg ccgccgtgga gcgttcgcgt 12420
cgtctcgaac aggaggcggc aggtttggcg aagtcgatga ccatcgacac gcgaggaact 12480
atgacgacca agaagcgaaa aaccgccggc gaggacctgg caaaacaggt cagcgaggcc 12540
aagcaggccg cgttgctgaa acacacgaag cagcagatca aggaaatgca gctttccttg 12600
ttcgatattg cgccgtggcc ggacacgatg cgagcgatgc caaacgacac ggcccgctct 12660
gccctgttca ccacgcgcaa caagaaaatc ccgcgcgagg cgctgcaaaa caaggtcatt 12720
ttccacgtca acaaggacgt gaagatcacc tacaccggcg tcgagctgcg ggccgacgat 12780
gacgaactgg tgtggcagca ggtgttggag tacgcgaagc gcacccctat cggcgagccg 12840
atcaccttca cgttctacga gctttgccag gacctgggct ggtcgatcaa tggccggtat 12900
tacacgaagg ccgaggaatg cctgtcgcgc ctacaggcga cggcgatggg cttcacgtcc 12960
gaccgcgttg ggcacctgga atcggtgtcg ctgctgcacc gcttccgcgt cctggaccgt 13020
ggcaagaaaa cgtcccgttg ccaggtcctg atcgacgagg aaatcgtcgt gctgtttgct 13080
ggcgaccact acacgaaatt catatgggag aagtaccgca agctgtcgcc gacggcccga 13140
cggatgttcg actatttcag ctcgcaccgg gagccgtacc cgctcaagct ggaaaccttc 13200

-continued

```
cgcctcatgt gcggatcgga ttccacccgc gtgaagaagt ggcgcgagca ggtcggcgaa  13260
gcctgcgaag agttgcgagg cagcggcctg gtggaacacg cctgggtcaa tgatgacctg  13320
gtgcattgca aacgctaggg ccttgtgggg tcagttccgg ctgggggttc agcagccagc  13380
gctttactgg catttcagga acaagcgggc actgctcgac gcacttgctt cgctcagtat  13440
cgctcgggac gcacggcgcg ctctacgaac tgccgataaa cagaggatta aaattgacaa  13500
ttcaatggca aggactgcca gcgctgccat ttttggggtg aggccgttcg cggccgaggg  13560
gcgcagcccc tggggggatg ggaggcccgc gttagcgggc cgggagggtt cgagaagggg  13620
gggcaccccc cttcggcgtg cgcggtcacg cgcacagggc gcagccctgg ttaaaaacaa  13680
ggtttataaa tattggttta aaagcaggtt aaaagacagg ttagcggtgg ccgaaaaacg  13740
ggcggaaacc cttgcaaatg ctggattttc tgcctgtgga cagcccctca aatgtcaata  13800
ggtgcgcccc tcatctgtca gcactctgcc cctcaagtgt caaggatcgc gcccctcatc  13860
tgtcagtagt cgcgcccctc aagtgtcaat accgcagggc acttatcccc aggcttgtcc  13920
acatcatctg tgggaaactc gcgtaaaatc aggcgttttc gccgatttgc gaggctggcc  13980
agctccacgt cgccggccga aatcgagcct gcccctcatc tgtcaacgcc gcgccgggtg  14040
agtcggcccc tcaagtgtca acgtccgccc ctcatctgtc agtgagggcc aagttttccg  14100
cgaggtatcc acaacgccgg cggccgcggt gtctcgcaca cggcttcgac ggcgtttctg  14160
gcgcgtttgc agggccatag acggccgcca gcccagcggc gagggcaacc agcccggtga  14220
gcgtcgcaaa ggcgctcggt cttgccttgc tcgtcgagat ctggggtcga tcagccgggg  14280
atgcatcagg ccgacagtcg gaacttcggg tccccgacct gtaccattcg gtgagcaatg  14340
gataggggag ttgatatcgt caacgttcac ttctaaagaa atagcgccac tcagcttcct  14400
cagcggcttt atccagcgat ttcctattat gtcggcatag ttctcaagat cgacagcctg  14460
tcacggttaa gcgagaaatg aataagaagg ctgataattc ggatctctgc gagggagatg  14520
atatttgatc acaggcagca acgctctgtc atcgttacaa tcaacatgct accctccgcg  14580
agatcatccg tgtttcaaac ccggcagctt agttgccgtt cttccgaata gcatcggtaa  14640
catgagcaaa gtctgccgcc ttacaacggc tctcccgctg acgccgtccc ggactgatgg  14700
gctgcctgta tcgagtggtg attttgtgcc gagctgccgg tcggggagct gttggctggc  14760
tggtggcagg atatattgtg gtgtaaacaa attgacgctt agacaactta ataacacatt  14820
gcggacgttt ttaatgtact ggggtggttt ttcttttcac cagtgagacg ggcaacagct  14880
gattgccctt caccgcctgg ccctgagaga gttgcagcaa gcggtccacg ctggtttgcc  14940
ccagcaggcg aaaatcctgt ttgatggtgg ttccgaaatc ggcaaaatcc cttataaatc  15000
aaaagaatag cccgagatag ggttgagtgt tgttccagtt tggaacaaga gtccactatt  15060
aaagaacgtg gactccaacg tcaaagggcg aaaaaccgtc tatcagggcg atggcccact  15120
acgtgaacca tcacccaaat caagtttttt ggggtcgagg tgccgtaaag cactaaatcg  15180
gaaccctaaa gggagccccc gatttagagc ttgacgggga aagccggcga acgtggcgag  15240
aaaggaaggg aagaaagcga aaggagcggg cgccattcag gctgcgcaac tgttgggaag  15300
gg                                                                 15302
```

IgG VARIANTS FOR INDUCTION OF IMMUNE RESPONSE WITHOUT ADJUVANT

Related Applications

This application is the U.S. National Stage of International patent application no. PCT/US2021/019090, filed Feb. 22, 2021, which claims the benefit of U.S. provisional patent application No. 62/980,012, filed Feb. 21, 2020 titled "IgG Variants for Induction of Neutralizing Immune Response Without Adjuvant," the contents of each of which are hereby incorporated by reference in their entireties.

STATEMENT REGARDING FEDERALLY FUNDED RESEARCH OR DEVELOPMENT

This invention was made with government support under R33 AI101329 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 416,572 byte ASCII (text) file named "SeqList" created on Feb. 21, 2021.

TECHNICAL FIELD

The disclosure relates to immunoglobulin variants that induce potent immune responses without an adjuvant and vectors for producing such variants in plants.

BACKGROUND

Subunit vaccines consisting of recombinant protein antigens are very promising due to their safety, ease of production, and capacity to elicit targeted immune responses tailored towards desired epitopes. When delivered by themselves, however, these antigens often fail to generate robust and long-lasting immune responses, necessitating strategies to enhance their immunogenicity. Accordingly, recombinant protein antigens have been candidates for therapeutic uses. Protein fusions to the immunoglobulin Fc domain have demonstrated tremendous potential as therapeutic candidates. Fusion of a protein of interest to Fc can enhance the solubility and stability of the fusion partner while also allowing simple and cost-effective purification via protein A/G affinity chromatography. Furthermore, by interacting with neonatal Fc receptors (FcRn) in the body, Fc-fusions can escape lysosomal degradation, thereby extending the serum half-life of the Fc-fusion.

While much of the work with Fc-fusions has focused on improving their therapeutic potential, fewer studies have investigated Fc-fusion as a strategy to enhance antigen immunogenicity. Antigen-presenting cells containing Fc7 receptors and the complement receptor C1q can uptake and process IgG-bound antigen. However, these interactions require high avidity binding for activation, and thus monovalent Fc-antigen fusions cannot efficiently utilize these pathways. On the other hand, larger antigen-antibody immune complexes with multivalent Fc domains can cross-link Fc receptors and efficiently bind C1q, resulting in greatly improved uptake and presentation by dendritic cells, as well as improved activation of T-cells. Immune complexes generated by mixing antibody with antigen often yields inconsistent results: immune responses may be skewed towards favorable antigenic sites, but overall immunogenicity may not be markedly improved.

By contrast, recombinant immune complexes (RICs), have been used to produce vaccine candidates for *Clostridium tetani*, Ebola virus, *Mycobacterium tuberculosis*, dengue virus, and human papillomavirus. An RIC is an IgG genetically fused to its cognate antigen, which allow the formation of larger highly immunogenic antigen-antibody clusters that mimic those found during native infection.

SUMMARY

This disclosure is directed to recombinant proteins that are immunoglobulin variants, for example immunoglobulin G (IgG) variants, and their methods of production and use. In some aspects, the IgG variants are based on the 6D8 antibody. In certain embodiments where the parts of antibody in the recombinant protein is the 6D8 antibody, the Fc fusion, which comprises the CH2 domain and the CH3 domain of the antibody, comprises the substitution mutations E345R, E430G, and S440Y.

In some embodiments, the recombinant protein comprises a unit of an antigen, a unit of a Fc fusion comprising a CH2 domain and a CH3 domain of an IgG, a unit of a variable heavy chain (VH) domain of the IgG, a unit of a CH1 domain of the IgG; and a unit of a light chain variable (VL) domain of the IgG. The unit of the antigen is not an epitope of the IgG, and it is linked to the unit of the VH domain of the IgG at the N-terminus or to the CH3 domain of IgG at the C-terminus. The unit of the CH1 domain of IgG is linked to the CH2 domain of the IgG, while the unit of the VL domain of the IgG is fused to the unit of the VH domain of the IgG and to the CH1 domain of the IgG. In some implementations, the recombinant protein further comprises a unit of an epitope tag, wherein the epitope tag is an epitope of the IgG.

In some aspects, the recombinant protein comprises two units of the antigen, two units of the Fc fusion, two units of the CH1 domain of the IgG, two units of the VH domain of the IgG, and two units of the VL domain of the IgG. A disulfide bond formed at the linkage of the CH2 domain and the CH1 domain of the IgG links the two units of the Fc fusion. In some aspects, the each unit of the VL domain of the IgG is linked to a unit of VH domain of the IgG and the CH1 domain of the IgG. In particular implementations, the recombinant protein does not comprise any light chain constant (CL) domain of the IgG. In some embodiments of the recombinant protein comprising two units of the antigen, two units of the Fc fusion, two units of the CH1 domain of the IgG, two units of the VH domain of the IgG, and two units of light chain variable (VL) domain of the IgG, the recombinant protein further comprises two units of an epitope tag, wherein the epitope tag is an epitope of the IgG. In some implementations, the two units of the epitope tag are linked to the two units of the Fc fusion at the C-terminus of the CH3 domain of the IgG, while the two units of the antigen are linked to the two units of the VH domain of the IgG. In other implementations, the two units of the epitope tag are linked to the two units of the antigen, while the two units of the antigen are linked to the two units of Fc fusion at the C-terminus of the CH3 domain of the IgG. In particular embodiments, the antibody is the 6D8 antibody and the epitope tag comprises the peptide sequence YKLDIS (SEQ ID NO. 1).

In other embodiments, the recombinant protein comprises a unit of an antigen, a unit of a Fc fusion comprising a CH2 domain and a CH3 domain of an IgG, a unit of a VH domain of the IgG, a unit of a CH1 domain of the IgG, a unit of a VL domain of the IgG; and a unit of a CL domain of the IgG. In such embodiments, the IgG is the 6D8 antibody, and the Fc fusion comprises the substitution mutations E345R, E430G, and S440Y. The unit of the antigen is not an epitope of the 6D8 antibody, and it is linked to the CH3 domain of IgG at the C-terminus. The unit of the VL domain of the IgG is linked to the unit of the CL domain of the IgG, and the unit of the CL domain of the IgG is linked to the CH1 domain of the IgG. The unit of the CH1 domain of IgG is then linked to the CH2 domain of the IgG. In some aspects, the recombinant protein further comprises an epitope tag for the 6D8 antibody, for example comprising the peptide sequence YKLDIS (SEQ ID NO. 1).

In some aspects, the epitope tag in the recombinant protein comprises the sequence VYKLDISEA (SEQ ID NO. 2). In other aspects, epitope tag consists of the sequence YKLDIS (SEQ ID NO. 1).

In still other embodiments of the recombinant protein, IgG variant comprises two units of an antigen, two units of the Fc fusion, two units of a VH domain of the IgG, and two unit of a CH1 domain of the IgG. The antigen is not an epitope of the IgG, and the two units of the antigen are linked to the two units of the VH domain of the IgG at the N-terminus. The two units of the CH1 domain of IgG are linked to the two units of the Fc fusion at the CH2 domain of the IgG. In some aspects, the recombinant protein does not comprise a CL domain of the IgG and does not comprise a VL domain of the IgG.

In certain implementations, the antigen of the recombinant protein is from Zika virus, for example, the unit of the antigen comprises K301-T406 of Accession No. AMC13911.1. In other implementations, the antigen of the recombinant protein is from norovirus, for example, the unit of the antigen comprises at least one portion from the major capsid protein of noroviruses and/or at least one portion from nonstructural protein 1 (NS1) of noroviruses. In some embodiments, the unit of the antigen comprises at least one 5- to 500-residue long portion from the protruding domain of the norovirus major capsid protein, the shell domain of the norovirus major capsid protein, or from NS1 of noroviruses. In some aspects, the antigen of the recombinant protein may comprise a plurality of antigenic peptides. For example, in some implementations, the unit of the antigen comprises at least one portion from the major capsid protein or at least one portion from NS1 of a plurality of norovirus strains or species, for example, from human norovirus virus GI.3, human norovirus virus GII.4, and murine norovirus (MNV). In some embodiments, the unit of the antigen comprises at least one sequence set forth in SEQ ID NOs. 34-72.

The methods of production described herein comprise expressing the recombinant protein in a plant. In other words, the recombinant protein is produced in a transgenic plant. In certain implementations, the recombinant protein is expressed in a transgenic plant silenced for xylosyltransferase and fucosyltransferase. In some aspects, the method of producing the recombinant protein described herein comprises introducing into agrobacteria a vector selected from the group consisting of: pBYR11eM-h6D8ZE3, pBYR11eMa-BAZE3-Hgp371, pBYR11eMa-BAZE3-H, pBYKEMd-HZE3, pBYKEMd-ZE3H, pBYKEMd-ZE3Hx, pBYKEMd-HVLZe, pBYKEMd2-HVL-Hx, pBYKEMd2-HVLZnt, pBYKEMd2-ZHVLnt, pBYKEMd2-ZHVLe, pBYKEMd2-ZHVLhx, pBYKEAM-N12MHd, pBYKEAM-NPHd, pBYKEAM-NSHd, pBYKEAM-NTHd, pBYKEHM-CPHd, pBYKEHM-CSHd, and pBYKEHM-CTHd and infiltrating a plant part with agrobacteria containing the vector to produce a transformed plant part. Crude protein is then extracted from the transformed plant followed by purification for the recombinant protein. For methods of production where the vector introduced into agrobacteria is selected from the group consisting of: pBYR11eM-h6D8ZE3, pBYR11eMa-BAZE3-Hgp371, pBYR11eMa-BAZE3-H, and pBYKEMd-HZE3, the method further comprises co-infiltration with agrobacteria containing pBYKEMd-6D8K and agrobacteria containing the vector.

The methods of use described herein include a method of inducing an immune response in a subject against the antigen in the recombinant protein. The method comprises administering the described recombinant protein to the subject. In certain embodiments, the method induces in the subject an immune response against Zika virus. In such embodiments, the recombinant protein comprises an antigen with an amino acid sequence comprising K301-T406 of Accession No. AMC13911.1. In other embodiments, the method induces in the subject an immune response against norovirus, including human norovirus and MNV. In such embodiments, the recombinant protein comprises an antigen from the VP1 of a norovirus, for example from its protruding domain or the shell domain, or from NS1 of a norovirus.

In some implementation, the subject is administering a composition comprising a recombinant protein with an antigen from VP1 of a plurality of noroviruses and a recombinant protein with an antigen from NS1 of a plurality of noroviruses. In still other implementations, the recombinant protein is produced in a transgenic plant. In some aspects, the transgenic plant is silenced for xylosyltransferase and fucosyltransferase.

BRIEF DESCRIPTION OF THE DRAWINGS

FIG. 1A is a schematic representation of certain IgG fusion constructs disclosed herein. As used in this figure, ZE3 refers to the Zika envelope domain III containing amino acids K301 to T406; e refers to an epitope tag with a peptide sequence consisting of VYKLDISEA (SEQ ID NO. 2), which is the 6D8 binding motif for recombinant immune complex (RIC) formation; e with lightning bolt refers to an epitope tag with a peptide sequence consisting of YKLD IS (SEQ ID NO. 1) to reduce RIC formation; VH refers to the variable heavy domain; VL refers to the variably light domain; H refers to the heavy chain constant CH1 domain; L refers to the light chain constant domain; Fc refers to a portion of heavy chain constant region, which consist of the CH2 and CH3 domains; and Fc with lightning bolt refers to the same as Fc but with E345R, E430G, and S440Y mutations to induce hexamer formation. FIG. 1B depicts C1q binding ELISA of purified IgG fusion constructs where the IgG fusion constructs are built on the mAb 6D8 human IgG1 backbone. ELISA plates were coated with g/ml human C1q and incubated with 10 g/ml each fusion, using 6D8 antibody with no fusion as a negative control. Constructs were detected using polyclonal goat anti-human IgG-HRP. Mean OD450 values from three samples are shown ±standard error with one star (*) indicating $p<0.05$ and three stars (***) indicating p<0.001 as measured by one-way ANOVA with comparisons between the indicated groups.

FIG. 2A depicts the ELISA and gel quantification of IgG fusion construct expression. Clarified protein extracts from leaf spots agroinfiltrated with each IgG fusion construct were analyzed by ELISA or SDS-PAGE followed by gel quantification. For ZE3 ELISA, plates were coated with polyclonal mouse anti-ZE3, incubated with serial dilutions of extracts from each IgG fusion using purified HLZ as a standard, and probed with goat anti-human IgG-HRP. For IgG ELISA, plates were coated with serial dilutions of extracts or human IgG standard and probed with goat anti-human IgG-HRP. For gel quantification, ImageJ software was used to compare the IgG fusion band intensity visualized on stain-free polyacrylamide gels using purified 6D8 as standard. Columns represent means±standard error from three independently infiltrated leaf samples. FIG. 2B depicts a representative gel image of clarified leaf extracts were separated by reducing SDS-PAGE. The band position corresponding to each respective heavy chain/ZE3 fusion is indicated "ZH/HZ." The small shift in size in HLZe and HLZd is due to epitope tag presence. The large subunit of Rubisco "RbcL" along with the ZFc and Fc bands are indicated.

FIGS. 5A-B depict, in accordance with certain embodiments, the stability and C1q binding of purified IgG fusions built on a 6D8 antibody backbone. Samples of purified IgG fusions were frozen and thawed once after purification (initial) or additionally subjected to either additional 5 freeze/thaw cycles, incubation for 2 weeks at 4° C., or incubation for 2 weeks at room temperature. FIG. 5A shows the relative proportion of fully assembled product (analyzed using ImageJ software) for each treatment. After the treatments, samples were separated on reducing and nonreducing SDS-PAGE gels. FIG. 5B shows the C1q binding ELISA results of the IgG constructs after each treatment. Columns represent the mean $OD_{450}$ value ±standard error from three samples.

FIG. 10 depicts, in accordance with certain embodiments, C1q binding comparison between IgG fusions built on a 6D8 antibody backbone. ELISA plates were coated with 10 g/ml human C1q and incubated with 10-fold serial dilutions of each purified construct starting at 50 g/ml. Constructs were detected using polyclonal goat anti-human IgG-HRP. Mean OD450 values from three replicates are shown. As used in this figure, wt refers to constructs made in wildtype *N. benthamiana* plants; GnGn, refers to constructs made in glycoengineered plants silenced for xylosyltransferase and fucosyltransferase; Ag refers to dengue consensus dengue E protein domain III (cE) tagged with the 6D8 epitope; and ZHL refers to the same as HL but with ZE3 fused to the N-terminus of the 6D8 heavy chain.

FIG. 11 depicts, in accordance with certain embodiments, epitope binding of single-chain antibody built on a 6D8 antibody bone (HVL) was compared to that of wildtype 6D8 antibody. ELISA plates coated with 900 ng of purified epitope-tagged protein were incubated with serial dilutions of either HVL (single-chain antibody with the variable heavy chain linked to the variable light chain region that is fused to the 6D8 heavy chain) or full-length 6D8 antibody.

FIG. 12 depicts, in accordance with certain embodiments, representative SDS-PAGE demonstrating RIC insolubility. Protein was extracted from leaves of *N. benthamiana* agroinfiltrated with the indicated constructs and separated by SDS-PAGE followed by western blotting under nonreducing conditions. The constructs were detected using goat anti-human IgG-HRP. Soluble (S) refers to the clarified crude leaf extract, while insoluble (IS) refers to the pellet following clarification that had been resuspended in SDS sample buffer.

In FIG. 14B, RIC constructs targeting conserved epitopes of VP1 protruding domain are labeled as P-RIC (the unit of the antigen comprises tandem-linked sequences of SEQ ID NOs. 34-42); VP1 shell domain, labeled as S-RIC (the unit of the antigen comprises tandem-linked sequences of SEQ ID NOs. 45-53); T-cell epitopes, labeled as T-RIC (the unit of the antigen comprises tandem-linked sequences of SEQ ID NOs. 58-72); and containing a unit of an antigen comprising epitopes from nonstructural protein 1 (NS1) of human norovirus GI.3, human norovirus GII.4, and murine norovirus (MNV), labeled as N-RIC (the unit of the antigen comprises tandem-linked sequences of SEQ ID NOs. 55-57). The RICs were purified, separated by SDS-PAGE under reducing conditions, and visualized under UV via stain-free 2,2,2-trichloroethanol (TCE) imaging. "+Inhibitors" refers to the addition of plant protease inhibitor cocktail to reduce degradation of N-RIC.

FIG. 16 depicts, in accordance with certain embodiments, serum binding to murine norovirus. Serum from mice immunized with 3 doses of 2 μg total antigen delivered via RIC constructs or with human norovirus GI.I (Norwalk virus)/human norovirus GII.4 (Minerva virus) VLPs mixed (labeled as "VLP") were tested for binding to murine norovirus 1 (MNV-1) virus by ELISA. Polystyrene 96-well plates were coated with rabbit anti-MNV capsid, blocked with 5% PBSTM, and then incubated with lysate from RAW267.4 cells infected with MNV-1. After incubation, serial dilutions of mouse sera were added to the plate, and then detected with goat anti-mouse IgG-HRP conjugate. Mean $OD_{450}$ values ±standard error from pooled mouse sera containing two technical replicates are shown. Abbreviations: P-RIC: serum from mice immunized with P-RIC; S-RIC: serum from mice immunized with S-RIC; T-RIC: serum from mice immunized with T-RIC; N-RIC: serum from mice immunized with N-RIC, PSTN-RIC: serum from mice immunized with P-RIC, S-RIC, T-RIC, and N-RIC but with a quarter of the dose used for the individual experiments.

FIG. 17 depicts, in accordance with certain embodiments, serum binding to GI.I VLPs. Serum from mice immunized with 3 doses of 2 μg total antigen delivered via RIC constructs were tested for binding to GI.I norovirus VLPs by ELISA. Polystyrene 96-well plates were incubated with plant-made Norwalk virus VLPs, blocked, and then incubated with serial dilutions of mouse sera. Bound antibodies were detected with goat anti-mouse IgG-IRP conjugate. Mean $OD_{450}$ values ±standard error from six samples containing two technical replicates are shown. Abbreviations: P-RIC: serum from mice immunized with P-RIC; S-RIC: serum from mice immunized with S-RIC; T-RIC: serum from mice immunized with T-RIC; N-RIC: serum from mice immunized with N-RIC, PSTN-RIC: serum from mice immunized with P-RIC, S-RIC, T-RIC, and N-RIC but with a quarter of the dose used for the individual experiments.

DETAILED DESCRIPTION

Figure 1A:
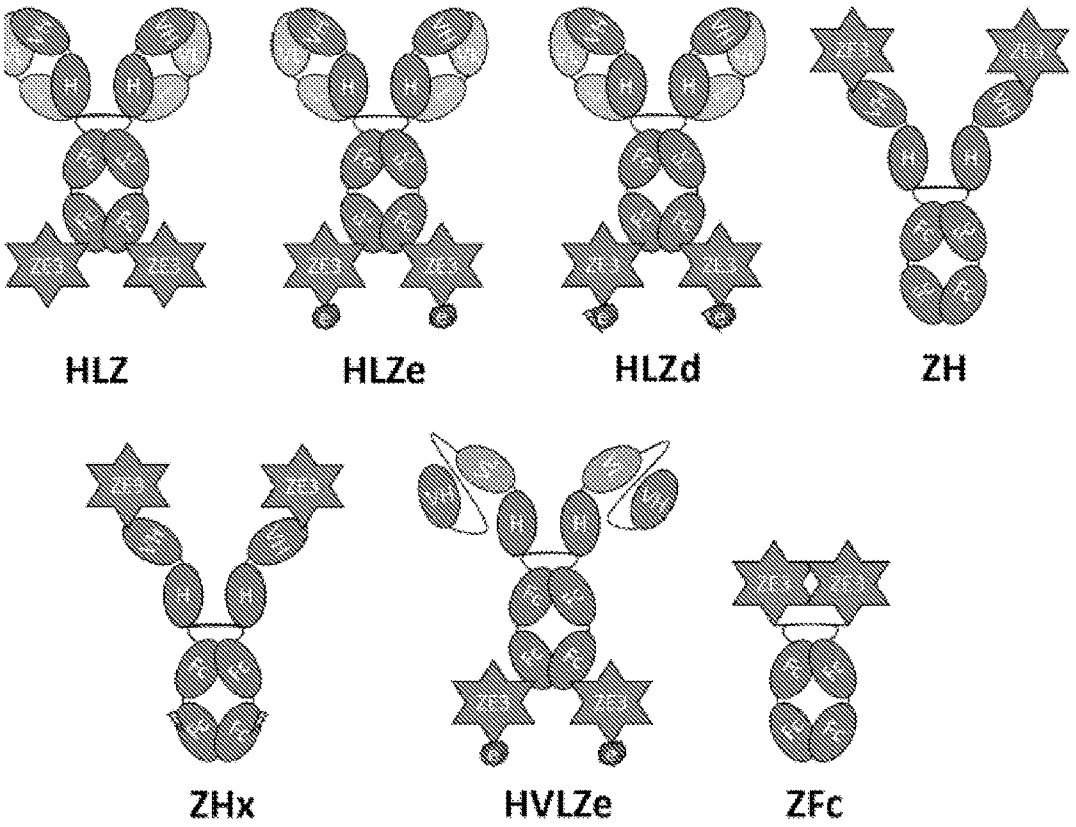
FIGS. 1A-B depict, in accordance with certain embodiments, IgG fusion constructs and a comparison of their respective ability to bind C1q.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "6D8 antibody" refers to a monoclonal antibody against the GP1 protein of Ebola virus (described in Wilson et al., 2000; plant optimized sequence described in Huang et al., 2010). In some embodiments, the CH1 domain of the 6D8 antibody refers to a peptide sequence comprising TKGPSVFPLAPSSKSTSGGTAAL-GCLVKDYFPEPVTVS WNSGALTSGVHTFPAVLQSSG-LYSLSSVVTVPSSSLGTQTYICNVNHKPSNTKVDKK-VEPKSC (SEQ ID NO. 5) or a peptide sequence having at least 80%, at least 85%, at least 90%, at least 95%, at least 98%, or at least 99% sequence similarity. In some embodiments, the CH2 domain of the 6D8 antibody refers to a peptide sequence comprising DKTHTCPPCPA-PELLGGPSVFLFPPKP KDTLMISRTPE-VTCVVVDVSHEDPEVKFNWYVDGVEHNAKTKPRE-EQYNSTYRVVSVLTVLHQD WLNGKEYKCKVSNKALAPIEKTISKAKG (SEQ ID NO. 6) or a peptide sequence having at least 80%, at least 85%, at least 90%, at least 95%, at least 98%, or at least 99% sequence similarity. In some embodiments, the CH3 domain of the 6D8 antibody refers to a peptide sequence comprising QPREPQVYTLPPSRDELTKNQVSLTCLVKGFYPSDIA-VEWESNGQPENNYKTTPPVLDSDGSFF LYSK-LTVDKSRWQQGNVFSCSVMHEALHNHYTQKSLSL-SPGK (SEQ ID NO. 7). In some embodiments, the variable heavy chain domain of the 6D8 antibody refers to a peptide sequence comprising GenBank Accession No. AEB96146 or a peptide sequence having at least 80%, at least 85%, at least 90%, at least 95%, at least 98%, or at least 99% sequence similarity. In some embodiments, the variable light chain domain of the 6D8 antibody refers to a peptide sequence comprising GenBank Accession No. AEB96146 or a peptide sequence having at least 80%, at least 85%, at least 90%, at least 95%, at least 98%, or at least 99% sequence similarity. In some aspects, nucleic acid encoding the light chain variant domain is set forth in GenBank Accession No. HQ407546. In some aspects, the nucleic acid encoding the heavy chain variant domain is set forth in GenBank Accession No. AEB96148.

As used herein, the term "linked" when used to describe a protein structure or configuration of protein domains refers to a linkage between two domains or structural portions, preferably where there are no other intervening domains or structural portions except a linker. In some aspects, the term "linker" as used herein refers to an amino acid sequence between protein domains or structural portions where its only function is to link the protein domains or structural portions. For example, the linker is sequence consisting of glycine, valine, and/or threonine residues. In some embodiments, the linker is sequence consisting of glycine, valine, threonine, alanine, and/or serine residues. In some aspects, the linker consists of 1 to 50 amino acids in length, for example, 3, 4, 6, 10, 12, 14, or 16 amino acids in length. In certain embodiments, the linker is a flexible linker.

As used herein, the term "unit" refers to a single peptide that is a functional fragment of a larger multi-component protein. The single peptide may be an antigenic fragment or a domain of a protein, for example a domain of an immunoglobulin. Accordingly, as used herein, the description of a recombinant protein comprising two units of a peptide refers to the recombinant protein having two such functional fragments that may or may not be linked together, for example, a dimer of the peptide.

As used herein, the term "immune complex" refers to a complex comprising immunoglobulin molecules or fragments thereof bound to its cognate antigen. As used herein, the term "recombinant immune complex" or "RIC" refers to an immune complex that is not produced by the original species that naturally produces the immunoglobulin molecule in the immune complex. For example, an exemplary recombinant immune complex comprises human immunoglobulin, which is synthesized in plants.

The disclosure relates to immunoglobulin variants. In particular preferred embodiments, the disclosure is directed to recombinant proteins that are variants of immunoglobulin G, also referred to herein as IgG fusions. In spite of the deviation from the natural structure of immunoglobulins, the described recombinant proteins do have immunogenic potential. In fact, the immune response induced by the recombinant protein is the same kind of immune response expected of the antigen in the recombinant protein. The recombinant proteins described herein are suitable for creating vaccines for targeting a variety of pathogens, for example Zika virus and norovirus.

Regardless of the variations in immunoglobulin structure, glycosylation state of the Fc strongly controls its function. By modulating the stability, conformation, and aggregation of the Fc, glycosylation can enhance or inhibit binding to Fc7 receptors, FcRn, and C1q. These alterations result in important differences in antibody effector functions, including antibody-dependent cellular cytotoxicity (ADCC), antibody-dependent cell-mediated phagocytosis (ADCP), complement-dependent cytotoxicity (CDC), and antibody-dependent enhancement of viral infection (ADE). Advances in glycoengineering have allowed targeted optimization of the Fc glycosylation state in a variety of recombinant expression systems. Using glycoengineered plants lacking core xylose and fucose N-glycans, an anti-CD20 antibody was produced with improved binding to FcγRI, FcγRIIIa, and C1q. The antibody had enhanced ADCC and CDC compared to a commercial anti-CD20 antibody produced in mammalian cells. Similarly, anti-DENV antibodies produced in glycoengineered plants have been shown to forgo their ADE activity and, consequently, have superior efficacy and safety profiles than their mammalian cell-produced counterparts. Antibody therapeutics made in glycoengineered plants have been used to treat rhesus macaques and humans with Ebola, HIV, and Chikungunya virus disease.

Mutations in the Fc region have been identified that confer desirable properties to antibodies. Introduction of M252Y, S254T, and T256E mutations increased the serum half-life of an anti-respiratory syncytial virus antibody from 20 days to 60 days in humans by improving interactions with FcRn under low pH conditions. An H237Y mutation reduced detrimental cleavage of the hinge region while improving FcγRIII binding and ADCC activity. Engineering additional disulfide bonds has been reported to prevent unfolding and aggregation of Fc-fusions. S239D and 1332E mutations improved FcγRIII binding and ADCC activity of a CD37 antibody. Replacing the IgG1 hinge region with the longer hinge region from IgG3 or from a camelid antibody increased ADCC of an epidermal growth factor receptor antibody. An IgG1 with E345R, E430G, and S440Y mutations formed hexamers that had greatly enhanced C1q binding and complement activation. The mutations T437R and K248E also promoted multimerization and improved effector functions of an OX40 receptor antibody.

The IgG variants described herein can be properly assembled with human-like glycosylation and expressed at very high levels in plants. These constructs can be efficiently made in plants, assemble appropriately, and purified via protein G column chromatography. As shown in the examples, the purified recombinant proteins are potently immunogenic.

As shown in the examples described herein, optimizing various aspects of the antibody design, such as complex size, to produce the described immunoglobulin variants resulted in optimized expression levels in plant and improved stability, solubility, and immune receptor binding. In certain embodiments where the immunoglobulin variants are designed with a portion of the Zika virus envelope protein domain III as the antigen, total IgG titers raised by the administration of the immunoglobulin variant was 150-fold higher compared to the total IgG titer raised by administration of the antigen alone. In fact, the endpoint titers was >1:500,000 with administration of only two doses of the immunoglobulin variant without any adjuvant. The recombinant proteins could be produced at levels exceeding the estimated thresholds for commercial viability of antibody therapeutics.

Recombinant Protein

The recombinant proteins described herein are variant immunoglobulin structures comprising a unit of an antigen, a unit of a Fc fusion, a unit of a variable heavy chain (VH) domain of the IgG, and a unit of a CH1 domain of the IgG. The Fc fusion comprises a CH2 domain and a CH3 domain of an IgG. Protein fusions to the immunoglobulin Fc domain are highly successful therapeutics. They can enhance the solubility and stability of the fusion partner, while also providing a means for simple and cost-effective purification. Furthermore, by interacting with neonatal Fc receptors (FcRn) in the body, Fc-fusions can escape lysosomal degradation, thereby extending the serum half-life of the Fc-fusion. The recombinant protein induces a greater immune response against the antigen attached to the recombinant protein than the antigen alone. Thus, the recombinant protein increases the immunogenicity of the antigen.

The unit of the antigen is not an epitope of the IgG. In certain embodiments, the unit of the antigen is from a different organism than the epitope of the IgG. The amino acid sequence of the unit of the antigen is between 5 and 500 residues long. In certain embodiments, the unit of the antigen is between 5 and 400 residues long. For example, the unit of the antigen is between 5 and 300 residues, between 5 and 250 residues, between 5 and 200 residues, between 5 and 100 residues, between 9 and 300 residues, between 9 and 250 residues, between 9 and 200 residues, between 9 and 100 residues, between 10 and 300 residues, between 10 and 250 residues, between 10 and 200 residues, between 10 and 100 residues, between 20 and 300 residues, between 20 and 250 residues, between 20 and 200 residues, between 20 and 100 residues, between 30 and 300 residues, between 30 and 250 residues, between 30 and 200 residues, between 30 and 100 residues, between 50 and 300 residues, between 50 and 250 residues, between 50 and 200 residues, or between 50 and 100 residues in length. In some aspects, the unit of the antigen comprises tandem-linked epitopes.

In some aspects, the tandem-linked epitopes comprise different epitopes, which may or may not be from the same or similar antigen protein. For example, a recombinant protein that targets a plurality of norovirus can comprise epitopes on the same target antigen from the plurality of noroviruses (see recombinant immune complexes studied in FIGS. 15-19) to address the diversity genotypes of noroviruses. Thus, the tandem-linked epitopes may comprise epitopes from the same antigenic protein. In other aspects, the tandem-linked epitopes are repetitions of a single epitope.

The unit of the antigen is linked to the unit of the VH domain of the IgG at the N-terminus or to the CH3 domain of IgG at the C-terminus. The unit of the CH1 domain of IgG is linked to the CH2 domain of the IgG. In some aspects, the unit of an antigen, the unit of the Fc fusion, the unit of the VH domain of the IgG, and the unit of a CH1 domain of the IgG forms half of the recombinant protein. For example, the recombinant protein self assembles upon production wherein a disulfide bond is formed at the linkage of the CH2 domain and the CH1 domain to link two units of the Fc fusion (see FIGS. 1A and 7). Accordingly in some embodiments, the recombinant protein comprises two units of the antigen, two units of the Fc fusion, two units of the VH domain of the IgG, and two units of the CH1 domain of the IgG. In certain embodiments, the antibody is the 6D8 antibody.

In certain embodiments, the recombinant protein comprises a unit of an antigen, a unit of a Fc fusion comprising a CH2 domain and a CH3 domain of an IgG, a unit of a VH domain of the IgG, a unit of a CH1 domain of the IgG; and a unit of a light chain variable (VL) domain of the IgG. The unit of the antigen is not an epitope of the IgG, and it is linked to the unit of the VH domain of the IgG at the N-terminus or to the CH3 domain of IgG at the C-terminus. The unit of the CH1 domain of IgG is linked to the CH2 domain of the IgG, while the unit of the VL domain of the IgG is fused to the unit of the VH domain of the IgG and to the CH1 domain of the IgG.

Figure 7:
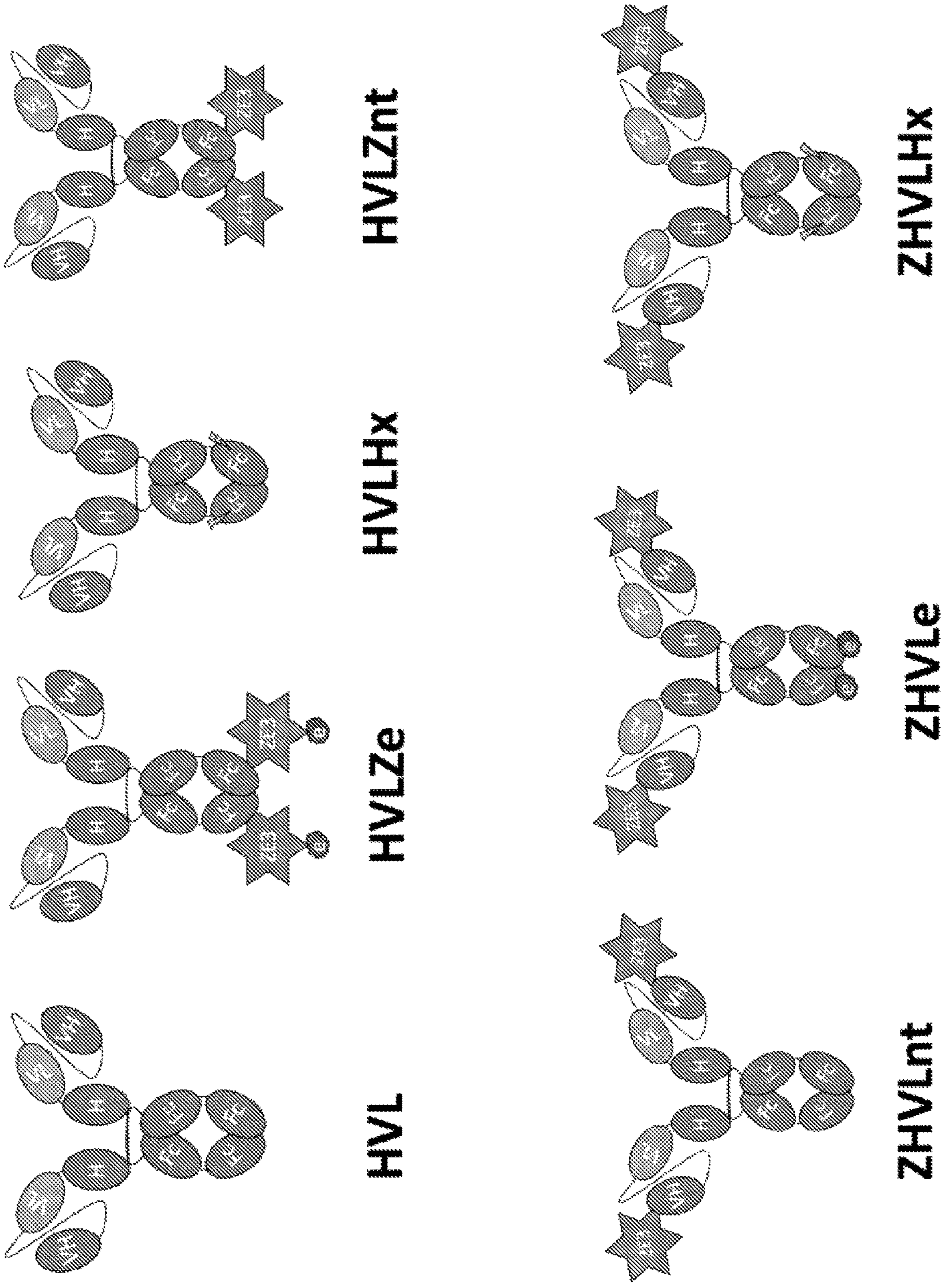
FIG. 7 depicts, in accordance with certain embodiments, a single-chain antibody (HVL) and HVL-related constructs. The single-chain antibody shown contains the 6D8 antibody variable heavy region linked to a variable light chain region that is directly fused to the 6D8 antibody heavy chain. As used in this figure, ZE3 refers to the Zika envelope domain III containing amino acids K301 to T406; e refers to an epitope tag with a peptide sequence consisting of VYKLDISEA (SEQ ID NO. 2), which is the 6D8 binding motif for RIC formation; VH refers to the variable heavy domain from the 6D8 antibody; VL refers to the variable light domain from the 6D8 antibody; H refers to the heavy chain constant region CH1 domain from the 6D8 antibody; Fc refers to the heavy chain constant region consisting of the CH2 and CH3 domains from the 6D8 antibody; and Fc with lightning bolt refers to the same as Fc but with E345R, E430G, and S440Y mutations to induce hexamer formation.
Figure 8:
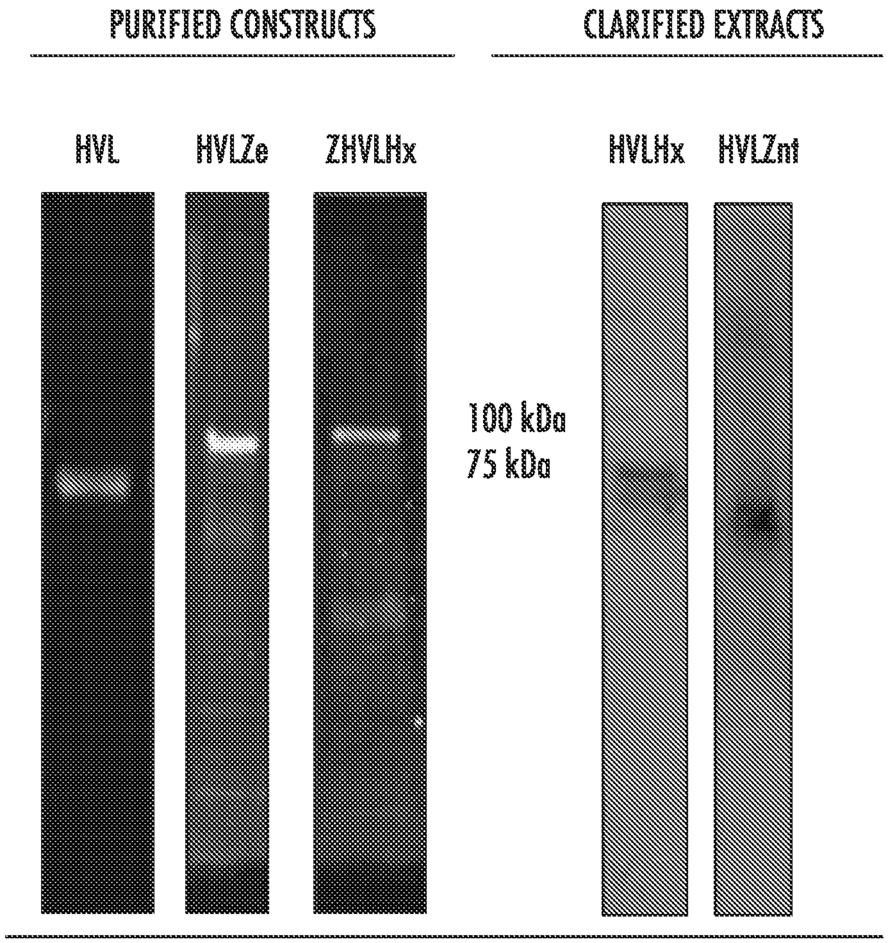
FIG. 8 depicts, in accordance with certain embodiments, the purification and western analysis of HVL and HVL-fusion constructs. After protein G purification of the HVL, HVLZe, and ZHVLHx constructs, samples from the peak elutions were separated on a 4-15% polyacrylamide, stain-free gel. Analysis of the HVLHX and HVLZnt constructs was conducted through a western blot containing small-scale leaf samples that had been clarified through centrifugation. The samples were separated on 4-15% polyacrylamide gel, transferred to a PVDF membrane, and detected with HRP-labeled goat anti-human IgG antibody.

In some aspects, the recombinant protein is self-assembled upon production, and a disulfide bond formed at the linkage of the CH2 domain and the CH1 domain of the IgG links the two units of the Fc fusion. Accordingly, the recombinant protein comprises two units of the antigen, two units of the Fc fusion, two units of the CH1 domain of the IgG, two units of the VH domain of the IgG, and two units of the VL domain of the IgG. In some aspects, the each unit of the VL domain of the IgG is linked to a unit of VH domain of the IgG and the CH1 domain of the IgG. In particular implementations, the recombinant protein does not comprise any light chain constant (CL) domain of the IgG. The recombinant protein of such embodiments is a single-chain antibody variant (see for example, FIG. 7). As shown in FIG. 8, the single-chain antibody variant can be produced in plants and efficiently purified. The single-chain antibody variant with the IgG being the 6D8 antibody also retains its ability to bind the 6D8 epitope (FIG. 11).

In some embodiments of the recombinant protein comprising two units of the antigen, two units of the Fc fusion, two units of the CH1 domain of the IgG, two units of the VH domain of the IgG, and two units of the VL domain of the IgG, the recombinant protein further comprises two units of an epitope tag, wherein the epitope tag is an epitope of the IgG. In some implementations, the two units of the epitope tag are linked to the two units of the Fc fusion at the C-terminus of the CH3 domain of the IgG, and the two units of the antigen are linked to the two units of the VH domain of the IgG. In other implementations, the two units of the epitope tag are linked to the two units of the antigen, and the two units of the antigen are linked to the two units of Fc fusion at the C-terminus of the CH3 domain of the IgG. Where the antibody is the 6D8 antibody, the epitope tag comprises the peptide sequence YKLDIS (SEQ ID NO. 1). In some aspects, the epitope tag comprises the sequence VYKLDISEA (SEQ ID NO. 2). In other aspects, the epitope tag consists of the sequence YKLDIS (SEQ ID NO. 1).

In other embodiments, the recombinant protein comprises a unit of an antigen, a unit of a Fc fusion comprising a CH2 domain and a CH3 domain of an IgG, a unit of a VH domain of the IgG, a unit of a CH1 domain of the IgG, a unit of a VL domain of the IgG; and a unit of a CL domain of the IgG. In such embodiments, the IgG is the 6D8 antibody, and the Fc fusion comprises at least one substitution mutation selected from the group consisting of: E345R, E430G, and S440Y. In certain embodiments, the Fc fusion comprises the substitution mutations E345R, E430G, and S440Y. The unit of the antigen is not an epitope of the 6D8 antibody, and it is linked to the CH3 domain of IgG at the C-terminus. The unit of the VL domain of the IgG is linked to the unit of the CL domain of the IgG, and the unit of the CL domain of the IgG is linked to the CH1 domain of the IgG. The unit of the CH1 domain of IgG is then linked to the CH2 domain of the IgG. In some aspects, the recombinant protein further comprises an epitope tag for the 6D8 antibody, for example comprising the peptide sequence YKLDIS (SEQ ID NO. 1). In some aspects, the epitope tag in the recombinant protein comprises the sequence VYKLDISEA (SEQ ID NO. 2). In other aspects, epitope tag consists of the sequence YKLDIS (SEQ ID NO. 1).

In still other embodiments of the recombinant protein, IgG variant comprises two units of an antigen, two units of the Fc fusion, two units of a VH domain of the IgG, and two unit of a CH1 domain of the IgG. The antigen is not an epitope of the IgG, and the two unit of the antigen are linked to the two units of the VH domain of the IgG at the N-terminus. The two units of the CH1 domain of IgG are linked to the two units of the Fc fusion at the CH2 domain of the IgG. In some aspects, the recombinant protein does not comprise a CL domain of the IgG and does not comprise a VL domain of the IgG.

Zika Virus

Zika virus (ZIKV) is a substantial global health threat that lacks safe, affordable, and efficacious vaccines. In addition to their widespread therapeutic value, IgG fusions are promising vaccine candidates due to their safety and self-adjuvating nature.

In exemplary embodiments, some IgG variants were designed to generate an immune response against ZIKV. Accordingly, the antigen in the recombinant protein is an antigen targeting ZIKV. In some aspects, the antigen targets Zika virus envelope domain III (ZE3). These IgG variants were highly stable and highly expressed in plants. Accordingly, the recombinant proteins described herein are vaccine candidates, for example against ZIKV.

In some aspects, the antigen targeting ZE3 comprises K301-T406 of Accession No. AMCC13911.1. In other aspects, the antigen targeting ZE3 comprises a peptide sequence having at least 80%, at least 85%, at least 90%, at least 95%, at least 97%, at least 98%, or at least 99% sequence similarity to K301-T406 of Accession No. AMC13911.1. In still other aspects, the antigen targeting ZE3 comprises a sequence that is a functionally equivalent version of corresponding regions of GenBank Accession No. AMC13911 from other strains of Zika virus, for example, the corresponding sequences of ZE3 in GenBank Accession Nos. AY632535, KU321639, KJ776791, KF383115, KF383116, KF383117, KF383118, KF383119, KF268948, KF268949, KF268950, EU545988, KF993678, JN860885, HQ234499, KU501215, KU501216, KU501217.

Figure 6A:
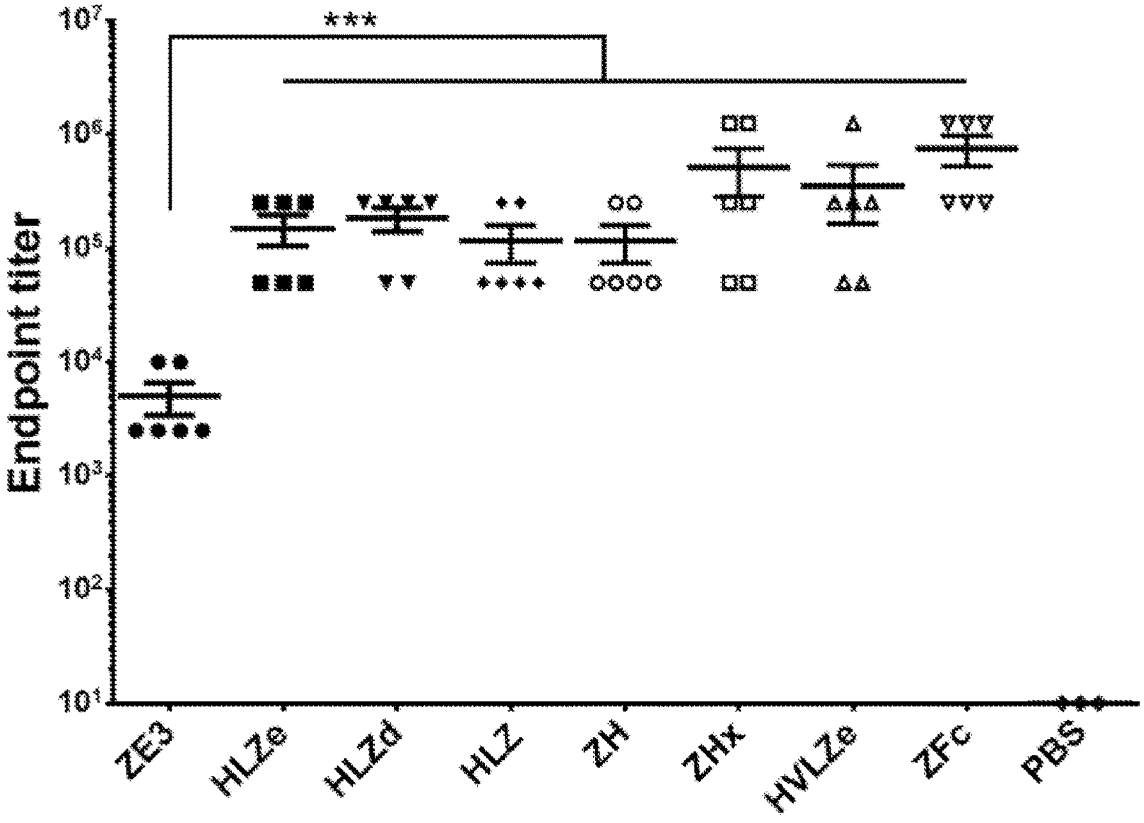
FIGS. 6A-6B depict, in accordance with certain embodiments, the results of mouse immunization with the IgG fusions and the serum titers. BALB/c mice (6 per group) were immunized twice two weeks apart subcutaneously with a dose that would deliver 8 g ZE3 for each IgG fusion or with PBS as a control. Mouse serum samples were collected two weeks after the final dose. For FIG. 6A, serially diluted mouse serum was analyzed for total IgG production by ELISA. The endpoint was taken as the reciprocal of the greatest dilution that gave an OD450 reading at least twice the background. Three stars (*) indicates p<0.01 by ANOVA comparing the indicated columns to ZE3. For FIG. 6B, mouse serum samples were diluted 1:100 and analyzed for IgG2a production by ELISA. () indicates p<0.05 and (***) indicates p<0.01 by ANOVA comparing the indicated columns to HLZ.
Figure 6B:
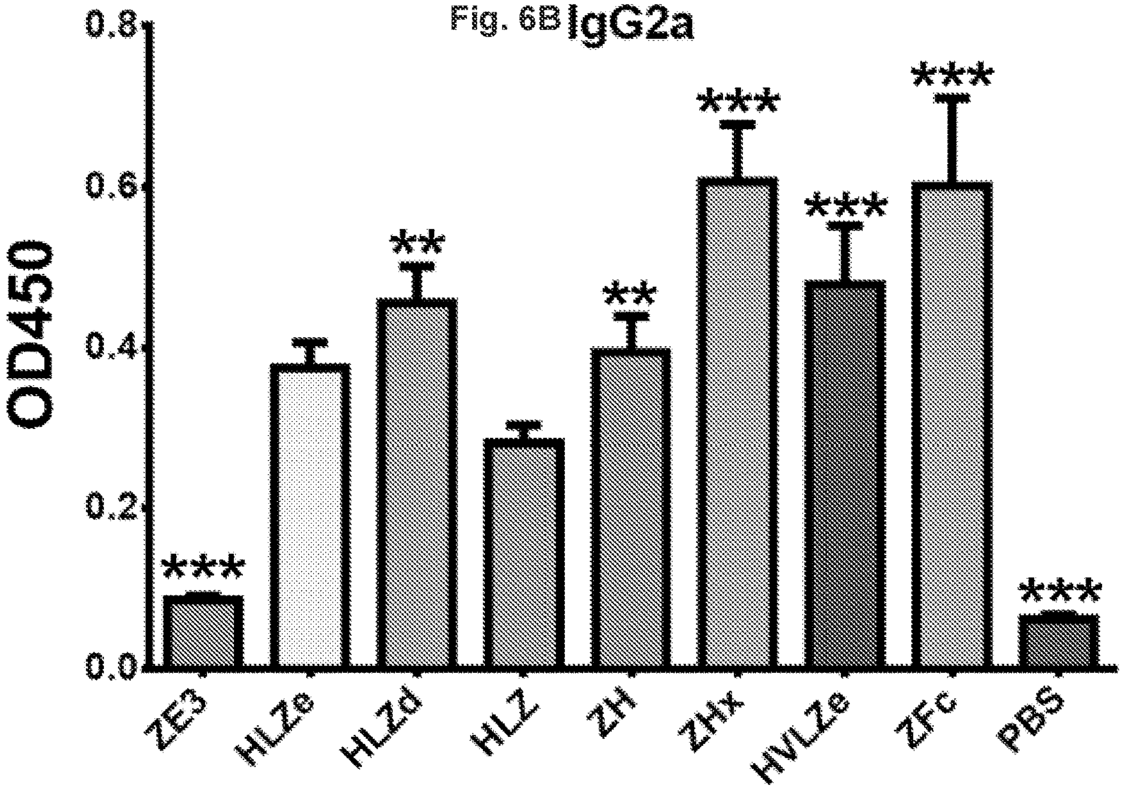

The recombinant proteins described herein targeting ZIKV elicited strong immune responses against ZIKV without adjuvants and only two doses (FIGS. 6A, 6B). Many of the recombinant proteins were produced at high levels in plants (0.5-1.5 mg/g LFW) (FIG. 2) and were stable upon repeated freeze-thaw and storage (FIG. 5). Compared to ZE3 antigen alone, the best IgG fusion groups produced over 100-fold higher antibody responses. This is in agreement with previous studies showing that ZE3 or ZIKV E are weakly immunogenic on their own, requiring an adjuvant and 3-4 doses.

Constructs expected to form polymeric structures were the most resistant to degradation and had the highest overall yield. By optimizing intermolecular binding of RIC, smaller complexes were generated that had greatly improved solubility, yielding 1.5 milligrams IgG fusion per gram leaf fresh weight (mg/g LFW), and equivalent or improved immunogenic properties. When used to immunize mice, the IgG fusions elicited high titers of Zika-specific antibodies using only two doses without adjuvant, exceeding the titers produced by ZE3 alone by 20-fold to 150-fold, and potently neutralized Zika virus. The IgG fusions were also found to strongly enhance IgG2a production compared to unfused ZE3 antigen in a manner that correlated with C1q binding. These findings demonstrate the excellent potential of IgG fusions as self-adjuvanting subunit vaccines for Zika virus that can be made efficiently in plants.

Figure 9:
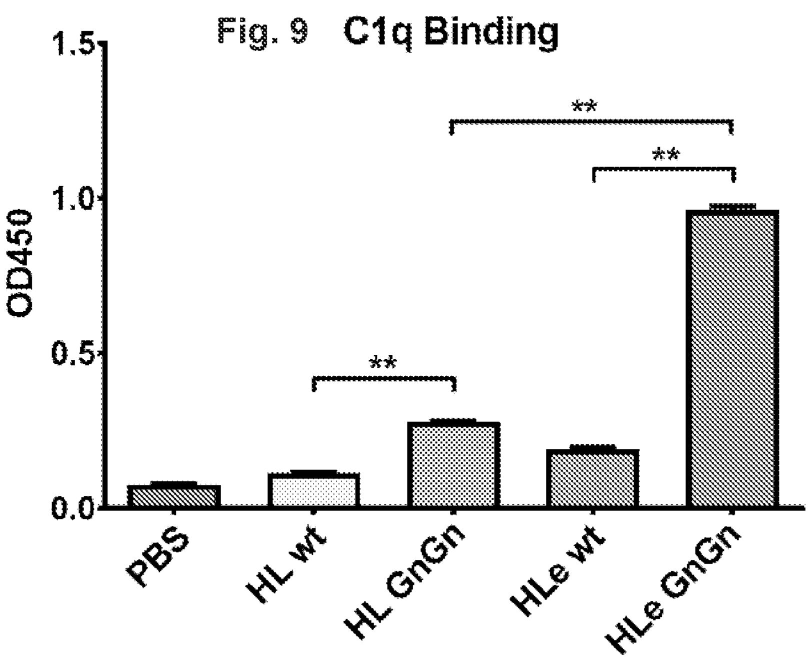
FIG. 9 depicts, in accordance with certain embodiments, the C1q binding comparison of IgG fusion constructs produced in wildtype and glycoengineered plants. ELISA plates were coated with 10 g/ml human C1q and incubated with 5 g/ml each purified construct. Constructs were detected using polyclonal goat anti-human IgG-HRP. Mean OD450 values from three replicates are shown ±standard error with two stars indicating p<0.01 as measured by one-way ANOVA with comparisons between the indicated groups. As used in this figure, wt refers to constructs made in wildtype *Nicotiana benthamiana* plants, while GnGn refers to constructs made in glycoengineered plants silenced for xylosyltransferase and fucosyltransferase.

C1q binding of the IgG fusions targeting ZIKV was enhanced by ZE3 fusion to the IgG N-terminus. The removal of the IgG light chain (HVL and HVL-related constructs) or Fab regions also enhanced C1q binding. The addition of hexamer-inducing mutations in the IgG Fc region enhanced C1q binding as well. C1q binding was also enhanced by adding a self-binding epitope tag to create RIC or producing IgG fusions in plants that lack plant-specific β1,2-linked xylose and α1,3-linked fucose N-glycans (for example, by silencing xylosyltransferase and fucosyltransferase, see FIGS. 9 and 10). Both the RIC construct (HLZe) and the modified immune complex based on the single-chain antibody variant (HVLZe) have significantly improved C1q binding compared to uncomplexed IgG (FIGS. 1, 9, and 10). The results after immunization showed that the HVLZe construct produced antibody titers similar to that of the traditional RIC containing the full heavy and light chains (FIGS. 6A and 6B).

In some aspects, the RIC construct is not preferred, because the large complex size renders them poorly soluble upon extraction (FIGS. 2A and 10) and high concentrations may precipitate during storage. Very large RIC may also be too big to efficiently drain to lymph nodes from the injection site, which favor particles <200 nm. Hexamer-sized IgG have been found be the optimal substrate for efficient C1q binding. Mutating the 6D8 epitope tag (construct HLZd) could also mitigate problems with the RIC construct. Notably, compared to the RIC, HLZd was significantly more soluble (FIG. 13B), had intermediate density (FIG. 4A), showed higher C1q binding (FIG. 1), reached higher expression levels (1.5 mg/g LFW) (FIG. 2A), and elicited higher IgG2a titers (FIGS. 6A and 6B). These improvements to the design of RIC vaccine candidates are applicable to other antigens.

The HVLZe fusion had slightly higher C1q binding than traditional RIC (FIG. 1B) and had high stability at the tested conditions (FIG. 5A). Since this single chain configuration reduced binding to the epitope tag when compared with the full 6D8 antibody, the HVLZe formed smaller complexes (sucrose gradient data showing reduced density compared to HLZe in FIG. 4A). However, some very dense material remained unlike with construct HLZd. Solubility could be improved by reducing the epitope binding of HVLZe.

Table 1 summarizes characteristics of the recombinant protein, an antigen targeting ZIKV. For expression, only the yield (mg/g LFW) of the fully assembled product is shown. A greater number of "+" symbols indicates either a statistically significant increase in the mean value for that property (for C1q, IgG, and IgG2a), or a repeatably observed difference (for density). For ZHx (*), peaks of both low-density and of high-density material were observed.

TABLE 1

| Construct | Expression | Solubility | Density | Stability | C1q | IgG | IgG2a |
|---|---|---|---|---|---|---|---|
| ZE3 | N.D. | N.D. | N.D. | N.D. | N.D. | + | + |
| HLZ | 0.17 mg/g | High | + | Medium | + | +++ | ++ |
| HLZe | 0.22 mg/g | Low | ++++ | High | ++ | +++ | ++ |
| HLZd | 1.50 mg/g | High | ++ | High | +++ | +++ | +++ |
| ZH | 0.83 mg/g | High | + | Medium | ++ | +++ | +++ |
| ZHx | 0.21 mg/g | Low | +++* | High | +++ | +++ | +++ |
| VHLZe | <0.1 mg/g | Low | ++++ | High | +++ | +++ | +++ |
| ZFc | 0.57 mg/g | High | + | Low | +++ | +++ | +++ |

Norovirus

The widespread occurrence of human norovirus (HNoV) infections causes tremendous economic damage and disease burden, however no approved vaccines or specific treatments are available. Efforts to control HNoV are hampered by the large genetic diversity of these viruses, which continually evolve to evade natural immunity. A wealth of published antibody mapping and T-cell data demonstrates the existence of broadly conserved HNoV B-cell and T-cell epitopes which, crucially, are targetable by the human immune system. Accordingly, it would be possible to design recombinant proteins for the purpose of eliciting immune responses against broadly conserved HNoV antigenic targets.

In exemplary embodiments, IgG variants were designed to generate an immune response against norovirus (NoV). In some aspects, the antigen of the recombinant protein comprises epitopes from a plurality of noroviruses, for example from human norovirus GI.3, human norovirus GII.4, and/or murine norovirus (MNV). The antigen in the recombinant protein targeting noroviruses comprises at least one epitope from the major capsid protein of NoV (VP1) or the non-structural protein of NoV. In some aspects, the antigen targets the protruding domain or the shell domain of VP1. Such recombinant proteins are vaccine candidates against NoV.

In certain implementations, the recombinant proteins targeting NoV may be used in combination as a vaccination composition. As shown in the examples and FIGS. 16-19, these antigens have been successfully used to produce immunoglobulin variants that are capable of broadly binding, blocking, and neutralizing a panel of diverse NoVs from different genogroups and genotypes.

In some aspects, the antigen targeting VP1 comprises 5- to 500-residue-long portion of VP1 and/or NS1. In some embodiments, the unit of the antigen comprises at least one sequence, at least three sequences, at least six sequences, at least nine sequence, at least twelve sequences, or at least fifteen sequences set forth in SEQ ID NOs. 34-72. For example, the unit of the antigen in recombinant proteins targeting VP1 comprises at least one sequence, at least two sequences, at least three sequences, at least four sequences, at least five sequences, at least six sequences, at least seven sequences, at least eight sequences, or at least nine sequences set forth in SEQ ID NOs. 34-54. In a particular embodiment, the unit of the antigen targeting the protruding domain of VP1 comprises at least one sequence, at least two sequences, at least three sequences, at least four sequences, at least five sequences, at least six sequences, at least seven sequences, at least eight sequences, or at least nine sequences selected from SEQ ID NOs. 34-44. In certain embodiments, the unit of the antigen of a recombinant protein targeting norovirus comprises the sequences set forth in SEQ ID NOs. 34-42. In another particular embodiment, the unit of the antigen of a recombinant protein targeting the shell domain of VP1 comprises at least one sequence, at least two sequences, at least three sequences, at least four sequences, at least five sequences, at least six sequences, at least seven sequences, at least eight sequences, or at least nine sequences selected from SEQ ID NOs. 45-54. In some aspects, the unit of the antigen of a recombinant protein targeting norovirus comprises the sequences set forth in SEQ ID NOs. 45-53. In still another particular embodiment, the unit of the antigen of a recombinant protein targeting NS1 comprises at least one sequence or at least two sequences selected from SEQ ID NOs. 55-57. In some aspects, the unit of the antigen of a recombinant protein targeting norovirus comprises the sequences set forth in SEQ ID NOs. 55-57. In yet another particular embodiment, the unit of the antigen of a recombinant protein designed to generate a T-cell mediated immune response comprises at least one sequence, at least two sequences, at least three sequences, at least four sequences, at least five sequences, at least six sequences, at least seven sequences, at least eight sequences, or at least nine sequences selected from SEQ ID NOs. 58-72, for example, the peptide sequence of the unit of the antigen comprises the sequences of SEQ ID NOs. 58-72.

Method of Production

Plant recombinant expression systems have inherent safety, high scalability, and low production costs compared to mammalian cell systems, making them particularly well suited to make IgG fusions vaccines. While previous work has shown that some IgG fusion vaccines can enhance antigen immunogenicity, the many fusion strategies that have been developed have not been directly compared, making it difficult to determine the key properties involved in creating an optimal vaccine candidate.

The methods of production described herein comprise expressing the recombinant protein in a transgenic plant. In certain implementations, the recombinant protein is expressed in a transgenic plant silenced for xylosyltransferase and fucosyltransferase. In some aspects, for example the recombinant protein is a RIC, it is preferable to produce the proteins using plants with xylosyltransferase and fucosyltransferase silenced. The method comprises introducing into agrobacteria a binary vector that expresses a unit of the antigen, a unit of the Fc fusion, a unit of the VH domain of the IgG; and a unit of the CH1 domain of the IgG. Accordingly, this binary vector encodes the heavy chain domains of the IgG. Next, a plant part is infiltrated with agrobacteria containing the binary vector to produce a transformed plant part. Crude protein from the plant part is extracted and then purified for the recombinant protein. In some aspects, the recombinant protein is purified using methods well-established in the art, for example, protein G affinity chromatography or metal affinity chromatography.

Where the recombinant protein comprises a unit of the VL domain of the IgG and a unit of the CL domain of the IgG, the method further comprises introducing into agrobacteria a different binary vector that encodes light chain domains of the IgG, namely the unit of the VL domain of the IgG and the unit of the CL domain of the IgG. The transformation of the plant part comprises co-infiltrating the plant part with agrobacteria containing the binary vector encoding the heavy chain domains of the IgG and agrobacteria containing the binary vector encoding the light chain domains of the IgG.

In particle implementations, the method of producing the recombinant protein described herein comprises introducing into agrobacteria a vector selected from the group consisting of: pBYR11eM-h6D8ZE3, pBYR11eMa-BAZE3-Hgp371, pBYR11eMa-BAZE3-H, pBYKEMd-HZE3, pBYKEMd-ZE3H, pBYKEMd-ZE3Hx, pBYKEMd-HVLZe, pBYKEMd2-HVL-Hx, pBYKEMd2-HVLZnt, pBYKEMd2-ZHVLnt, pBYKEMd2-ZHVLe, pBYKEMd2-ZHVLhx, pBYKEAM-N12MHd, pBYKEAM-NPHd, pBYKEAM-NSHd, pBYKEAM-NTHd, pBYKEHM-CPHd, pBYKEHM-CSHd, and pBYKEHM-CTHd and infiltrating a plant part with agrobacteria containing the vector to produce a transformed plant part. Crude protein is then extracted from the transformed plant followed by purification for the recombinant protein. For methods of production where the vector introduced into agrobacteria is selected from the group consisting of: pBYR11eM-h6D8ZE3, pBYR11eMa-BAZE3-Hgp371, pBYR11eMa-BAZE3-H, and pBYKEMd-HZE3, the method further comprises co-infiltrating with agrobacteria containing pBYKEMd-6D8K and agrobacteria containing the vector.

Illustrative, Non-Limiting Example in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

A. Design and C1q Binding of IgG-Fusions with ZIKV Envelope Domain III

ZE3 is a promising subunit vaccine candidate, however it is not strongly immunogenic on its own, necessitating high antigen doses with adjuvant and repeated immunizations. A panel of human IgG1 variants was designed based on the humanized Ebola monoclonal antibody 6D8 fused to ZE3 (FIG. 1A). A RIC construct was created by fusing ZE3 via flexible linker to the C-terminus of the 6D8 heavy chain. ZE3 was tagged with the 6D8 epitope binding site to allow immune complex formation. The construct is referred to as "HLZe" as it contains the Heavy chain, Light chain, C-terminal ZE3 fusion, and epitope tag. As a control for immune complex formation, an otherwise identical construct was created without the epitope tag (construct "HLZ") and thus would not be expected to form immune complexes. First, C1q binding by IgG variants was studied. To improve immune receptor binding, all constructs were expressed in glycoengineered *Nicotiana benthamiana.* 6D8 antibody or RIC made in glycoengineered plants showed highly improved C1q binding compared to constructs expressed in wildtype plants (FIG. 9). RIC are thought to engage C1q with high avidity due to densely clustered antigen-antibody complexes, and as expected, HLZe showed greatly improved C1q binding compared to HLZ ($p<0.001$) (FIG. 1*i*). A small increase in C1q binding was also noted with HLZ compared to HL, perhaps suggesting low-level aggregation of the construct ($p<0.05$) (FIG. 1).

It has been reported that the antibody Fab arms may play a regulatory role in complement activation by inhibiting C1q binding unless cognate antigens are bound by the antibody. In agreement with these data, the addition of soluble antigen carrying the 6D8 epitope tag improved C1q binding (FIG. 10, compare HL vs HL+Ag), and C1q binding was greatly enhanced either by removal of the 6D8 light chain or, interestingly, by antigen fusion to the 6D8 heavy chain N-terminus (FIG. 10, compare HL, H, and ZHL). Therefore, a construct with ZE3 fused to the N-terminus of 6D8 (construct "ZH") in the absence of the light chain was created and found to efficiently bind C1q (FIG. 1*i*). To further improve interaction with C1q, a construct was created that was identical to ZH except that E345R, E430G, and S440Y mutations were introduced to the 6D8 Fc region, which favor formation of hexamers. This construct (ZHx) had further improved C1q binding compared to ZH ($p<0.001$) (FIG. 1*i*). Interestingly, while IgG1-Fc fusions have been shown to have variable C1q binding, ZE3 fused to the 6D8 Fc (construct "ZFc") showed very strong C1q binding (FIG. 1*i*). To build a simplified RIC that also lacked the light chain constant region, first a construct was made such that the variable light (VL) domain of 6D8 was inserted between the variable heavy (VH) and CH1 domains of 6D8, yielding construct HVL. This construct was found to bind antigen tagged with the 6D8 epitope, albeit at a somewhat reduced level compared to unaltered 6D8 (FIG. 11). This configuration was inserted into HLZe to create the single chain RIC HVLZe, which displayed potent C1q binding (FIG. 1).

Figure 1B:
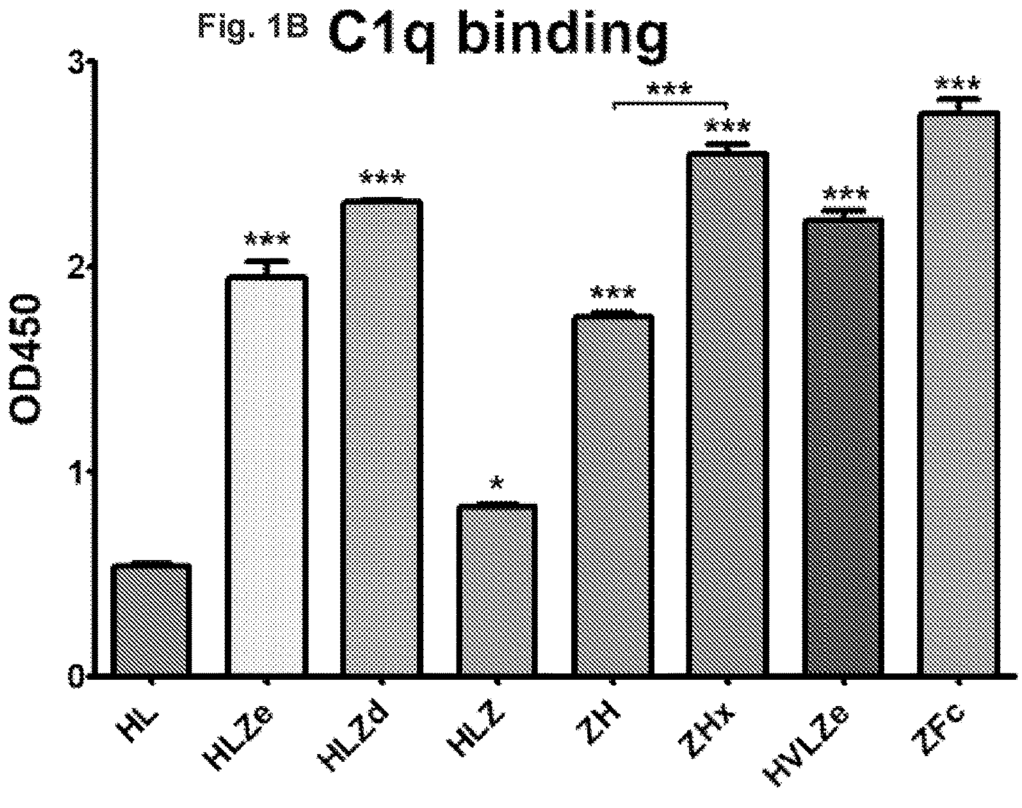
Figure 2A:
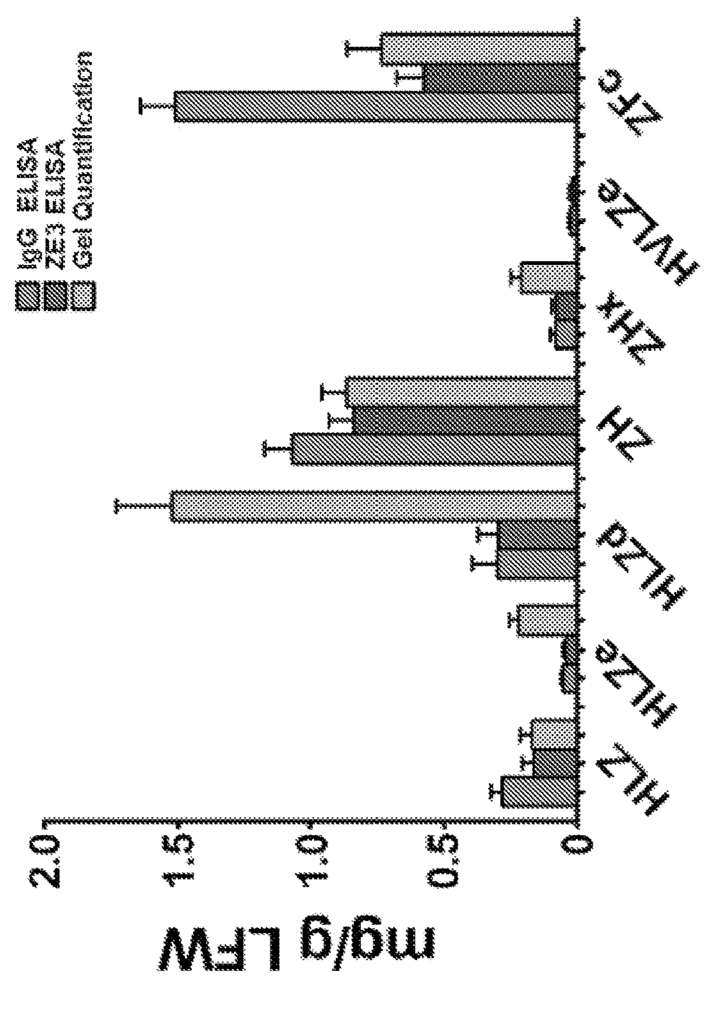
FIGS. 2A-B depict, in accordance with certain embodiments, the expression of the IgG fusions built on 6D8 antibody backbone.
Figure 3:
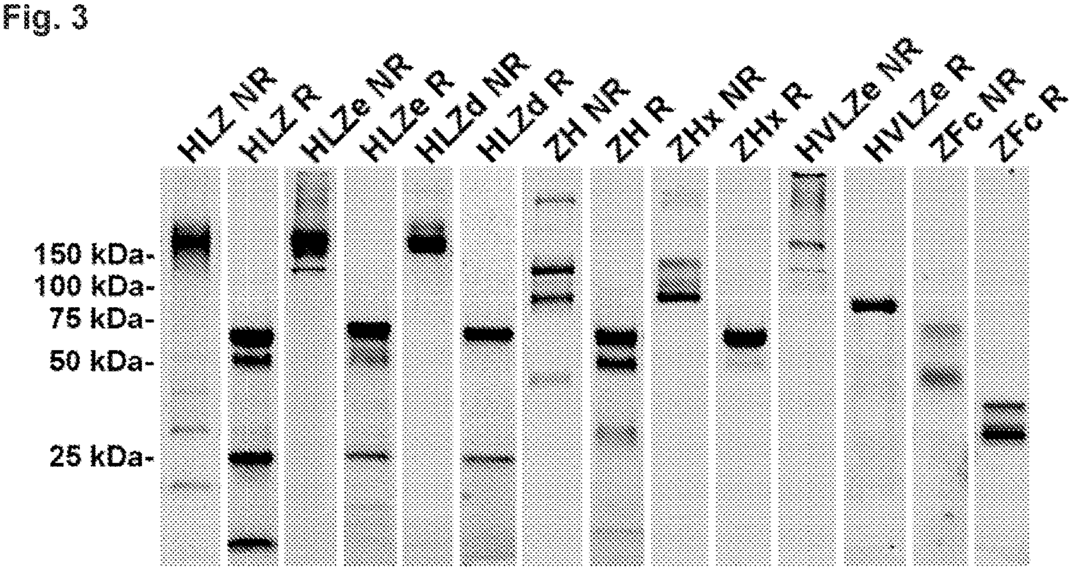
FIG. 3 depicts, in accordance with certain embodiments, the purification of IgG fusions built on a 6D8 antibody backbone. Agroinfiltrated leaf material from 1-3 plants per construct was homogenized, clarified, and purified by protein G affinity chromatography. The peak elutions were pooled and separated on nonreducing and reducing SDS-PAGE using stain-free polyacrylamide gels. Representative lanes for each construct are shown.
Figure 4A:
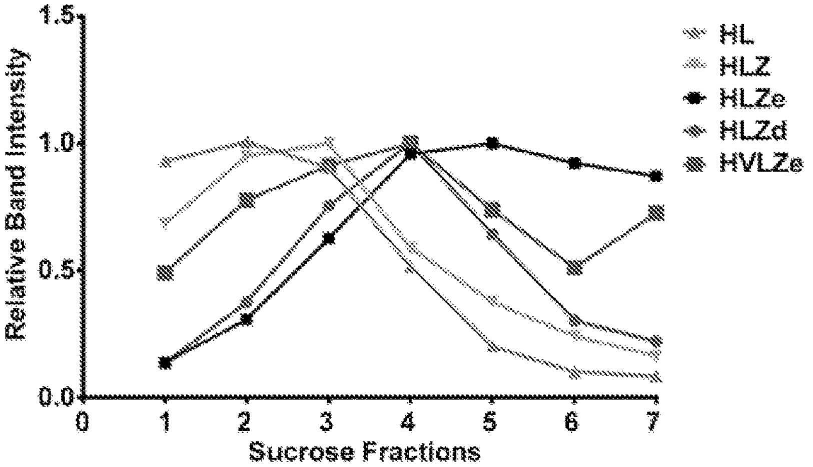
FIGS. 4A-B depict, in accordance with certain embodiments, the sucrose gradient density centrifugation of IgG fusions built on a 6D8 antibody backbone. Purified IgG fusions were separated by sucrose gradient centrifugation using 5/10/15/20/25% discontinuous sucrose layers. Gradient fractions were analyzed by SDS-PAGE and representative results are shown. The relative band intensity was quantified using ImageJ software and the peak band was arbitrarily assigned the value of 1.

It is interesting to note that the theoretically monomeric construct HLZ (consisting of ZE3 fused to the C-terminus of 6D8 without any epitope tag) produced a small but repeatable improvement in C1q binding (FIG. 1). This may suggest some low-level aggregation due to the ZE3 fusion (FIG. 4A, compare HL and HLZ). Furthermore, it has been reported that Fab-mediated events impact C1q binding, as deletion of the IgG Fab arms induced the formation of oligomers and further enhanced C1q binding via an unknown mechanism. The expression of HLZ was generally low, suggesting C-terminal ZE3 fusion may interfere with folding or otherwise cause instability (FIG. 2A). Many degradation products are visible by SDS-PAGE following purification (FIG. 3) and, interestingly the C1q binding of HLZ continued to increase upon further degradation by incubation for 2 weeks at RT or repeated freeze-thaw cycles (FIG. 5B). These data suggest that the degradation products may be more highly immunogenic than the original construct, a finding that may explain the relatively high total IgG titers produced by HLZ (FIG. 6A). However, HLZ IgG2a titers were reduced compared to the other constructs (FIG. 6B). As IgG2a is a general indicator of a Th1 response, HLZ may still have impaired effector functions that lead to T-cell activation, such as reduced complement activation. Notably, all IgG fusions strongly enhanced IgG2a production compared to unfused ZE3 (FIG. 6B). While human antibodies have recently been shown to have similar binding affinities to mouse Fc receptors compared to mouse antibodies, human IgG1 has reduced binding to low affinity mouse FcγRIII/CD16. It was also shown that a polymeric dengue IgG fusion vaccine showed enhanced immunogenicity in human adenotonsillar tissue compared to a monomeric form of the same IgG fusion, however both showed equivalent immunogenicity in mice expressing human FcγRI/CD64. Therefore, further testing in other animal models is needed to more fully evaluate the immunogenicity of these constructs.

Antigen binding may induce conformational changes in the IgG, which may improve C1q binding. Mixing 6D8 with an antigen containing the 6D8 epitope produced only a small increase in C1q binding (FIG. 10) and was found to be poorly immunogenic compared to RIC constructs (data to be presented elsewhere). However, N-terminal antigen fusion had a more pronounced effect on C1q binding (FIG. 1*i*), perhaps by strongly inducing conformational changes similar to antigen binding. In general, antigen fusion to the 6D8 N-terminus greatly enhances C1q binding for a variety of large and small antigens. Furthermore, deletion of the 6D8 light chain (construct ZH) also substantially enhanced C1q binding (FIG. 1). These findings agree with the hypothesis that the Fab portions of the antibody plays a regulatory role in C1q binding. Additionally, removal of the light chain may also impact glycosylation and thus C1q binding. Construct ZHx synergistically combines the effects of light chain removal and N-terminal ZE3 fusion with hexamer-inducing mutations, resulting in an even more potent enhancement of C1q binding (FIG. 1B) and high total IgG and IgG2a titers (FIG. 6B). Despite its strong immunogenicity, ZHx had reduced yield compared to ZH (FIG. 2A). Additionally, ZHx appeared to have some very large material found in the very bottom of the sucrose gradients that was not found in construct ZH (FIG. 4B), suggesting the hexamer mutations may contribute to aggregation. Further work is needed to optimize the solubility of these constructs.

N-terminal ZE3 fusion to the 6D8 CH1 domain (construct ZFc) greatly improved C1q binding (FIG. 1), elicited very high antibody titers (FIG. 6A). Many properties of Fc fusions, including C1q binding, seem to vary based on the individual fusion partner and thus must be determined empirically for each fusion. Interestingly, some Fc fusion constructs have been shown to form hexamers, which may explain the strong immunogenicity of ZFc observed here. Despite its strong immunogenicity, ZFc was remarkably unstable: 50% of the ZE3 was cleaved off before or during extraction (FIG. 2A, 2B) even when directly extracted in SDS sample buffer, and less than 25% of full-size ZFc molecules remained intact upon repeated freeze-thaw or storage (FIG. 5A). Unlike HLZ, this degradation was associated with a loss in C1q binding (FIG. 5B), suggesting impairment of the Fc receptor binding domains. ZFc has fewer disulfide bonds than whole IgG, and in general Fc fusions often suffer from instability or undesirable aggregation. While ZFc elicited high titers, to deliver 8 g ZE3 (discounting the weight of the IgG fusion partner), the total amount of purified sample used for immunization had to be nearly tripled to account for the high degradation and resulting loss of the ZE3 fusion. Whether this increased delivery of unfused Fc as well as other possible degradation products may have contributed to the high immunogenicity is unknown. By contrast, the larger and more highly oligomeric constructs HLZe, HLZd, ZHx, and HVLZe (FIGS. 4A and 4B) were more stable both prior to and during extraction, as well as upon storage (FIG. 5A). Consistent with their inaccessibility to antibody probes during ELISA (FIG. 2A), the intramolecular and intermolecular associations of these constructs may protect them from proteolysis or other degradative processes.

B. Expression and Characterization of HVL Fusion Constructs

RICs are known to be immunogenic; however, they require the co-expression of a heavy and light chain in order to form the fully assembled product. This process can be simplified by creating a single chain antibody fusion. The benefit of single-chain antibody fusions is that the entire antibody-antigen fusion can be produced in a single coding sequence, thereby eliminating the need for co-expression of heavy and light chains. In addition, the new construct will still retain the variable regions of both the heavy and light chain. The core single-chain antibody contains the variable heavy regions linked to a variable light chain region that is directly fused to an antibody heavy chain (FIG. 7) While a similar construct expressed in *N. benthamiana* plants has been previously characterized and published, there is very little work that explores the potential of single-chain antibody fusions, in which the core single-chain antibody is fused to an antigen of interest. Several single-chain antibody fusions were created and tested (FIG. 7). The results from the purified constructs can be expressed in plants and appear at the correct size when run under non-reducing conditions on an SDS-PAGE gel.

C. Expression of IgG Fusion Constructs

Figure 13A:
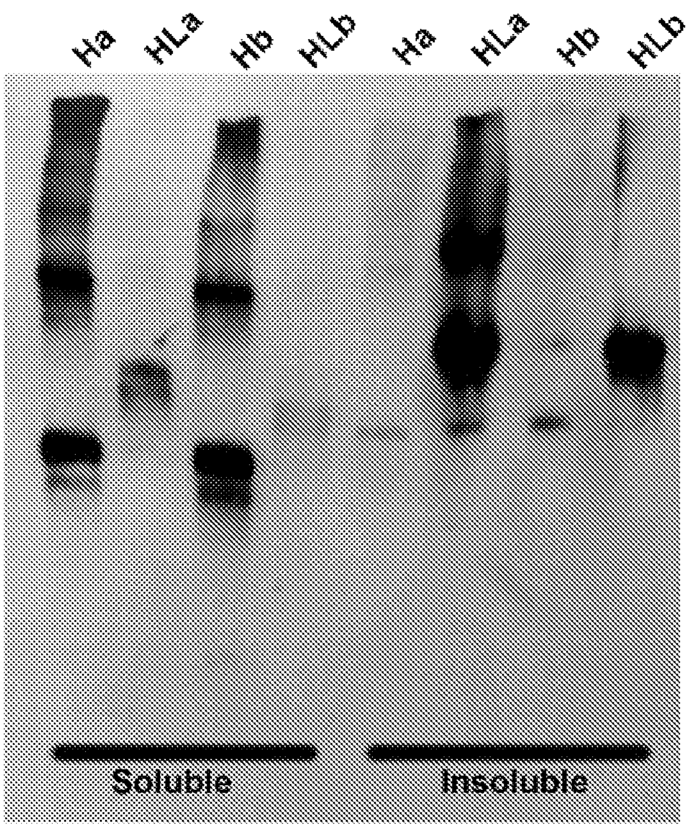
FIGS. 13A-C depict, in accordance with certain embodiments, studies on the solubility and binding of 6D8 epitope tag mutants. For FIGS. 13A-B, protein was extracted from leaves of *N. benthamiana* agroinfiltrated with the indicated constructs and separated under nonreducing conditions by SDS-PAGE followed by western blotting using goat anti-human IgG-HRP as probe. Soluble refers to the clarified crude leaf extract, while insoluble refers to the pellet following clarification that had been resuspended in SDS sample buffer. The epitope mutant designated "a" has a peptide sequence consisting of VYKLDISEA (SEQ ID NO. 2). The epitope mutant designated "b" has a peptide sequence consisting of VYKLDISE (SEQ ID NO. 3). The epitope mutant designated "c" has a peptide sequence consisting of YKLDISE (SEQ ID NO. 4). The epitope mutant designated "d" has a peptide sequence consisting of YKLDIS (SEQ ID NO. 1). For FIG. 13C, ELISA plates coated with serial dilutions of purified heavy chains containing the indicated epitope tag mutants were probed with full-size 6D8 followed by goat anti-human kappa-HRP. Mean OD450 values are shown from three replicates ±standard error.
Figure 13B:
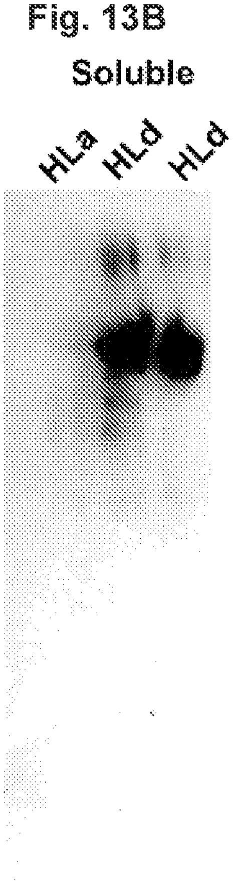
Figure 13C:
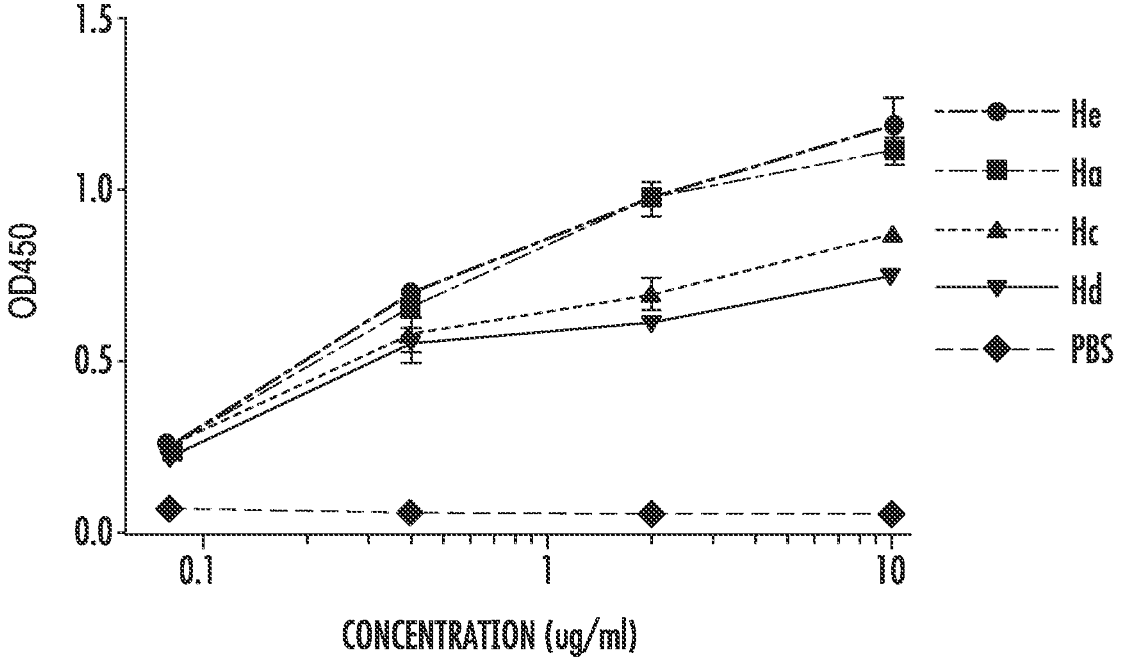

RIC suffer from low yield of soluble product. Addition of the 6D8 epitope tag to the C-terminus of 6D8 renders the antibody mostly insoluble; however this is prevented by removal of the light chain, suggesting the insolubility arises from large complexes of antibody bound to the epitope tag (FIG. 12). To improve RIC solubility, the 6D8 epitope tag was mutated to reduce antibody binding. Reducing the epitope tag on HLZe to the minimal reported binding region for 6D8 (Wilson et al., 2000) (construct "HLa," epitope sequence VYKLDISEA, SEQ ID NO. 2) showed no improvement in solubility, nor did removal of a single amino acid from the 3' end (construct "HLb," VYKLDISE, SEQ ID NO. 3) (FIG. 13A). However, further removal of a single amino acid from the 5' end (construct "HLc," YKLDISE, SEQ ID NO. 4) and additional truncation in construct "HLd" (YKLDIS, SEQ ID NO. 1) resulted in greatly improved solubility (FIG. 13B). This mutation was introduced to HLZe (construct HLZd) and characterized. Despite reducing epitope binding by approximately 25-fold by ELISA (FIG. 13C), HLZd still maintained very strong C1q binding (FIG. 1), suggesting efficient complex forming activity remained.

Figure 2B:
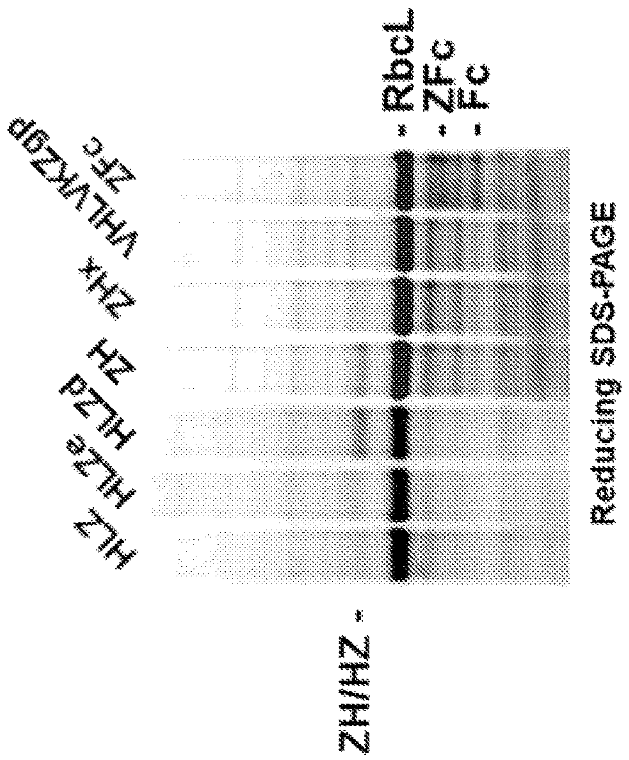

To measure the yield of fully assembled IgG fusions, an ELISA assay was employed that first captured ZE3 and then detected human IgG. To detect cleavage of ZE3, an ELISA measuring only total IgG was also used as a comparison. When probed for both ZE3 and IgG, the highly soluble monomeric construct ZH yielded 0.83 mg fully formed product per gram leaf fresh weight (mg/g LFW), and the similar ZFc yielded 0.58 mg/g LFW (FIG. 2A). However, when measuring the total IgG content, the yield of ZH was roughly 20% higher and, for ZFc, 2.5-fold higher, which suggests that ZH and especially ZFc are susceptible to proteolytic cleavage, probably of the ZE3 linker (FIG. 2A). This finding which was confirmed by visualization of the ZFc cleavage products on SDS-PAGE (FIG. 2B). HLZ accumulated only 0.17 mg/g LFW fully assembled product, with roughly 40% ZE3 lost to cleavage, suggesting general instability of the construct (FIG. 2A, 2B). By ELISA, the RIC constructs seemingly performed worse than the monomeric constructs: HLZe and HLZd only accumulated 0.04 mg/g LFW and 0.30 mg/g LFW respectively, and the hexameric ZHx accumulated only 0.08 mg/g LFW (FIG. 2A). However, when visualized under reducing SDS-PAGE conditions, HLZd was the highest expressing construct, accumulating an estimated 1.5 mg/g LFW (FIG. 2A, 2B). This discrepancy may arise due to complexed HLZd being rendered inaccessible to the antibody probe by ELISA. Similarly, the total yield of HLZe and ZHx was also higher when measured by gel quantification (FIG. 2A, 2B). Despite its low solubility, HLZe had similar yields to HLZ, and HLZd greatly exceeded the yield of HLZ. This finding suggests complex formation may protect HLZe and HLZd either inside the cell or during extraction, though the possibility that the short epitope tag plays some other role in enhancing stability of HLZe and HLZd cannot be excluded. HVLZe yielded only 0.02 mg/g LFW soluble product by ELISA and was not detectable by SDS-PAGE (FIG. 2A); however it accumulated very high levels when extracted with 7.5 M urea, which suggests insolubility resulted in the low yield.

D. Purification, Aggregation, and Stability of IgG Fusions

Figure 4B:
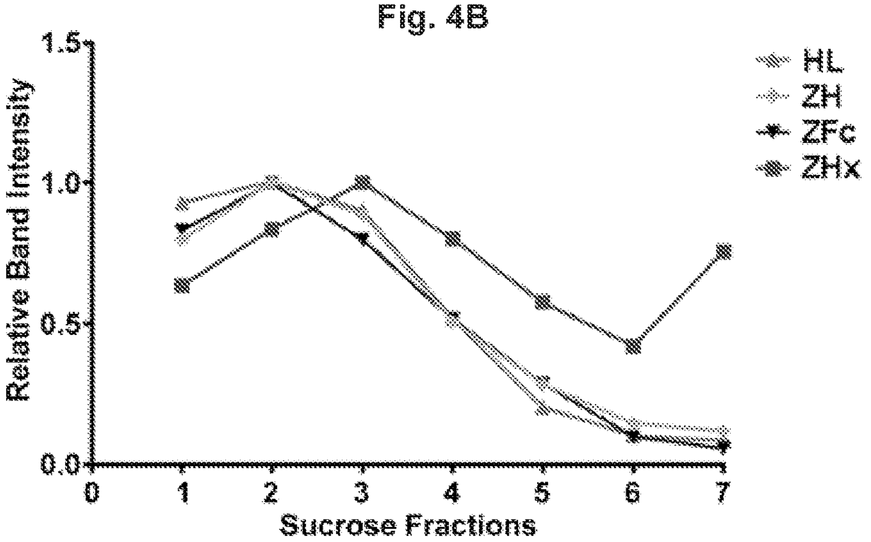

IgG fusions were purified to >95% homogeneity using a simple one-step purification via protein G affinity chromatography. In agreement with the expression data, the more highly oligomeric constructs showed less degradation than the other constructs, and the ZFc fusion had particularly high levels of degradation (FIG. 3). To investigate the aggregation characteristics of each construct, purified IgG fusions were analyzed by sucrose gradient centrifugation. Consistent with the formation of large immune complexes, HLZe and HVLZe were found mostly in the bottom of the gradient while HLZ, ZH, and ZFc were found mostly at the top of the gradient (FIGS. 4A and 4B). Solutions of ZHx contained both low-density material as well as some very high-density material (FIG. 4B). Solutions of HLZd showed intermediate density compared to HLZ and HLZe (FIG. 4A) which, when taken together with the expression data and C1q binding, are consistent with HLZd forming smaller, more soluble immune complexes compared to HLZe.

The stability of each construct was analyzed by comparing fully formed products and degradation products on SDS-PAGE after treatment with various temperature conditions. After five freeze-thaw cycles or two weeks at 4° C., small amounts of degradation were observed with all constructs (FIG. 5A). High concentrations (>1 mg/ml) of HLZe and HVLZe were found to precipitate after several days at 4° C. At room temperature, most constructs had 10-15% degradation after two weeks (FIG. 5A). Overall, the oligomerizing constructs retained the highest stability, while the monomeric constructs, and especially the Fc fusion, were more rapidly degraded (FIG. 5A). Most constructs retained strong C1q binding after storage, however after room temperature storage or repeated freeze-thaw cycles but not 4° C. storage, construct HLZ displayed increased C1q binding (FIG. 5B). This may be due to degradation of the Fab regions or loss of light chain, as degradation products are visible on SDS-PAGE (FIG. 3), or aggregation. Conversely, construct ZFc lost C1q binding ability as it became more degraded, probably due to degradation of the C1q binding regions (FIG. 5B).

E. Mouse Immunizations, Titers, IgG2a, Cytokines

To investigate the immunogenicity of the IgG fusions, BALB/c mice (n=6) were immunized subcutaneously without adjuvant with two doses of each IgG variant such that the total dose of ZE3 delivered was 8 g. As a control, mice were also immunized with 8 g unfused plant-expressed ZE3. All IgG fusions very strongly enhanced the production of ZE3-specific antibodies, producing 20-fold to 150-fold higher total IgG titers than ZE3 alone (FIG. 6A, $p<0.01$ compared to ZE3). All IgG fusions significantly enhanced the production of IgG2a compared to ZE3 alone (FIG. 6B, $p<0.01$ compared to ZE3). While no significant differences in total titer production were observed between the IgG fusions, the construct HLZ had a significantly reduced production of IgG2a compared to all other fusions except for HLZe (FIG. 6B, $p<0.05$ compared to HLZ). The constructs ZHx and ZFc produced the highest levels of total IgG and IgG2a (FIG. 6A, FIG. 6B).

F. Design, Expression, and Purification of IgG-Fusions with Norovirus Epitopes

The norovirus (NoV) capsid protein VP1 consists of an inner shell domain (S), which forms the core surrounding the viral genome, and a protruding domain (P), which is further subdivided into P1 and P2 subdomains. Traditional human norovirus (HNoV) vaccine approaches, as well as natural infection, elicit immune responses primarily targeting immunodominant epitopes on the viral capsid that are poorly conserved, resulting in limited protection against novel strains and against related viruses from different genotypes. Nearly all HNoV vaccine candidates have focused on virus-like particles (VLPs) made from the VP1 capsid protein. Based on sequence divergence of the major capsid protein VP1, ten genogroups (GI-GX) which contains over forty genotypes of NoVs have been identified. Of these ten genogroups, GI and GII cause the most human disease. Yet, even the best attempts at generating conserved VLPs have produced only modest reductions of disease severity in human clinical trials and generally struggled to induce broadly protective immunity.

One broadly reactive antibody mapped to a strongly conserved epitope at the base of P1: LPQEWVQYFYQEAAPA (SEQ ID NO. 34). Critically, this antibody binds linear epitopes in P1, and thus the native VP1 conformation is not necessary to elicit functional antibodies. Antibodies targeting this epitope bind with high affinity to VLPs from 8 GI, 13 GII, and 1 GIV genotype. Antibodies directed against a second broadly reactive, linear epitope (ALLRFVNPDTGRVLFE, SEQ ID NO. 37) bind VLPs from at least 3 GI and 7 GII genogroups. A third broadly conserved linear epitope at the base of the P1 domain is DSWVNQFYTLAP (SEQ ID NO. 41). The S domain is the most highly conserved region of VP1. Antibodies targeting the strongly conserved linear epitopes QNVIDPWIRNNF (SEQ ID NO. 45), QAPGGEFTVSPRNAPGE (SEQ ID NO. 46), and KVIFAAVPP (SEQ ID NO. 47) have been identified with broad cross-reactivity to NoV genogroups. Conserved HNoV T-cell epitopes were identified in humans13, namely the epitope TMFPHIIVDV (SEQ ID NO. 54) in the VP1 S domain elicited broad T-cell activation against both GI and GII HNoV. In addition, a dominant T-cell epitope (SWVSRFYQL, SEQ ID NO. 64) in the P1 C-terminal domain that is highly conserved between all NoV genogroups, including HNoV, was critical for viral clearance in NoV-infected mice. This region plays a vital role in capsid assembly, and thus structural constraints limit the potential for mutational escape. The nonstructural protein NS1, which is proteolytically cleaved from NS1-2, is secreted from cells infected with murine NoV (GV) or transfected with HuNoV NS1-2. Secreted NS1 suppresses IFN-λ production in the intestinal tract of mice. Importantly, vaccination with NS1 alone protected mice better than vaccination with P-domain, highlighting NS1 as a vaccine target. Vaccination with NS1-2 yielded antibodies directed against NS1.

For the development of antigens to make immunoglobulin variants targeting norovirus, epitopes from the protruding domain of VP1 of human norovirus GI.3, human norovirus GII.4, and murine norovirus (MNV) have been identified (SEQ ID NOs. 34-44). Also identified are epitopes from the shell domain of VP1 of GI.3, GII.4, and MNV (SEQ ID NOs. 45-54). The NS1 epitopes of MNV is set forth in SEQ ID NO. 55. The NS1 epitope of GI.3 is set forth in SEQ ID NO. 56. The NS1 epitope of GII.4 is set forth in SEQ ID NO. 57. The T-cell response epitopes are set forth in SEQ ID NOs. 58-72.

Accordingly, RIC constructs targeting conserved epitopes of the NoV protruding domain (P-RIC), shell domain (S-RIC), T-cell epitopes (T-RIC), or containing tandem linked nonstructural protein 1 (NS1) from murine norovirus (N-RIC) are designed and produced. The unit of the antigen for P-RIC is formed from nine tandem-linked epitopes from the protruding domain of VP1 from GI.3, GII.4, and MNV. The unit of the antigen for P-RIC is formed from nine tandem-linked epitopes from the protruding domain of VP1 of GI.3, GII.4, and MNV. The unit of the antigen for S-RIC is formed from nine tandem-linked epitopes from the shell domain of VP1 of GI.3, GII.4, and MNV. The unit of the antigen for T-RIC is formed from fifteen tandem-linked epitopes that have been found to cause a T-cell mediated immune response against GI.3, GII.4, and MNV. The unit of the antigen for N-RIC is formed from tandem-linked epitopes from NS1 of GI.3, GII.4, and MNV. The plant expression vector for producing these RIC constructs are pBYKEAM-N12MHd, pBYKEAM-NPHd, pBYKEAM-NSHd, pBYKEAM-NTHd, pBYKEHM-CPHd, pBYKEHM-CSHd, and pBYKEHM-CTHd.

Figure 14A:
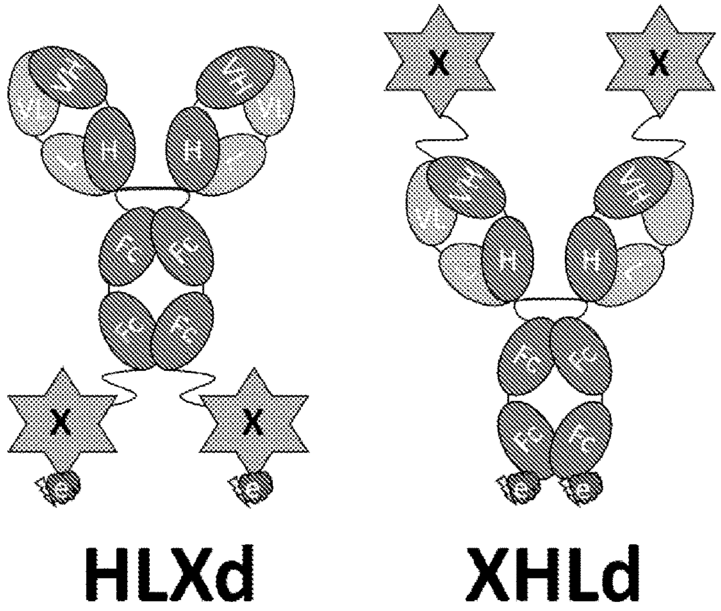
FIGS. 14A and 14B depict, in accordance with certain embodiments, a schematic of recombinant immune complex (RIC) constructs targeting norovirus (NoV) and a SDS-PAGE of the purified RIC constructs, respectively.
Figure 14B:
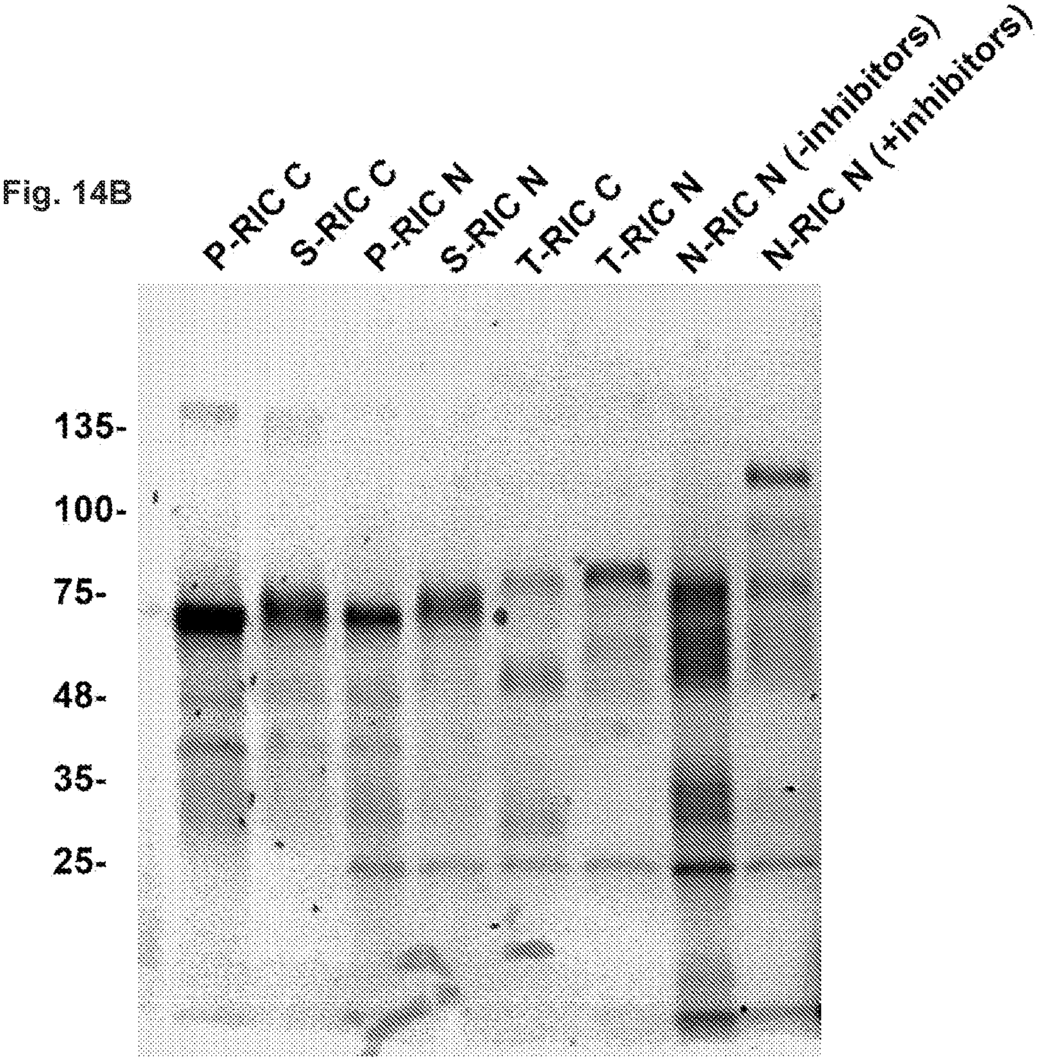
Figure 15:
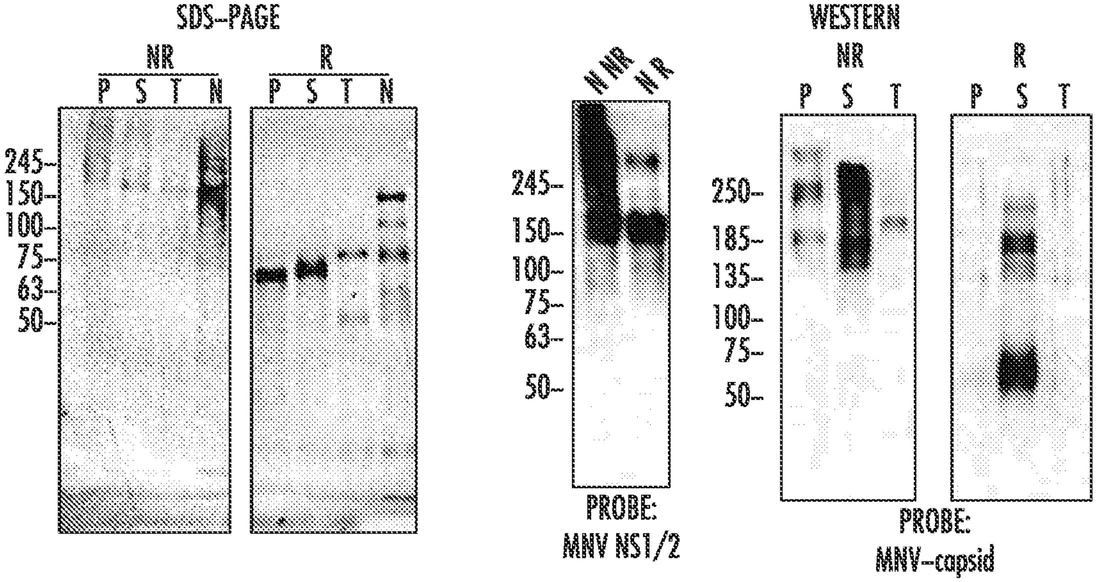
FIG. 15 depicts, in accordance with certain embodiment, a SDS-PAGE (left) and western blot (right) of purified RIC constructs targeting norovirus. The purified RICs were separated by SDS-PAGE under nonreducing (NR) or reducing (R) conditions and visualized under UV via stain-free 2,2,2-trichloroethanol (TCE) imaging (left). Western blot was performed with anti-murine norovirus 1 (MNV) NS1/2 antibodies, or anti-MNV capsid antibodies. P, P-RIC; S, S-RIC; T, T-RIC; N-RIC.
Figure 18:
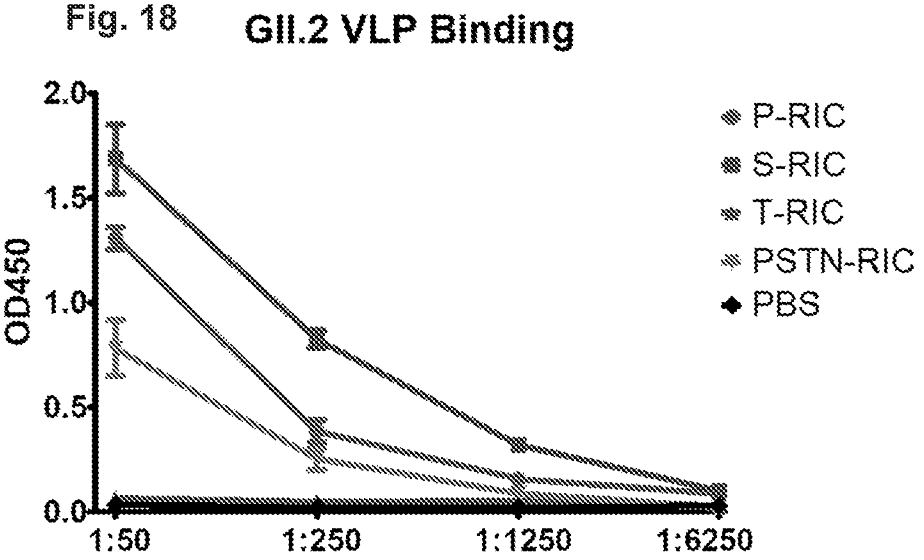
FIG. 18 depicts, in accordance with certain embodiments, serum binding to human norovirus GII.2 VLPs. Serum from mice immunized with 3 doses of 2 μg total antigen delivered via RIC constructs were tested for binding to human norovirus GII.2 (Snow Mountain virus) VLPs by ELISA. Polystyrene 96-well plates were incubated with plant-made GII.2 VLPs, blocked, and then incubated with serial dilutions of mouse sera. Bound antibodies were detected with goat anti-mouse IgG-RP conjugate. Mean $OD_{450}$ values ±standard error from pooled serum samples containing two technical replicates are shown. Abbreviations: P-RIC: serum from mice immunized with P-RIC; S-RIC: serum from mice immunized with S-RIC; T-RIC: serum from mice immunized with T-RIC; N-RIC: serum from mice immunized with N-RIC, PSTN-RIC: serum from mice immunized with P-RIC, S-RIC, T-RIC, and N-RIC but with a quarter of the dose used for the individual experiments.
Figure 19:
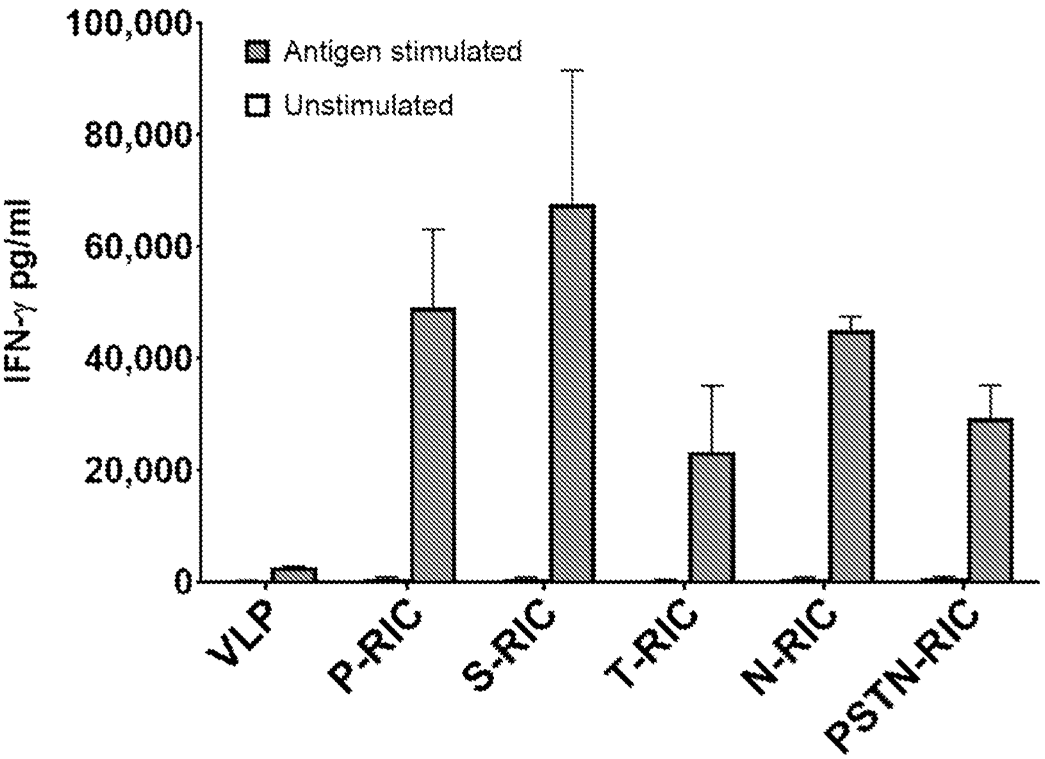
FIG. 19 depicts, in accordance with certain embodiments, IFN-7 production from mice immunized with the VLP or RIC constructs targeting norovirus. Splenocytes were harvested from immunized mice and stimulated with their corresponding antigen for 72 hours. Supernatants from stimulated and unstimulated splenocytes were collected and assayed IFN-7 production by ELISA. Polystyrene 96-well plates were coated with serially diluted splenocyte supernatants or recombinant mouse IFN-7 standard, blocked with 5% PBSTM, and then probed with rat anti-mouse IFN-7 and goat anti-rat IgG horseradish peroxidase conjugate. $OD_{450}$ values were used to construct a standard curve, and the mean IFN-7 production ±standard error from six samples each containing two technical replicates are shown. Abbreviations: P-RIC: serum from mice immunized with P-RIC; S-RIC: serum from mice immunized with S-RIC; T-RIC: serum from mice immunized with T-RIC; N-RIC: serum from mice immunized with N-RIC, PSTN-RIC: serum from mice immunized with P-RIC, S-RIC, T-RIC, and N-RIC but with a quarter of the dose used for the individual experiments.
Figure 20:
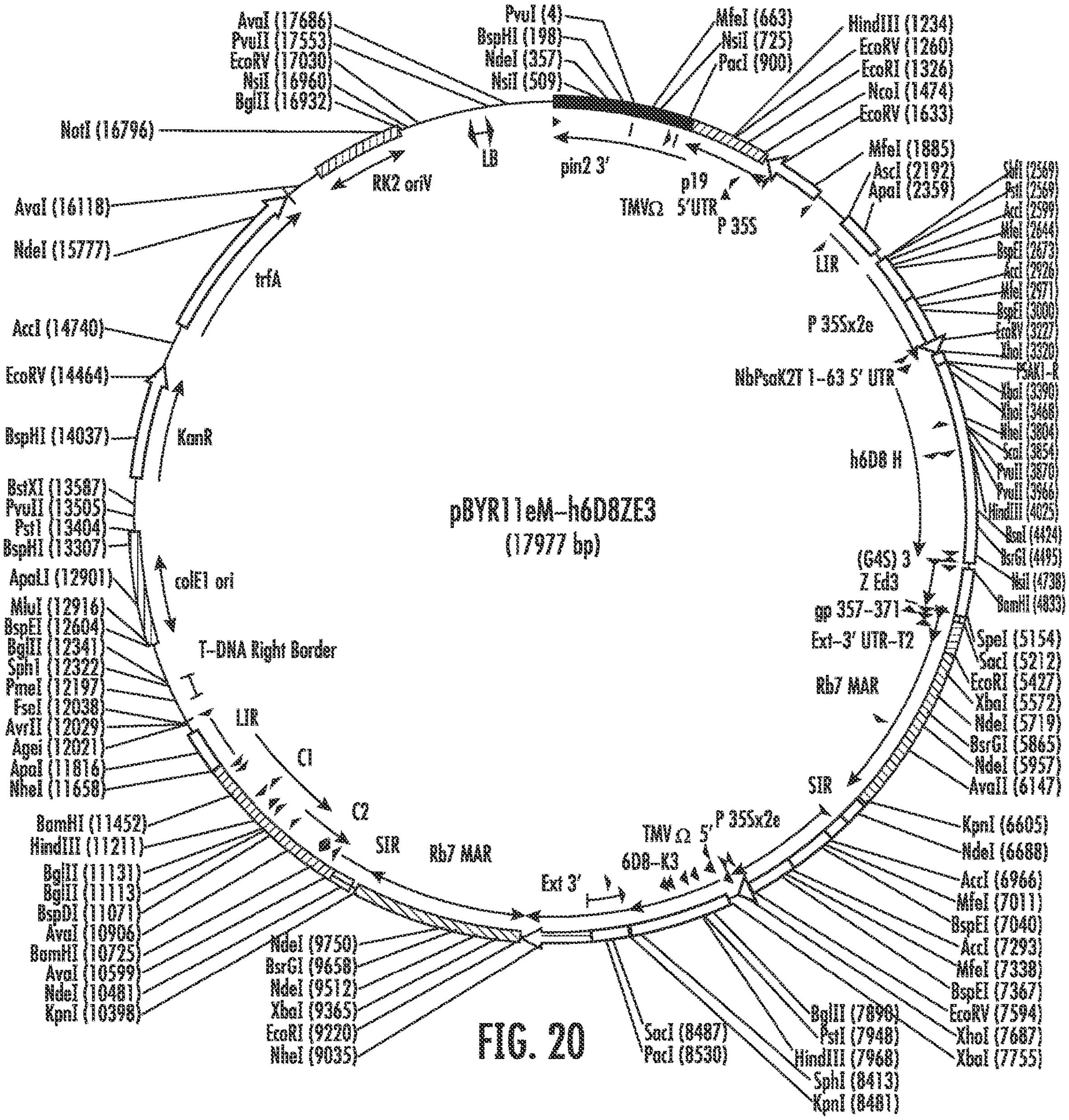
FIGS. 20-39 depict maps of pBYR11eM-h6D8ZE3, pBYR11eMa-BAZE3-Hgp371, pBYR11eMa-BAZE3-H, pBYKEMd-HZE3, pBYKEMd-ZE3H, pBYKEMd-ZE3Hx, pBYKEMd-HVLZe, pBYKEMd2-HVL-Hx, pBYKEMd2-HVLZnt, pBYKEMd2-ZHVLnt, pBYKEMd2-ZHVLe, pBYKEMd2-ZHVLhx, pBYKEMd-6D8K, pBYKEAM-N12MHd, pBYKEAM-NPHd, pBYKEAM-NSHd, pBYKEAM-NTHd, pBYKEHM-CPHd, pBYKEHM-CSHd, and pBYKEHM-CTHd.
Figure 21:
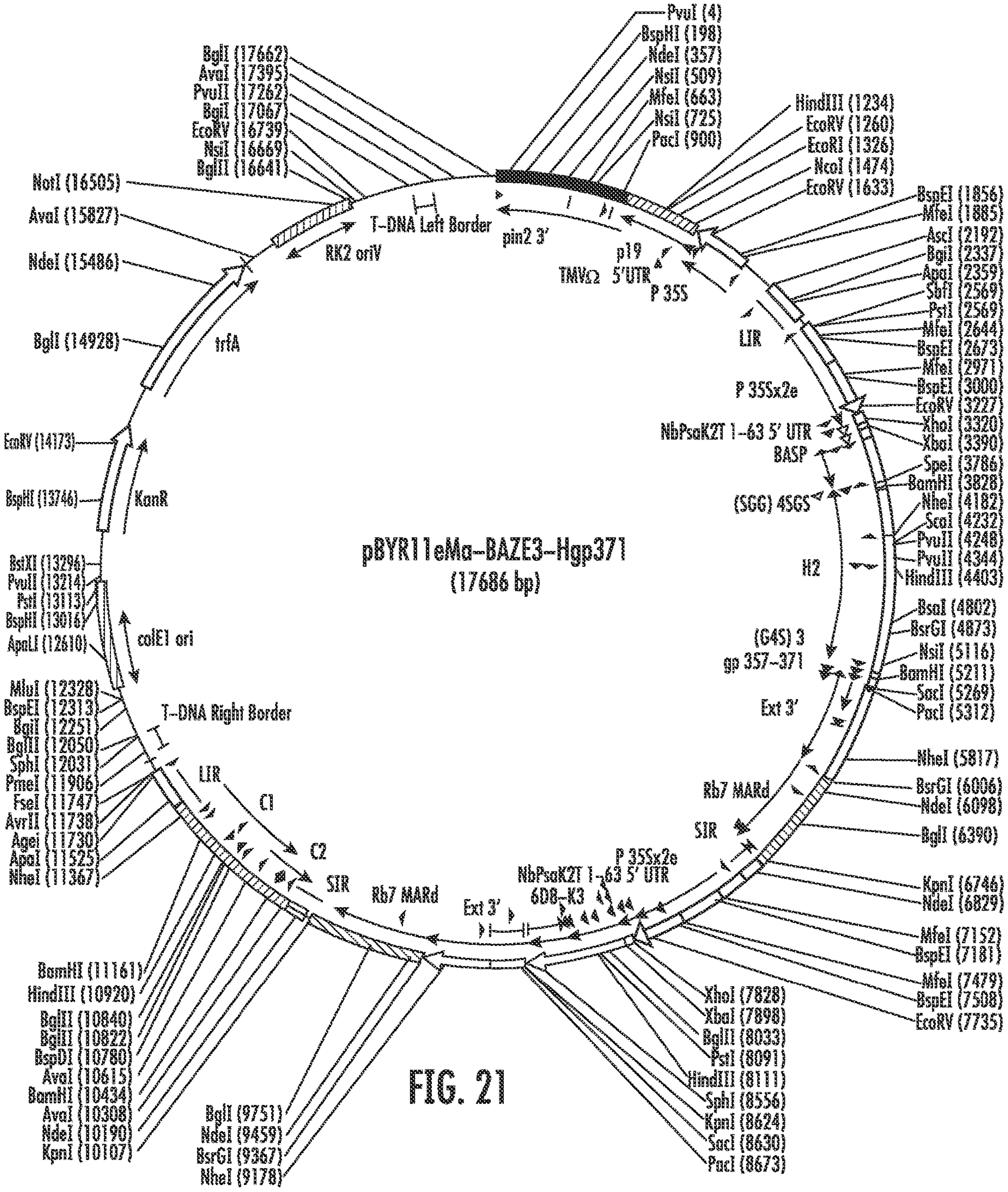
Figure 22:
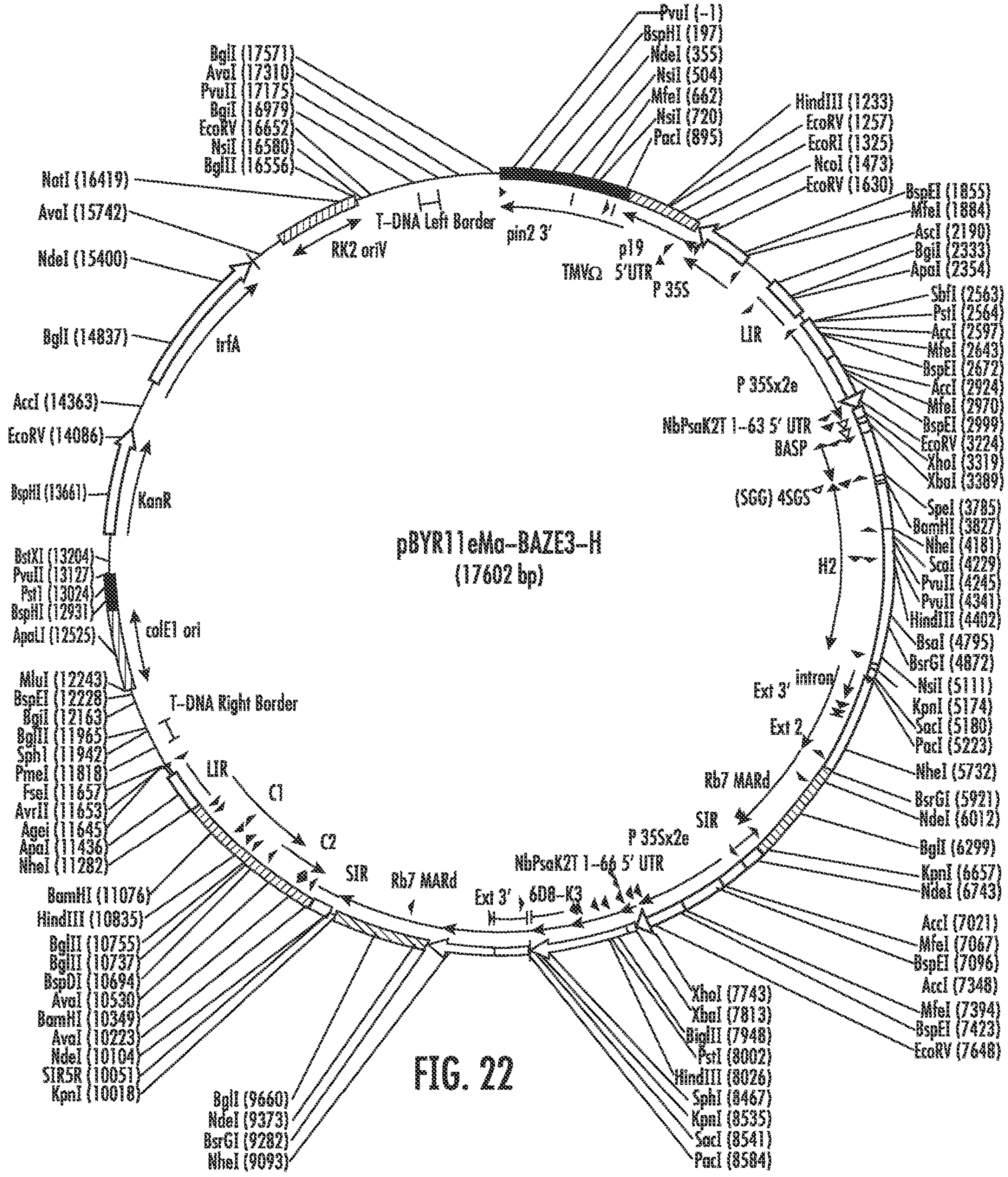
Figure 23:
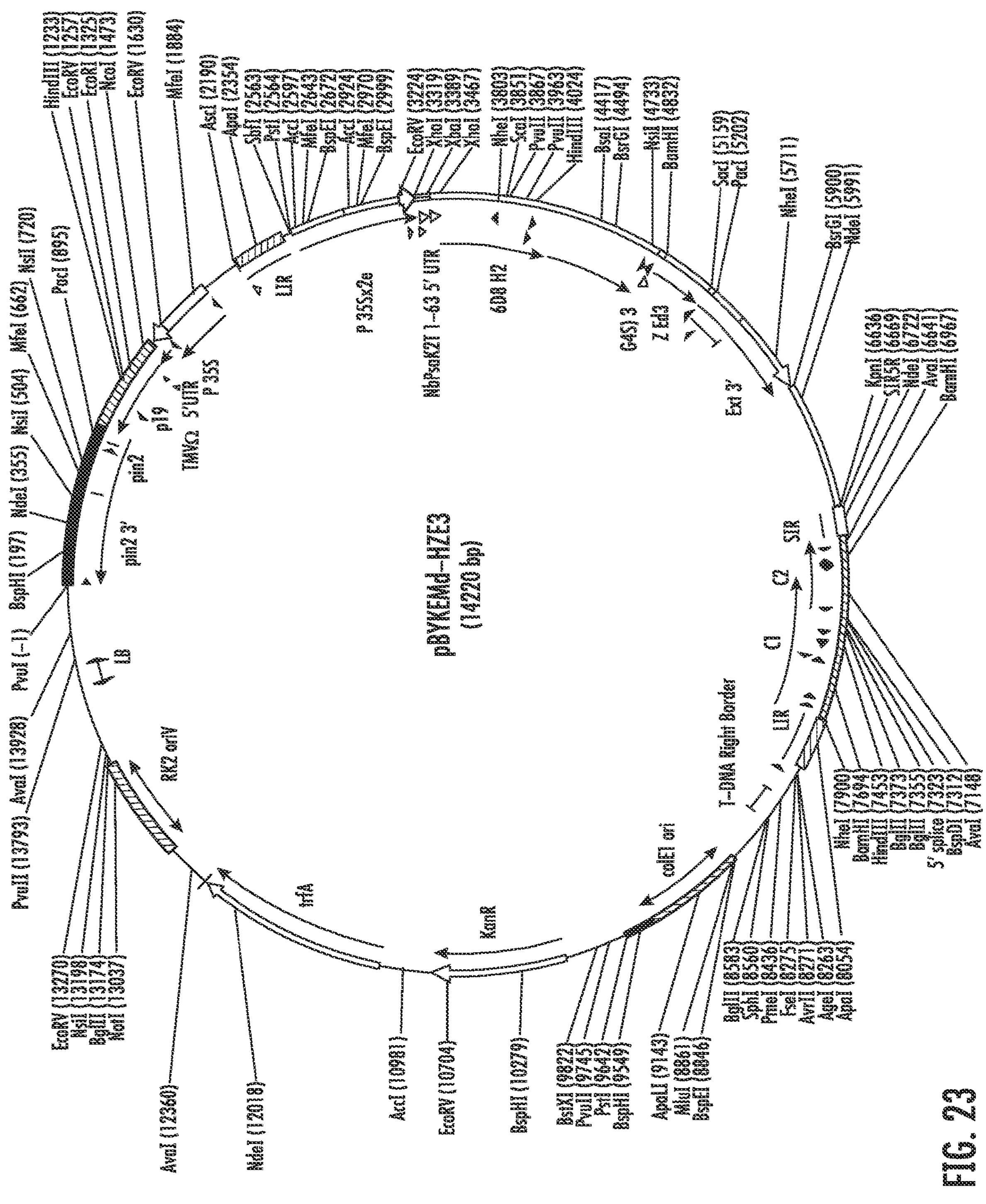
Figure 24:
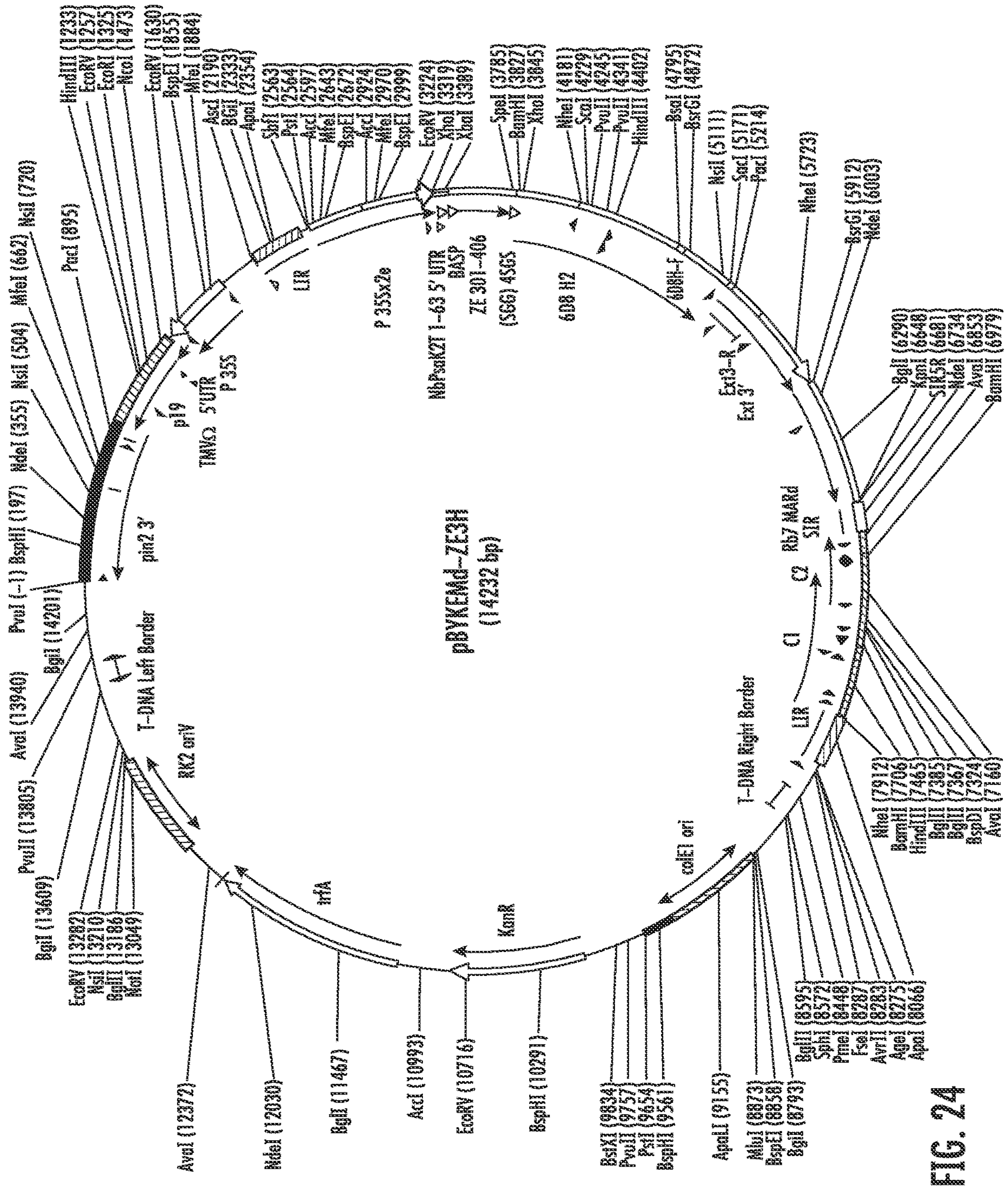
Figure 25:
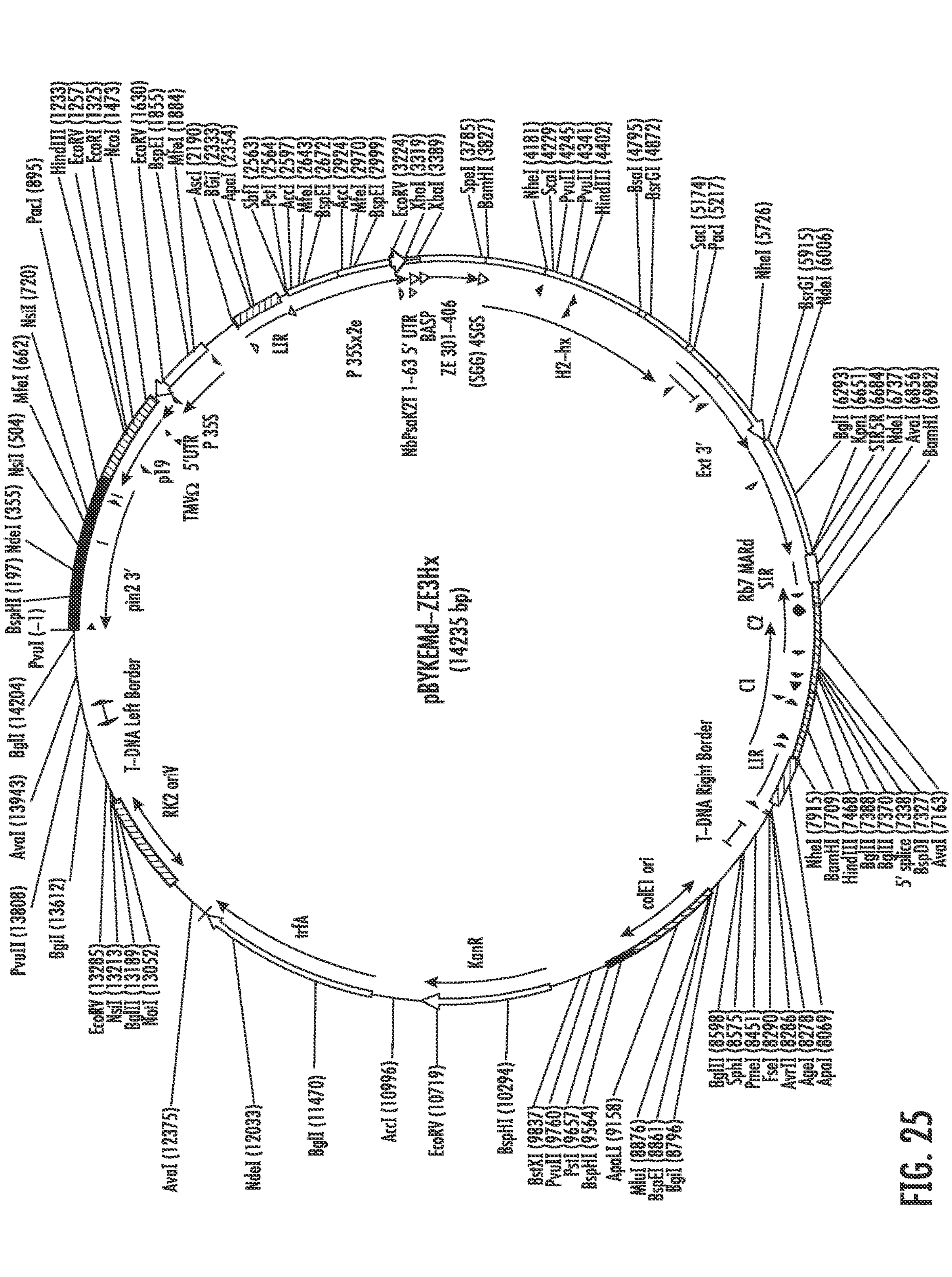
Figure 26:
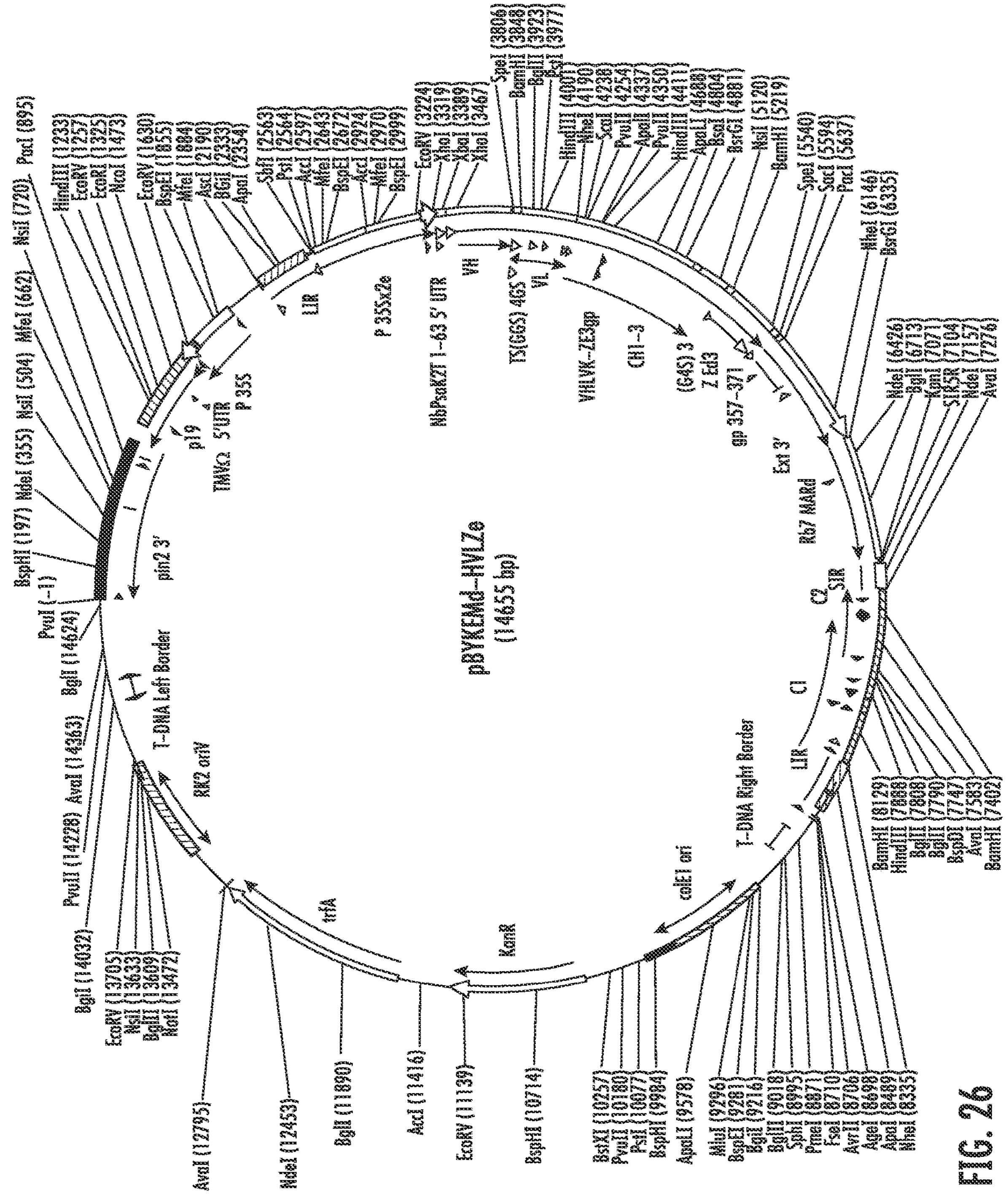
Figure 27:
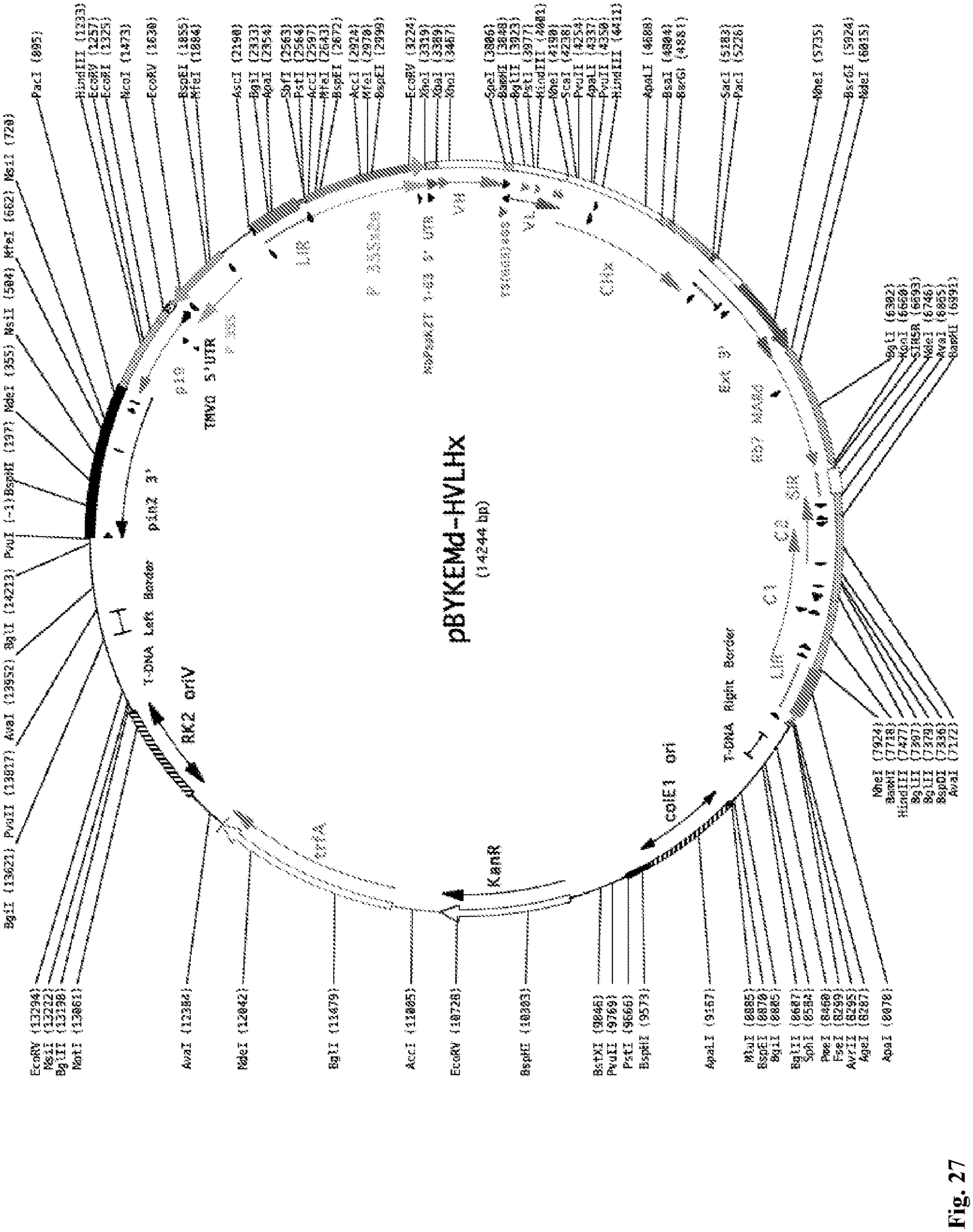
Figure 28:
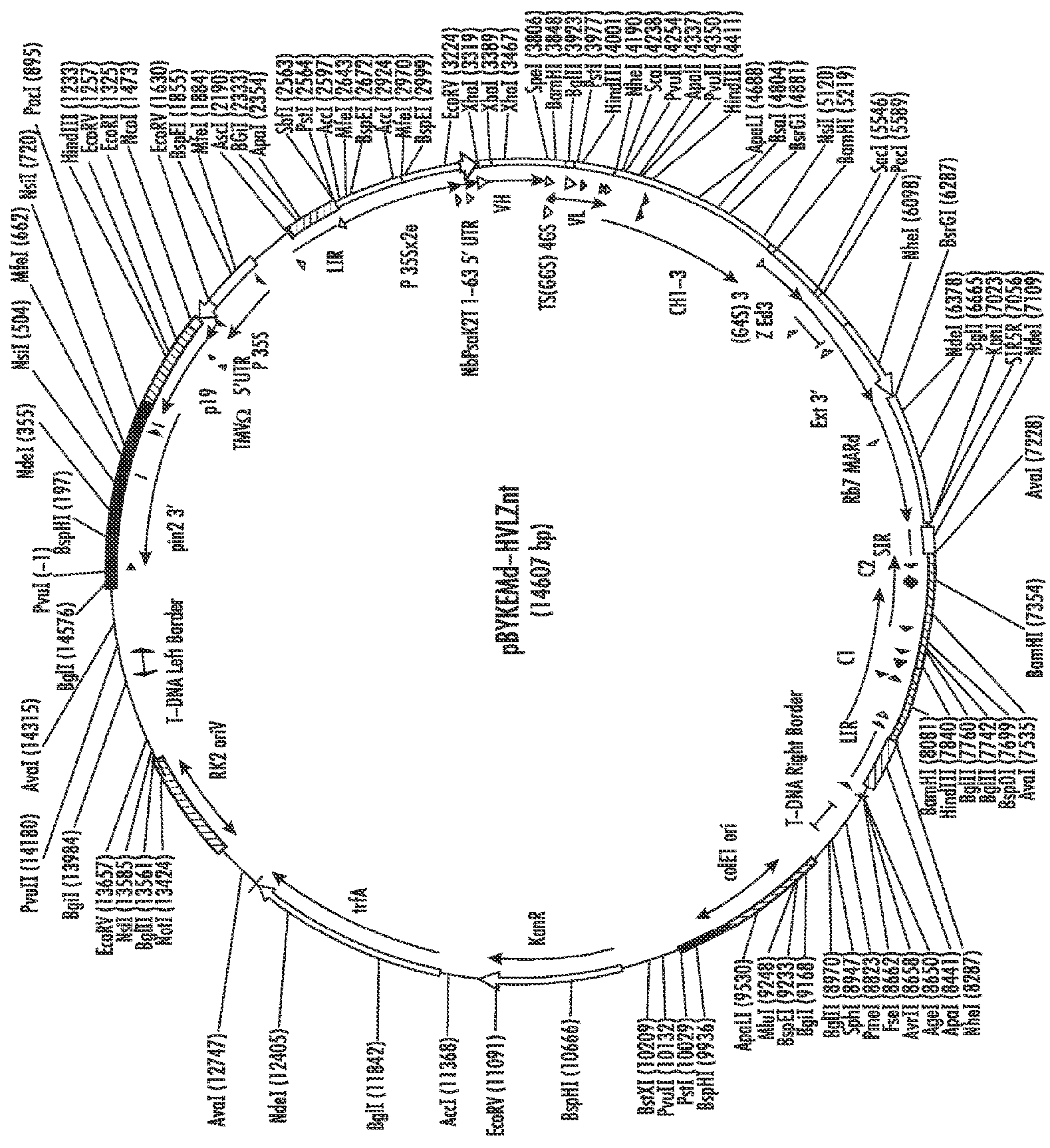
Figure 29:
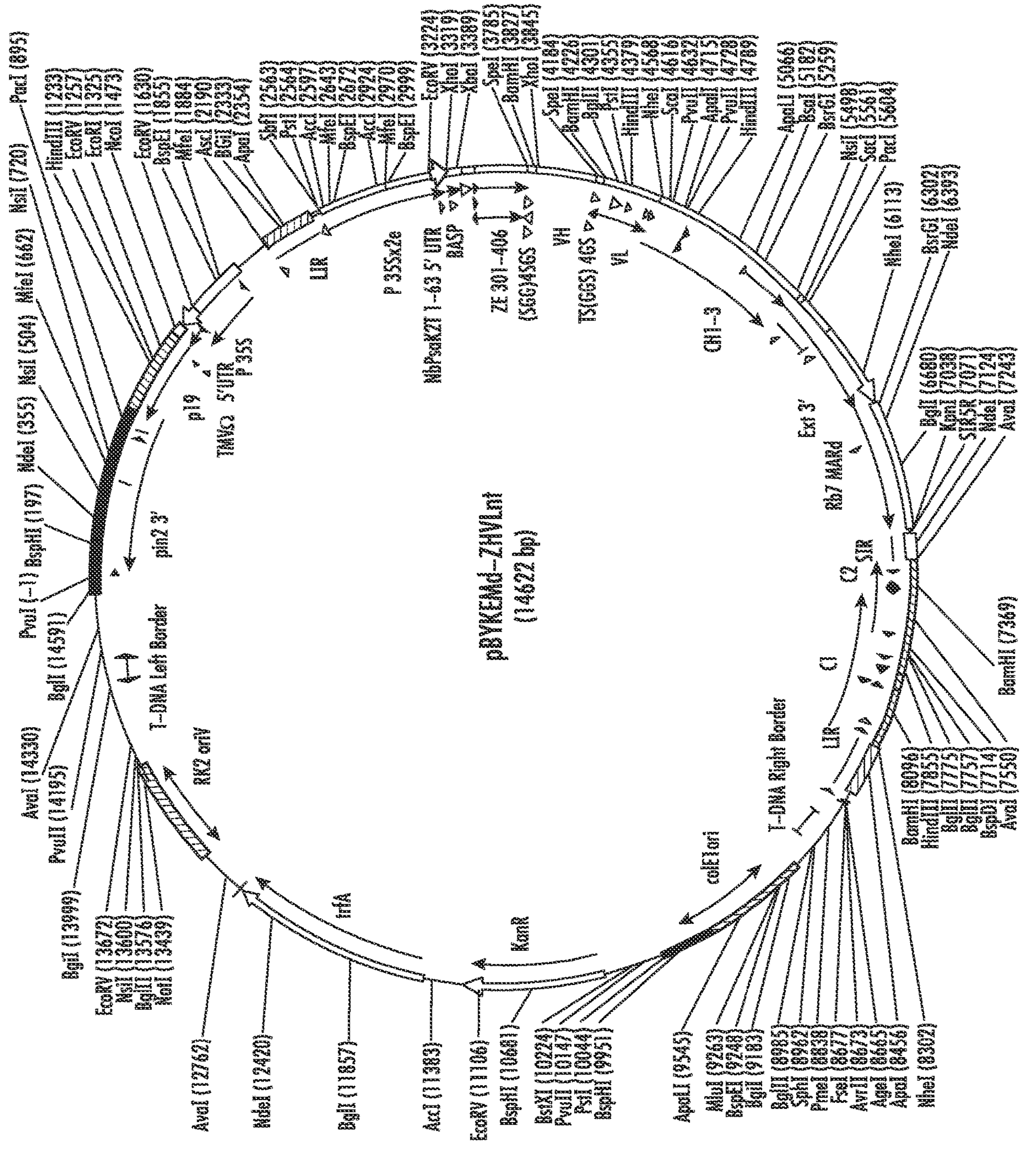
Figure 30:
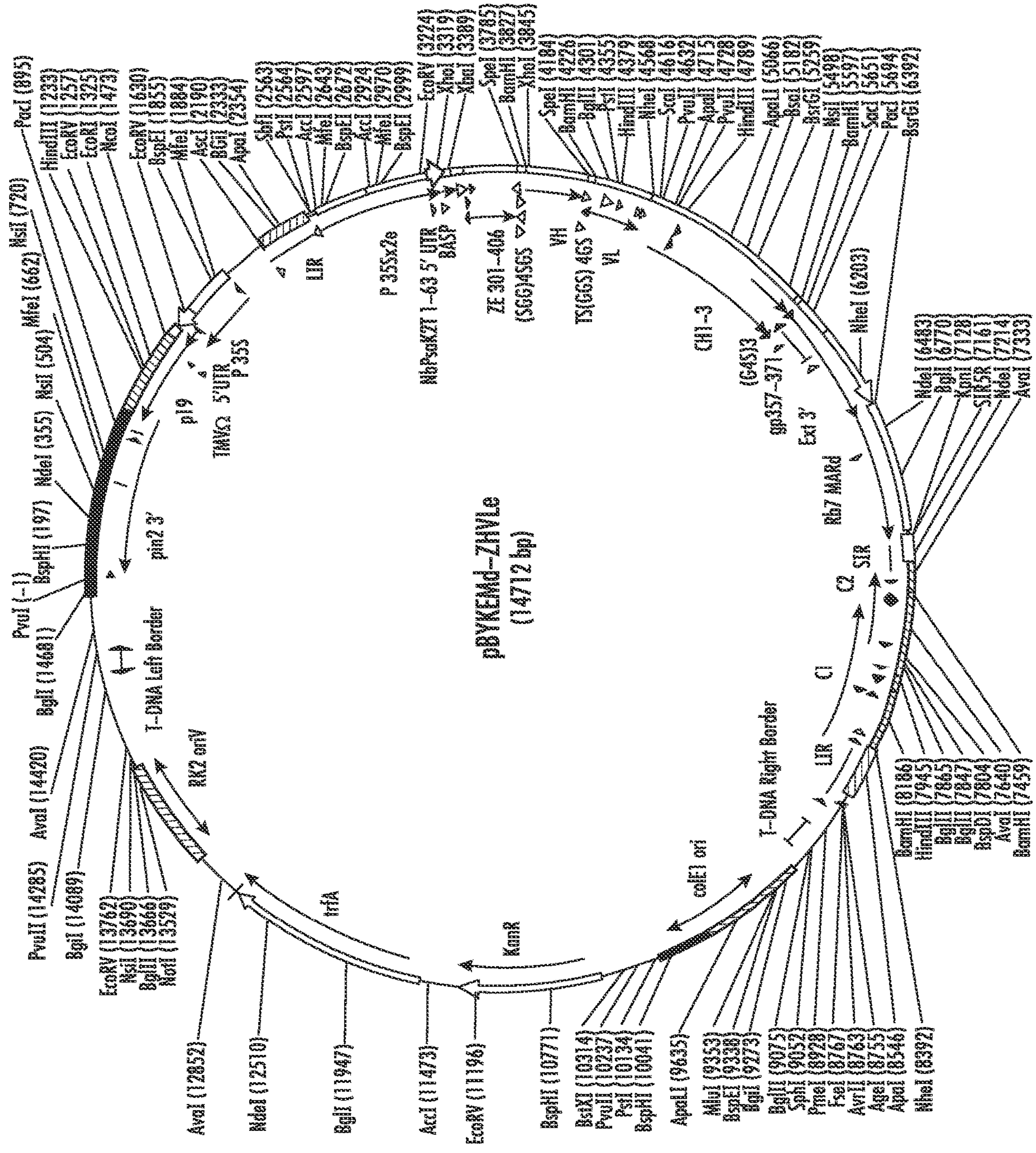
Figure 31:
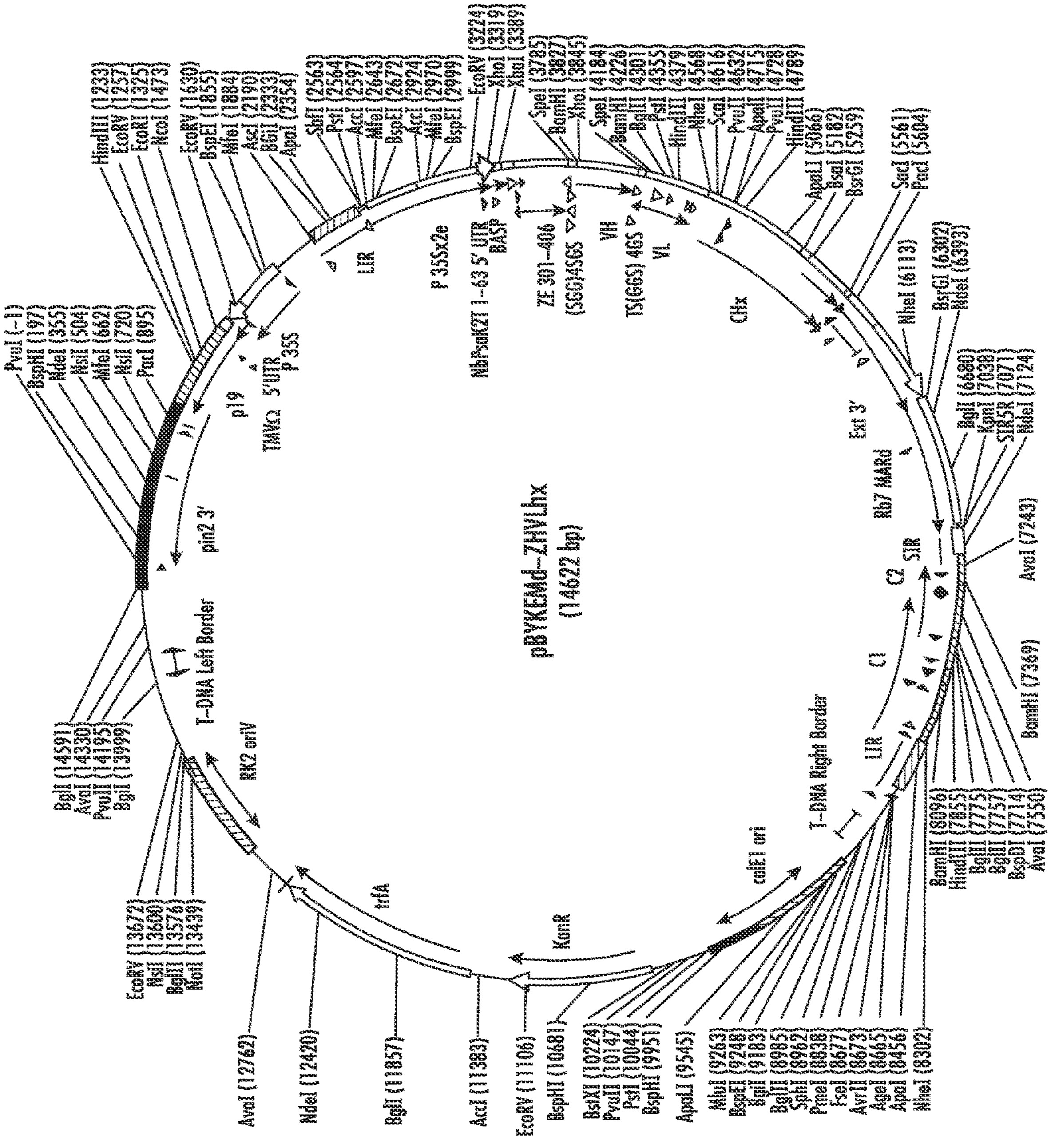
Figure 32:
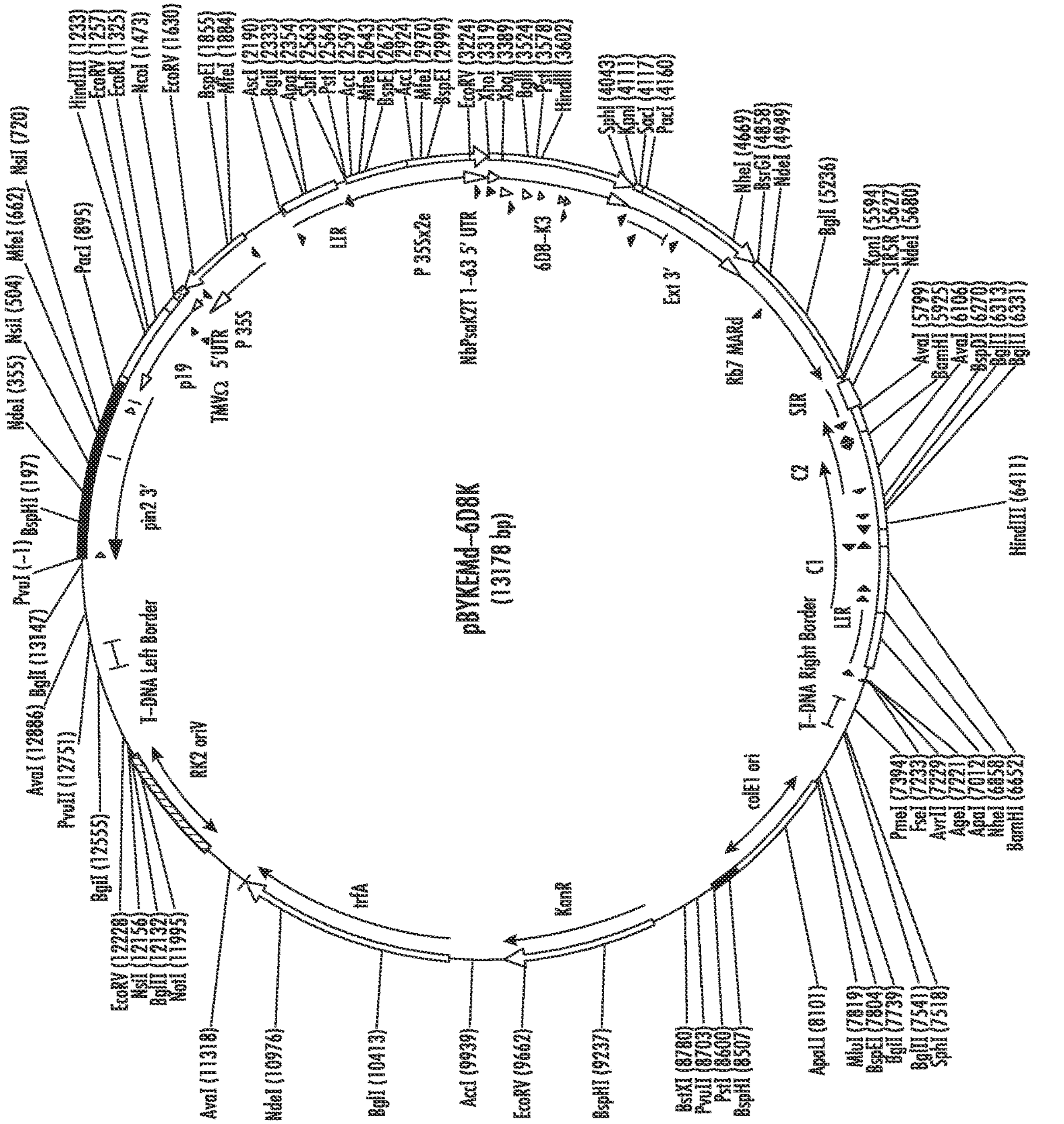
Figure 33:
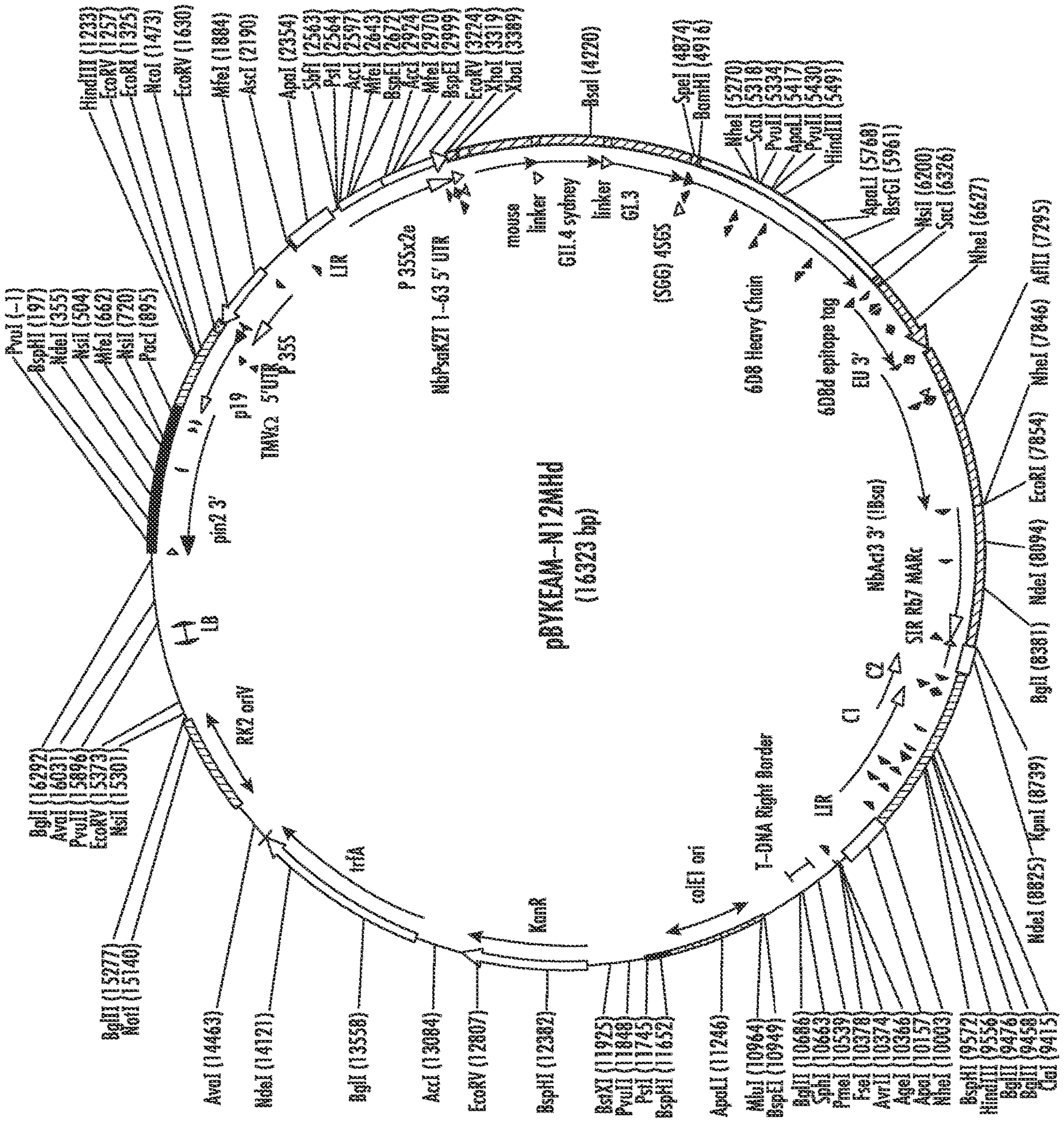
Figure 34:
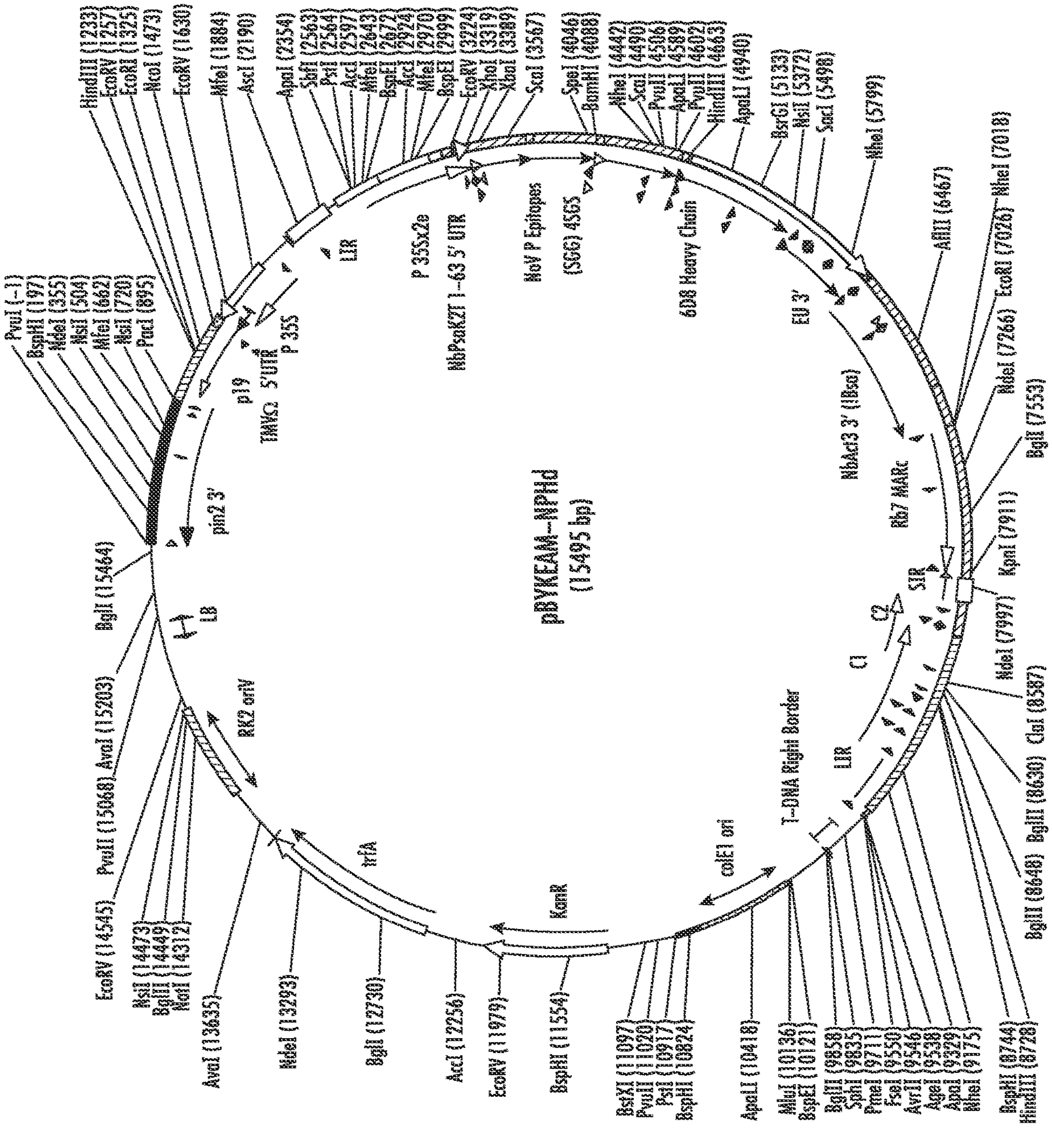
Figure 35:
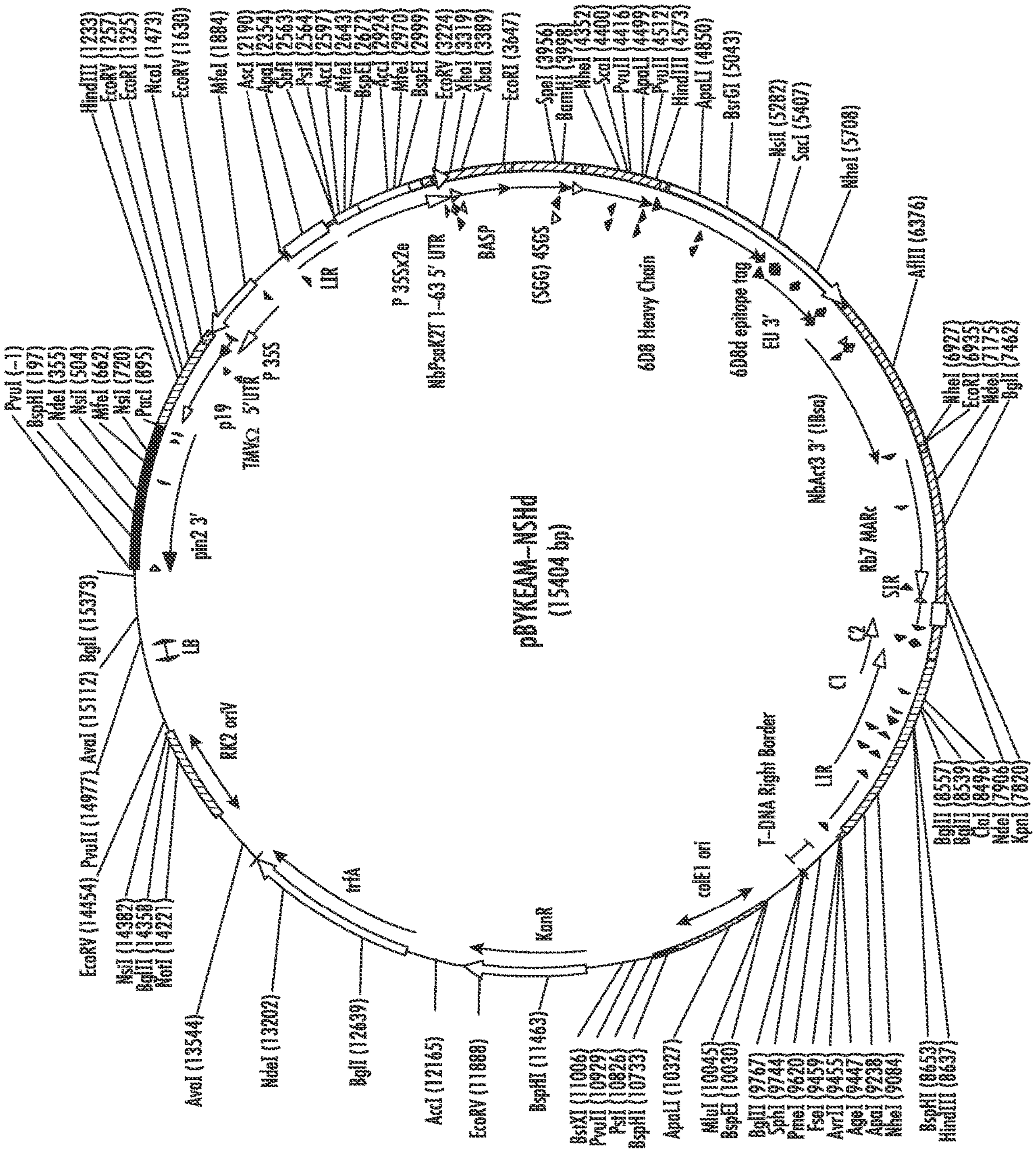
Figure 36:
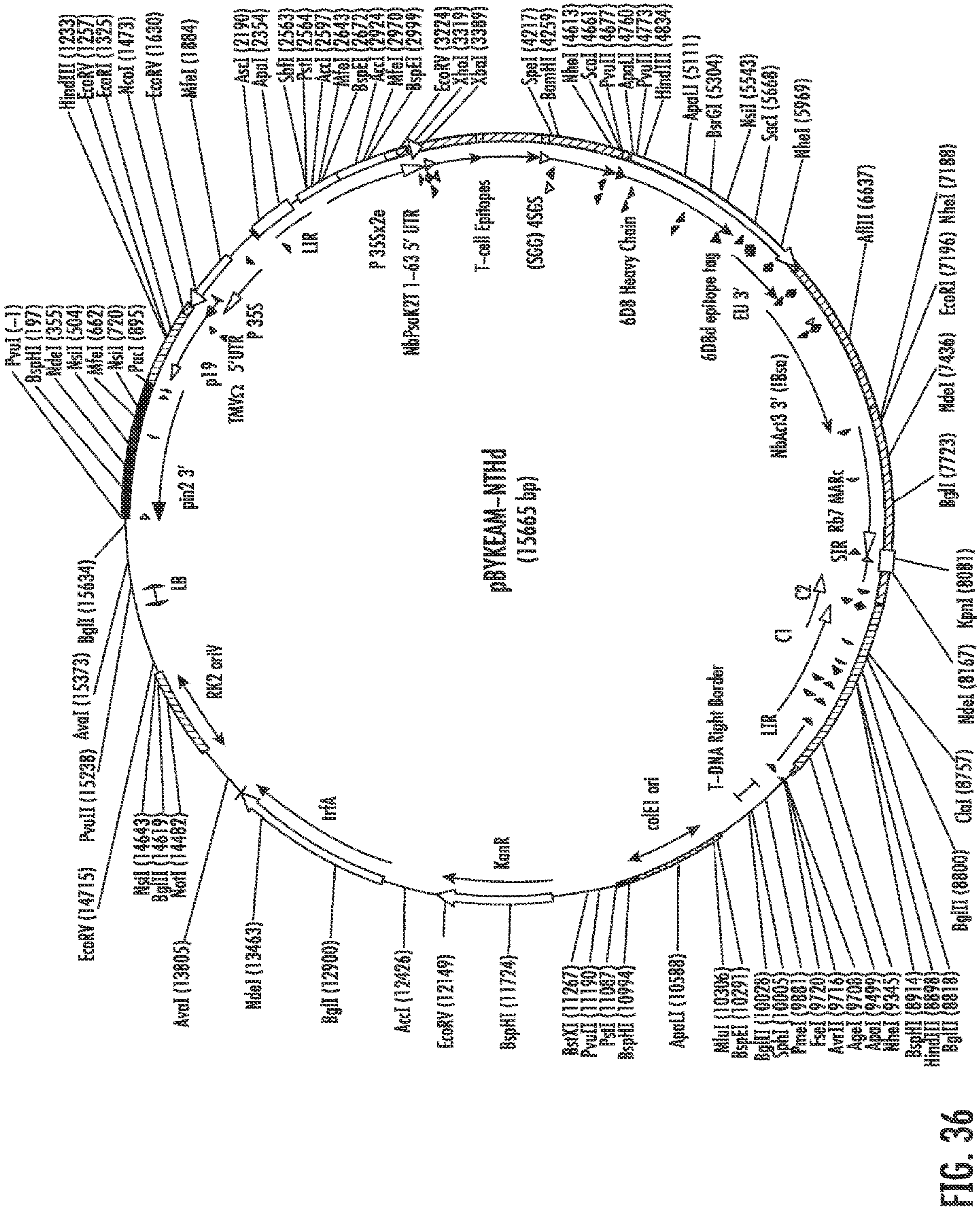
Figure 37:
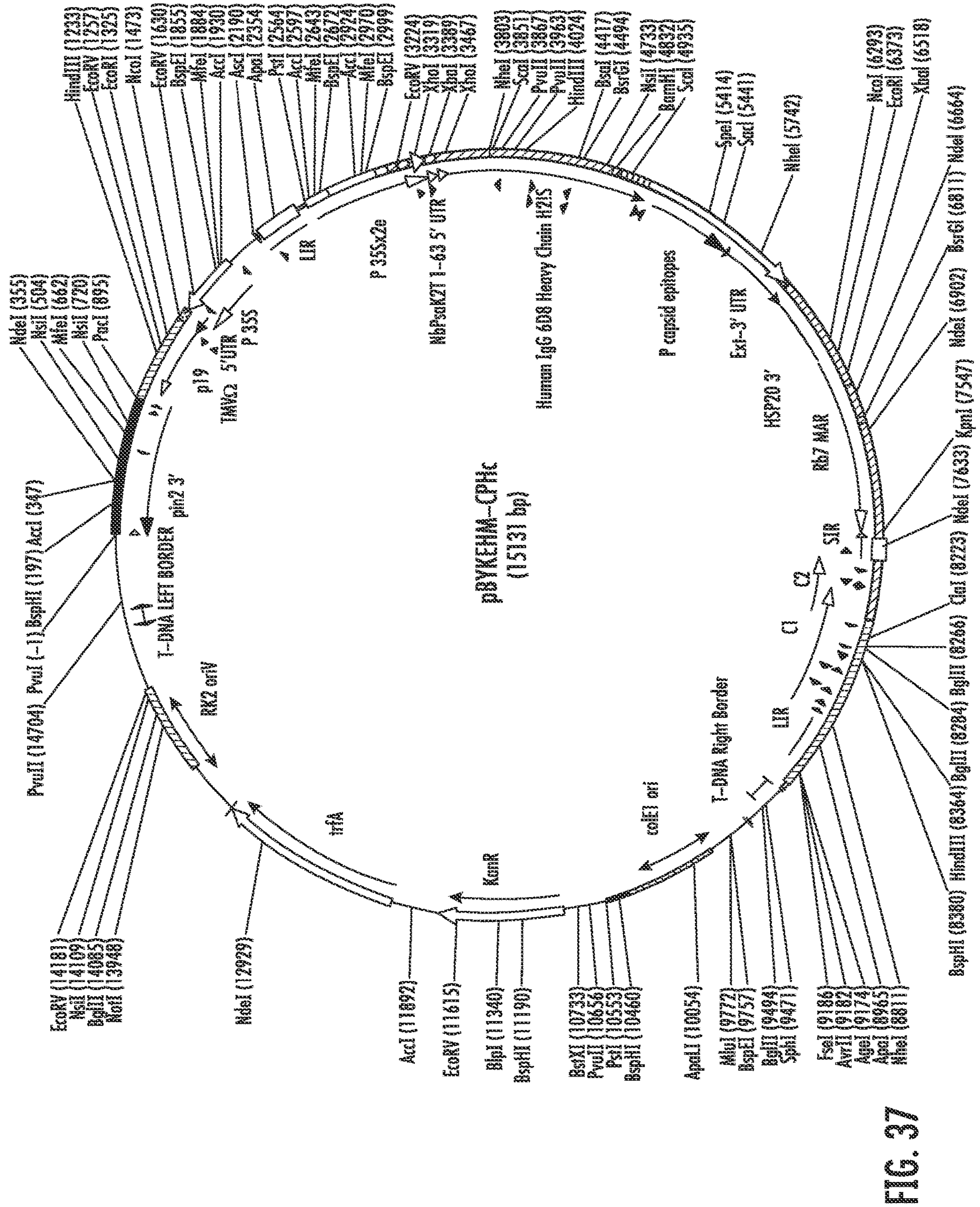
Figure 38:
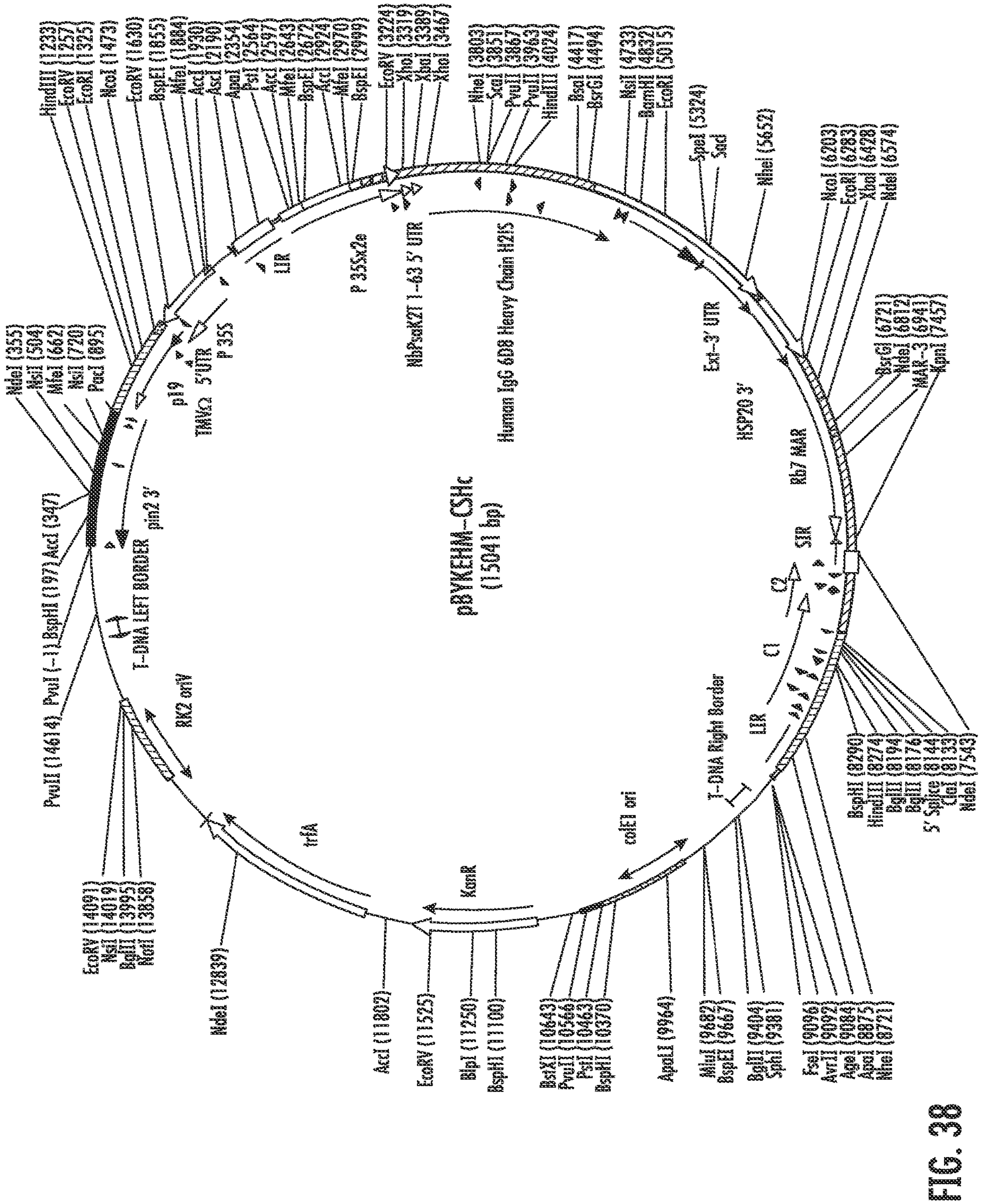
Figure 39:
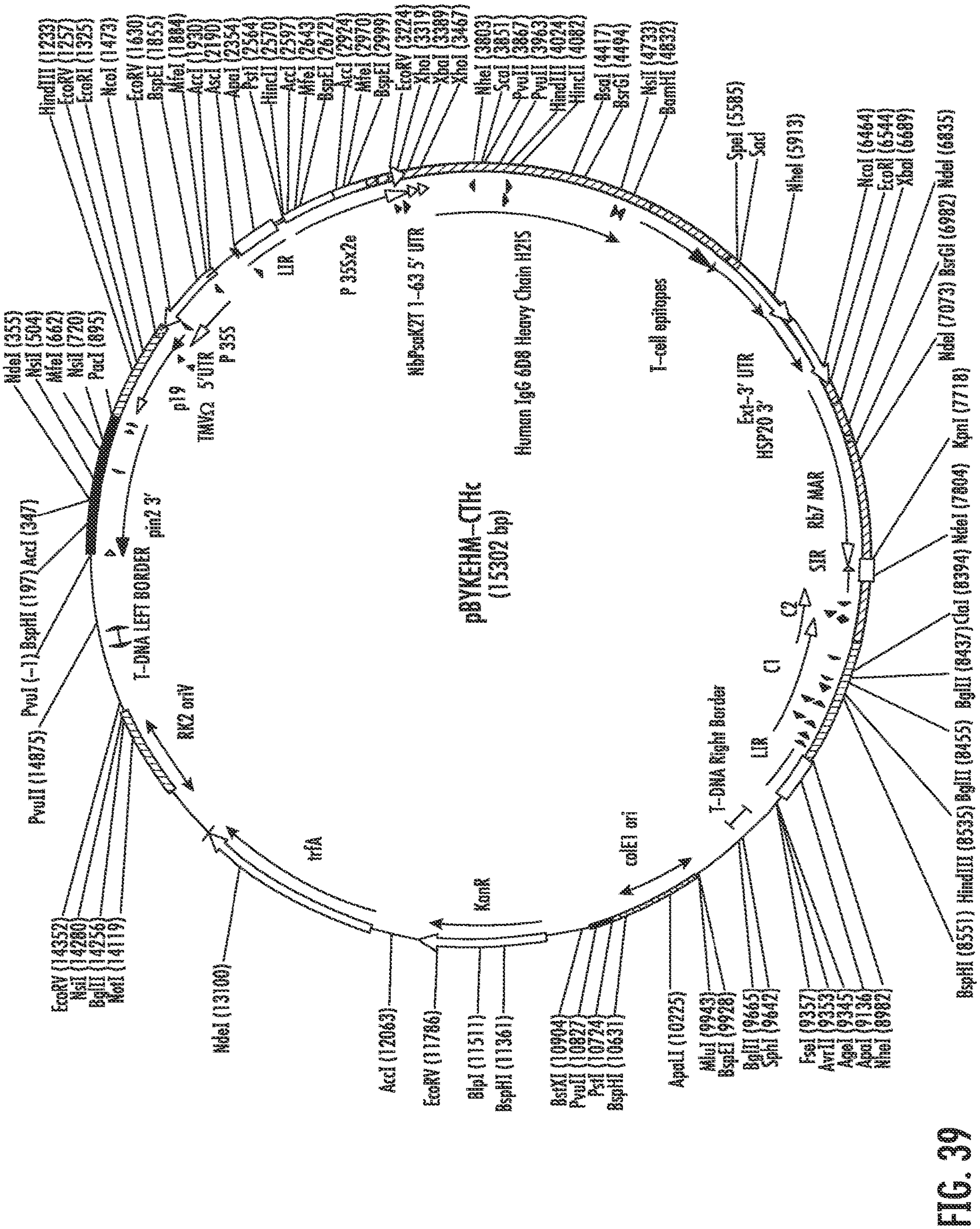

For each epitope, RIC constructs where the epitopes are linked to at the N-terminus or the C-terminus could be successfully expressed in plants (FIG. 14A). All of these RIC constructs could be purified (FIG. 14B and FIG. 15). Serum from mice immunized with these RIC constructs could bind to mouse norovirus (FIG. 16) and VLPs modeling GI.3 and GII.2 noroviruses (FIGS. 17 and 18). Increase increased IFN-7 production by splenocytes of mice immunized with the RICs (FIG. 19) suggest that RICs successfully induced immunity norovirus.

G. Methods

1. Vector Construction

The construction of a BeYDV plant expression vector for ZE3, as well as its fusion to the 6D8 C-terminus (pBYR11eM-h6D8ZE3), referred to here as construct "HLZe") or N-terminus with epitope tag (pBYR11eMa-BAZE3-Hgp371) or without epitope tag (pBYR11eMa-BAZE3-H) was described in Diamos et al., 2019. A vector pBYKEMd2-6D8 expressing the full 6D8 mAb without ZE3 fusion (construct "HL") was also described in Diamos et al., 2019. To create a vector expressing only the light chain of 6D8, pBYKEMd2-6D8 was digested with XhoI and the vector was self-ligated to yield pBYKEMd-6D8K. A vector expressing only the heavy chain of 6D8 (construct "H") was created by digesting pBYKEMd2-6D8 with SacI and self-ligating the vector, to yield pBYKEMd-6D8H. The 6D8 epitope binding tag was added to pBYKEMd-6D8H by digesting pBYR11eMa-BAZE3-Hgp371 with BsaI-SacI and inserting the tag-containing fragment into pBYKEMd-6D8H digested with BsaI-SacI, yielding pBYKEMd-6D8Hgp371 (construct "HLe" when coexpressed with light chain). To remove the epitope tag from HLZe, pBYR11eM-h6D8ZE3 was digested with BamHI-SacI and ligated with a fragment containing ZE3 obtained via amplification with primers ZE3-Bam-F (5'-gcgggatccaagggcgtgtcatactcc, SEQ ID NO. 8) and ZE3-Sac-R (5'-acagagctcttaagtgctaccactcctgtg, SEQ ID NO. 9) and subsequent digestion with BamHI-SacI. The resulting vector, pBYKEMd-HZE3, was coinfiltrated with pBYKEMd-6D8K to produce construct "HLZ." To produce ZE3 fused to the 6D8 N-terminus without light chain, pBYR11eMa-BAZE3-H was digested with SacI and the vector was self-ligated, yielding pBYKEMd-ZE3H (construct "ZH"). To introduce hexamer mutations, a region of the 6D8 heavy chain constant region was synthesized (Integrated DNA Technologies, Iowa, USA) containing the E345R, E430G, and S440Y mutations, then digested with BsaI-SacI and used to replace the BsaI-SacI region of 6D8 in pBYKEMd-ZE3H, yielding pBYKEMd-ZE3Hx (construct "ZHx"). RIC epitope tag mutant "a" was generated by annealing oligos 6D89-F (5'-ctagtgtttacaagctggacatatctgaggcataagagct, SEQ ID NO. 10) and 6D89-R (5'-cttatgcctcagatatgtccagcttgtaaaca, SEQ ID NO. 11) and ligating them into pBYR11eM-h6D8ZE3 digested SpeI-SacI; mutant "b" was generated by first amplifying mutant "a" with primers gpDISE-Sac-R: (5'-tttgagctcttactcagatatgtccagcttgtaaac, SEQ ID NO. 12) and 35S-F (5'aatcccactatccttcgc, SEQ ID NO. 13), then digesting the product with SpeI-SacI and ligating it into pBYR11eM-h6D8ZE3 digested with SpeI-SacI. Mutants "c" and "d" were created similarly to mutant "a" using overlapping oligos 6D87-F (5'-ctagttacaagctggacatatctgagtaagagct, SEQ ID NO. 14) and 6D87-R (5'-cttactcagatatgtccagcttgtaa, SEQ ID NO. 15) for "c" and 6D86-F (5'-ctagttacaagctggacatatcttaagagct, SEQ ID NO. 16) and 6D86-R (5'-cttaagatatgtccagcttgtaa, SEQ ID NO. 17).

In order to make a construct in which the variable heavy (VH) domain is linked to a variable light chain (VL) domain that, in turn, is directly fused to the constant region of the 6D8 antibody, the variable regions were first obtained through PCR amplification and end-tailoring of segments from pBYR11eM-h6D8ZE3. For the VH domain, the primers LIR-H3A (5'-aagcttgttgttgtgactccgag, SEQ ID NO. 18) and 6D8VH-Spe-R (5'-cggactagtagctgaagacactgtgac, SEQ ID NO. 19) were used. The VL region was obtained through PCR amplification of pBYR11eM-h6D8ZE3 with primers 35S-F (5'-aatcccactatccttcgc, SEQ ID NO. 13) and 6D8VK-Nhe-R (5'-cgtgctagccttgatctccactttggtc, SEQ ID NO. 20). In order to fuse VL region to the constant region of a human IgG antibody, a subclone was created by digesting the PCR fragment with XhoI-NheI and inserting it into a vector, pKS-HH-gp371, that contained the 6D8 heavy chain. This subclone was named pKS-VL. Next, pBYKEM-6D8K was digested with SbfI-SacI, the PCR product that amplified the variable heavy chain fragment was digested SbfI-SpeI, and the variable light chain subclone was digested SpeI-SacI. These fragments were assembled to create pBYKEMd2-VHLVK (HVL). Finally, this construct was used to create pBYKEMd2-HVLZe by a two-fragment ligation. The pBYKEMd2-VHLVK construct was digested with BsaI and SacI to obtain the vector fragment along with the variable regions of the heavy and light chains. To obtain the ZE3 antigen segment and the epitope tag, pBYR11eM-h6D8ZE3 was also digested BsaI-SacI. The resulting construct, which was used to produce HVLZe, was named pBYKEMd-HVLZe.

The HVL panel of constructs were created as follows. HVL-Hx, a construct containing a single-chain antibody with three point mutations in the Fc region in order to facilitate formation of single-chain hexamers, was created by a two-fragment ligation. The backbone was derived by a BsaI-SacI digest of pBYKEMd2-VHLVK and the insert containing the mutations for hexamer formation was derived from a BsaI-SacI digest of pBYKEMd-ZE3Hx. The final construct was named pBYKEMd2-HVL-Hx.

HVLZnt, a single-chain fusion with the ZE3 antigen on the C-terminus but no epitope tag, was created by ligating a BsaI-SacI digested backbone from pBYKEMd2-VHLVK to an insert derived from pBYKEMd-HZE3. This construct was named pBYKEMd2-HVLZnt ZHVLnt, a single-chain RIC with the ZE3 antigen linked to the antibody N-terminus and no epitope tag, was created by the following ligation. The insert fragment containing the ZE3 antigen and the VH segment was amplified from pBYR11eMa-BAZE3-Hgp371 using the 35S-F and VH-BsaS-R primers. The VH-BsaS-R primer end-tailored the 5' end to include a BsaI site that would result in a SpeI overhang upon digestion with BsaI. This PCR fragment was digested XhoI-BsaI and ligated with a backbone XhoI-SpeI fragment obtained from pBYKEMd2-VHLVK. The final construct was named pBYKEMd2-ZHVLnt.

ZHVLe, a single-chain antibody RIC with an N-terminally fused ZE3 antigen and an epitope tag was created by a two-fragment ligation. pBYKEMd2-ZHVLnt was digested BsaI-SacI to produce the vector segment containing the N-terminal ZE3 antigen and the HVL construct. The insert containing the 6D8 epitope tag was derived from a BsaI-SacI digest of pBYR11eMa-BAZE3-Hgp371. The final construct was named pBYKEMd2-ZHVLe.

ZHVLhx, a single-chain antibody with a N-terminally fused ZE3 antigen and point mutations to facilitate hexamer formation, was obtained by a two-fragment ligation. The vector fragment was obtained by a BsaI-SacI digest of pBYKEMd2-ZHVLnt and the insert fragment was derived from a BsaI-SacI digest of pBYKEMd2-HVL-Hx. The final construct was named pBYKEMd2-ZHVLhx.

The specific constructs described herein listed below:

pBYR11 em-h6D8ZE3 (sequence set forth in SEQ ID NO. 21)

pBYR11eMa-BAZE3-Hgp371 (sequence set forth in SEQ ID NO. 22)

pBYR11eMa-BAZE3-H (sequence set forth in SEQ ID NO. 23)

pBYKEMd-HZE3 (sequence set forth in SEQ ID NO. 24)

pBYKEMd-ZE3H (sequence set forth in SEQ ID NO. 25)

pBYKEMd-ZE3Hx (sequence set forth in SEQ ID NO. 26)

pBYKEMd-HVLZe (sequence set forth in SEQ ID NO. 27)

pBYKEMd2-HVL-Hx (sequence set forth in SEQ ID NO. 28)

pBYKEMd2-HVLZnt (sequence set forth in SEQ ID NO. 29)

pBYKEMd2-ZHVLnt (sequence set forth in SEQ ID NO. 30)

pBYKEMd2-ZHVLe (sequence set forth in SEQ ID NO. 31)

pBYKEMd2-ZHVLhx (sequence set forth in SEQ ID NO. 32)

pBYKEMd-6D8K (sequence set forth in SEQ ID NO. 33)

2. Agroinfiltration of *Nicotiana benthamiana* Leaves

Binary vectors were separately introduced into *Agrobacterium tumefaciens* EHA105 by electroporation. The resulting strains were verified by restriction digestion or PCR, grown overnight at 30° C., and used to infiltrate leaves of 5- to 6-week-old *N. benthamiana* maintained at 23-25° C. Briefly, the bacteria were pelleted by centrifugation for 5 min at 5,000 g and then resuspended in infiltration buffer (10 mM 2-(N-morpholino)ethanesulfonic acid (MES), pH 5.5 and 10 mM $MgSO_4$) to $OD_{600}$=0.2, unless otherwise described. The resulting bacterial suspensions were injected by using a syringe without needle into leaves through a small puncture (Huang and Mason, 2004). To evaluate the effects of glycosylation, transgenic plants silenced for xylosyltransferase and fucosyltransferase were employed. Plant tissue was harvested at 5 DPI.

3. Protein Extraction and Purification

Crude protein was extracted by homogenizing agroinfiltrated leaf samples with 1:5 (w:v) ice cold extraction buffer (25 mM Tris-HCl, pH 8.0, 125 mM NaCl, 3 mM EDTA, 0.1% Triton X-100, 10 mg/mL sodium ascorbate, 0.3 mg/mL phenylmethylsulfonyl fluoride) using a Bullet Blender machine (Next Advance, Averill Park, NY) following the manufacturer's instruction. Homogenized tissue was rotated at room temperature or 4° C. for 30 min. The crude plant extract was clarified by centrifugation at 13,000 g for 15 min at 4° C. and the supernatant was analyzed by SDS-PAGE or ELISA. Alternatively, to evaluate solubility of proteins in the original homogenate, the pellet was designated the insoluble fraction and treated with SDS sample buffer at 100° C. for 10 min before loading on SDS-PAGE.

IgG variants, including HVLZe, were purified by protein G affinity chromatography. Agroinfiltrated leaves were blended with 1:3 (w:v) ice cold extraction buffer (25 mM Tris-HCl, pH 8.0, 125 mM NaCl, 3 mM EDTA, 0.1% Triton X-100, 10 mg/mL sodium ascorbate, 0.3 mg/mL phenylmethylsulfonyl fluoride), stirred for 30 min at 4° C., and filtered through miracloth. To precipitate endogenous plant proteins, the pH was lowered to 4.5 with 1 M phosphoric acid for 5 min while stirring, then raised to 7.6 with 2 M tris base. Following centrifugation for 20 min at 16,000 g, the clarified extract was loaded onto a Pierce Protein G column (Thermo Fisher Scientific, Waltham, MA, USA) following the manufacturer's instructions. Purified proteins were eluted with 100 mM glycine, pH 2.5, directly into collection tubes containing 1 M Tris-HCl pH 8.0 to neutralize the elution buffer. The HVL and ZHVLhx constructs were purified in a similar fashion; however, the acid precipitation step was skipped.

ZE3-His expressed from pBYe3R2K2Mc-BAZE3 was purified by metal affinity chromatography. Protein was extracted as described above, but without acid precipitation. The clarified extract was loaded onto a column containing TALON Metal Affinity Resin (BD Clontech, Mountain View, CA) according to the manufacturer's instructions. The column was washed with PBS and eluted with elution buffer (PBS, 150 mM imidazole, pH 7.4). Peak ZE3 elutions were pooled, dialyzed against PBS, and analyzed by SDS-PAGE and western blot.

4. SDS-PAGE and Western Blot

Plant protein extracts or purified protein samples were mixed with SDS sample buffer (50 mM Tris-HCl, pH 6.8, 2% SDS, 10% glycerol, 0.02% bromophenol blue) and separated on 4-15% stain-free polyacrylamide gels (Bio-Rad, Hercules, CA, USA). For reducing conditions, 0.5M DTT was added, and the samples were boiled for 10 min prior to loading. Polyacrylamide gels were visualized and imaged under UV light, then transferred to a PVDF membrane. For IgG detection, the protein transferred membranes were blocked with 5% dry milk in PBST (PBS with 0.05% tween-20) overnight at 4° C. and probed with goat anti-human IgG-HRP (Sigma-Aldrich, St. Louis, MO, USA diluted 1:5000 in 1% PBSTM). Bound antibody was detected with ECL reagent (Amersham, Little Chalfont, United Kingdom).

5. C1q Binding 96-well high-binding polystyrene plates (Corning Inc, Corning, NY, USA) were coated with 15 g/ml human complement C1q in PBS for 2 h at 37° C. The plate was washed 3 times with PBST, and then blocked with 5% dry milk in PBST for 15 minutes. After washing 3 times with PBST, purified human IgG (Southern Biotech, Birmingham, AL, USA) and purified IgG-ZE3 fusions were added at 0.1 mg/ml with 10-fold serial dilutions and incubated for 1.5 h at 37° C. After washing 3 times with PBST, bound IgG was detected by incubating with 1:1000 polyclonal goat anti human IgG-HRP (Southern Biotech, Birmingham, AL, USA) for Ih at 37° C. The plate was washed 4 times with PBST, developed with TMB substrate (Thermo Fisher Scientific, Waltham, MA, USA), stopped with 1M HCl, and the absorbance was read at 450 nm.

6. 6D8 Epitope Binding

To test the ability of HVL to bind to the 6D8 epitope tag, 900 ng of purified dengue consensus envelope domain III tagged with 6D8 epitope were bound to 96-well high-binding polystyrene plates (Corning Inc, Corning, NY, USA). After a 1-hour incubation at 37° C., the plate was washed thrice with PBST and blocked with 5% dry milk in PBST for 30 minutes. Then, the plate was washed thrice with PBST and various dilutions of either purified HLV or full-length 6D8 antibody were added to the plate. The plate was incubated at 37° C. for 1-hour, washed thrice with PBST and detected with HRP-conjugated mouse anti-human IgG (Fc only) (Southern Biotech, Birmingham, AL, USA) antibody at a 1:2000 dilution. Then, the plate was thoroughly washed with PBST and developed with TMB substrate (Thermo Fisher Scientific, Waltham, MA, USA). The absorbance was read at 450 nm.

7. Sucrose Gradient Density Centrifugation

Purified samples of each IgG fusion (100 μl) were loaded onto discontinuous sucrose gradients consisting of 350 μl layers of 5, 10, 15, 20, and 25% sucrose in PBS in a 2.0 ml microcentrifuge tube and centrifuged at 21,000 g for 16 h at 4° C. Fractions were collected and analyzed by SDS-PAGE followed by visualization on stain-free gels (Bio-Rad, Hercules, CA, USA). The relative band intensity of each fraction was determined using ImageJ software, with the peak band arbitrarily assigned the value of 1.

8. Immunization of Mice and Sample Collection

All animals were handled in accordance to the Animal Welfare Act and Arizona State University IACUC. Female BALB/C mice, 6-8 weeks old, were immunized subcutaneously with purified IgG fusion variants. In all treatment groups, the total weight of antigen was set to deliver an equivalent 8 μg of ZE3. Doses were given on days 0 and 14. Serum collection was done as described in Santi et al., 2008 by submandibular bleed on days 0, 14, and 28.

9. Antibody Measurements

Mouse antibody titers were measured by ELISA. Plant-expressed 6-His tagged ZE3 at 50 ng/well was bound to 96-well high-binding polystyrene plates (Corning Inc, Corning, NY, USA), and the plates were blocked with 5% nonfat dry milk in PBST. After washing the wells with PBST (PBS with 0.05% Tween 20), the mouse sera were diluted with 1% PBSTM (PBST with 1% nonfat dry milk) and incubated. Mouse antibodies were detected by incubation with polyclonal goat anti-mouse IgG-horseradish peroxidase conjugate (Sigma-Aldrich, St. Louis, MO, USA). The plate was developed with TMB substrate (Thermo Fisher Scientific, Waltham, MA, USA), stopped with 1M HCl, and the absorbance was read at 450 nm. Endpoint titers were taken as the reciprocal of the lowest dilution which produced an OD450 reading twice the background produced using PBS as the sample. IgG2a antibodies were measured from sera diluted 1:100 in 1% PBSTM and detected with IgG2a horseradish peroxidase conjugate (Santa Cruz Biotechnology, Dallas, TX, USA).

REFERENCES CITED AND INCORPORATED BY REFERENCE

Diamos, A. G., Larios, D., Brown, L., Kilbourne, J., Kim, H. S., Saxena, D., et al. (2019) Vaccine synergy with virus-like particle and immune complex platforms for delivery of human papillomavirus L2 antigen. 37, 137-144.

Huang Z, Phoolcharoen W, Lai H, Piensook K, Cardineau G, Zeitlin L, Whaley K J, Arntzen C J, Mason H S, Chen Q. (2010) High-level rapid production of full-size monoclonal antibodies in plants by a single-vector DNA replicon system. Biotechnol Bioeng. 106(1):9-17.

Santi, L., Batchelor, L., Huang, Z., Hjelm, B., Kilbourne, J., Arntzen, C. J., et al. (2008) An efficient plant viral expression system generating orally immunogenic Norwalk virus-like particles. Vaccine, 26, 1846-1854.

Wilson, J. A., Hevey, M., Bakken, R., Guest, S., Bray, M., Schmaljohn, A. L., and Hart, M. K. (2000) Epitopes involved in antibody-mediated protection from Ebola virus. Science, 287, 1664-6.

We claim:

1. A recombinant protein comprising:

a unit of a Fc fusion comprising a CH2 domain and a CH3 domain of an IgG;

a unit of an antigen, wherein the unit of the antigen is not an epitope of the IgG;

a unit of a variable heavy chain (VH) domain of the IgG; and a unit of a CH1 domain of the IgG;

an epitope tag consisting of the sequence YKLDIS (SEQ ID NO. 1);

a unit of a light chain variable (VL) domain of the IgG; and a unit of a light chain constant (CL) domain of the IgG, wherein:

the unit of the antigen is linked to the unit of the VH domain of the IgG at the N-terminus or to the CH3 domain of IgG at the C-terminus;

the unit of the CH1 domain of the IgG is linked to the CH2 domain of the IgG and to the unit of the VH domain of the IgG;

the unit of the VL domain of the IgG is linked to the unit of the CL domain of the IgG;

the unit of CL domain of the IgG is linked to the CH1 domain of the IgG; and the unit of the antigen is linked:

(1) to the CH3 domain of IgG at the C-terminus and the epitope tag is linked to the C-terminus of the antigen; or (2) to the unit of the VH domain of the IgG at the N-terminus and the epitope tag is linked to the C-terminus of the CH3 domain of the IgG.

2. The recombinant protein of claim 1, wherein the unit of the antigen comprises SEQ ID NO. 34.

3. A method of inducing an immune response in a subject, the method comprising administering to the subject the recombinant protein of claim 1, thereby inducing the immune response against the antigen in the recombinant protein.

4. The recombinant protein of claim 1, comprising:

two units of the antigen;

two units of the Fc fusion;

two units of the VH domain of the IgG; and two units of the CH1 domain of the IgG;

two epitope tags;

two units of the VL domain of the IgG; and two units of the CL domain of the IgG, wherein the two units of the Fc fusion are linked together by a disulfide bond formed at the linkage of the CH1 domain of the IgG and the CH2 domain of the IgG.

5. The recombinant protein of claim 4, wherein the unit of the antigen comprises SEQ ID NO. 34.

* * * * *